(12) United States Patent
Evans et al.

(10) Patent No.: US 7,981,615 B2
(45) Date of Patent: Jul. 19, 2011

(54) COMPOSITIONS AND METHODS FOR TREATING DISEASES ASSOCIATED WITH T-BOX AND N-MYC

(75) Inventors: Sylvia Evans, Del Mar, CA (US); Ju Chen, San Diego, CA (US); Chenleng Cai, San Diego, CA (US); Wenlai Zhou, San Diego, CA (US); Michael G. Rosenfeld, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/611,047

(22) Filed: Nov. 2, 2009

(65) Prior Publication Data
US 2010/0047810 A1 Feb. 25, 2010

Related U.S. Application Data

(62) Division of application No. 11/734,267, filed on Apr. 11, 2007, now Pat. No. 7,625,874.

(60) Provisional application No. 60/791,176, filed on Apr. 11, 2006.

(51) Int. Cl.
*C12Q 1/68* (2006.01)
*C07H 21/02* (2006.01)
*C07H 21/04* (2006.01)
*C07K 16/00* (2006.01)

(52) U.S. Cl. ........ 435/6; 536/23.1; 536/24.5; 530/387.1

(58) Field of Classification Search .................. None
See application file for complete search history.

(56) References Cited

U.S. PATENT DOCUMENTS
6,506,559 B1  1/2003  Fire et al.

OTHER PUBLICATIONS

Cai et al., Development. May 2005;132(10):2475-87. Epub Apr. 20, 2005. T-box genes coordinate regional rates of proliferation and regional specification during cardiogenesis.*
Elbashir et al., The EMBO Journal, vol. 20, No. 23, pp. 6877-6888, 2001.*
Devroe and Silver, "Retrovirus-Delivered siRNA," *BMC Biotechnology* (2002), 2(15):1-5.
Mahato et al., "Modulation of Gene Expression by Antisense and Antigene Oligodeoxynucleotides and Small Interfering RNA," *Expert Opin. Drug Deliv.* (2005), 2(1):3-28, Ashley Publications Ltd.
Prince et al., "Tbx2 Directly Represses the Expression of the $p21^{WAF1}$ Cyclin-Dependent Kinase Inhibitor," *Cancer Research* (2004), 64:1669-1674.
Scherer and Rossi, "Approaches for the Sequence-Specific Knockdown of mRNA," *Nature Biotechnology* (2003), 21(12):1457-1465, Nature Publishing Group.

* cited by examiner

*Primary Examiner* — Amy Bowman
(74) *Attorney, Agent, or Firm* — DLA Piper LLP (US)

(57) ABSTRACT

The invention herein provides a mode of treating a disease associated with the regulation of T-Box and N-Myc gene, which includes cancers and heart disease in human and other subjects by identifying and administering a compound which modulates T-Box or N-Myc function. The invention also provides polynucleotides, polypeptides, vectors, cells, tissues and organisms useful in the identification and treatment of metabolic syndrome. A number of desirable cell proliferation and senescence regulating aspects are achieved by various embodiments of the present invention.

7 Claims, 44 Drawing Sheets

MLC2a

α-MHC

Tbx5

Wnt11

Tbx20

Tbx3 ccna2

BMP7

Hand2

Isl1

US 7,981,615 B2

COMPOSITIONS AND METHODS FOR TREATING DISEASES ASSOCIATED WITH T-BOX AND N-MYC

CROSS-REFERENCE TO RELATED APPLICATIONS

This application is a divisional application of U.S. application Ser. No. 11/734,267 filed Apr. 11, 2007, now U.S. Pat. No. 7,625,874; which claims the benefit under 35 USC §119 (e) to U.S. Application Ser. No. 60/791,176 filed Apr. 11, 2006, now abandoned. The disclosure of each of the prior applications is considered part of and is incorporated by reference in the disclosure of this application.

GRANT INFORMATION

This invention was made with government support under Grant No. HL070867 awarded by National Institutes of Health Heart Lung and Blood Institute. The government has certain rights in the invention.

INCORPORATION-BY-REFERENCE OF MATERIAL SUBMITTED VIA .TXT FILE

The sequence listing, which is a part of the present disclosure, includes a sequence listing comprising nucleotide and/or amino acid sequences of the present invention. The subject matter of the Sequence Listing is incorporated herein by reference in its entirety,

BACKGROUND OF THE INVENTION

1. Field of the Invention

The present invention relates to T-box transcription factors and their effects on the N-Myc promoter during cell proliferation and senescence. Diseases associated with such effects include cancers and heart disease. Also provided are the genes and their homologs, methods for screening for inducers and repressors of T-box transcription factors and N-Myc, effectors such as siRNA, antibodies and other compounds, methods for manipulating cell cycle by effecting the expression of those genes or the functions of the gene products, and methods for preventing and treating diseases associated with the regulation of T-box transcription factors and N-Myc.

2. Background Information

T-Box (Tbx) transcription factors are highly conserved across species, expressed in a wide variety of tissue types, often in an overlapping manner, and are required for development of diverse organs and tissues. T-Box genes regulate patterning and cell fate, cell survival and/or proliferation.

Although much is known about the individual biochemical components of T-box and N-Myc, what has not been determined is a mechanism for controlling proliferation and/or senescence to provide a target for drug studies for the treatment of, e.g., cancers and heart disease. Therefore, what are needed are methods for designing such drugs and treatments for those ailments and methods for screening for markers predictive of such ailments.

SUMMARY OF THE INVENTION

The present invention provides a method for identifying a candidate N-Myc up regulating compound, the method comprising (a) contacting Tbx2 or biologically-active fragment with a known compound that binds Tbx2 to form an assay mixture, (b) contacting the assay mixture with a test compound, and (c) determining the ability of the test compound to interact with Tbx2, wherein an increased ability of the test compound to interact with Tbx2 in the presence of the known compound indicates that the test compound is an N-Myc up regulating compound.

In accordance with a further aspect of the invention, a method is provided for identifying a candidate Tbx2 up regulating compound, the method comprising (a) contacting Tbx20 or biologically-active fragment with a known compound that binds Tbx20 to form an assay mixture, (b) contacting the assay mixture with a test compound, and (c) determining the ability of the test compound to interact with Tbx20, wherein an increased ability of the test compound to interact with Tbx20 in the presence of the known compound indicates that the test compound is an Tbx2 up regulating compound.

In the methods above, the test compound can be an antibody, preferably a monoclonal antibody. The test compound can also include a ribozyme, antisense compound, triplex-forming molecule, siRNA, and aptamer. Preferably, the siRNA comprises a sequence selected from the group consisting of SEQ ID NOs: 107-324, 326-523, and 525-550.

In a further aspect of the invention, a method is provided for expressing a siRNA targeting a TBX2, TBX3 or TBX20 gene in a cell in vitro or in vivo, comprising
providing an expression vector encoding a siRNA specific to the TBX2, TBX3 or TBX20 gene; introducing the vector into a cell in vitro or in vivo; and maintaining the cell in vitro or in vivo under conditions permitting expression of the siRNA in the cell.

In yet another aspect, a method is provided for identifying a subject having or susceptible to acquiring a cancer or heart disease, the method comprising detecting a level of TBX20, TBX2 and N-Myc activity in the subject and comparing the subject TBX20, TBX2 and N-Myc activity level to predetermined normal standards, wherein a TBX20 or TBX 2 activity level below the normal standard and a N-Myc activity level above the normal standard indicates that the subject has or is susceptible to acquiring a cancer or heart disease.

In another aspect, a method is provided for treating an animal, preferably human, having a cancer associated with T-Box or N-Myc protein expression, the method comprising:
administering to a subject in need thereof a therapeutically effective amount of at least one of an antisense nucleic acid, ribozyme, triplex-forming oligonucleotide, siRNA, probe, primer, T-Box-specific antibody, N-Myc-specific antibody, and any combination thereof, such that expression of the T-Box or N-Myc protein is inhibited.

In yet another embodiment, a method is provided for controlling the proliferative state of a stem cell the method comprising administering a siRNA to the stem cell in an amount effective to inhibit the expression of T-box.

In a further aspect, a method is provided for controlling the senescent state of a stem cell, the method comprising administering a siRNA to the stem cell in an amount effective to inhibit the expression of T-box.

In yet another embodiment, a method is provided for diagnosing heart disease in a subject comprising (a) obtaining a sample from the subject; (b) detecting T-box or N-Myc expression in the sample; and (c) comparing to the expression of T-box or N-Myc of the sample to a control sample, wherein an elevated expression of T-box or N-Myc in the sample is diagnostic for heart disease.

In yet another embodiment, a method is provided for treating heart disease comprising modulating an activity of T-box or N-Myc, preferably by decreasing the activity of T-box or N-Myc.

In another aspect, a method is provided for determining whether a compound up-regulates or down-regulates the transcription of a T-box or N-Myc gene, comprising contacting the compound with a RNA polymerase and said gene, followed by measuring T-box or N-Myc gene transcription initiated by the RNA polymerase acting on the gene, wherein measuring enhanced transcription is indicative of up-regulation and measuring decreased transcription is indicative of down-regulation.

In another aspect, a method is provided for determining whether a compound up-regulates or down-regulates translation of an T-box or N-Myc gene in a cell, comprising contacting the compound with the cell, the cell further comprising the gene, and measuring T-box or N-Myc gene translation, wherein measuring enhanced translation is indicative of up-regulation and measuring decreased translation is indicative of down-regulation.

In yet another embodiment, a method is provided for treating an animal having a heart disease associated with T-Box or N-Myc protein expression, the method comprising administering to the animal a therapeutically effective amount of at least one of an antisense nucleic acid, ribozyme, triplex-forming oligonucleotide, siRNA, probe, primer, T-Box-specific antibody, N-Myc-specific anybody, and any combination thereof, such that expression of the T-Box or N-Myc protein is inhibited.

In a further aspect, a method is provided for manipulating cell cycle of an animal, comprising administering to the animal an effective amount of at least one of an antisense nucleic acid, ribozyme, triplex-forming oligonucleotide, siRNA, probe, primer, T-Box-specific antibody, N-Myc-specific antibody, and any combination thereof, such that expression of T-Box or N-Myc protein is inhibited.

An expression vector is also provided comprising a nucleic acid encoding a sequence selected from the group consisting of SEQ ID NOs: 107-324, 326-523, and 525-550, wherein the nucleic acid is operably linked to an expression control sequence. In addition, a cultured cell is provided comprising the vector of claim 51 or nucleic acid of claim 51 or RNA including SEQ ID NOs: 107-324, 326-523, and 525-550. In a further aspect, a kit is provided comprising an expression vector comprising a nucleic acid encoding a sequence selected from the group consisting of SEQ ID NOs: 107-324, 326-523, and 525-550.

These and other features, aspects and advantages of the present teachings will become better understood with reference to the following description, examples and appended claims.

BRIEF DESCRIPTION OF THE DRAWINGS

Those of skill in the art will understand that the drawings, described below, are for illustrative purposes only. The drawings are not intended to limit the scope of the present teachings in any way.

Figure 1A:
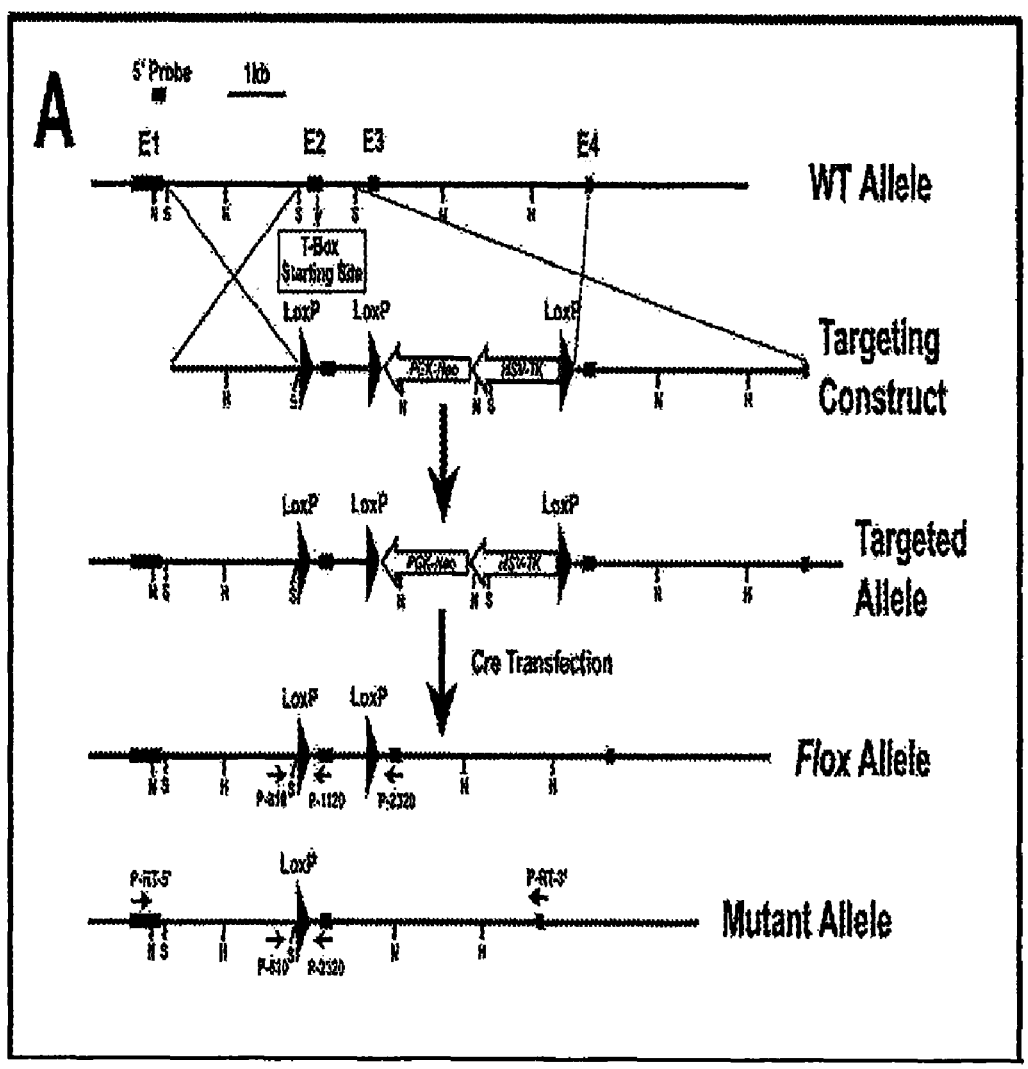
FIGS. 1A-1L. Generation of Tbx20 Targeted Allele, Whole Mount and Histological View of Tbx20-Null Mice and Littermate Controls at E8.5 and E9.5.
Figures 1B, 1C, 1D:
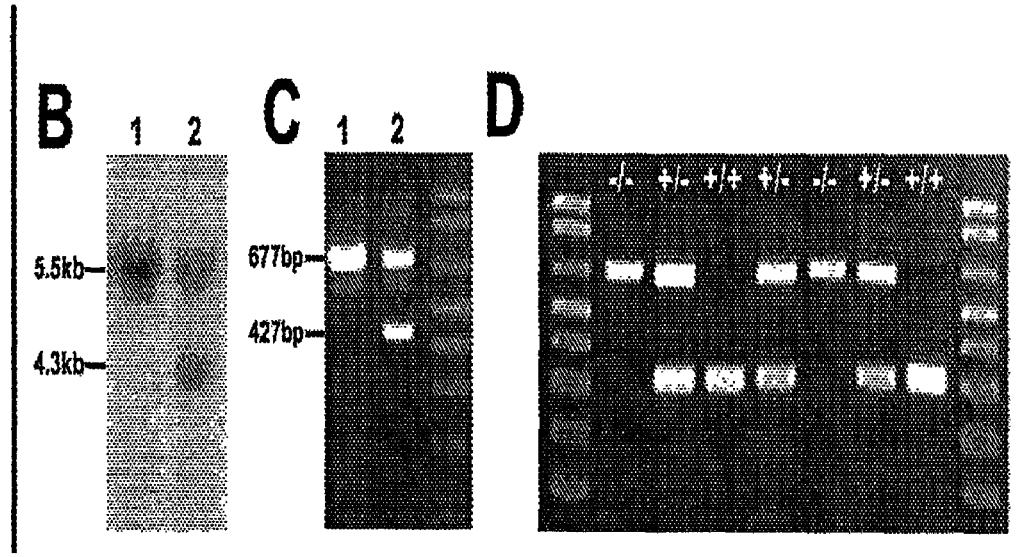
Figures 1E, 1F, 1G, 1H:
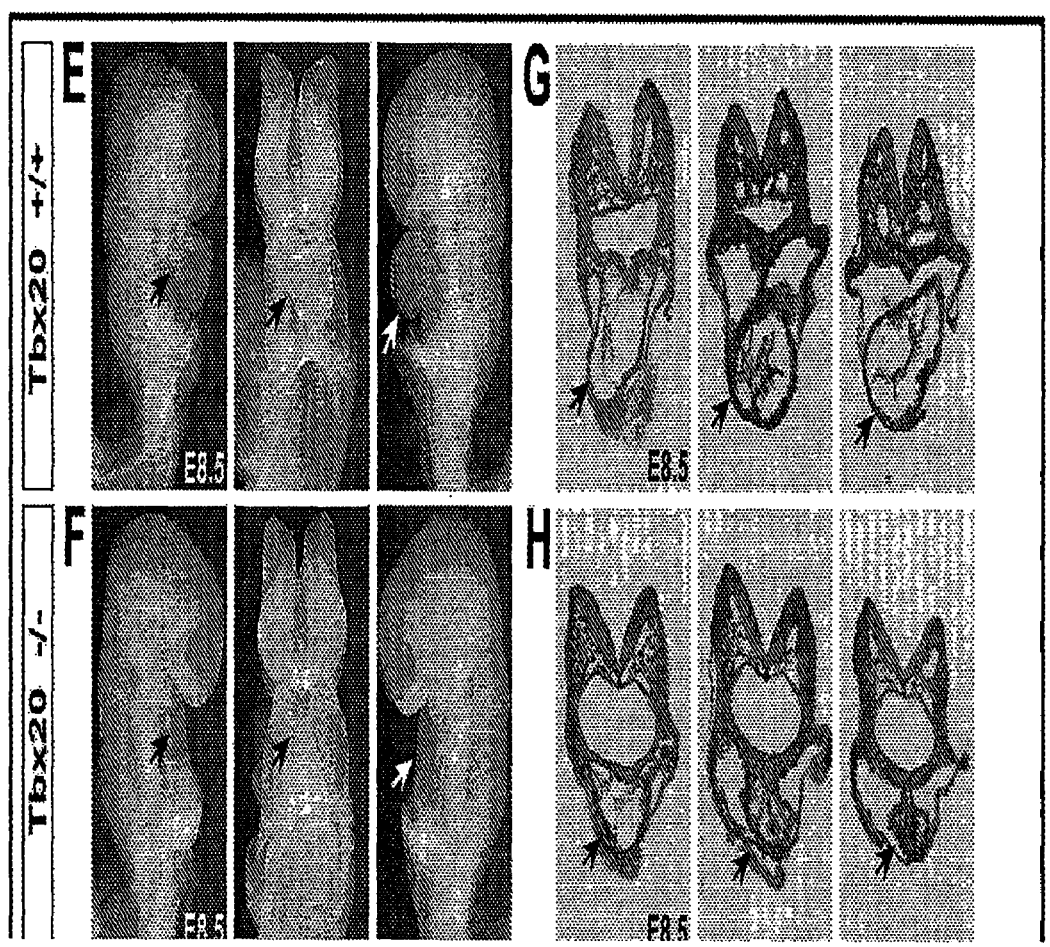
Figures 1I, 1J, 1K, 1L:
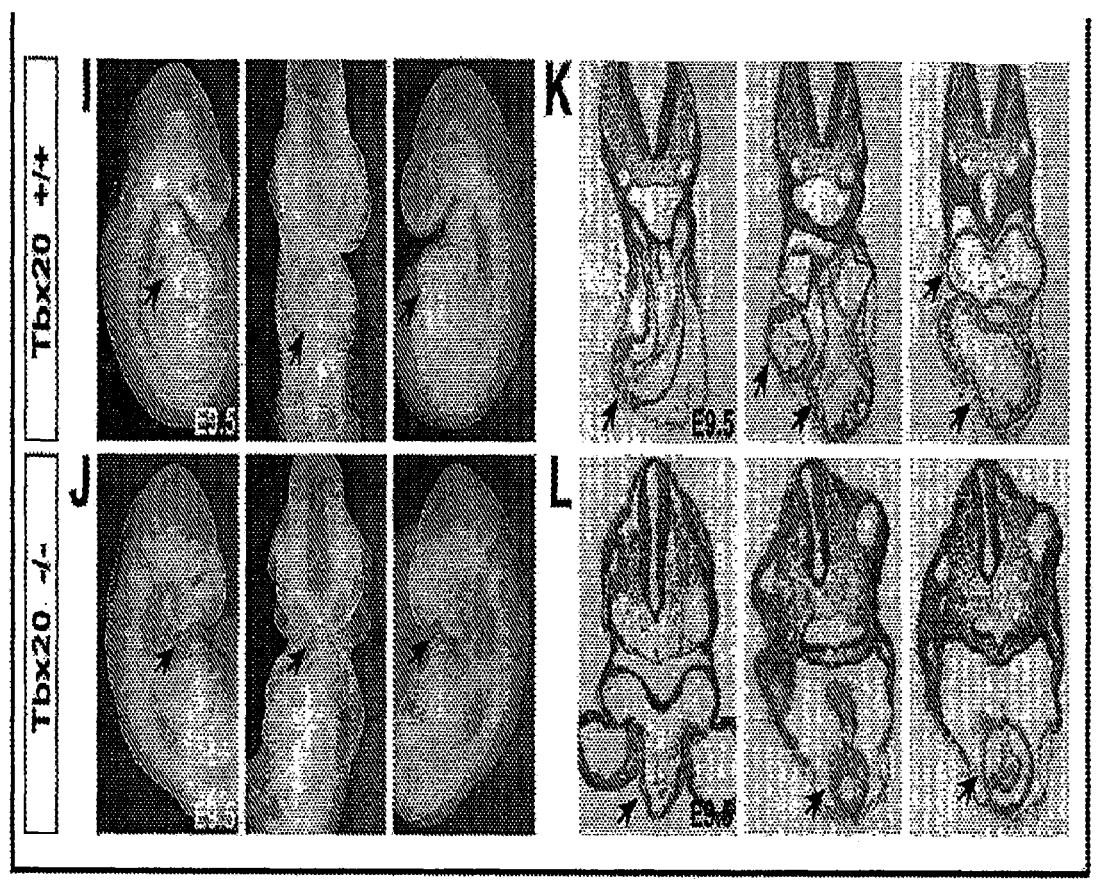

(A) Vector and allele maps showing generation of Tbx20 targeted allele using two LoxP sites that were induced into Tbx20 exon 2 where T-Box domain starts.

(B) Southern Blot of digested (Ncol) ES cell DNA, hybridized to show wild type band 5.5 kb and recombinant band 4.3 kb.

(C) RT-PCR using whole heart RNA obtained from adult wild type (C-1) and heterozygous mice (C-2) show the wild type band 677 bp and mutant band 427 bp.

(D) Genotypes determined by PCR of one littermate embryos from heterozygous cross (wild type allele band was 310 bp and the mutant allele band was 650 bp).

(E-L) Whole-mount and histological views of mice at embryonic stages as indicated in each panel, with arrows indicating heart region and showing that hearts of Tbx20 null mice are severely hypoplastic relative to control littermates at both stages.

Figures 2A, 2B:
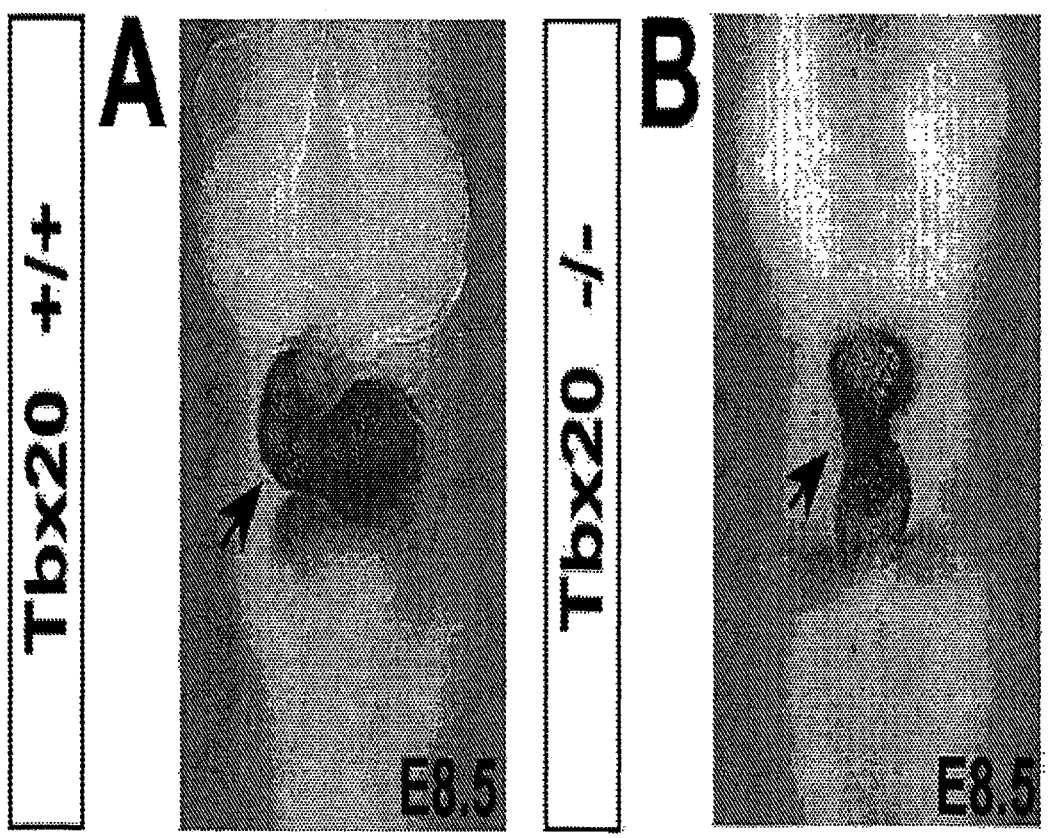
Figures 2C, 2D:
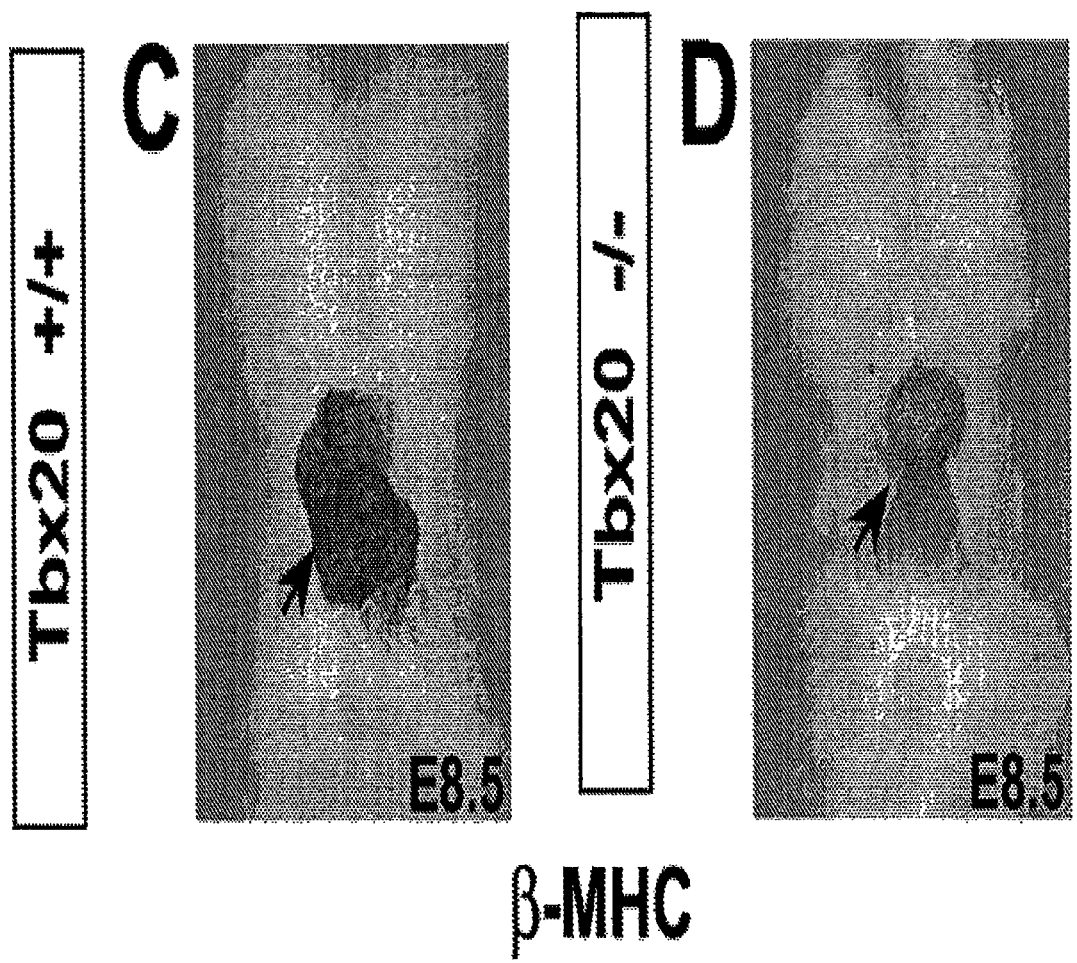
Figures 2E, 2F:
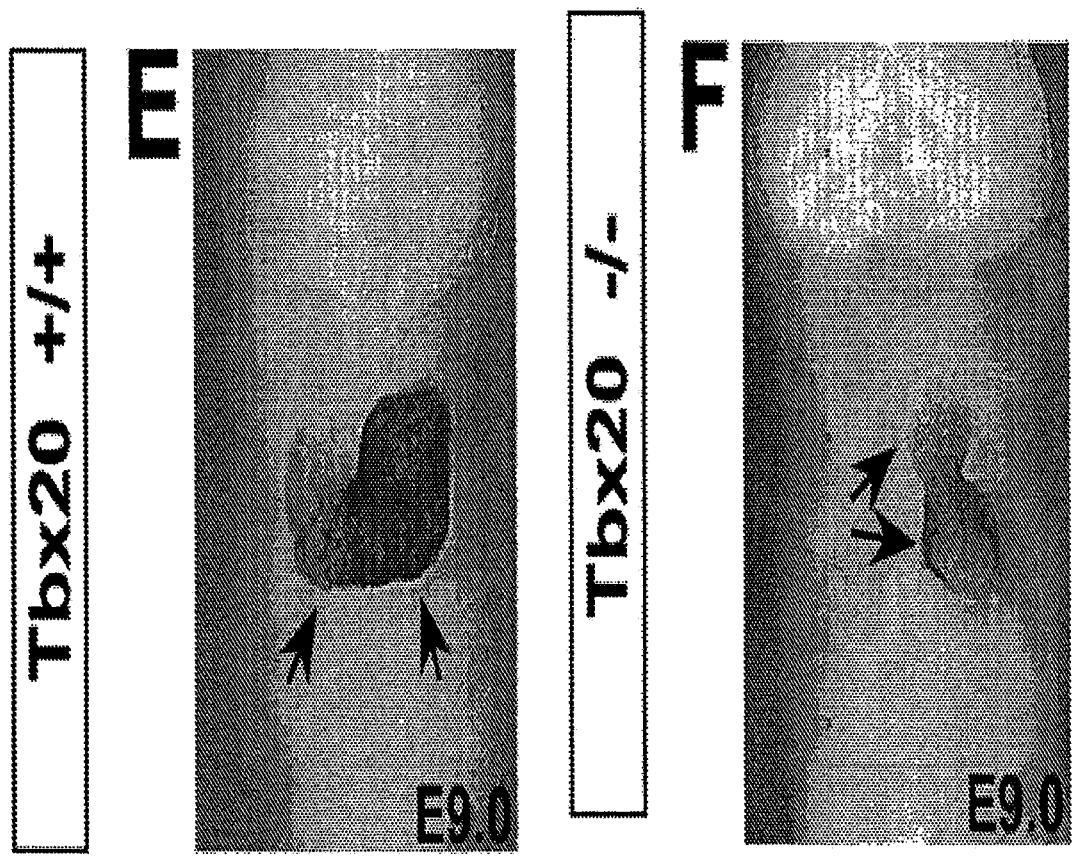
Figures 2G, 2H:
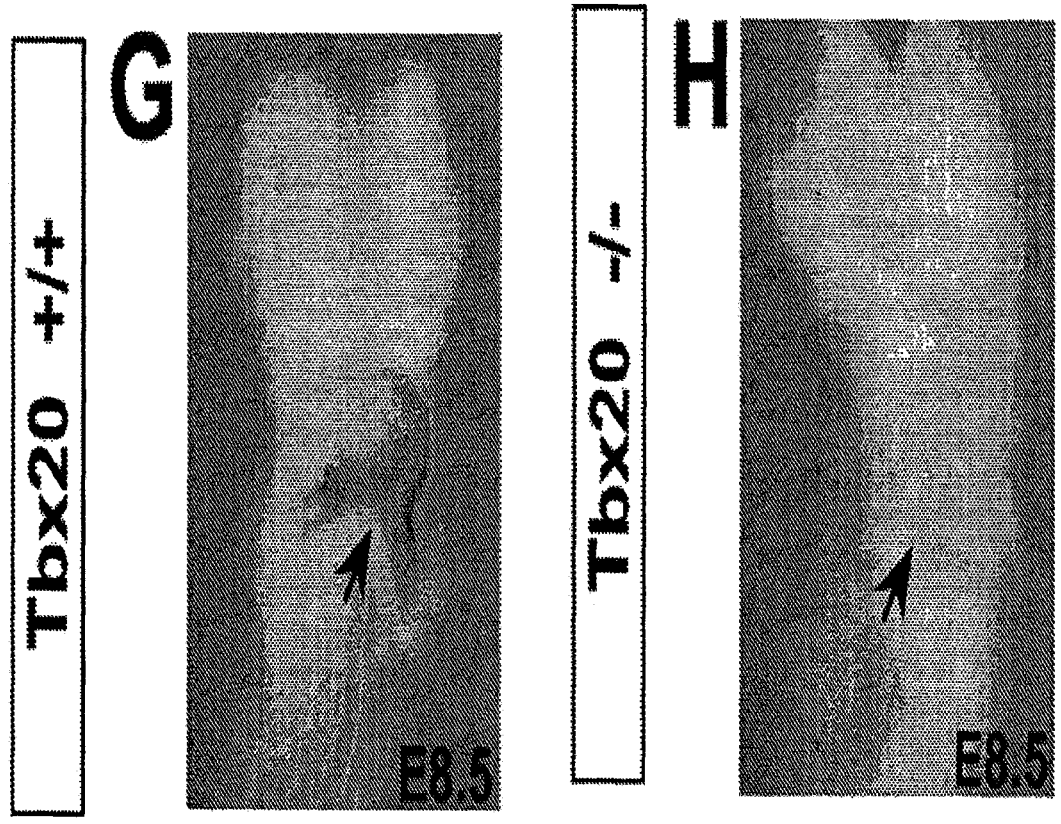
Figures 2I, 2J:
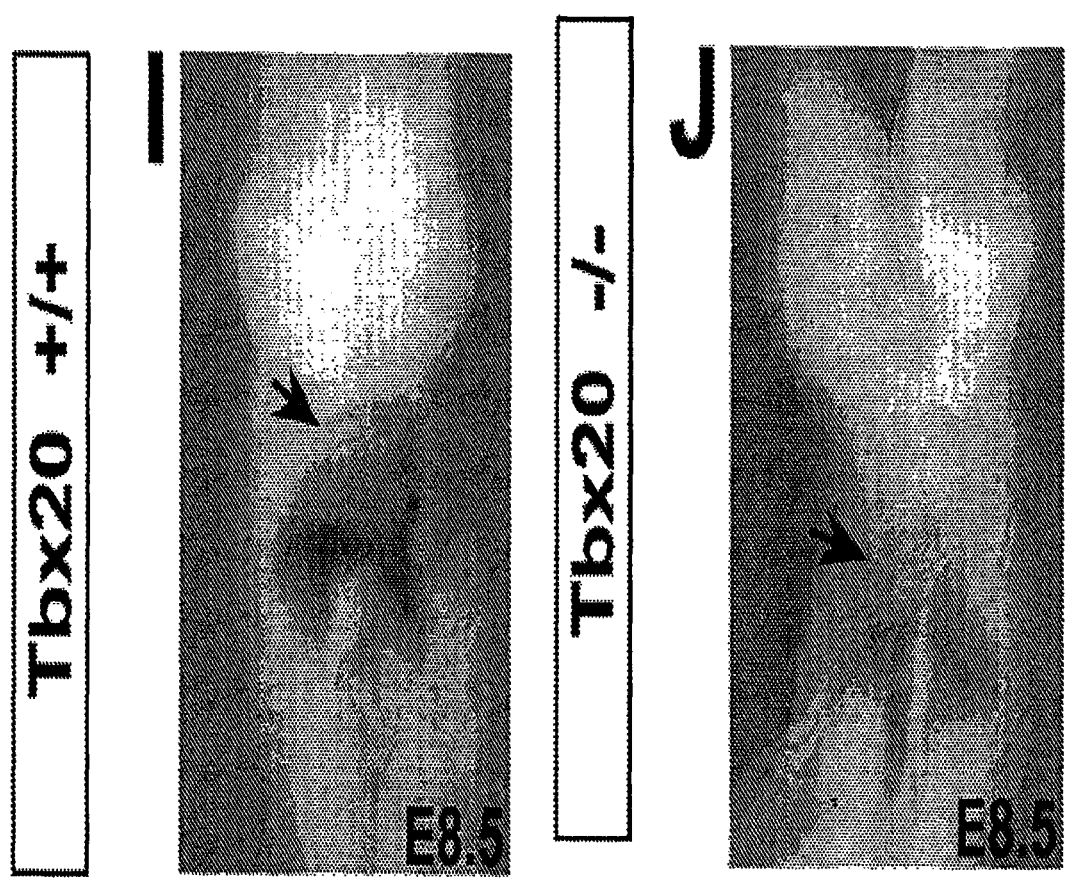
Figures 2K, 2L:
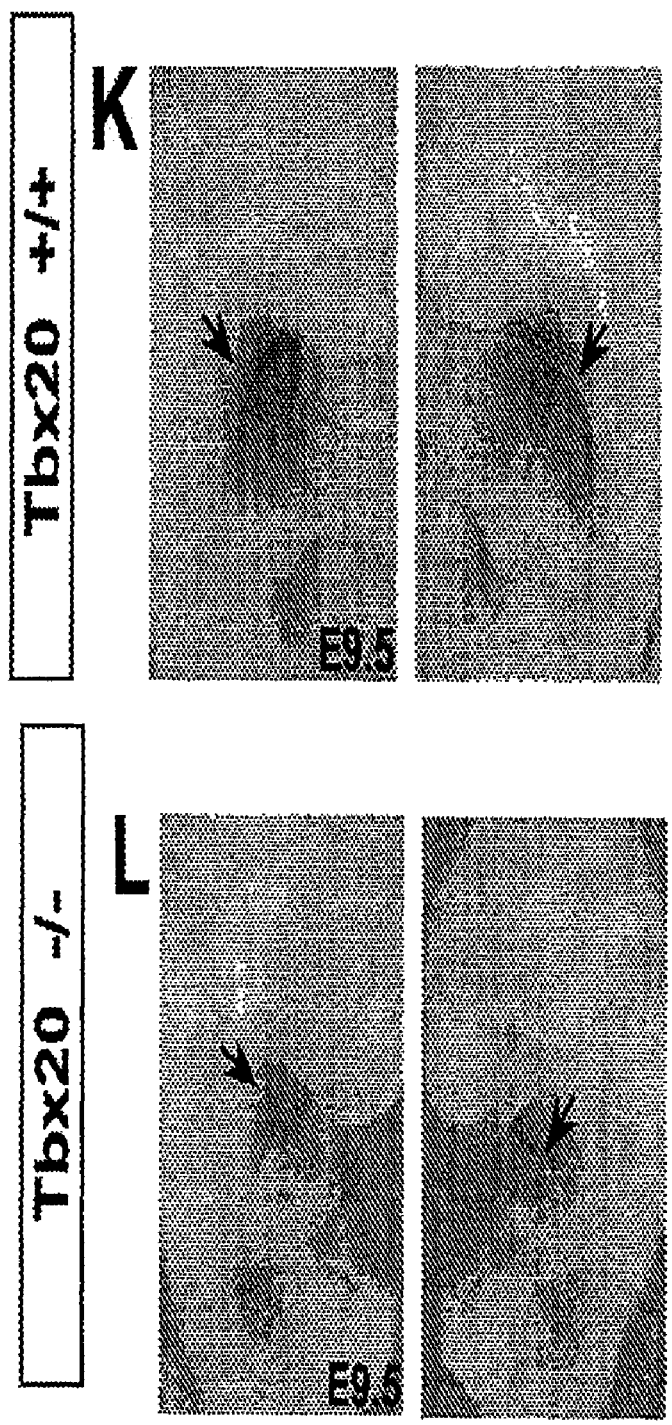
Figures 2M, 2N:
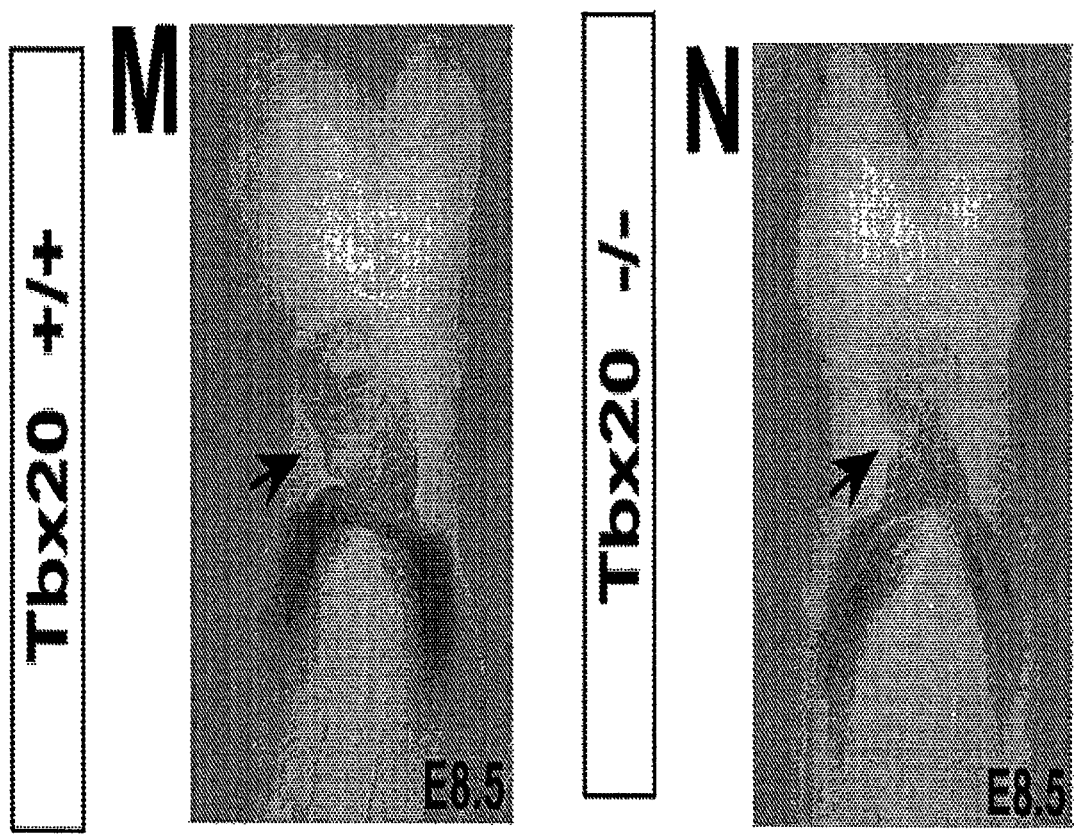

FIGS. 2A-2N. Whole Mount in situ Analysis of Tbx20 Null Mutants and Control Littermates:

(A-H) Panel series showing whole mount in situ hybridization with differentiation markers MLC2a, β-MHC, MLC2v indicating normal expression in Tbx20 mutants, but down-regulation of α-MHC.

(I, J) Tbx5 is expressed in left ventricular, atrioventricular, and atrial progenitors in an anteroposterior gradient, which is maintained in Tbx20 mutants.

(K,L) Wnt11 is expressed in outflow tract and atrioventricular canal.

(M,N) GATA4 expression throughout the heart in BO anterior-posterior gradient is maintained in Tbx20 mutants.

Figures 3A, 3B, 3C, 3D, 3E, 3F:
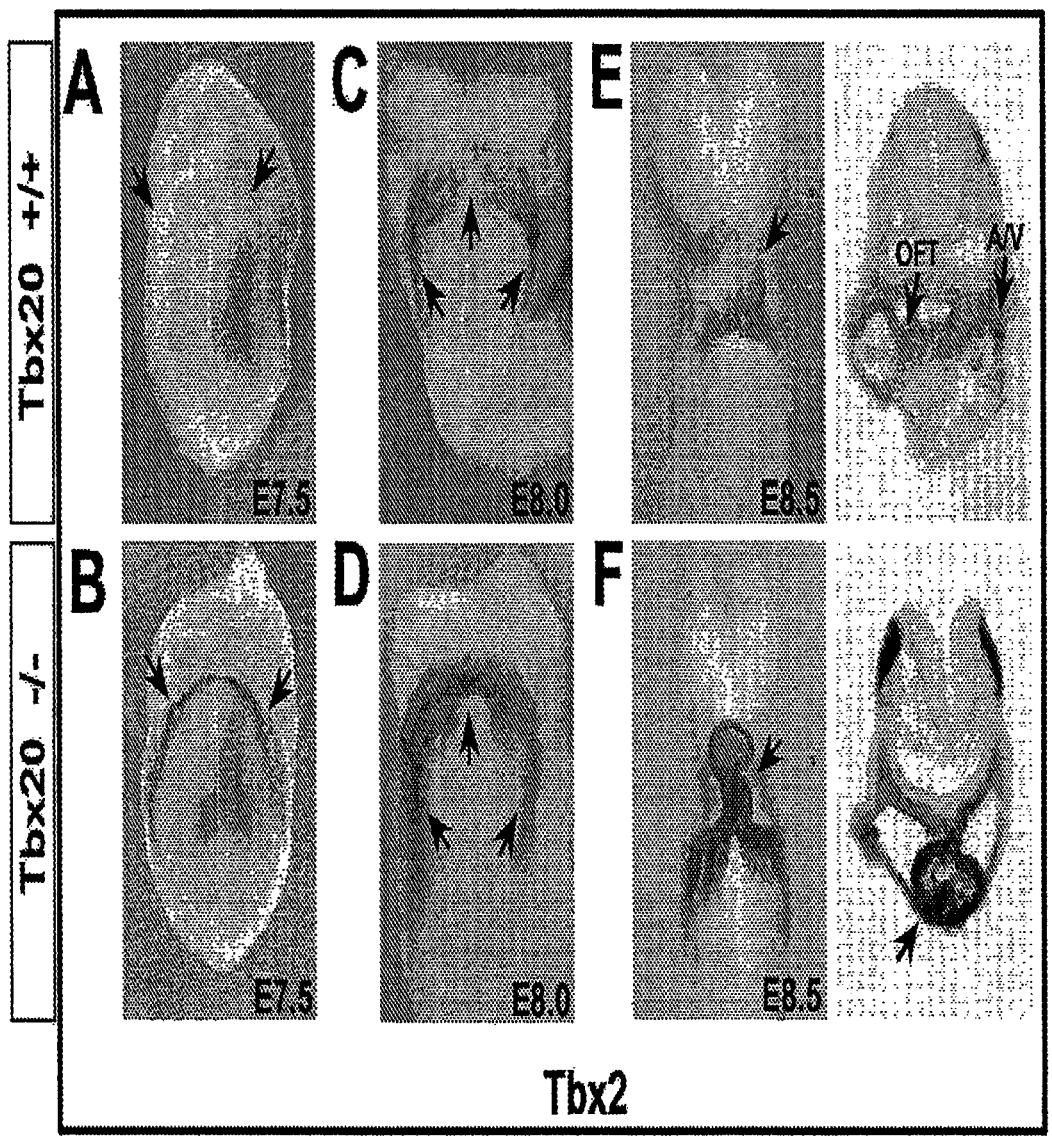
Figures 3G, 3H, 3I, 3J, 3K, 3L:
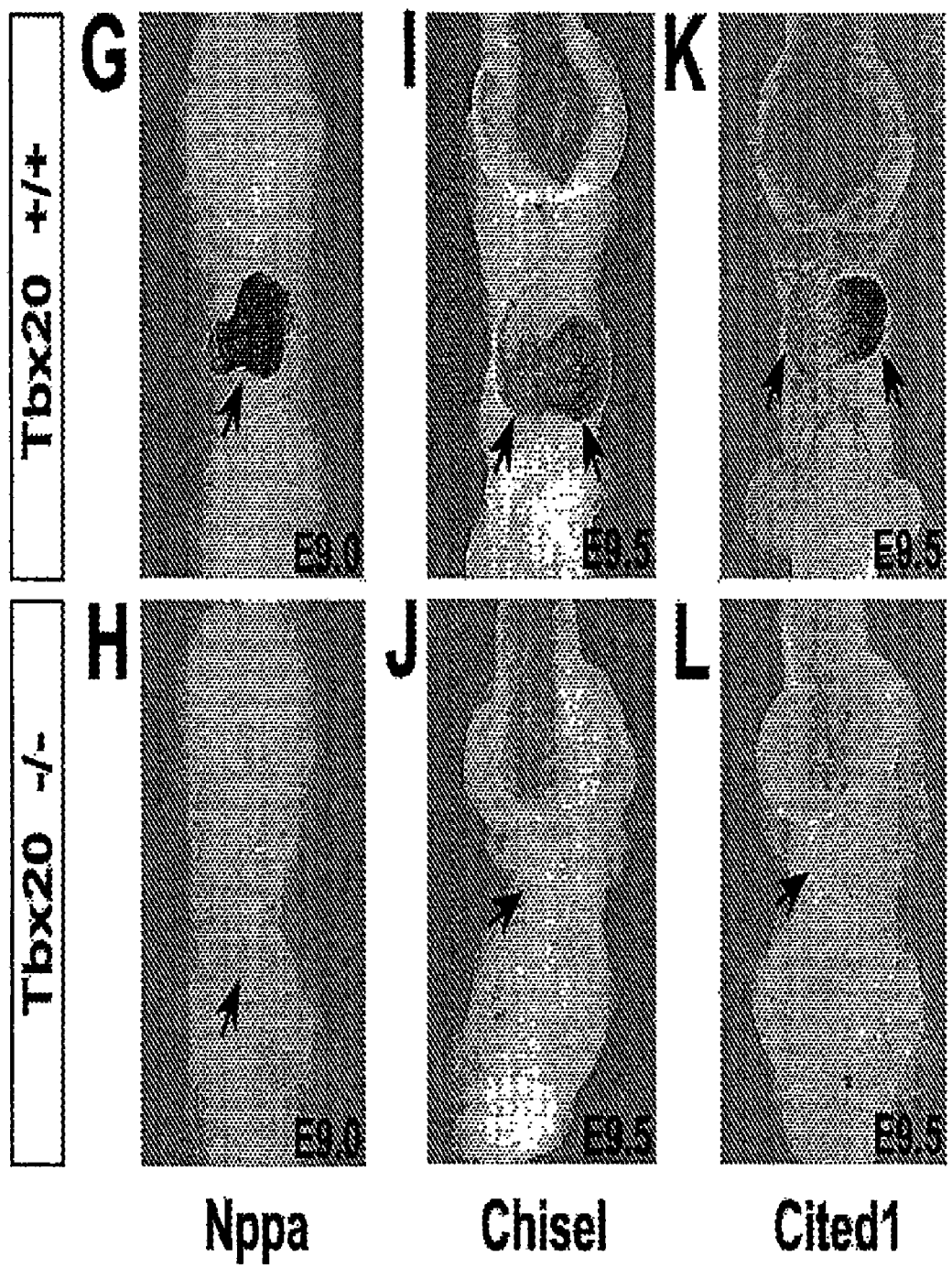
Figures 3M, 3N:
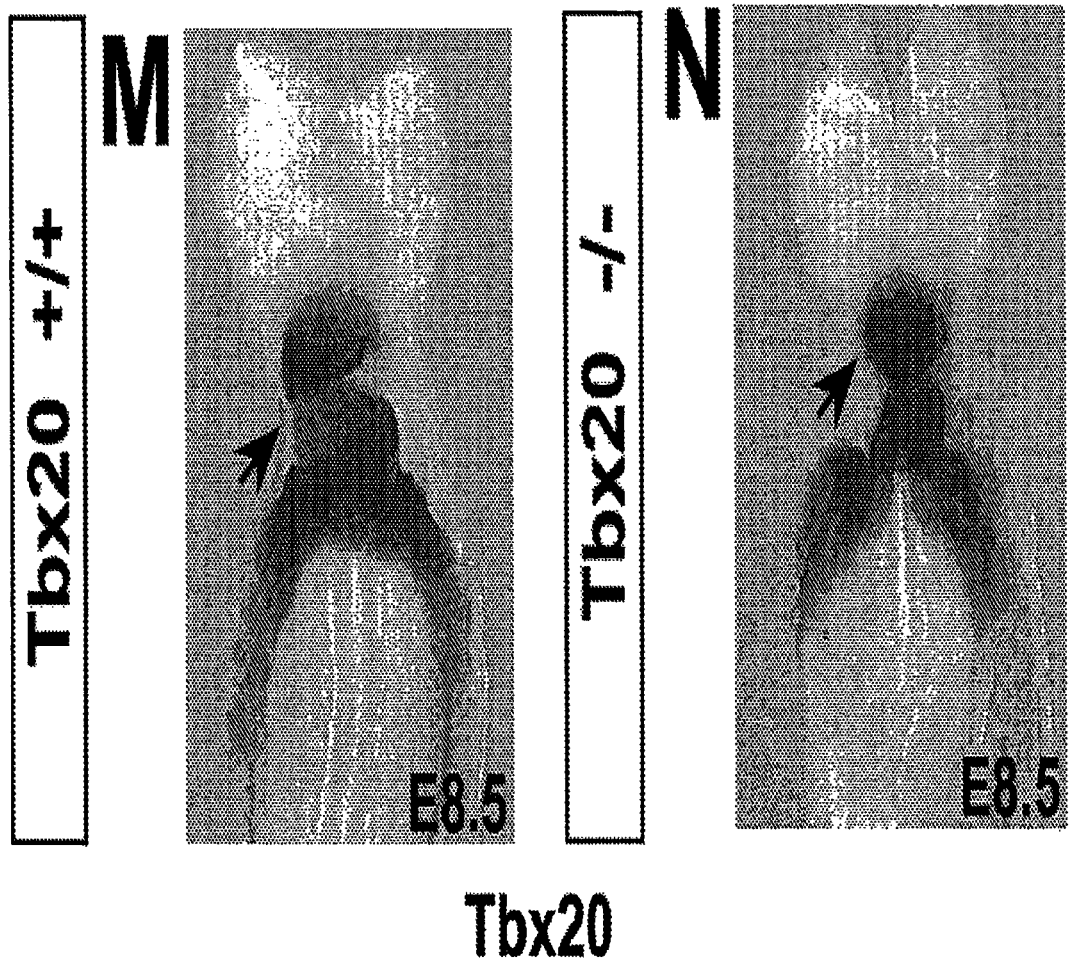
Figures 3O, 3P:
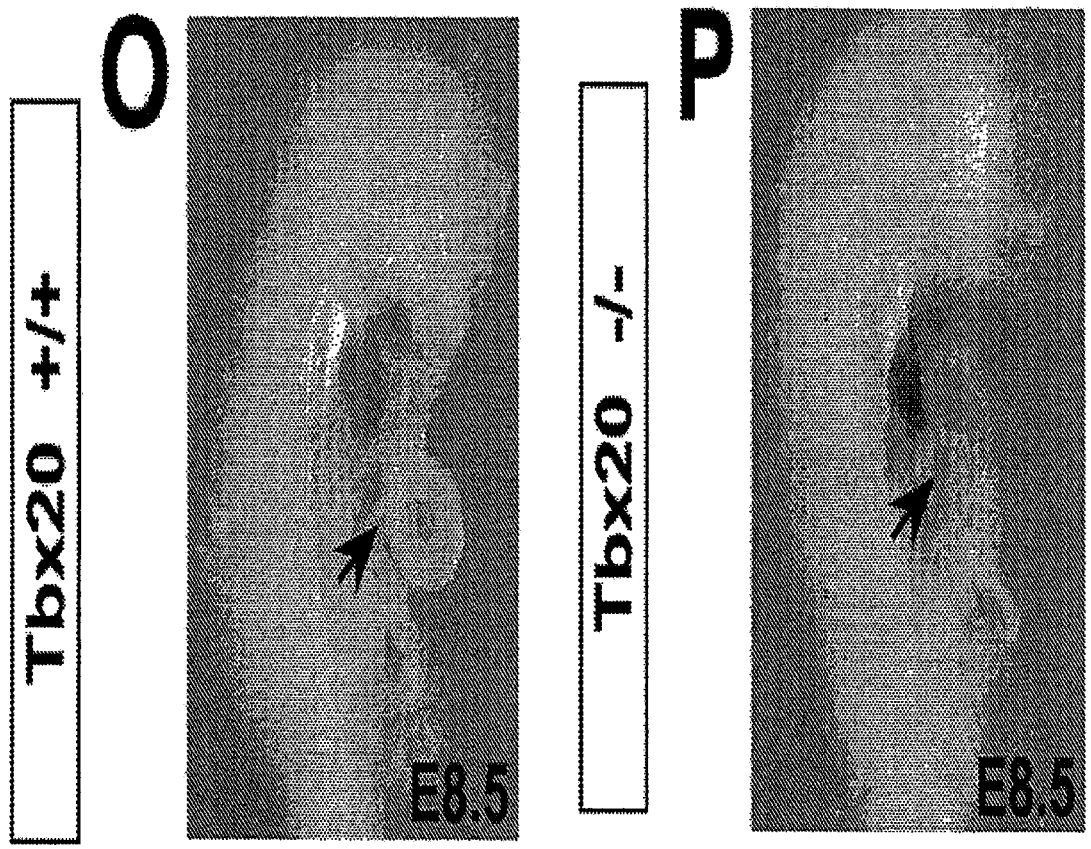
Figure 3Q:
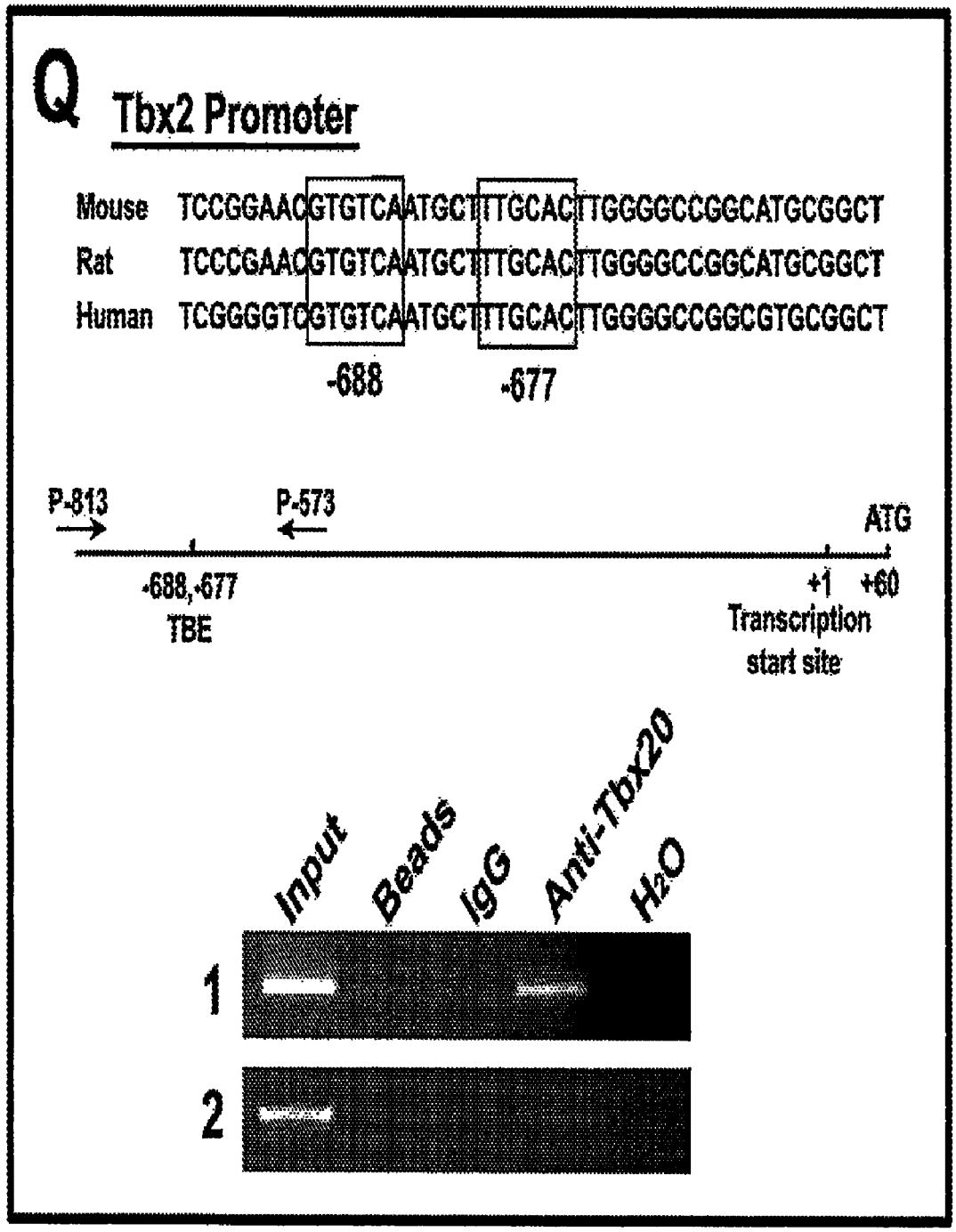
Figure 3R:
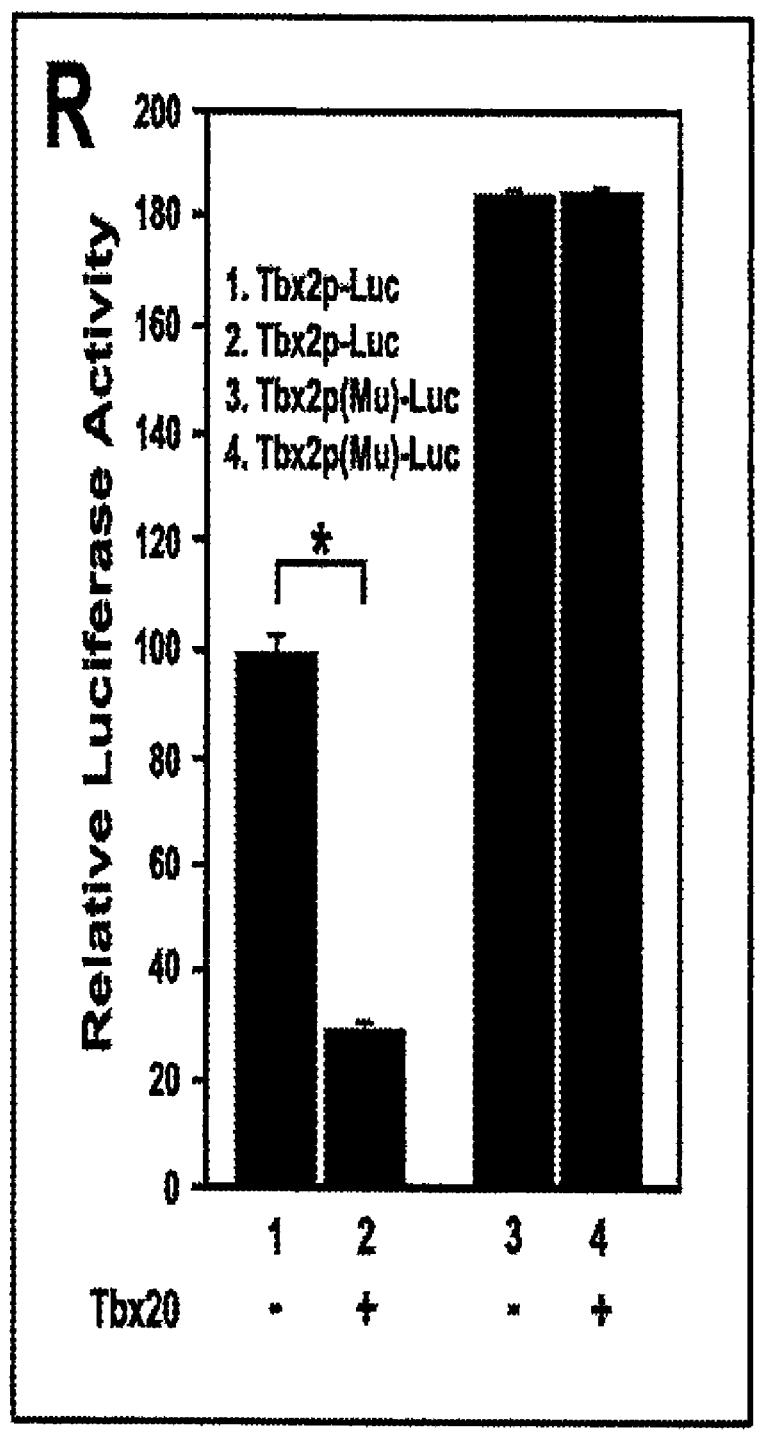
Figures 4A, 4B, 4C, 4D:
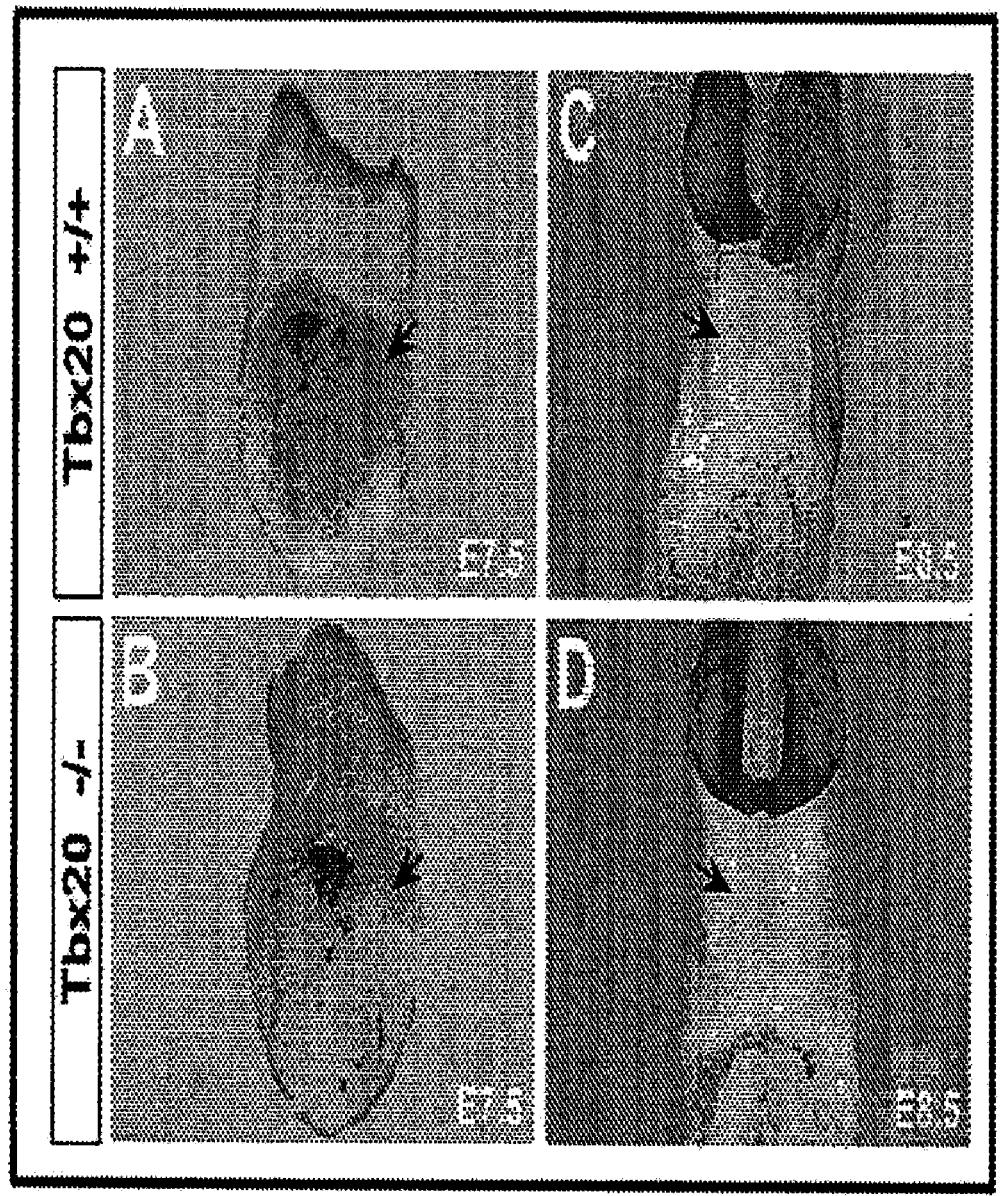
Figures 4E, 4F, 4G, 4H:
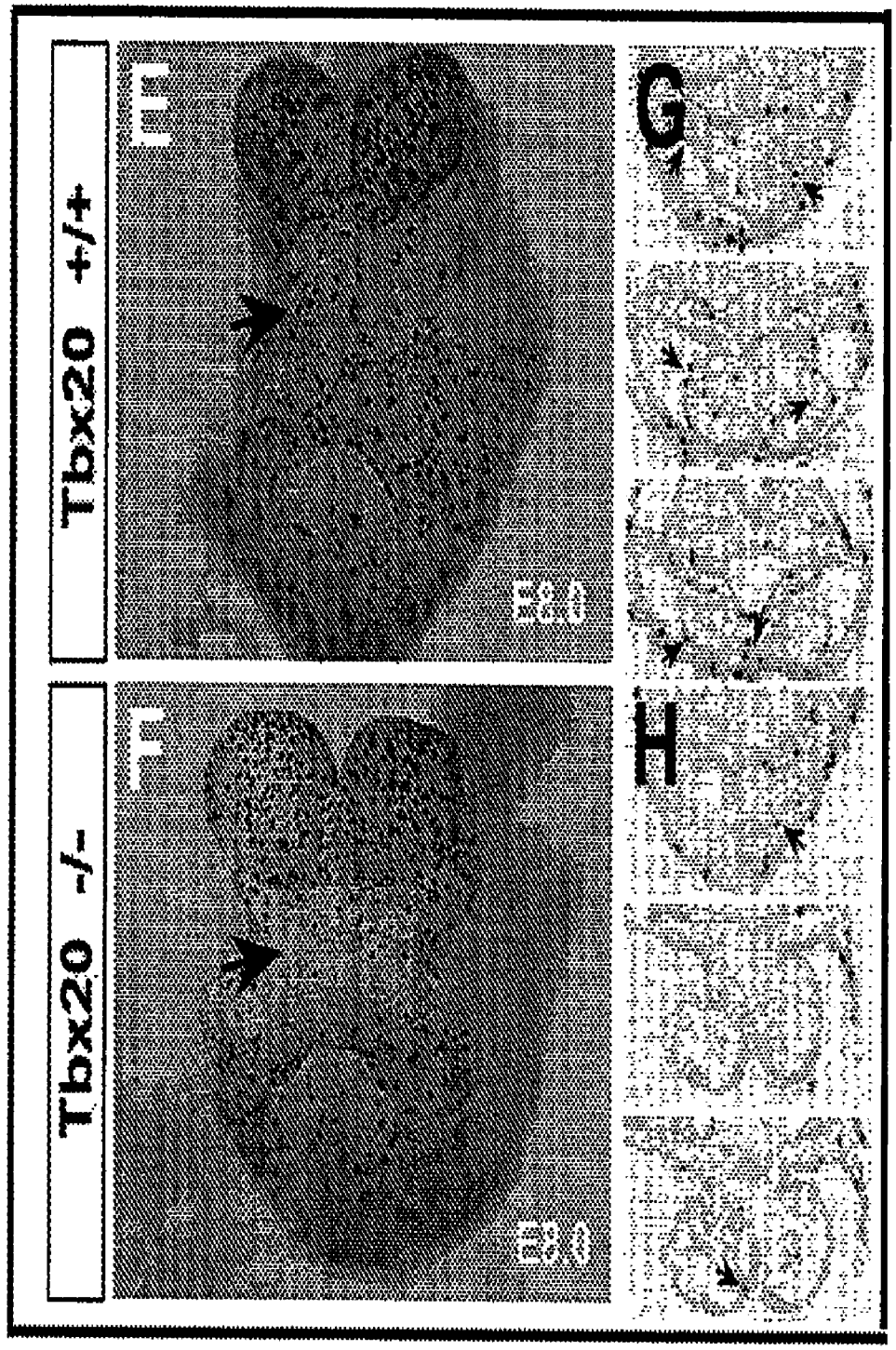
Figures 4I, 4J, 4K, 4L:
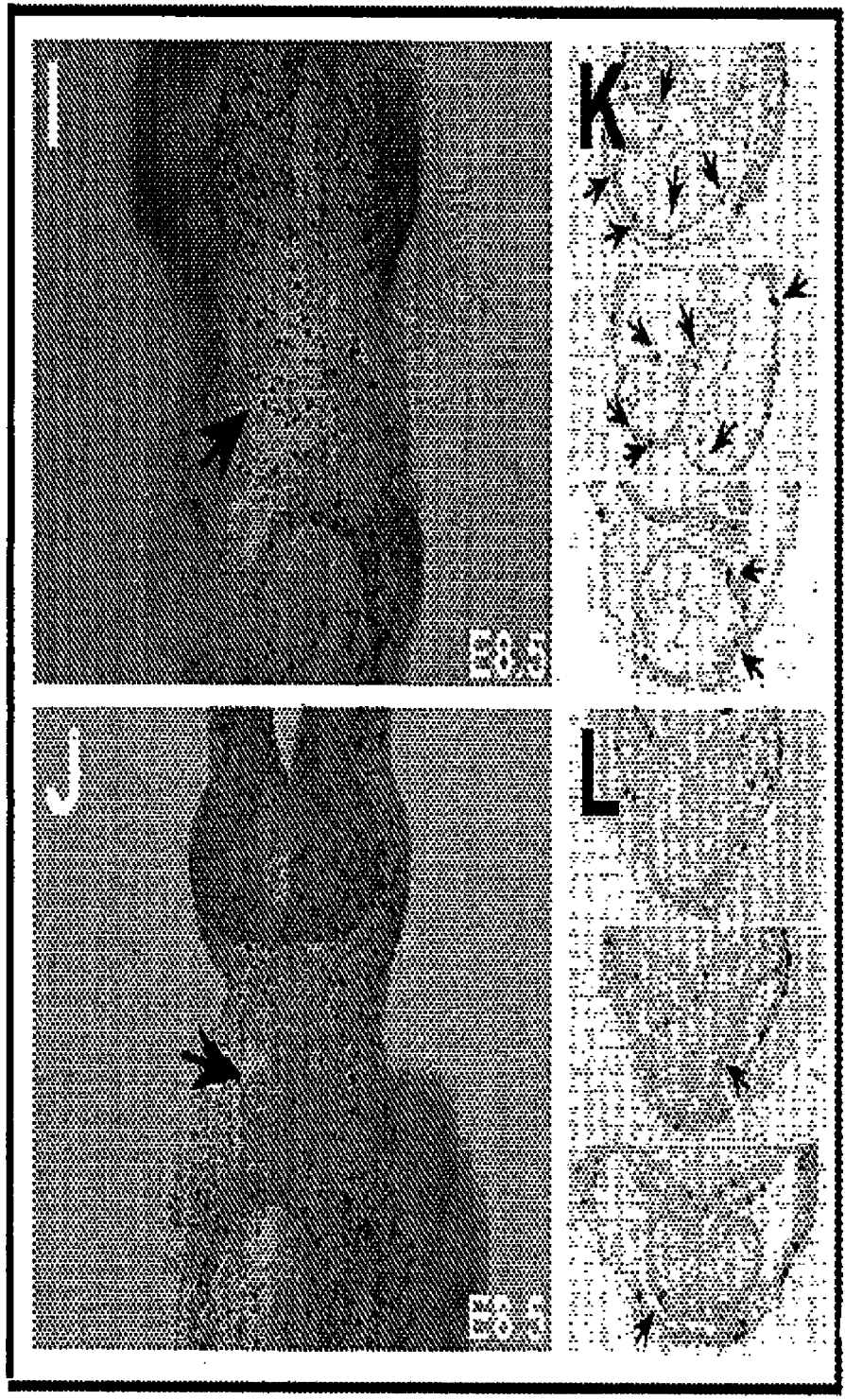

FIGS. 3A-3R. Tbx2 is Up Regulated in Tbx20 Mutants and is a Direct Target for Repression by Tbx20:

(A-F) Whole mount RNA in situ and section analysis for Tbx2 expression in Tbx20 null embryos and wild type littermates.

(G-L) Whole mount RNA in situ analysis demonstrates down regulation of Nppa, chisel, and cited1 in Tbx20 mutants.

(M-P) Expression of Tbx20 and Tbx3 is unaffected.

(Q) ChIP analysis with embryonic heart extracts reveals binding of Tbx20 to region containing conserved T-Box sites within the Tbx2 promoter of mouse (SEQ ID NO: 554), rat (SEQ ID NO: 555), and human (SEQ ID NO: 556).

(R) Cotransfection of Tbx20 expression vector with Tbx2 promoter-luciferase constructs into HEK293 cells showing repression by Tbx20 which is abrogated by mutation (Mu) of conserved T Box elements within the Tbx2 promoter.

FIGS. 4A-4L. Apoptosis and Proliferation Assays in Tbx20 Null Mutants and Control Littermates:

(A-D) TUNEL analysis revealed no increase in apoptosis in Tbx20 null embryos relative to control littermates, with arrows indicating cardiac crescent (A,B) and heart tube (C,D).

(E-L) Antibody staining for phosphorylated histone H3 reveals decreased proliferation in Tbx20 null mutants relative to control littermates, with arrows indicating positive phosphorylated histone H3 staining in cardiomyocytes.

Figures 5A, 5B:
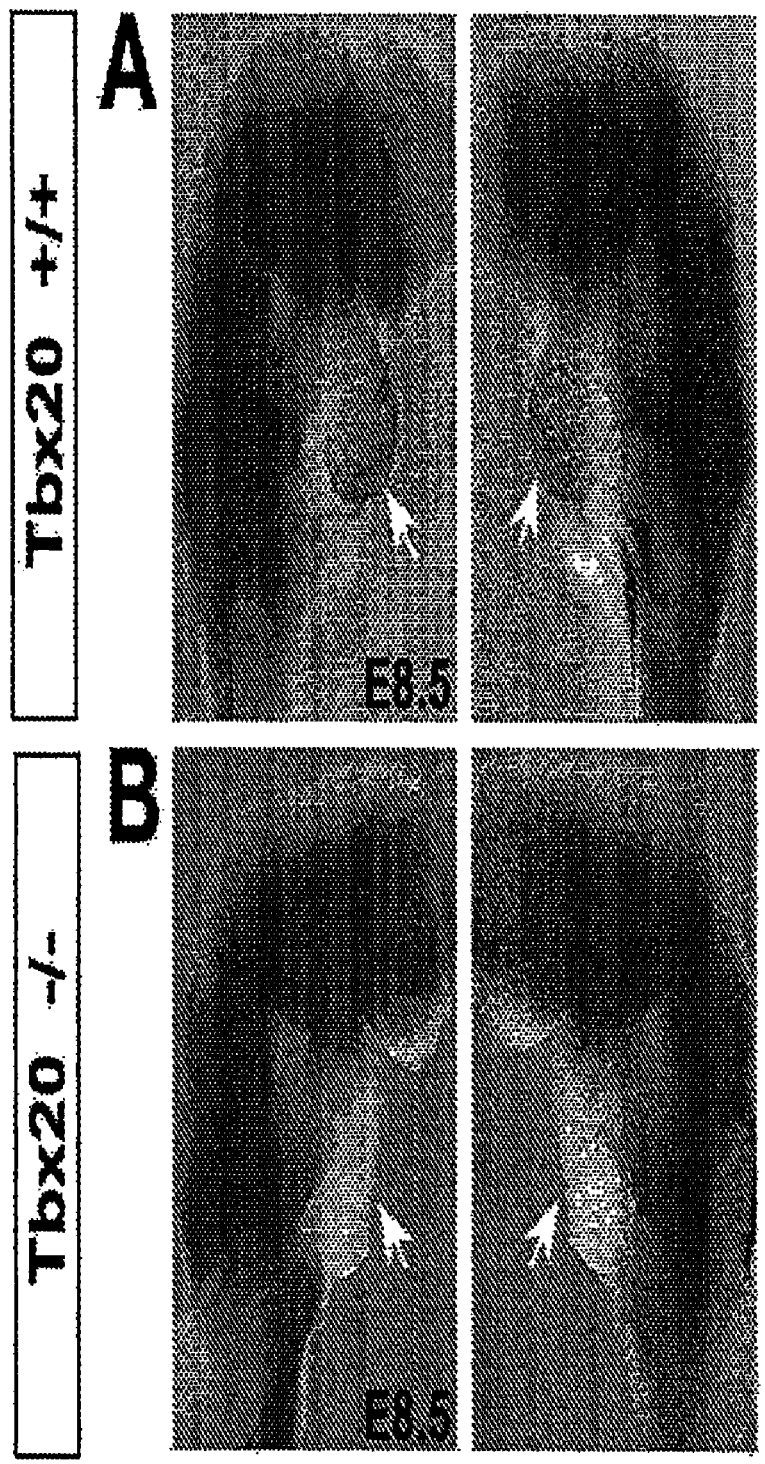
Figures 5C, 5D:
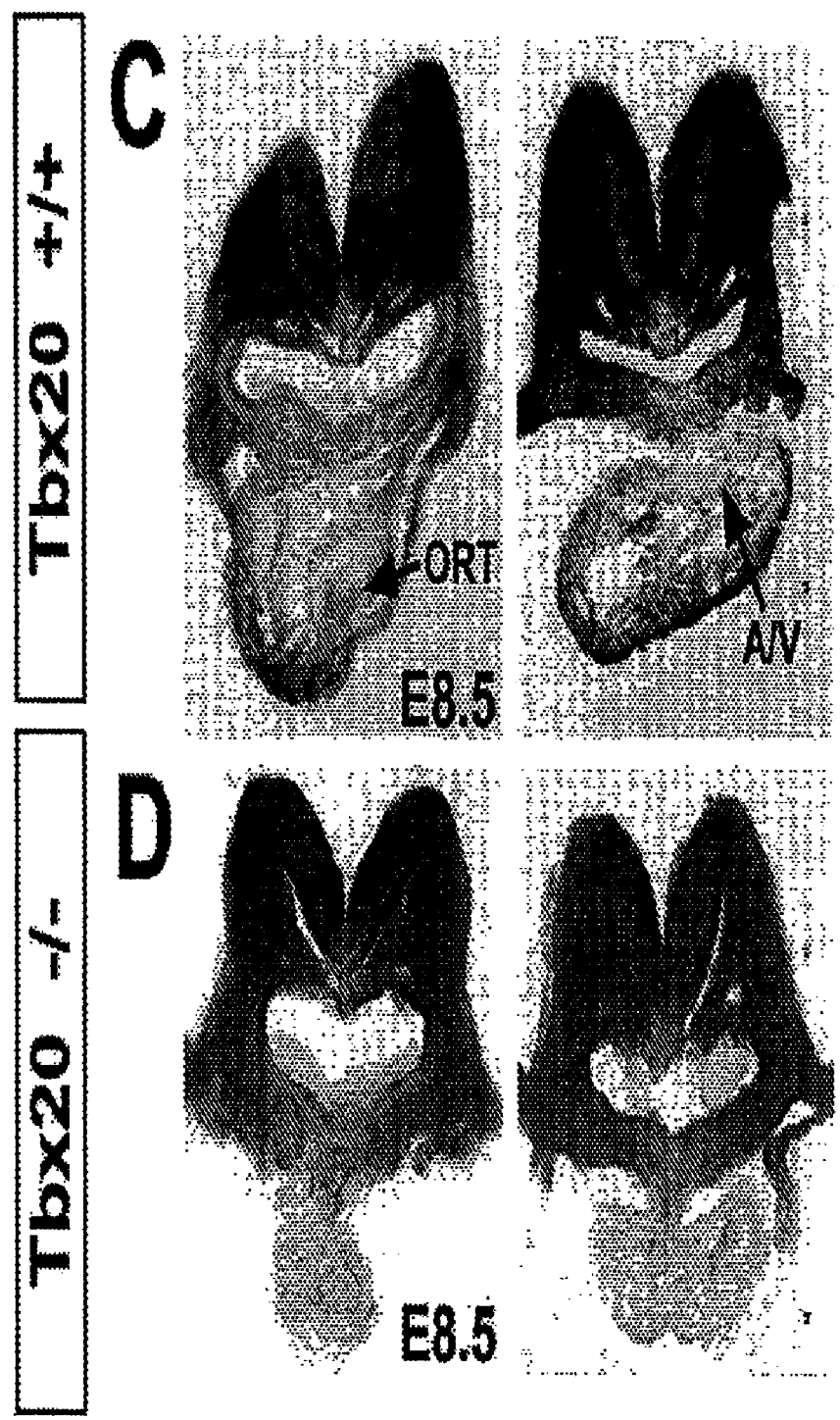
Figures 5E, 5F:
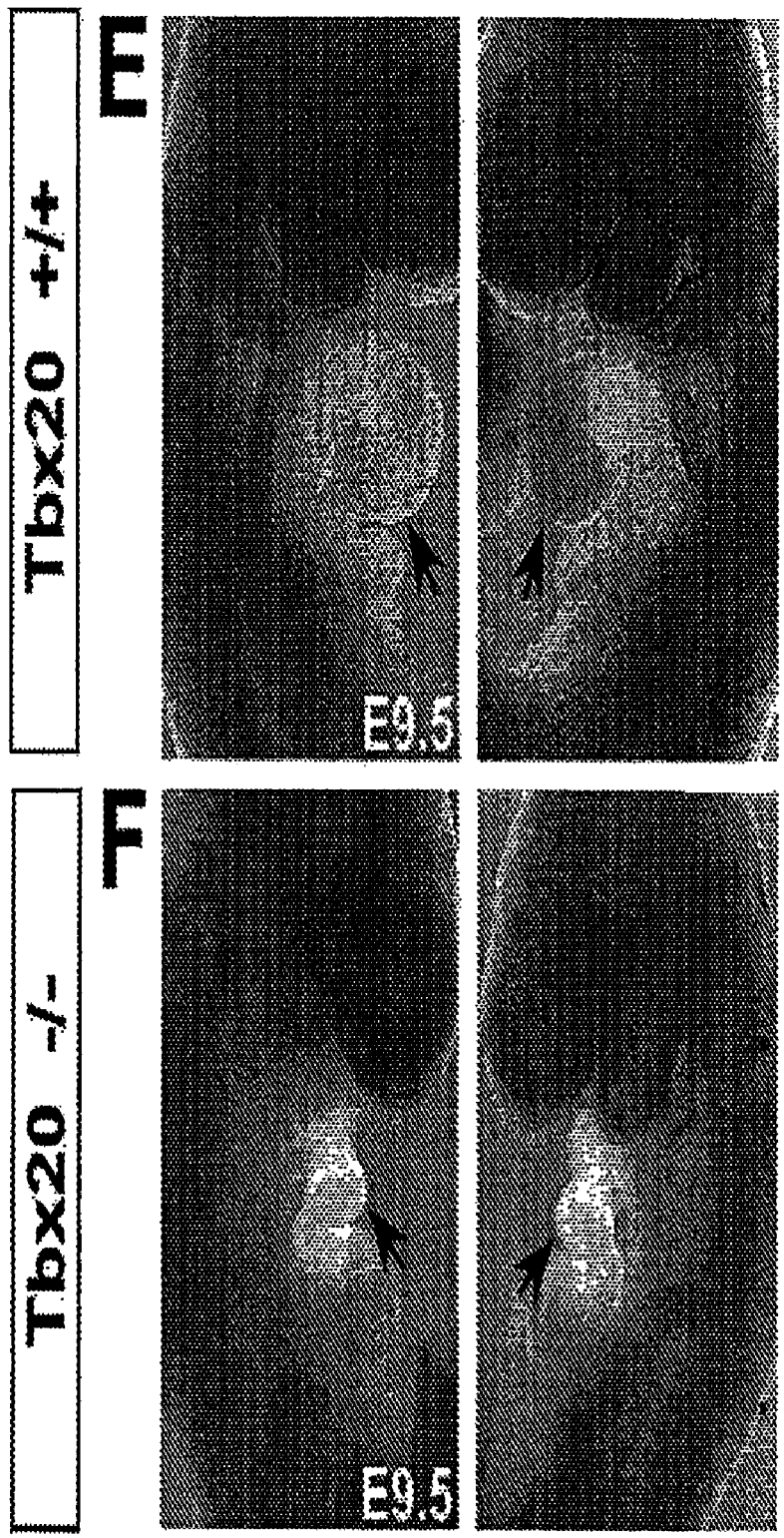
Figures 5G, 5H:
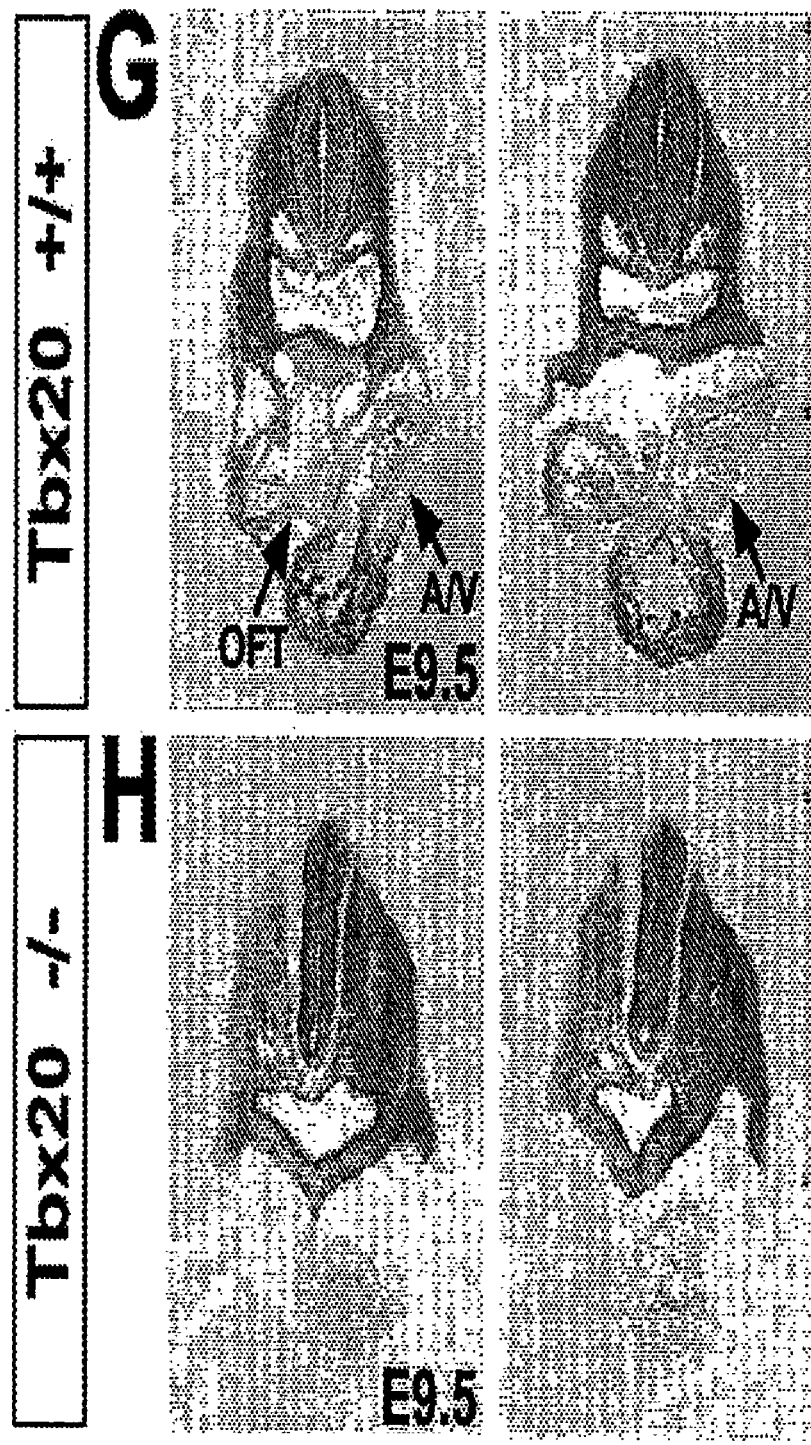
Figures 5I, 5J:
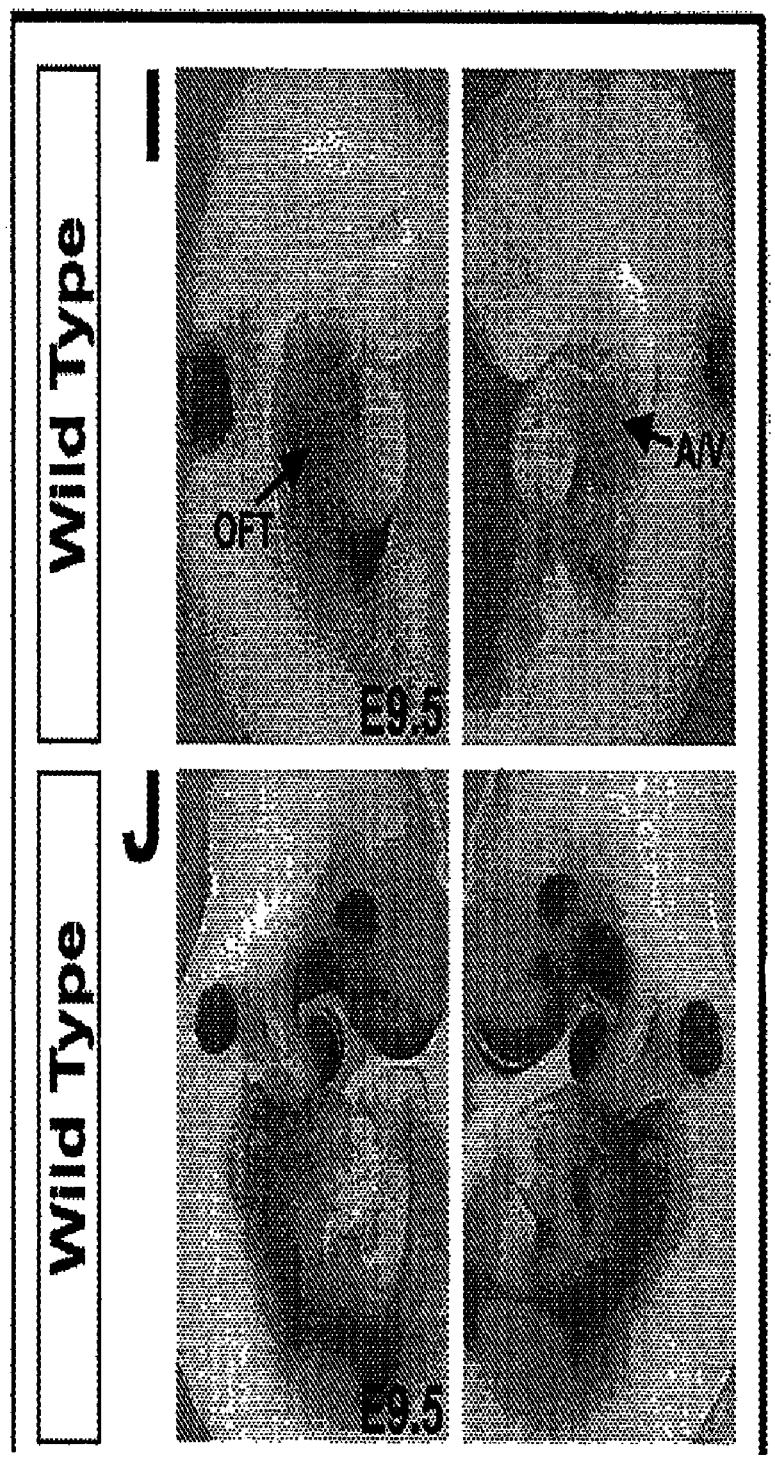
Figure 5K:
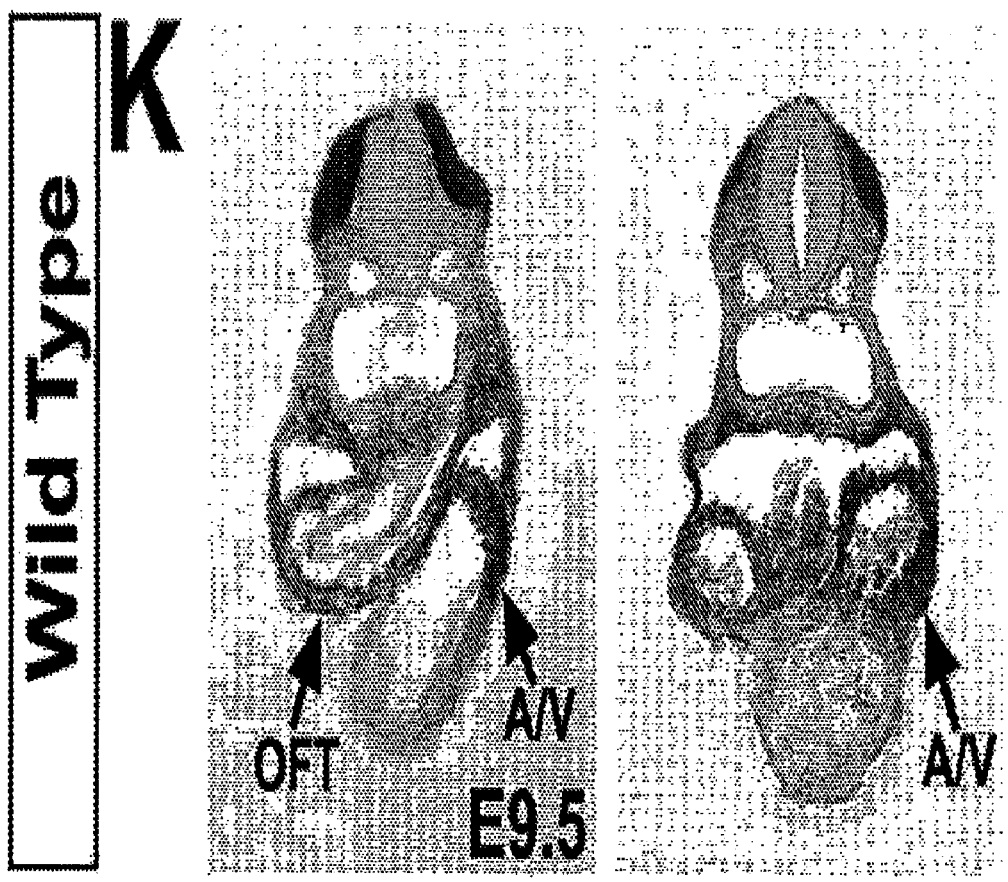
Figure 5L:
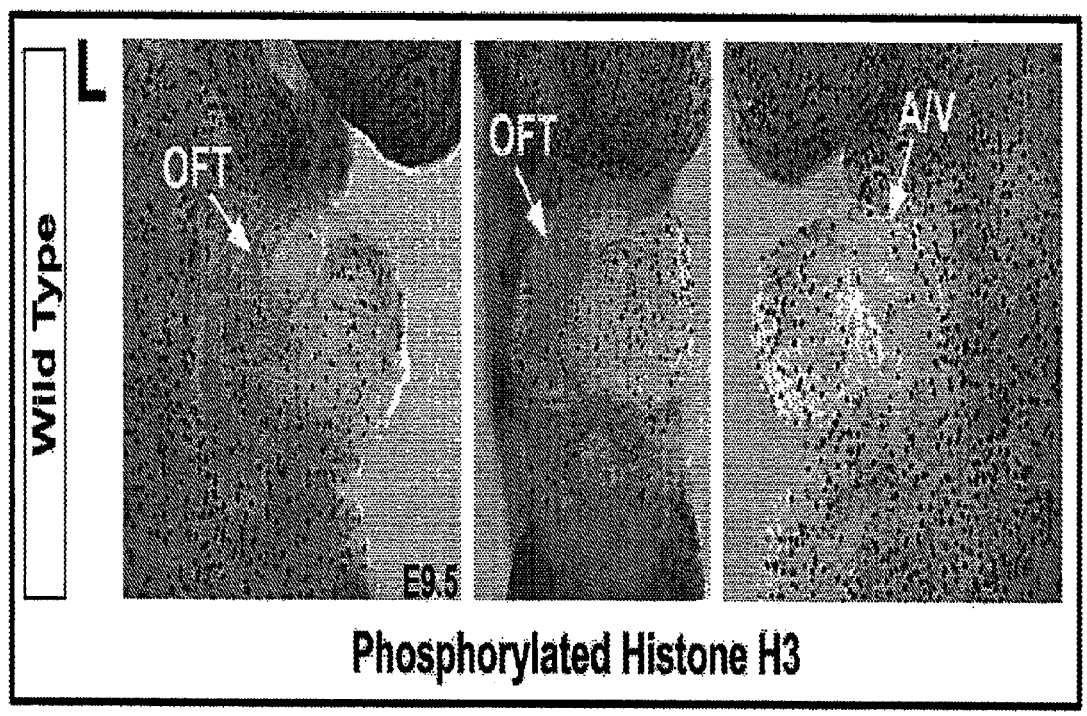
Figure 5M:
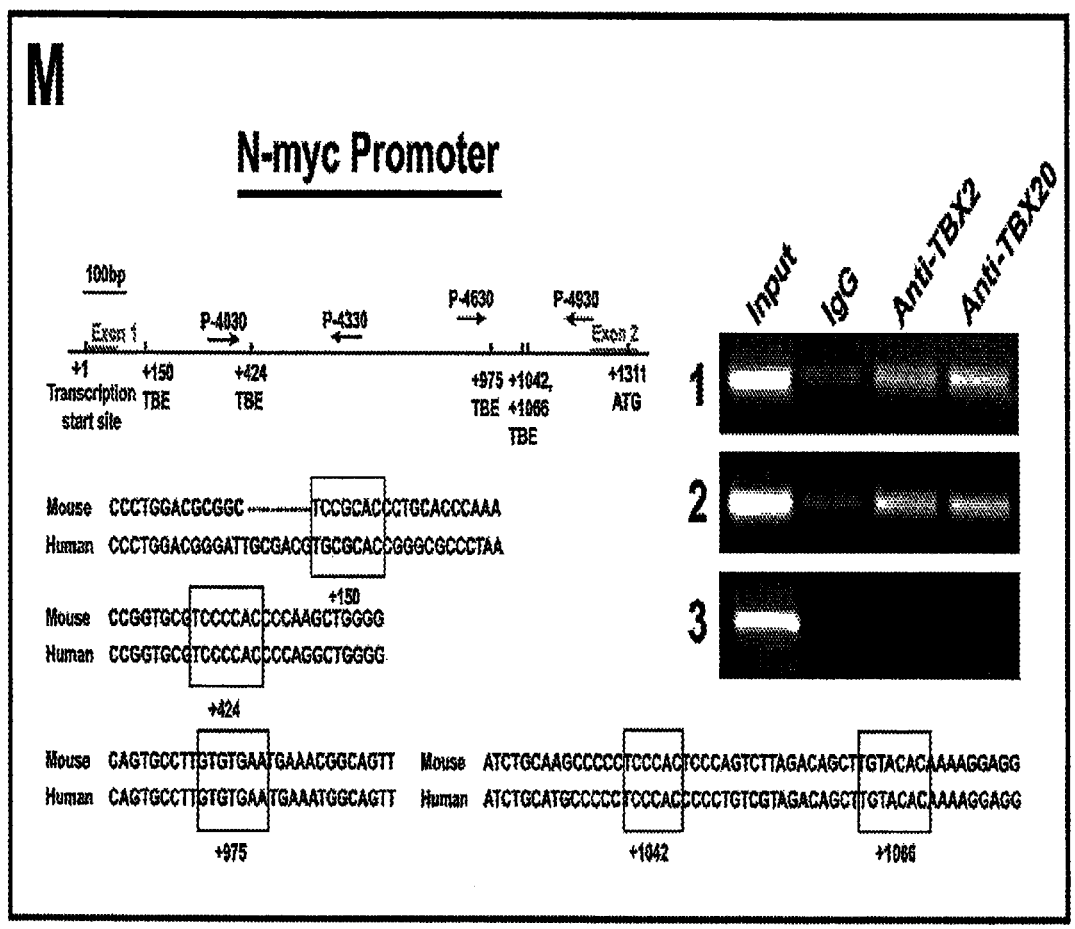
Figure 5N:
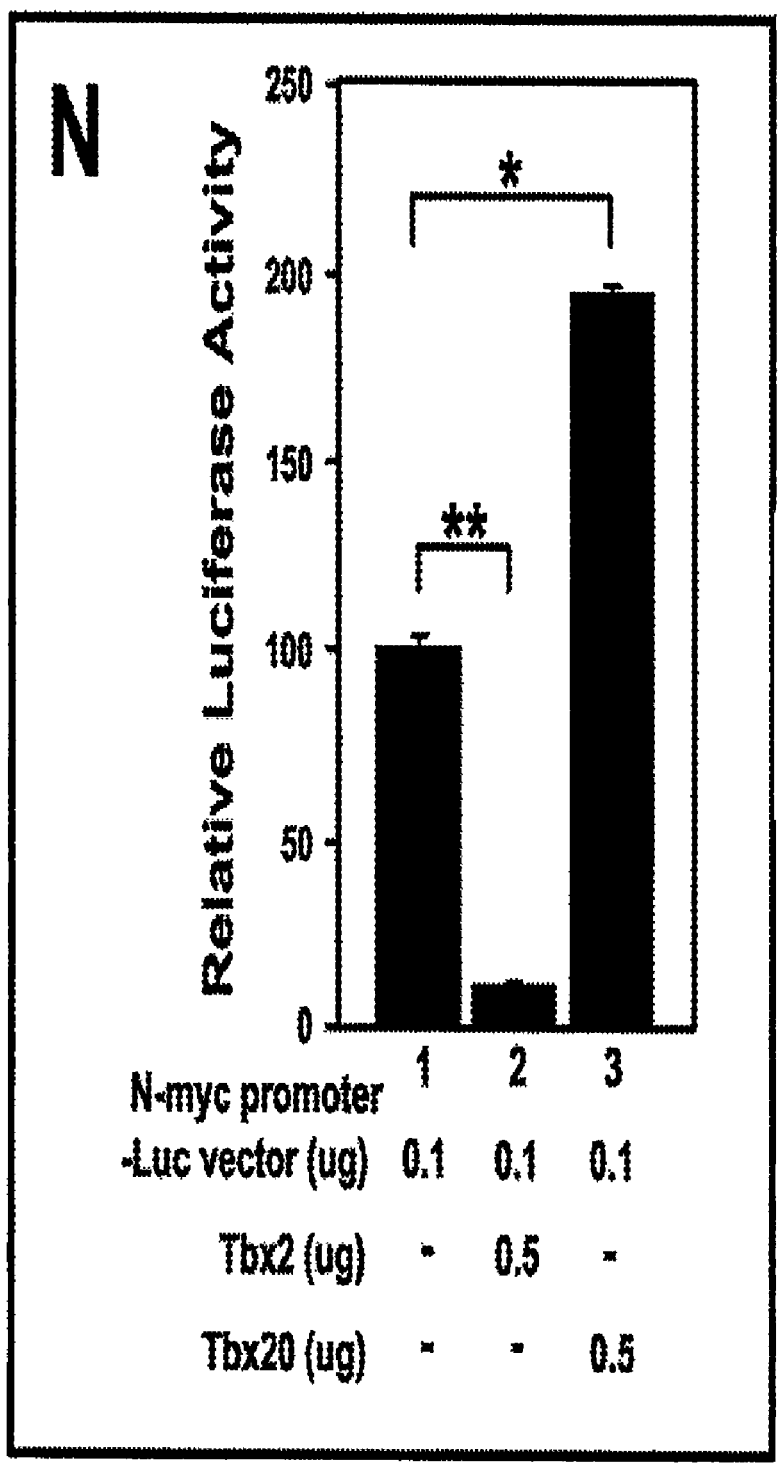
Figure 50:
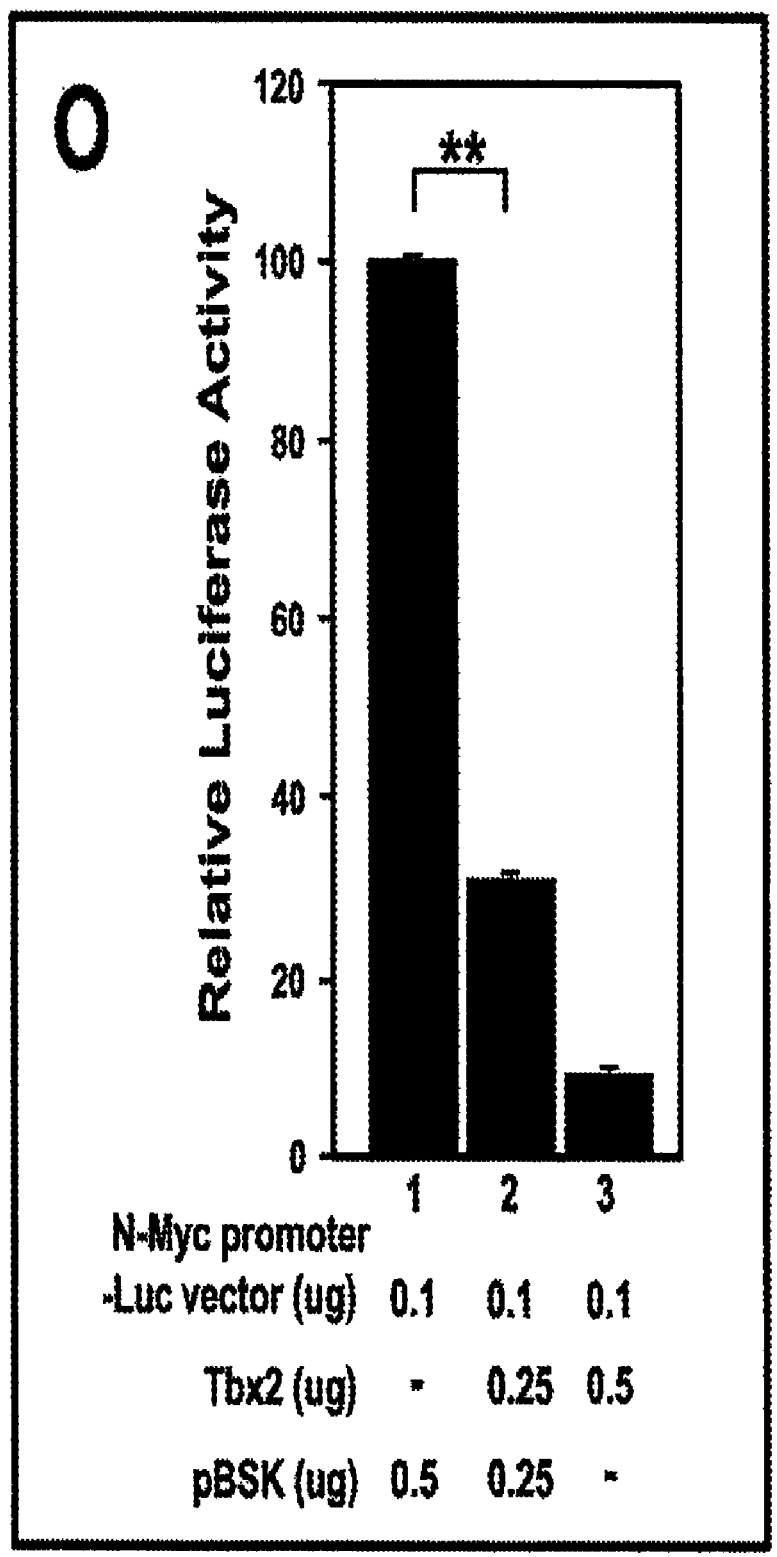
Figures 6A, 6B:
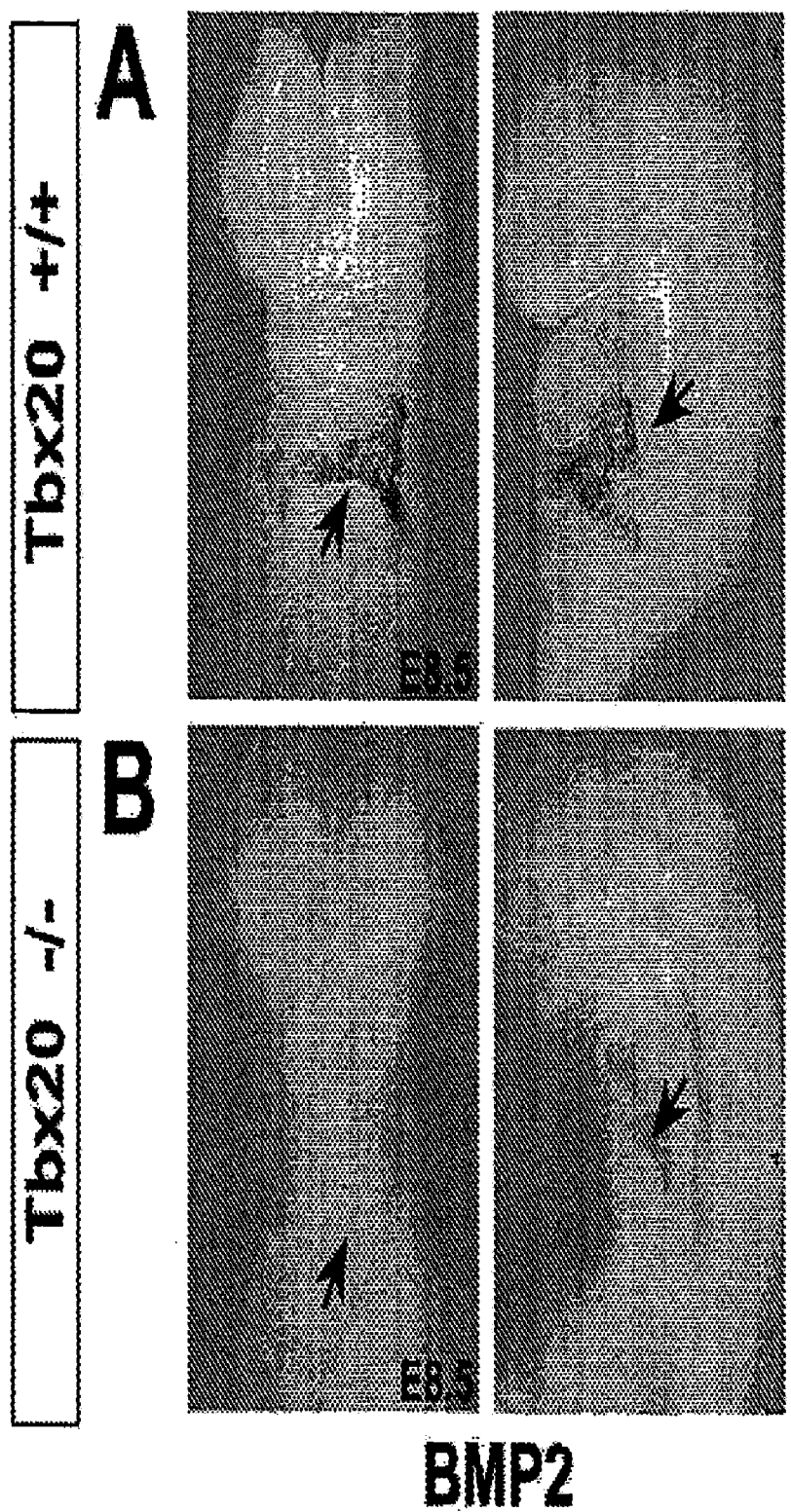
Figures 6C, 6D:
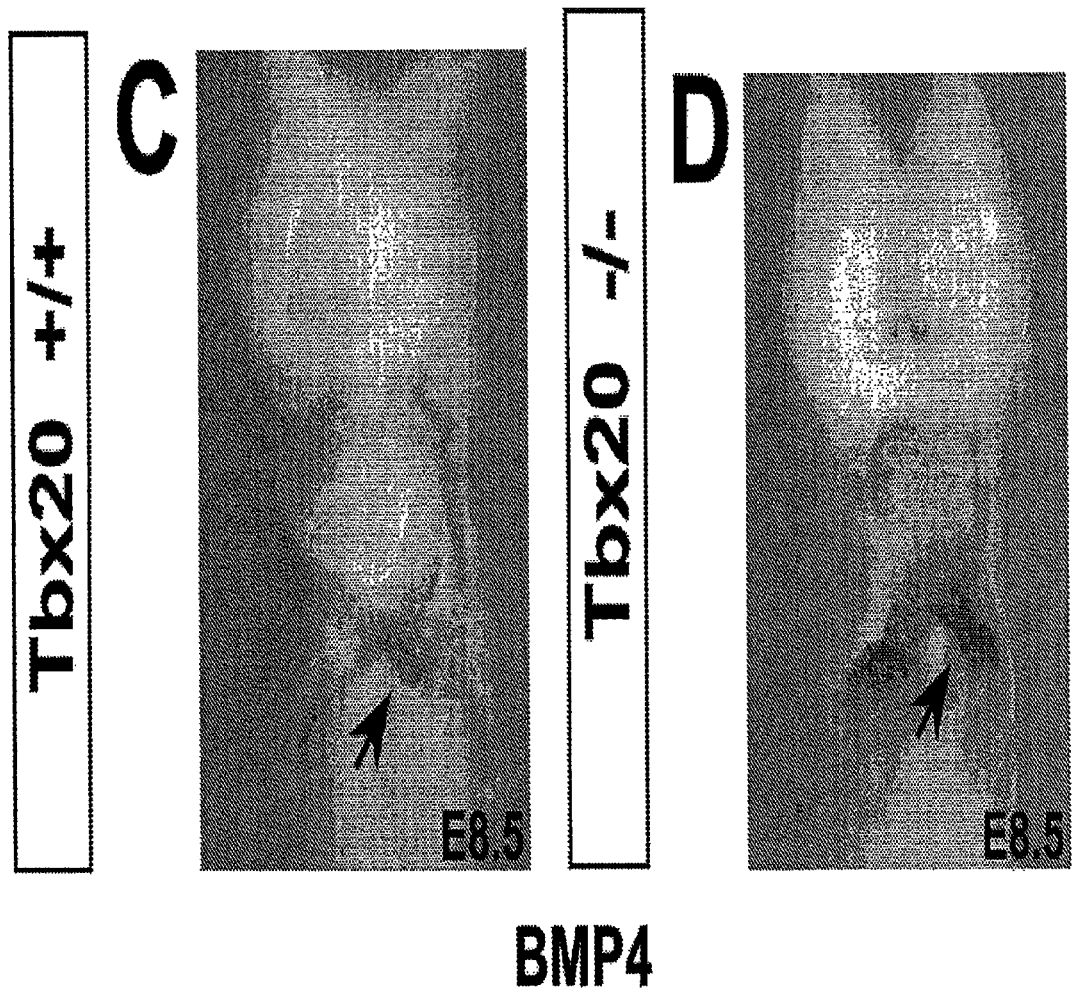
Figures 6E, 6F:
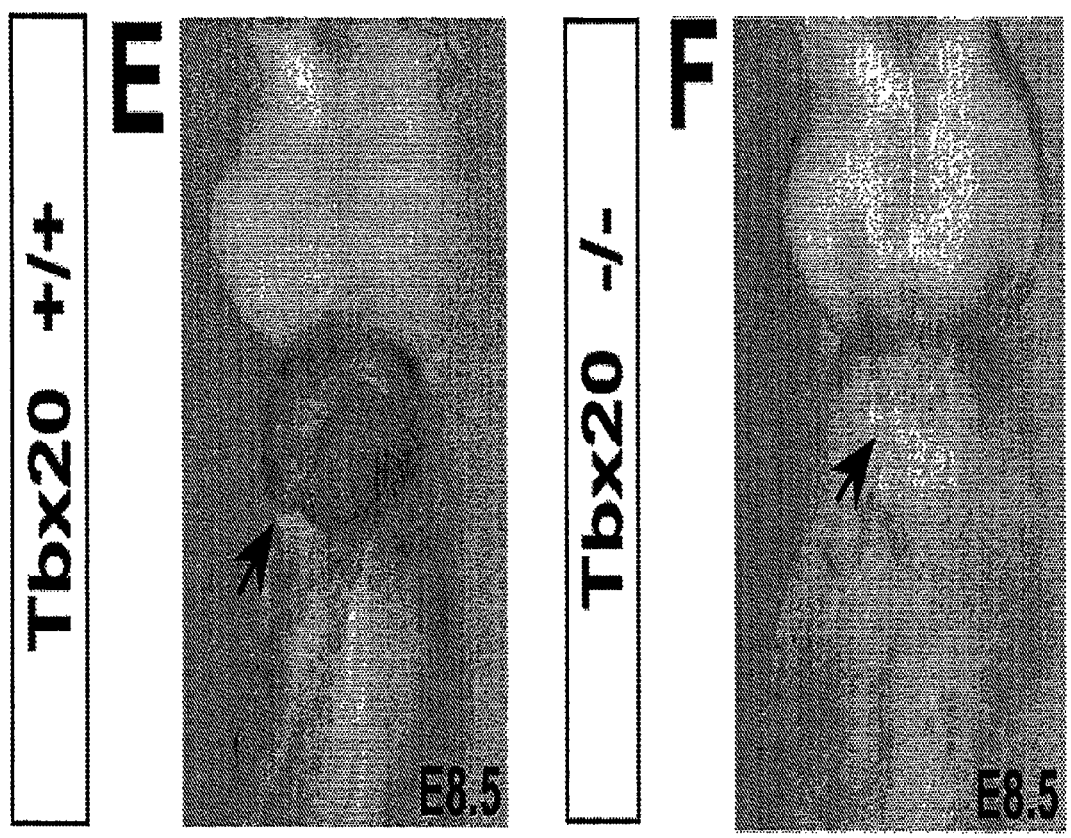
Figures 6G, 6H:
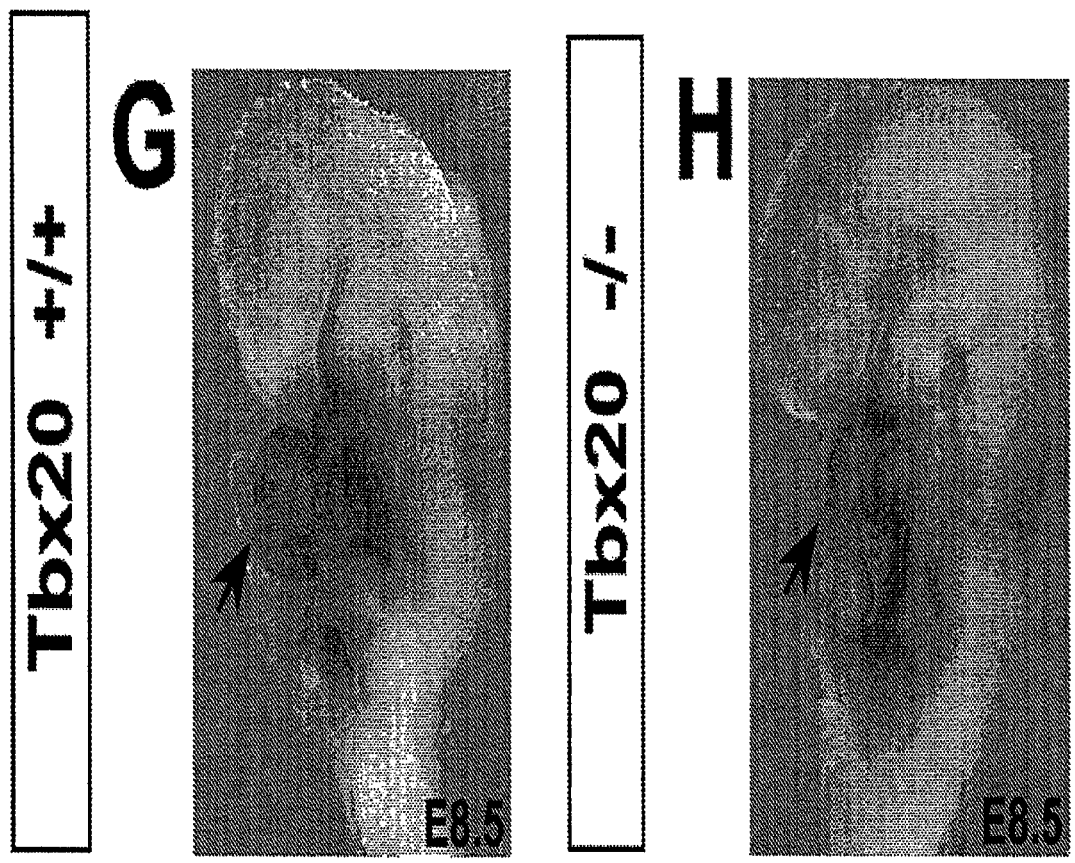
Figures 7A, 7B:
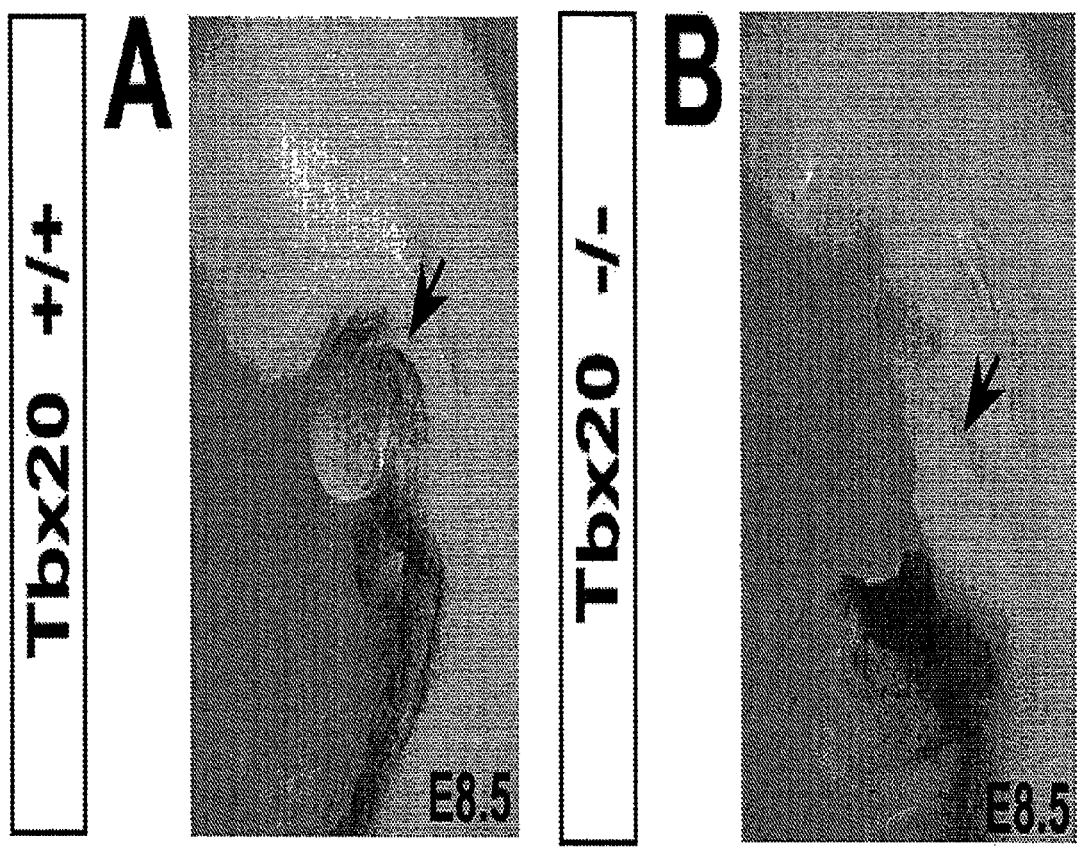
Figures 7C, 7D:
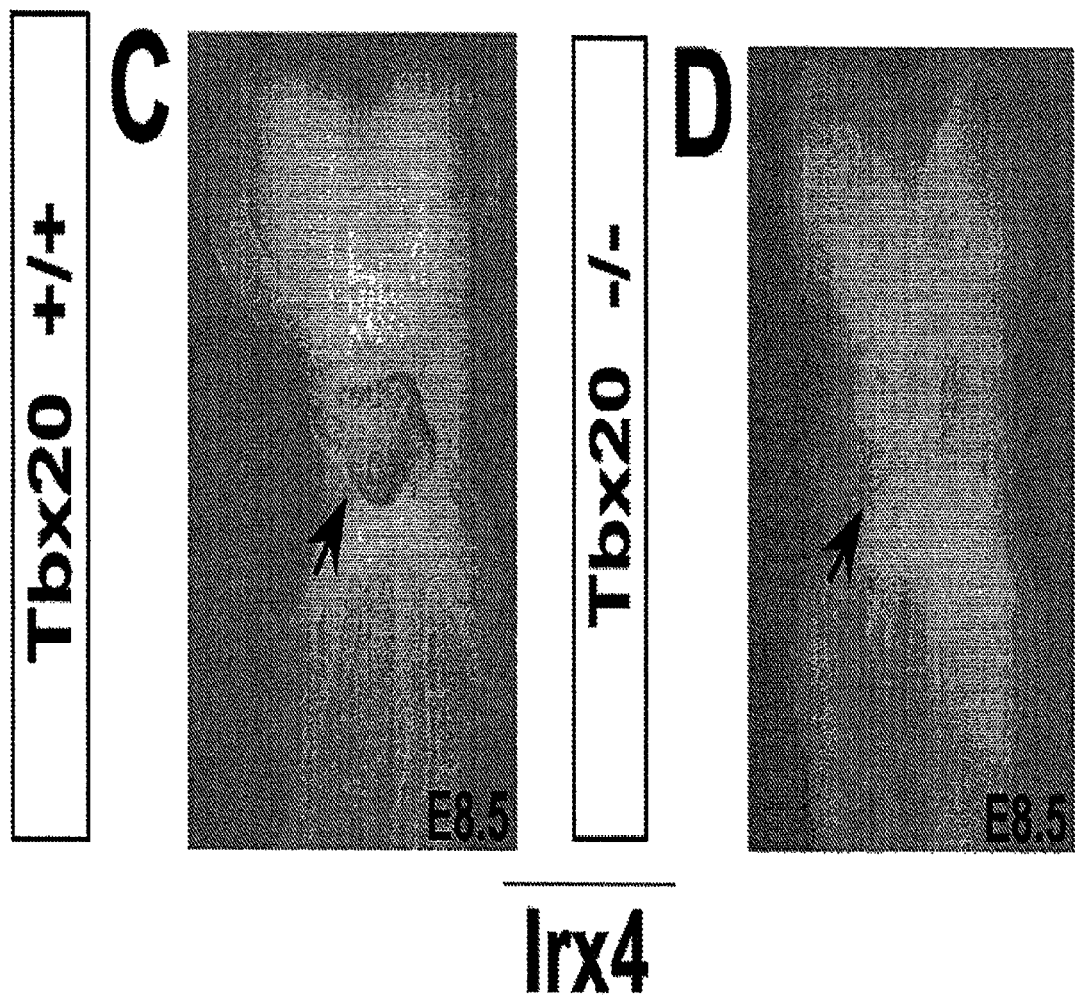
Figures 7E, 7F:
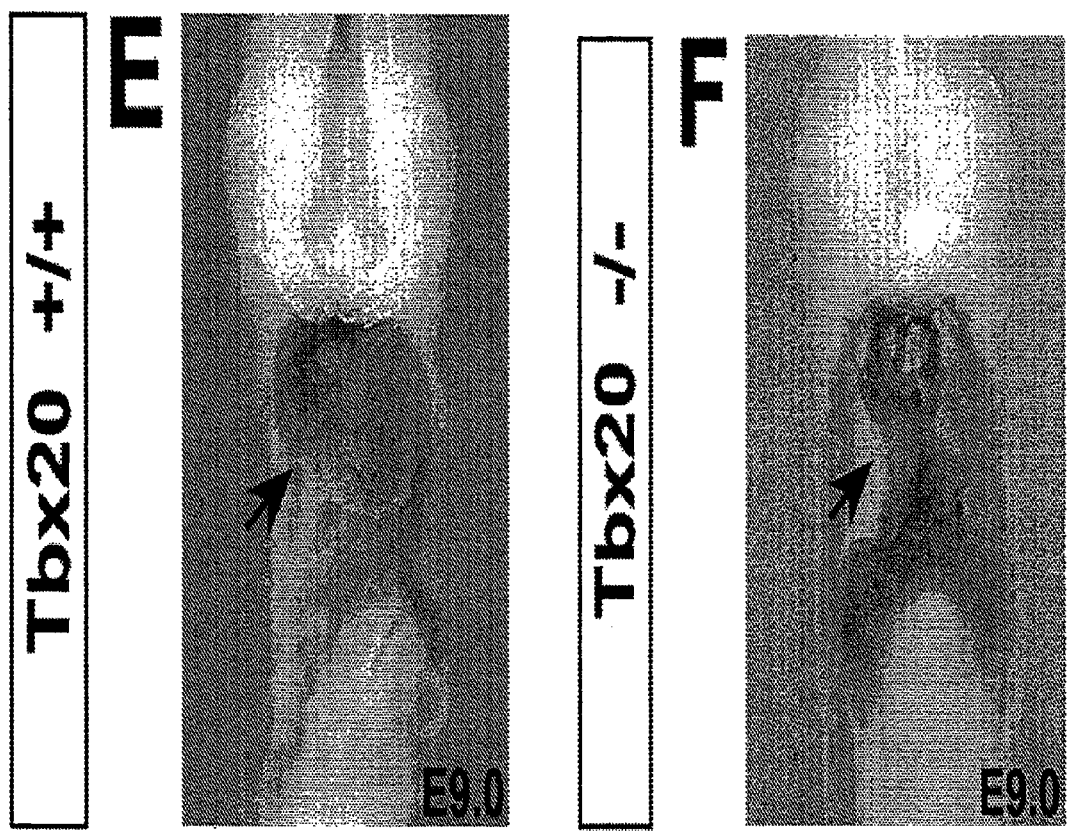
Figures 7G, 7H, 7I, 7J:
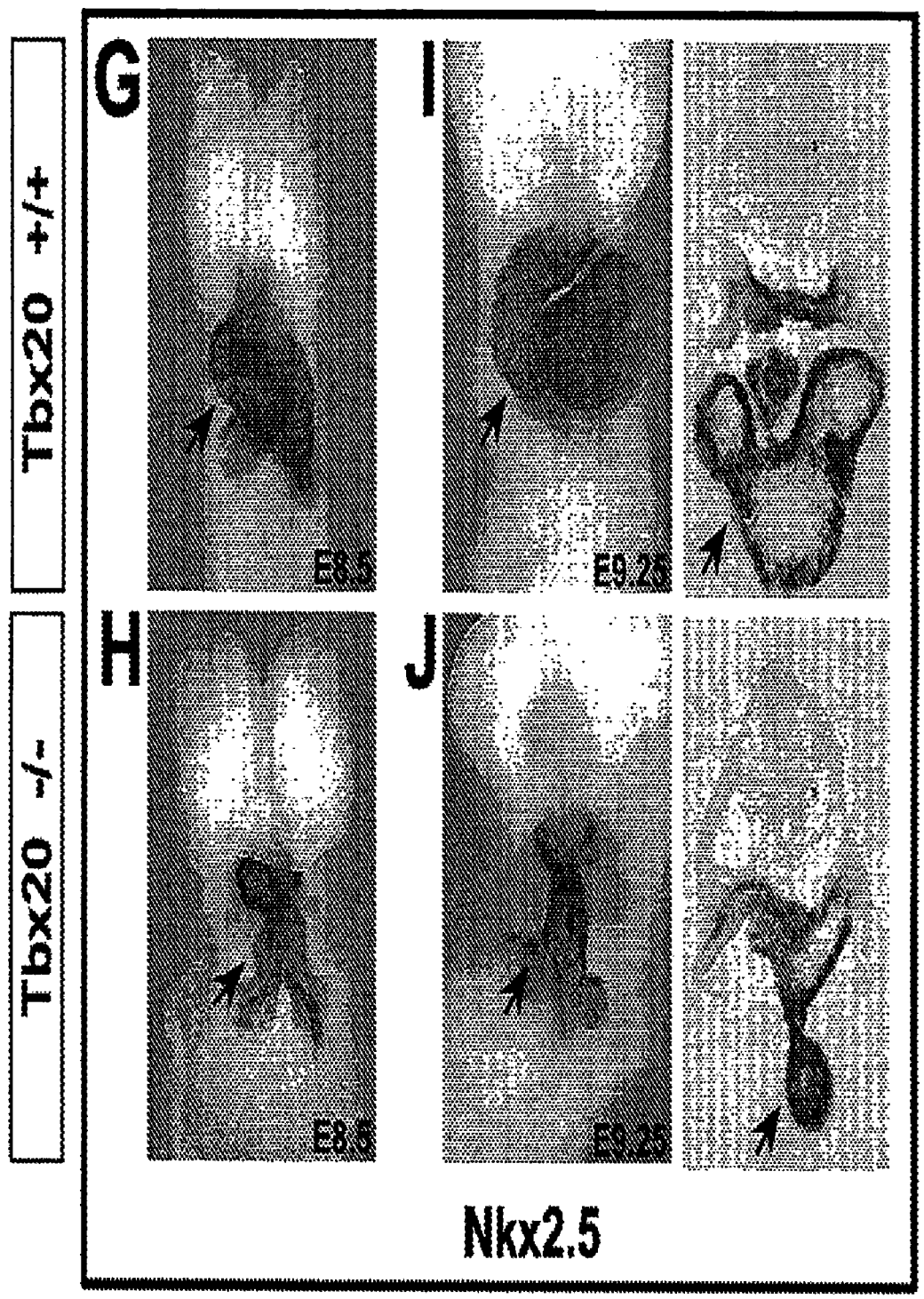
Figures 8A, 8B:
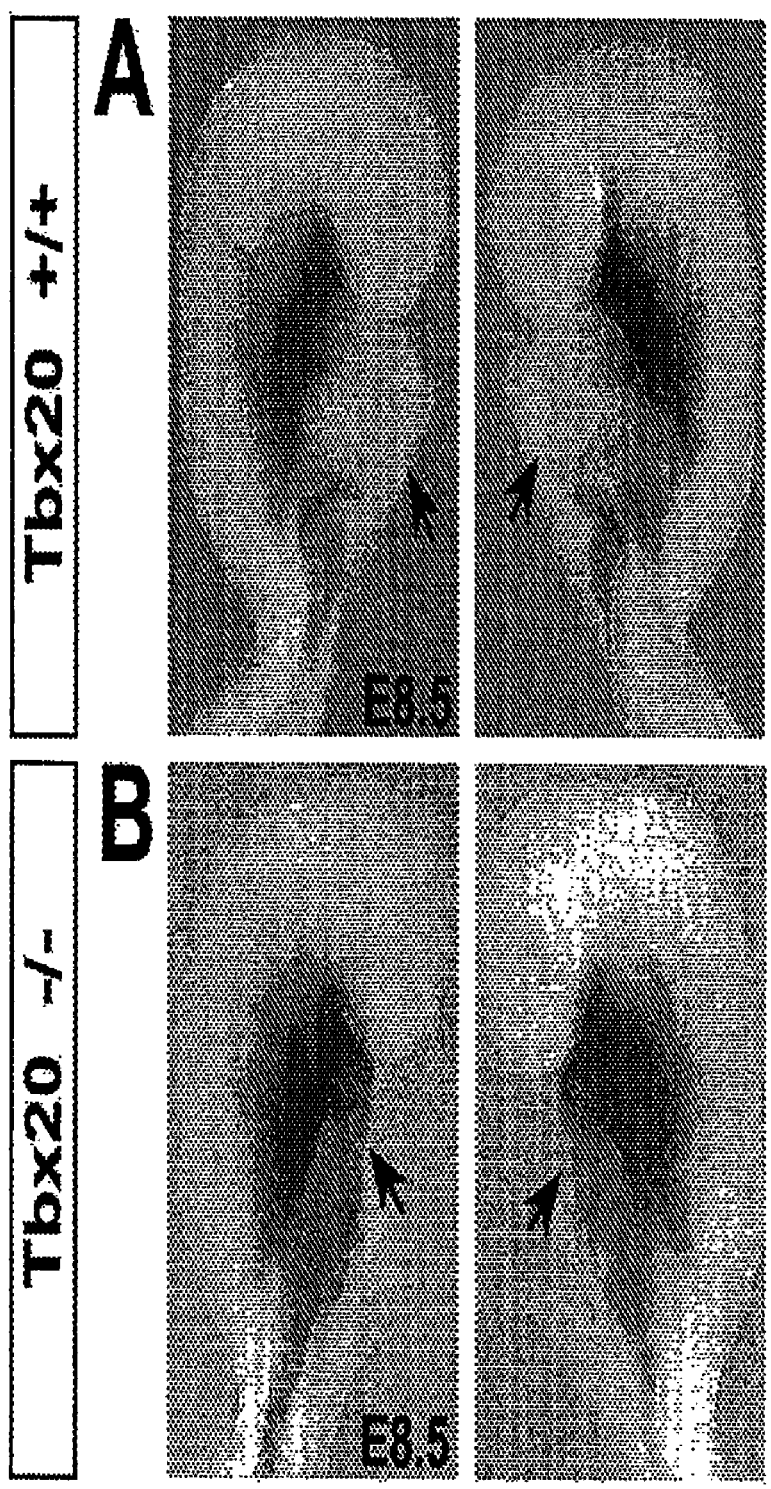
Figures 8C, 8D:
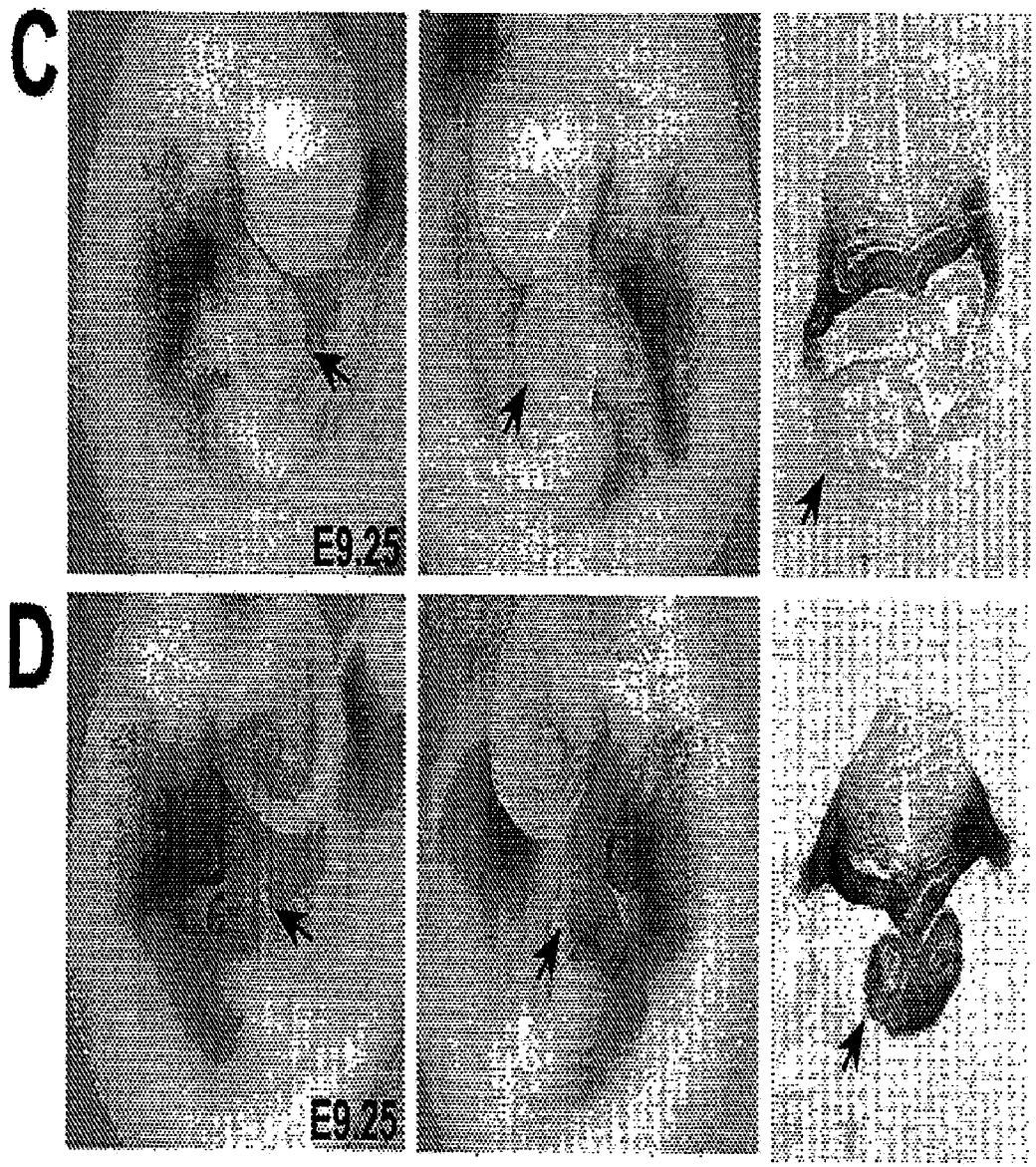
Figure 8E:
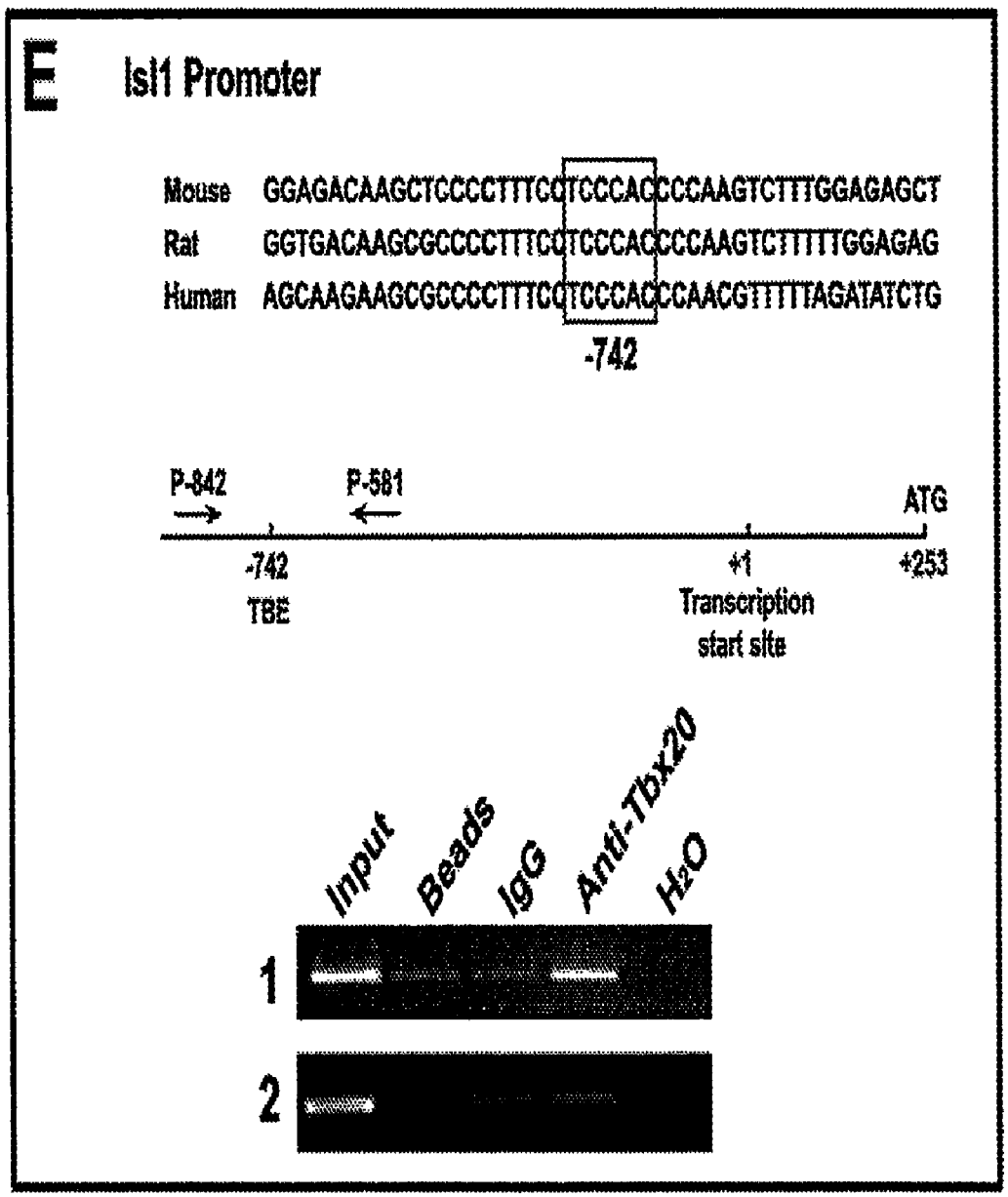
Figure 8F:
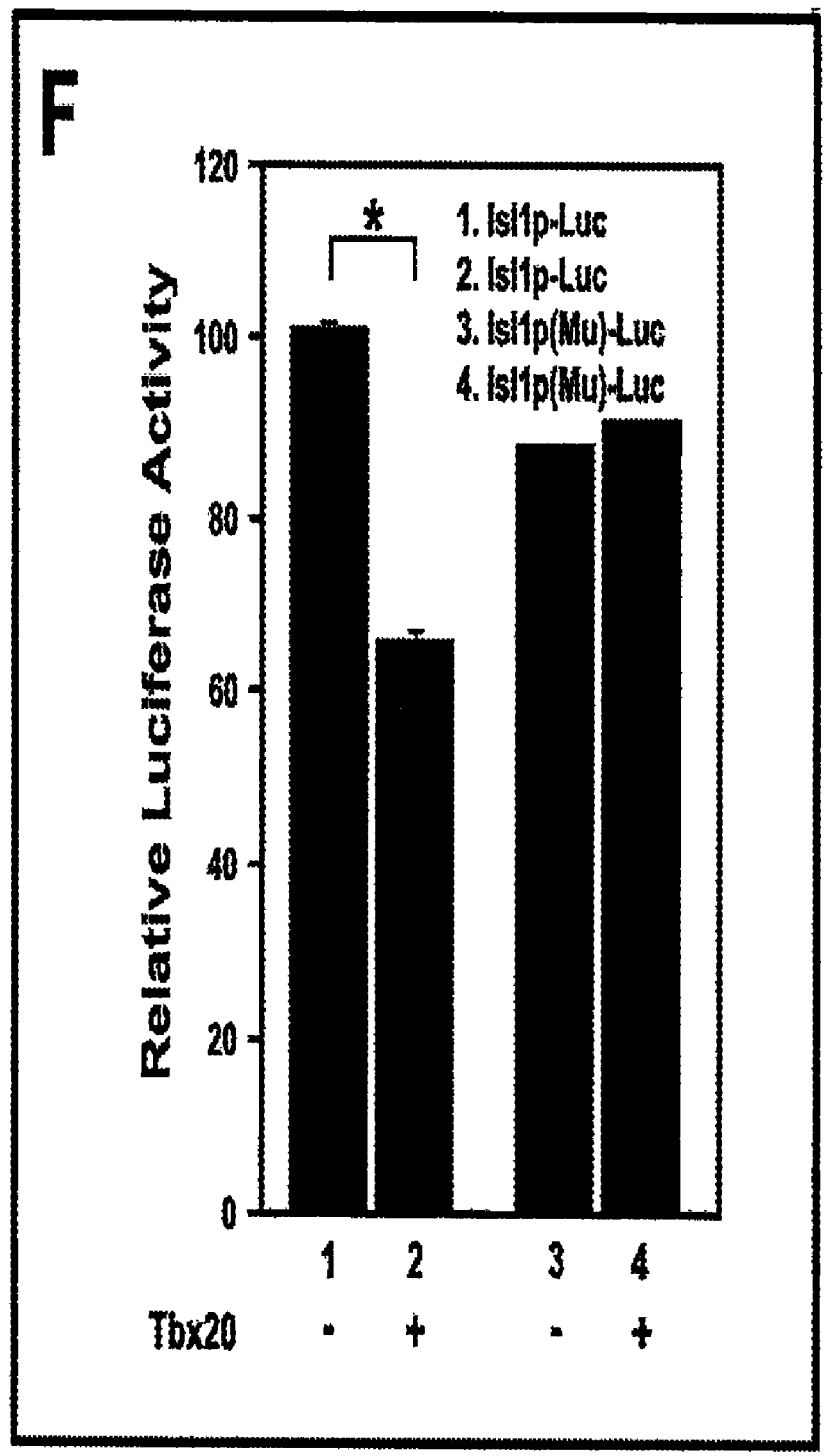
Figures 8G, 8H:
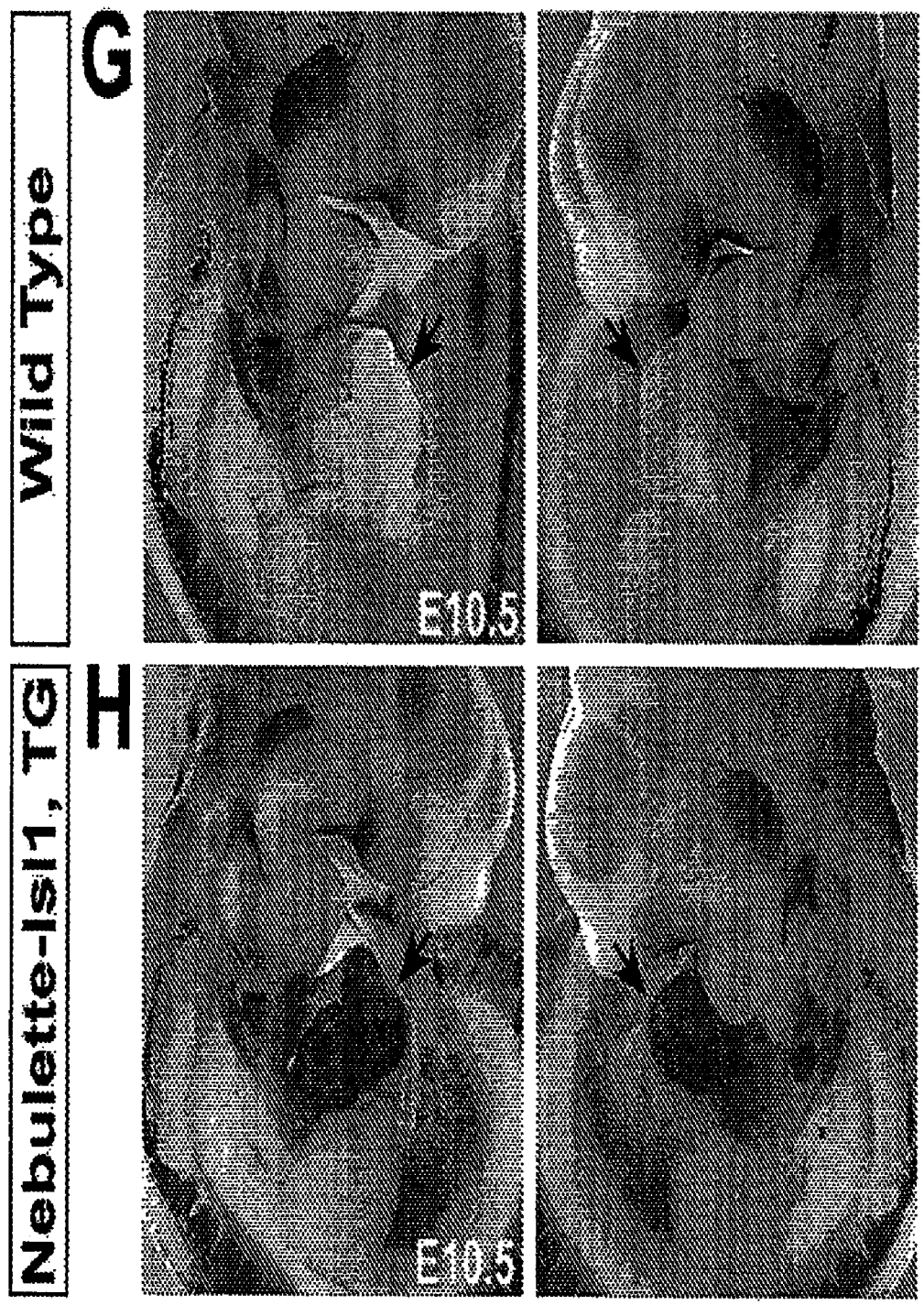
Figures 8I, 8J:
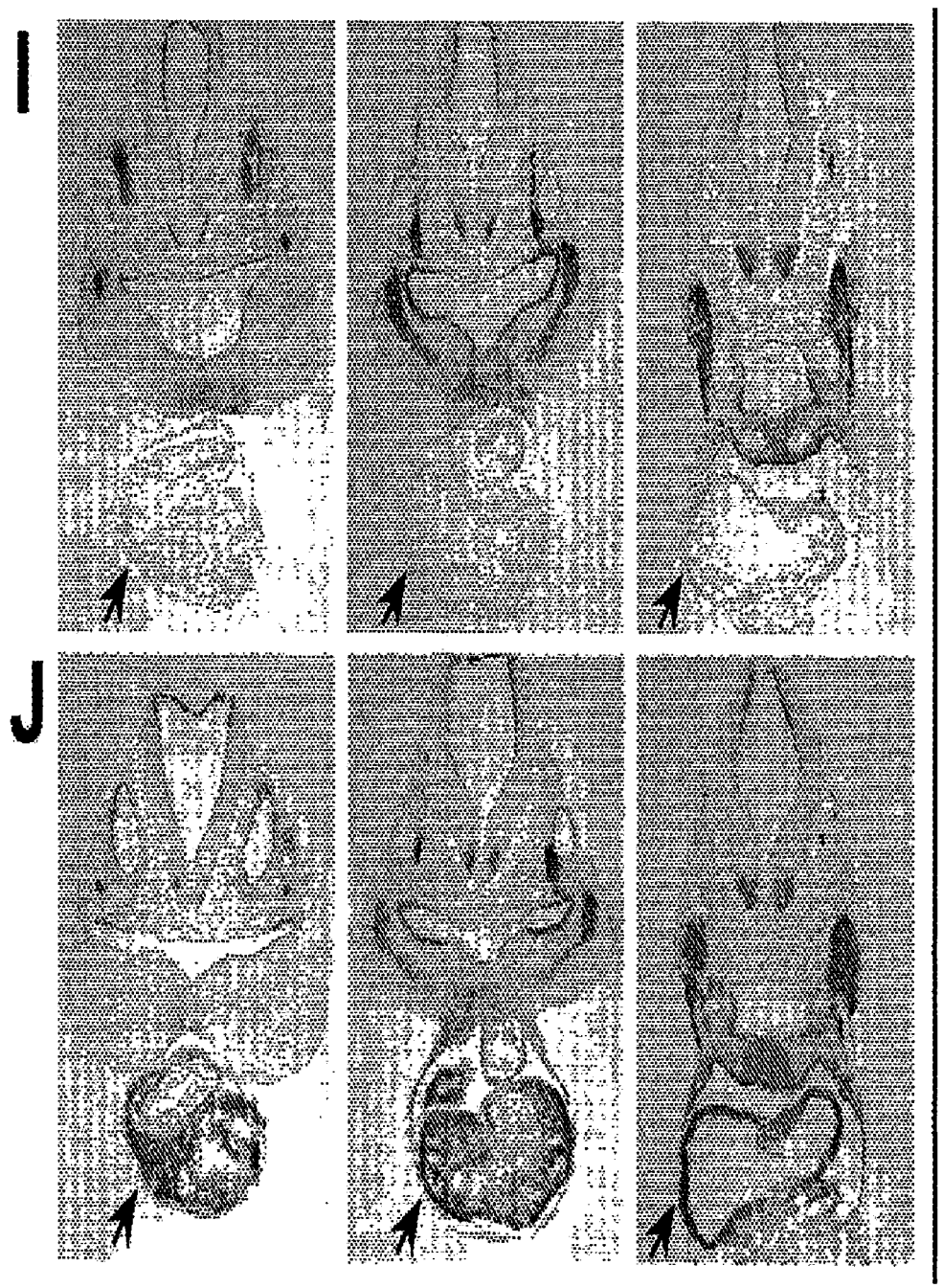

FIGS. 5A-5O. Tbx2 Directly Binds and Represses N myc Expression in Regions of Relatively Low Proliferation within the Heart:

(A-D) Expression of Nmyc is downregulated in Tbx20 null mutants.

(E-H) Expression of cyclin A2 is downregulated in Tbx20 null mutants.

(I-K) Wild type Tbx2 expression is complementary to that of N myc and cyclinA2.

(L) Expression of phosphorylated histone H3 in wild type embryos revealed regions of low proliferation within developing heart.

(M) ChIP analysis with embryonic heart extracts demonstrated recruitment of Tbx2 and Tbx20 to regions containing T-Box consensus sites within intron 1 of the N-myc gene of mouse (SEQ ID NOS: 557, 559, 561 and 563) and human (SEQ ID NOS: 558, 560, 562 and 564).

(N) Cotransfections of Tbx2 or Tbx20 expression vectors with N myc intron 1 luciferase reporter into HEK293 cells demonstrated repression or activation, respectively.

(O) Co-transfections of Tbx2 expression vector with N myc intron 1-luciferase reporter into HEK293 cells demonstrated dose-dependent repression by Tbx2.

FIGS. 6A-6H. Tbx20 Regulates Expression of a Subset of BMP Genes:

(A,B) Frontal and left view images showing expression of Bmp2 in Tbx20 mutants is severely downregulated in the heart.

(C,D) Expression of Bmp4 is not down-regulated in Tbx20 mutants.

(E,F) Expression of Bmp2 in Tbx20 mutants is also severely downregulated in the heart.

(G,H) Expression of Bmp7 is not down-regulated in Tbx20 mutants.

FIGS. 7A-7J. Tbx20 and Nkx2.5 Independently Regulate Common Downstream Targets:

(A,B) Left side views showing that expression of Hand1 and Irx4 is downregulated in Tbx20 mutants.

(C-J) Frontal views showing that expression of Hand1 and Irx4 is down-regulated in Tbx20 mutants (C, D); that Hand2 expression is unaffected (E, F); and that Nkx2-5 expression is unaffected (G-J) in Tbx20 mutants.

FIGS. 8A-8J. Tbx20 Directly Binds and Represses Isl1 in Myocardium:

(A-D) Isl1 is expressed throughout myocardium in Tbx20 mutants.

(E) ChIP analysis revealing Tbx20 recruitment to region of the Isl1 promoter of mouse (SEQ ID NO: 565), rat (SEQ ID NO: 566), and human (SEQ ID NO: 567) with conserved T-Box site (E-1), and with primers against an unrelated promoter region revealing no Tbx20 recruitment (E-2).

(F) Co-transfection of Tbx20 expression vector with Isl1 promoter-luciferase reporter showing repression of Isl1 by Tbx20 that is abrogated by mutation of the consensus T Box element within the Isl1 promoter.

(G-J) Section series through whole-mount in situ hybridization showing expression of Isl1 throughout normal-appearing myocardium in transgenic mice at E10.5, and that the nebulette promoter is utilized to drive expression of Isl1 in transient transgenic mice.

DETAILED DESCRIPTION OF THE INVENTION

Abbreviations and Definitions

To facilitate understanding of the invention, a number of terms and abbreviations as used herein are defined below as follows:

Unless otherwise defined, all technical terms used herein have the same meaning as commonly understood by one of ordinary skill in the art to which this invention belongs. Commonly understood definitions of molecular biology terms can be found in Rieger et al., GLOSSARY OF GENETICS: CLASSICAL AND MOLECULAR, 5th edition, Springer-Verlag: New York, 1991; and Lewin, Genes V. Oxford University Press: New York, 1994. To facilitate understanding of the invention, a number of terms and abbreviations as used herein are defined below as follows:

Abs: As used herein, the term "Abs" refers to antibodies which may be, e.g., a single anti-Tbx2 or -Tbx20 monoclonal Abs (including agonist, antagonist, and neutralizing Abs), anti-Tbx2 or -Tbx20 antibody compositions with poly-epitopic specificity, single chain anti-Tbx2 or -Tbx20 Abs, and fragments of anti-Tbx2 or -Tbx20 Abs. A "monoclonal antibody" refers to an antibody obtained from a population of substantially homogeneous Abs, i.e., the individual Abs comprising the population are identical except for naturally-occurring mutations that may be present in minor amounts.

Active Polypeptide: As used herein, the term "active polypeptide" refers to a, e.g., Tbx2 or Tbx20 protein, Tbx2 or Tbx20 fragment or Tbx2 or Tbx20 variant which retains a biological and/or an immunological activity of native or naturally occurring Tbx2 or Tbx20 protein. Immunological activity refers to the ability to induce the production of an antibody against an antigenic epitope possessed by a native Tbx2 or Tbx20 protein; biological activity refers to a function, either inhibitory or stimulatory, caused by a native Tbx2 or Tbx20 protein that excludes immunological activity. A biological activity of Tbx2 or Tbx20 protein includes, for example, its regulation of cell proliferation and senescence.

Bind(s) or Interacts With: As used herein, the terms "bind," or "interacts with" refers to an activity wherein one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ moles/liter for that second molecule.

Conservative Changes: As used herein, when referring to mutations in a nucleic acid molecule, "conservative changes" are those in which at least one codon in the protein-coding region of the nucleic acid has been changed such that at least one amino acid of the polypeptide encoded by the nucleic acid sequence is substituted with a another amino acid having similar characteristics. Examples of conservative amino acid substitutions are ser for ala, thr, or cys; lys for arg; gln for asn, his, or lys; his for asn; glu for asp or lys; asn for his or gln; asp for glu; pro for gly; leu for ile, phe, met, or val; val for ile or leu; ile for leu, met, or val; arg for lys; met for phe; tyr for phe or trp; thr for ser; trp for tyr; and phe for tyr.

Control Sequences: As used herein, the term "control sequences" refers to DNA sequences that enable the expression of an operably-linked coding sequence in a particular host organism. Prokaryotic control sequences include promoters, operator sequences, and ribosome binding sites. Eukaryotic cells utilize promoters, polyadenylation signals, and enhancers.

Fragment: As used herein, the term "fragment" refers to a portion of an T-Box or N-Myc nucleic acid that is less than full-length and comprises at least a minimum length capable of hybridizing specifically with a native T-Box or N-Myc nucleic acid under stringent hybridization conditions. The length of such a fragment is preferably at least 15 nucleotides, more preferably at least 20 nucleotides, and most preferably at least 30 nucleotides of a native T-Box or N-Myc nucleic acid sequence. With respect to an T-Box or N-Myc polypeptide, a "fragment" of an T-Box or N-Myc polypeptide is a portion of an T-Box or N-Myc polypeptide that is less than full-length (e.g., a polypeptide consisting of 5, 10, 15, 20, 30, 40, 50, 75, 100 or more amino acids of a native T-Box or N-Myc protein), and preferably retains at least one functional activity of a native T-Box or N-Myc protein.

Functional Activity: As used herein, the term "functional activity" refers to a protein having any activity associated with the physiological function of the protein (e.g., functional activities of a native T-Box or N-Myc protein affecting proliferation and senescence of certain cancer cells, stem cells and heart cells).

Gene: As used herein, the term "gene" refers to a nucleic acid molecule that codes for a particular protein, or in certain cases, a functional or structural RNA molecule. For example, the TBX2 gene encodes the Tbx2 protein.

Homolog: As used herein, the term "homolog" refers to an T-Box or N-Myc gene encoding an T-Box or N-Myc polypeptide isolated from an organism other than a human being. Similarly, a "homolog" of a native T-Box or N-Myc polypeptide is an expression product of a T-Box or N-Myc gene homolog.

Labeled: As used herein, when referring to a probe or antibody, the term "labeled," generally refers to direct labeling of a probe or antibody by coupling (i.e., physically linking) a detectable substance to the probe or antibody.

Native: As used herein, when referring to a nucleic acid, molecule or polypeptide, the term "native" refers to a naturally-occurring (e.g., a "wild-type") nucleic acid or polypeptide.

N-Myc Gene: As used herein, the terms "N-Myc gene" refers to a native N-Myc-encoding nucleic acid sequence, e.g., the native N-Myc gene; a nucleic acid having sequences from which an N-Myc cDNA can be transcribed; and/or allelic variants and homologs of the foregoing. The terms encompass double-stranded DNA, single-stranded DNA, and RNA. The N-Myc gene has previously been described and can be identified as the Accession Nos. provided herein.

N-Myc Marker: As used herein, an "N-Myc marker" refers to any molecule whose presence in a sample (e.g., a cell, tissue or organ) indicates that an N-Myc gene is expressed in the sample. N-Myc markers include N-Myc nucleic acids and N-Myc proteins. "Expressing an N-Myc gene" or like phrases mean mat a sample contains a transcription product (e.g., messenger RNA, i.e., "mRNA") of an N-Myc gene or a translation product of an N-Myc protein-encoding nucleic acid (e.g., an N-Myc protein). A cell expresses an N-Myc gene when it contains a detectable level of an N-Myc nucleic acid or an N-Myc protein.

N-Myc Protein, Polypeptide: As used herein, the terms "N-Myc protein," or "N-Myc polypeptide" refers to an expression product of an N-Myc gene such as a native N-Myc protein (e.g., SEQ ID NO: 2) or a protein that shares at least 65% (preferably, 75, 80, 85, 90, 95, 96, 97, 98, or 99%) amino acid sequence identity with those of Appendix A plays a functional activity of a native N-Myc protein. The N-Myc protein has previously been described and can be identified as the Accession Nos. provided herein.

N-Myc-Specific Antibody: As used herein, the term "N-Myc-specific antibody" refers to an antibody that binds an N-Myc protein and displays no substantial binding to other naturally occurring proteins other than those sharing the same antigenic determinants as the N-Myc protein. The term includes polyclonal and monoclonal antibodies as well as antibody fragments.

Nucleic Acid or Nucleic Acid Molecule: As used herein, the terms "nucleic acid" or "nucleic acid molecule" refer to a chain of two or more nucleotides such as RNA (ribonucleic acid) and DNA (deoxyribonucleic acid). A "purified" nucleic acid molecule is one that is substantially separated from other nucleic acid sequences in a cell or organism in which the nucleic acid naturally occurs (e.g., at least 30, 40, 50, 60, 70, 80, 90, 95, 96, 97, 98, 99, or 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR) nucleic acids formed by restriction enzyme treatment of genomic nucleic acids, recombinant nucleic acids, and chemically synthesized nucleic acid molecules, e.g., the modified, variant and chimeric nucleic acid molecules provided below. Additionally, ribozymes, siRNAs and antisense nucleic acid molecules are included within the scope of this definition.

Operably Linked: As used herein, the term "operably linked" refers to a first nucleic-acid sequence physically linked with a second nucleic acid sequence creating a functional relationship with the second nucleic acid sequence. For example, a promoter is operably linked to a coding sequence if the promoter affects the transcription or expression of the coding sequence. Generally, operably linked nucleic acid sequences are contiguous and, where necessary to join two protein coding regions, in reading frame.

Pharmaceutically Acceptable: As used herein, the term "pharmaceutically acceptable" means approved by a regulatory agency of the Federal or a state government or listed in the U.S. Pharmacopeia or other generally recognized pharmacopeia for use in animals, and more particularly in humans.

Pharmaceutical Acceptable Carrier: As used herein, the term "pharmaceutically acceptable carrier" refers to a diluent, adjuvant, excipient, or vehicle with which a composition is administered. Such carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when a composition is administered intravenously. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. A composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier.

Pharmaceutically Acceptable Salt: As used herein, the term "pharmaceutically acceptable salt" includes those salts of a pharmaceutical acceptable composition formed with free amino groups such as those derived from hydrochloric, phosphoric, acetic, oxalic, tartaric acids, and those formed with free carboxyl groups such as those derived from sodium, potassium, ammonium, calcium, ferric hydroxides, isopropylamine, triethylamine, 2-ethylamino ethanol, histidine, and procaine. If the composition is basic, salts may be prepared from pharmaceutically acceptable non-toxic acids including inorganic and organic acids. Such acids include acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Particularly preferred are besylate, hydrobromic, hydrochloric, phosphoric and sulfuric acids. If the composition is acidic, salts may be prepared from pharmaceutical acceptable organic and inorganic bases. Suitable organic bases include, but are not limited to, lysine, N,N'-dibenzylethylenediamine, chloroprocaine, choline, diethanolamine, ethylenediamine, meglumine (N-methylglucamine) and procaine. Suitable inorganic bases include, but are not limited to, alkaline and earth-alkaline metals such as aluminum, calcium, lithium, magnesium, potassium, sodium and zinc.

Pro-drug: As used herein, the term "pro-drug" refers to any composition which releases an active drug in vivo when such a composition is administered to a mammalian subject. Pro-drugs can be prepared, for example, by functional group modification of a parent drug. The functional group may be cleaved in vivo to release the active parent drug compound. Pro-drugs include, for example, compounds in which a group that may be cleaved in vivo is attached to a hydroxy, amino or carboxyl group in the active drug. Examples of pro-drugs include, but are not limited to esters (e.g., acetate, methyl, ethyl, formate, and benzoate derivatives), carbamates, amides and ethers. Methods for synthesizing such pro-drugs are known to those of skill in the art.

Protein or Polypeptide: As used herein, the terms "protein" or "polypeptide" mean any peptide-linked chain of amino acids, regardless of length or post-translational modification, e.g., glycosylation or phosphorylation. A "purified" polypeptide is one that is substantially separated from other polypeptides in a cell or organism in which the polypeptide naturally occurs (e.g., at least 30, 40, 50, 60, 70, 80, 90, 95, 96, 97, 98, 99, or 100% free of contaminants).

Recombinant: As used herein, the term "recombinant" refers to a nucleic acid molecule is one made by an artificial combination of two otherwise separated segments of sequence, e.g., by chemical synthesis or by the manipulation of isolated segments of nucleic acids by genetic engineering techniques.

Sequence Identity: As used herein, the term "sequence identity" means the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Sequence identity is typically measured using sequence analysis software (e.g., the Sequence Analysis Software Package of the Genetics Computer Group, University of Wisconsin Biotechnology Center, 1710 University Avenue, Madison, Wis. 53705).

Silent Changes: As used herein, when referring to mutations in a nucleic acid molecule, "silent changes" are those that substitute of one or more base pairs in the nucleotide sequence, but do not change the amino acid sequence of the polypeptide encoded by the sequence.

Stringency or Stingent Conditions: When referring to hybridization of one nucleic acid to another, "low stringency conditions" means in 10% formamide, 5×Denhart's solution, 6×SSPE, and 0.2% SDS at 42° C., followed by washing in 1×SSPE, 0.2% SDS, at 50° C.; "moderate stringency conditions" means in 50% formamide, 5×Denhart's solution, 5×SSPE, 0.2% SDS at 42° C., followed by washing in 0.2× SSPE, 0.2% SDS, at 65° C.; and "high stringency conditions" means in 50% formamide, 5×Denhart's solution, 5×SSPE, 0.2% SDS at 42° C., followed by washing in 0.1×SSPE, and 0.1% SDS at 65° C. The phrase "stringent hybridization conditions" means low, moderate, or high stringency conditions.

T-Box: As used herein, the term "T-Box" refers to Tbx2 and Tbx20 proteins. Those of skill in the art will recognize that, in various embodiments, Tbx2 can include other members of the entire Tbx2 family of transcription factors, including Tbx2, Tbx3, Tbx4 and Tbx5. Those of skill in the art will also recognize that in various embodiments, Tbx20 can include other members of the entire Tbx20 family of transcription factors, including Tbx 15, Tbx18 and Tbx20.

TBX2 or TBX20 Gene: As used herein, the terms "TBX2 gene," or "TBX20 gene" refer to a native TBX2- or TBX20-encoding nucleic acid sequence, e.g., the native TBX2 or TBX20 gene; a nucleic acid having sequences from which a TBX2 or TBX20 cDNA can be transcribed (SEQ ID NOs: 551 and 552); and/or allelic variants and homologs of the foregoing. The terms encompass double-stranded DNA, single-stranded DNA, and RNA. The T-box gene has previously been described and can be identified as the Accession Nos. provided herein. Those of skill in the art will recognize that in various embodiments, TBX2 can include other members of the entire TBX2 family of transcription factor genes, including TBX2, TBX3, TBX4 and TBX5. Those of skill in the art will also recognize that in various embodiments, TBX20 can include other members of the entire TBX20 family of transcription factor genes, including TBX15, TBX18 and TBX20.

TBX2 or TBX20 Marker: As used herein, an "TBX2 marker" or "TBX20 marker" refers to any molecule whose presence in a sample (e.g., a cell, tissue or organ) indicates that a TBX2 or TBX20 gene is expressed in the sample. TBX2 or TBX20 markers include TBX2 or TBX20 nucleic acids and TBX2 or TBX20 proteins. "Expressing a TBX2 or TBX20 gene" or like phrases mean that a sample contains a transcription product (e.g., messenger RNA, i.e., "mRNA") of a TBX2 or TBX20 gene or a translation product of an TBX2 or TBX20 protein-encoding nucleic acid (e.g., a TBX2 or TBX20 protein). A cell expresses a TBX2 or TBX20 gene when it contains a detectable level of a TBX2 or TBX20 nucleic acid or a Tbx2 or Tbx20 protein.

Tbx2 or Tbx20 Protein, Polypeptide: As used herein, the terms "Tbx2 protein," "Tbx2 polypeptide," "Tbx20 protein," or "Tbx20 polypeptide" refers to an expression product of an T-box gene such as a native Tbx2 protein (e.g., SEQ ID NO: 1), native Tbx20 protein (e.g., SEQ ID NO: 106) or a protein that shares at least 65% (preferably, 75, 80, 85, 90, 95, 96, 97, 98, or 99%) amino acid sequence identity with those of SEQ ID NOs 1, 106 and 325 provides a functional activity of a native Tbx2 or Tbx20 protein. The Tbx2 or Tbx20 protein has previously been described and can be identified as the Accession Nos. provided herein. Those of skill in the art will recognize that, in various embodiments, Tbx2 can include other members of the entire Tbx2 family of transcription factors, including Tbx2, Tbx3, Tbx4 and Tbx5. Those of skill in the art will also recognize that, in various embodiments, Tbx20 can include other members of the entire Tbx20 family of transcription factors, including Tbx15, Tbx18 and Tbx20.

Tbx2- or Tbx20-Specific Antibody: As used herein, the terms "Tbx2-specific antibody" or "Tbx20-specific antibody" refer to an antibody that binds a Tbx2 or Tbx20 protein and displays no substantial binding to other naturally occurring proteins other than those sharing the same antigenic determinants as the Tbx2 or Tbx20 protein. The term includes polyclonal and monoclonal antibodies as well as antibody fragments.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below.

Transformed, Transfected or Transgenic: As used herein, the terms "transformed," "transfected" or "transgenic" refer to a cell, tissue, or organism into which has been introduced a foreign nucleic acid such as a recombinant vector. The terms "transformed" or "transgenic" includes progeny of a cell or organism, including progeny produced from a breeding program employing such a "transgenic" cell or organism, as a parent in a cross. For example, a transgenic T-Box or N-Myc organism is one in which an T-Box or N-Myc nucleic acid has been introduced or progeny thereof.

Vector: As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and expression of nucleic acids to which they are linked. Vectors capable of directing the expression of genes to which they are operatively linked are referred to herein as "expression vectors."

Compositions and Methods for Treating Diseases Associated with T-Box and N-Myc

The present invention relates to the discovery that Tbx2 as a direct target for repression by Tbx20 in proliferating and senescing cells, including cancers and developing heart. The invention also relates to the discovery that Tbx2 can directly bind to the N-myc promoter, and can repress expression of the N-myc promoter. Repression of N-myc by aberrantly regulated Tbx2 affects cell proliferation and/or senescence, which can account for the proliferation and/or senescence of certain cancer cells, differentiation of stem cells, and the formation of abnormal heart morphogenesis. For example, Tbx2 can directly repress N-myc in outflow tract and atrioventricular canal of the developing heart, resulting in relatively low proliferation and hypoplasia. Also provided are genes and their homologs, methods for screening for inducers and repressors of Tbx2, Tbx20 and N-Myc, effectors such as siRNAs, antibodies and other compounds, methods for manipulating cell cycle by effecting the expression of those genes or the functions of the gene products, and methods for preventing and treating diseases associated with the regulation of Tbx20, Tbx2 and N-Myc.

Thus, Tbx2 (and, in various embodiments, the Tbx2 family of transcription factors including Tbx2, Tbx3, Tbx4 and Tbx5) is a critical direct target for repression by Tbx20 (and, in various embodiments, the Tbx20 family of transcription factors including Tbx15, Tbx18 and Tbx20), and Tbx2 (and, in various embodiments, the Tbx2 family of transcription factors including Tbx2, Tbx3, Tbx4 and Tbx5) itself directly represses N-myc activity, Tbx2 and its close family member Tbx3 play critical roles in cell cycle control via suppression of senescence genes. Senescence genes are well known the art and can include the INK4a/Arf gene locus, e.g. p19ARF and p16INK4a. In addition to its role in regulating regional proliferation, Tbx20 regulates expression of a number of genes which specify regional identity within the heart, thereby coordinating these two important aspects of organ development and cell proliferation. T-box genes can deferentially regulate N-Myc—the Tbx2 family of transcription factors can repress N-Myc expression and the Tbx20 family can activate N-Myc.

The TBX20 gene sequence for human (SEQ ID NO; 1; Accession No. NM_020417.1), TBX2 gene sequence for human (SEQ ID NO: 106; Accession No. NM_005994.3) and TBX3 gene sequence for human (SEQ ID NO: 325; Accession No. AF170708.2), and N-Myc gene sequence for human (SEQ ID NO: 524; Accession No. AF320053.1) are provided. SEQ ID NOs: 2-105 are sense and antisense sequences of siRNAs targeting various sequences within TBX20 (even numbered sense strands followed by odd numbered antisense sequences). SEQ ID NOs: 107-324 are sense and antisense sequences of siRNAs targeting various sequences within TBX2 (odd numbered sense strands followed by even numbered antisense sequences). SEQ ID NOs: 326-523 are sense and antisense sequences of siRNAs targeting various sequences within TBX3 (even numbered sense strands followed by odd numbered antisense sequences). SEQ ID NOs: 525-550 are sense and antisense sequences of siRNAs targeting various sequences within N-Myc (odd numbered sense strands followed by even numbered antisense sequences). SEQ ID NOs 551-553 are TBX20, TBX2 and TBX3 cDNAs respectively. Those of skill in the art will recognize that homologs to the above human T-Box and N-Myc gene sequences are available on public databases.

Roles of T-Box and N-Myc in Proliferation, Morphogenesis and Senescence

The present invention provides two direct targets for repression by Tbx20, including Tbx2, and Isl1. Interactions between Tbx20 and Tbx2 are required for regional proliferation, morphogenesis, and aspects of specification in early heart, while Isl1 is required for proliferation, survival and migration of a subset of undifferentiated cardiac progenitors (Cai et al., 2003). As these progenitors enter the heart and differentiate, Isl1 is down regulated. Evidence from transgenic mice expressing Isl1 throughout myocardium (FIG. 8 G-J) demonstrate that upregulation of Isl1 does not account for the cardiac phenotype in Tbx20 mutants.

T-Box genes regulate the N-myc promoter which contribute to organ morphogenesis and human congenital disease and cancer. In one non-limiting example, Tbx2, normally expressed in outflow tract and atrioventricular canal, is up regulated throughout the heart in Tbx20 mutants. The cardiac phenotype of Tbx20 mutants mimics that of mice over expressing Tbx2 in myocardium (Christoffels et al., 2004). The present invention provides that Tbx2 is a direct target of Tbx20 in developing heart. In vivo ChIP analysis performed on embryonic heart extracts demonstrates direct binding of Tbx20 to a region of the Tbx2 promoter containing conserved T-box consensus sites. Transfection studies demonstrate that activity of this promoter is repressed by co-transfection with a Tbx2 expression vector, in a manner dependent on presence of conserved T-box sites within the promoter.

Two cell cycle genes previously implicated in cardiomyocyte proliferation were examined—cyclinA2 and N-myc (Chaudhry et al., 2004; Davis and Bradley, 1993; Murphy et al., 1997)—and were down regulated in Tbx20 mutant hearts. Similar regional differences were observed in expression of both these genes in wild type heart. Regions of relatively low expression coincide with regions expressing Tbx2, suggesting that Tbx2 suppresses proliferation by acting directly on N-myc (no consensus T-Box sites were identified in putative promoter regions of cyclinA2). A cluster of conserved T-Box sites was identified within intron 1 of N-myc. This intron is within a human N-myc transgene which recapitulates expression pattern of the endogenous N-myc gene in newborn mice (Zimmerman et al., 1990).

Sequences within exon1 and/or intron 1 of N-myc direct tissue specific expression in cancer cell lines, and contain both positive and negative regulatory elements, some acting at a post-transcriptional level (Strieder and Lutz, 2002). N-myc is expressed in early myocardial cells, and is required for normal proliferative growth of me heart (Charron et al., 1992; Moens et al., 1993; Sawai et al., 1993). Mice which are homozygous null for N-myc arrest development at approximately E9.5, and die between E10.5 and E11.5, with severely hypoplastic hearts, undivided thin-walled ventricles, and few trabeculae.

Tbx2 directly binds to N-myc enhancer elements with conserved T-Box sites in early developing heart, and can repress N-myc promoter activity in transfection studies. Tbx20 is also able to bind to this N-myc enhancer, but does not repress its activity in our in vitro assay system. This observation suggests the possibility that Tbx20 blocks Tbx2 repression of N-myc by competitive binding. Although both Tbx20 and N-myc mutants have hypoplastic hearts, the cardiac hypoplasia in Tbx20 mutants is more severe than that of N-myc mutant mice.

Regional expression of Tbx2, e.g., in outflow tract and atrioventricular canal, suppresses N-myc expression to result in relatively low rates of proliferation. In contrast, in chamber myocardium, Tbx20 represses Tbx2, preventing its repression of N-myc, and allowing for higher rates of proliferation. Regulation of N-myc by Tbx2 is dose dependent, suggesting that differential proliferation rates can be regulated by the amount of Tbx2 present. Thus, Tbx20 is involved in the control of regional proliferation at the early heart tube stage.

One of skill in the art will recognize that Tbx2 may regulate N-myc in other contexts. Down regulation of N-myc is an early response in retinoic acid-induced differentiation of neuroblastoma cells, and Tbx2 is expressed in neuroblastoma cells as demonstrated by microarray analysis (Schulte et al., 2005; Thiele et al., 1985). In melanocytes and melanoma cells, Tbx2 is a direct target of Mitt a basic helix-loop-helix leucine zipper transcription factor which is central to pathways controlling proliferation and differentiation of melanoblasts and melanocytes, and is likely to be a negative regulator of cell cycle progression (Vance and Goding, 2004). B16 melanoma cells differentiate in response to retinoic acid and Tbx2 is an immediate early target (Niles, 2003). These data suggest that Tbx2 plays a key role in cell cycle regulation in both melanocytes and melanoma cells, and that N-myc may be a target of Tbx2 in this context.

Without being bound by a particular theory, Tbx2 may be involved in cancer cell proliferation when over expression of Tbx2 allows bypass of senescence in cells predisposed to senesce. In addition, Tbx2 is amplified in breast, ovarian, and pancreatic cancer cells (Rowley et al., 2004). Tbx2 can bypass senescence by direct repression of senescence genes. Consequences of Tbx2 repression of N-myc in cancer cells may depend on relative expression levels of Tbx2 and N-myc. For example, high levels of N-myc can trigger senescence. Therefore moderate down regulation of N-myc by Tbx2 in this context could bypass senescence, promoting immortalization. On the other hand, severe down regulation of N-myc by Tbx2 could prevent proliferation, promoting differentiation, and rendering transformation less likely. Bypass of senescence is a property of stem cells (Park et al., 2004). The ability of Tbx2 to bypass senescence, either by targeting of senescence genes or down regulation of N-myc suggests that Tbx2 might play a role in stem cell maintenance. Tbx2 and Tbx20 can maintain normal regulation of N-myc which suggests that a stem cell can maintain cell cycle and not senesce. In addition, Tbx2 and Tbx20 can up regulate N-Myc to promote entry of stem cells in to a more proliferative mode— from omnipotential to pluripotential. This provides a way to regulate proliferative or senescent state of stem cell.

Tbx2 and Tbx3 display functional redundancy as both have been shown to repress the same senescence genes, both are amplified in breast cancer, and cooperate with oncogenes to transform cells (Rowley et al., 2004). These observations suggest that Tbx3 may also target N-myc.

These observations demonstrate that, in addition to the control of regional proliferation detailed here, Tbx20 is required for other critical aspects of heart development. Although both Tbx20 and N-myc mutants have severely hypoplastic hearts, the cardiac phenotype in Tbx20 mice is slightly more severe than that of N-myc mutant mice, suggesting that factors in addition to N-myc down regulation contribute to the phenotype.

Accordingly, the present invention provides a novel role, for Tbx2, Tbx20 and N-Myc in proliferation and senescence. Therefore, those of skill in the art will recognize that Tbx2, Tbx20 and N-Myc are targets for drug discovery and designing new treatments for diseases associated with Tbx2, Tbx20 and N-Myc, including certain cancers and heart disease.

Accordingly, the invention provides a method for identifying a candidate N-Myc up regulating compound, the method comprising: (a) contacting Tbx2 or biologically-active fragment with a known compound that binds Tbx2 to form an assay mixture, (b) contacting the assay mixture with a test compound, and (c) determining the ability of the test compound to interact with Tbx2, wherein an increased ability of the test compound to interact with Tbx2 in the presence of the known compound indicates that the test compound is an N-Myc up regulating compound.

The invention also provides a method for identifying a candidate Tbx2 up regulating compound, the method comprising: (a) contacting TBX20 or biologically-active fragment with a known compound that binds TBX20 to form an assay mixture, (b) contacting the assay mixture with a test compound, and (c) determining the ability of the test compound to interact with TBX20, wherein an increased ability of the test compound to interact with TBX20 in the presence of the known compound indicates that the test compound is an Tbx2 up regulating compound.

In one embodiment, an isolated T-Box molecule can be used to express T-Box (e.g., via a recombinant expression vector in a host cell in gene therapy applications), to detect T-Box mRNA (e.g., in a biological sample) or to modulate a T-Box activity. In addition, T-Box polypeptides can be used to screen drugs or compounds that modulate the T-Box activity or expression as well as to treat disorders characterized by insufficient or excessive production of T-Box or production of T-Box forms that have decreased or aberrant activity compared to T-Box wild-type protein, or modulate biological function that involve T-Box. In addition, the anti-Tbx2 or anti-Tbx20 Abs of the invention can be used to detect and isolate T-Box and modulate T-Box activity.

Accordingly, the present invention provides a method for identifying a candidate cell proliferation or senescence regulating compound, i.e., candidate or test compounds or agents (e.g., peptides, peptidomimetics, small molecules or other drugs), and combinations thereof, that effect T-Box, a stimulatory or inhibitory effect, including translation, transcription, activity or copies of the gene in cells. In addition, the cell proliferation or senescence regulating compounds of the invention can include other candidate or test compounds or agents which are effective in modulating an activity of T-Box either upstream or downstream. The present invention also includes compounds identified in screening assays provided herein.

Testing for compounds that increase or decrease T-Box or N-Myc gene activity are desirable. A compound may modulate T-Box or N-Myc gene activity by affecting: (1) the number of copies of the gene in the cell (amplifiers and deamplifiers); (2) increasing or decreasing transcription of the T-Box or N-Myc (transcription up-regulators and down-regulators); (3) by increasing or decreasing the translation of T-Box or N-Myc mRNA into protein (translation up-regulators and down-regulators); or (4) by increasing or decreasing the activity of T-Box itself (agonists and antagonists).

To identify compounds that affect T-Box or N-Myc at the DNA, RNA and protein levels, cells or organisms are contacted with a candidate compound and the corresponding change in T-Box or N-Myc DMA, RNA or protein is assessed. For DNA amplifiers and deamplifiers, the amount of T-Box or N-Myc DNA is measured, for those compounds that are transcription up-regulators and down-regulators the amount of T-Box or N-Myc mRNA is determined; for translational up- and down-regulators, the amount of T-Box or N-Myc polypeptides is measured. Compounds that are agonists or antagonists may be identified by contacting cells or organisms with the compound.

Modulators of T-Box or N-Myc expression can be identified in a method where a cell is contacted with a candidate compound and the expression of T-Box or N-Myc mRNA or protein in the cell is determined. The expression level of T-Box or N-Myc mRNA or protein in the presence of the candidate compound is compared to T-Box or N-Myc mRNA or protein levels in the absence of the candidate compound. The candidate compound can then be identified as a modulator of T-Box or N-Myc mRNA or protein expression based upon this comparison. For example, when expression of T-Box or N-Myc mRNA or protein is greater (i.e., statistically significant) in the presence of the candidate compound than in its absence, the candidate compound is identified as a stimulator of T-Box or N-Myc mRNA or protein expression. Alternatively, when expression of T-Box or N-Myc mRNA or protein is less (statistically significant) in the presence of the candidate compound than in its absence, the candidate compound is identified as an inhibitor of T-Box or N-Myc mRNA or protein expression. The level of T-Box or N-Myc mRNA or protein expression in the cells can be determined by methods described for detecting T-Box or N-Myc mRNA or protein.

Methods of making recombinant cells and expressing cellular proteins such as T-Box or N-Myc are well known in the art. For an introduction to recombinant methods, see, Berger and Kimmel, Guide to Molecular Cloning Techniques, Methods in Enzymology, volume 152, Academic Press, Inc., San Diego, Calif. ("Berger"); Sambrook et al. (1989) Molecular Cloning—A Laboratory Manual (2nd ed.) Vol. 1-3, Cold Spring Harbor Laboratory, Cold Spring Harbor Press, N.Y., ("Sambrook"); and Current Protocols in Molecular Biology, F. M. Ausubel et al., eds., Current Protocols, a joint venture between Greene Publishing Associates, Inc. and John Wiley & Sons, Inc., (e.g., current through 1999, e.g., at least through supplement 37) ("Ausubel"), each of which are incorporated herein by reference in its entirety. Culture of mammalian cell lines and cultured cells from tissue or blood samples is well known in the art. Freshney (Culture of Animal Cells, a Manual of Basic Technique, Third Edition, Wiley-Liss, New York (1994)) and the references cited therein provides a general guide to the culture of animal cells. Culture of plant cells is described in Payne et al. (1992) Plant cell and Tissue Culture in Liquid Systems, John Wiley & Sons, Inc., New York, N.Y. Additional information on cell culture, including prokaryotic cell culture, is found in Berger, Sambrook, and Ausubel, supra. Cell culture media are described in Atlas and Parks (eds.) The Handbook of Microbiological Media (1993) CRC Press, Boca Raton, Fla. Additional information is found in commercial literature such as the Life Science Research Cell Culture catalogue (various editions) from Sigma-Aldrich, Inc. (St. Louis, Mo.) and, e.g., the Plant Culture Catalogue and supplement (1997) also from Sigma-Aldrich, Inc. (St. Louis, Mo.).

Many other assays for screening candidate or test compounds that bind to or modulate the activity of T-Box or N-Myc polynucleotide or polypeptide or biologically active portion are available to those of skill in the art. Test compounds can be obtained using any of the numerous approaches in combinatorial library methods, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptides, while the other four approaches encompass peptide, non-peptide oligomer or small molecule libraries of compounds.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries are also optionally used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with $\alpha$-D-glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see, Berger and Kimmel, Guide to Molecular Cloning Techniques, Methods in Enzymology, volume 152, Academic Press, Inc., San Diego, Calif. ("Berger"), Sambrook, supra, and Ausubel, supra; peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569, 588; thiazolidinones and metathiazanones, U.S. Pat. No. 5,549,974; pyrrolidines, U.S. Pat. Nos. 5,525,735 and 5,519, 134; morpholino compounds, U.S. Pat. No. 5,506,337; benzodiazepines, U.S. Pat. No. 5,288,514, and the like).

A "small molecule" refers to a composition that has a molecular weight of less than about 5 kD and more preferably less than about 4 kD, and most preferable less than 0.6 kD. Small molecules can be nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Cell-Free Assays

In one embodiment, a cell-free assay is provided which comprises contacting T-Box or N-Myc gene, or biologically-active fragment thereof, with a known compound that binds T-Box or N-Myc gene to form an assay mixture, contacting the assay mixture with a test compound, and determining the ability of the test compound to interact with T-Box or N-Myc gene, where determining the ability of the test compound to interact with T-Box or N-Myc gene comprises determining the ability of T-Box or N-Myc gene to preferentially bind to or modulate the activity of a T-Box or N-Myc target molecule.

Immobilizing either T-Box or N-Myc gene can facilitate separation of complexed from uncomplexed forms of one or both of the proteins, as well as to accommodate high throughput assays. Binding of a test compound to T-Box or N-Myc gene, or interaction of T-Box or N-Myc gene with a target molecule in the presence and absence of a candidate compound, can be accomplished in any vessel suitable for containing the reactants, such as microtiter plates, test tubes, and micro-centrifuge tubes. A fusion protein can be provided that provides a domain that allows one or both of the proteins to be bound to a matrix. The complexes can be dissociated from the matrix, and the level of T-Box or N-Myc gene binding or activity determined using standard techniques.

Other techniques for immobilizing proteins on matrices can also be used in screening assays. Either T-Box or N-Myc gene can be immobilized using biotin-avidin or biotin-streptavidin systems. Biotinylation can be accomplished using many reagents, such as biotin-NHS (N-hydroxy-succinimide; PIERCE Chemicals, Rockford, Ill.), and immobilized in wells of streptavidin-coated 96 well plates (PIERCE Chemical). Alternatively, Abs reactive with T-Box or target molecules, but which do not interfere with binding of the T-Box to N-Myc, can be derivatized to the wells of the plate, and unbound N-Myc or T-Box trapped in the wells by antibody conjugation. Methods for detecting such complexes, in addition to those described for the GST-immobilized complexes, include immunodetection of complexes using Abs reactive with T-Box or N-Myc gene, as well as enzyme-linked assays that rely on detecting an enzymatic activity associated with the T-Box or N-Myc gene.

Many other embodiments of such drug screening assays are available to those of skill in the art. For example, Sambrook and Ausubel provide multiple screening protocols which may be adapted for use with T-Box or N-Myc gene.

Agonists and Antagonists

"Antagonist" includes any molecule that partially or fully blocks, inhibits, or neutralizes a biological activity of endogenous T-Box or N-Myc gene. Similarly, "agonist" includes any molecule that mimics a biological activity of endogenous T-Box or N-Myc gene. Molecules that can act as agonists or antagonists include Abs or Ab fragments, fragments or variants of endogenous T-Box or N-Myc gene, peptides, antisense oligonucleotides, small organic molecules, etc.

To assay for antagonists, T-Box or N-Myc gene is added to, or expressed in, a cell along with the compound to be screened for a particular activity. If the compound inhibits the activity of interest in the presence of the T-Box or N-Myc gene, that compound is an antagonist to the T-Box or N-Myc gene; if T-Box or N-Myc gene activity is enhanced, the compound is an agonist.

In another embodiment, T-Box-expressing cells can be easily identified using any of the disclosed methods. For example, antibodies that recognize the amino- or carboxy-terminus of human T-Box can be used to screen candidate cells by immunoprecipitation, Western blots, and immunohistochemical techniques. Likewise, SEQ ID NOs: 1, 106 and 325 can be used to design primers and probes that can detect TBX20, TBX2 and TBX3 mRNA, respectively, in cells or samples from cells.

Any molecule that alters T-Box cellular effects is a candidate antagonist or agonist. Screening techniques well known to those skilled in the art can identify these molecules. Examples of antagonists and agonists include: (1) small organic and inorganic compounds, (2) small peptides, (3) Abs and derivatives, (4) polypeptides closely related to T-Box, (5) antisense DNA and RNA, (6) ribozymes, (7) triple DNA helices, (8) siRNAs, (9) nucleic acid aptamers, and (10) cDNAs.

Small molecules that bind to the T-Box active site or other relevant part of the polypeptide and inhibit the biological activity of the T-Box are antagonists. Examples of small molecule antagonists include small peptides, peptide-like molecules, preferably soluble, and synthetic non-peptidyl organic or inorganic compounds. These same molecules, if they enhance T-Box activity, are examples of agonists.

Almost any antibody that affects T-Box function is a candidate antagonist, and occasionally, agonist. Examples of antibody antagonists include polyclonal, monoclonal, single-chain, anti-idiotypic, chimeric Abs, or humanized versions of such Abs or fragments. Abs may be from any species in which an immune response can be raised. Humanized Abs are also contemplated.

Alternatively, a potential antagonist or agonist may be a closely related protein, for example, a mutated form of the T-Box that recognizes a T-Box-interacting protein but imparts no effect, thereby competitively inhibiting T-Box action. Alternatively, a mutated T-Box may be constitutively activated and may act as an agonist.

Therapeutics

For therapeutics, an animal, preferably a human, suspected of suffering from an heart disease which can be treated by modulating the expression of T-Box or N-Myc is treated by administering the antisense nucleic acids, ribozymes, triplex-forming oligonucleotides, siRNAs, probes, primers, T-Box or N-Myc-specific antibodies, and other compositions identified herein which modulate the expression of T-Box or N-Myc can be utilized in accordance with this invention.

The present invention provides a key diagnostic assay for early detection of heart disease, as well as a therapy that may be used in conjunction with surgical or chemotherapeutic techniques. Use of the instant invention as an assay can be used to determine the level of expression of T-Box or N-Myc, enabling diagnosticians to determine with highly sensitive assays whether there is an abnormality in the expression levels.

Detection Assays

Portions or fragments of T-Box cDNA sequences identified herein as SEQ ID NOs: 551-553 for TBX20, TBX2 and TBX3 respectively, (and the complete T-Box gene sequences) are useful in themselves. By way of non-limiting example, these sequences can be used to: (1) identify an individual from a minute biological sample (tissue typing); and (2) aid in forensic identification of a biological sample.

The T-Box sequences of the invention can be used to identify individuals from minute biological samples. In this technique, an individual's genomic DNA is digested with one or more restriction enzymes and probed on a Southern blot to yield unique bands. The sequences of the invention are useful as additional DNA markers for "restriction fragment length polymorphisms" (RFLP).

Furthermore, the T-Box sequences can be used to determine the actual base-by-base DNA sequence of targeted portions of an individual's genome. T-Box sequences can be used to prepare two PCR primers from the 5'- and 3'-termini of the sequences that can then be used to amplify the corresponding sequences from an individual's genome and then sequence the amplified fragment.

Panels of corresponding DNA sequences from individuals can provide unique individual identifications, as each individual will have a unique set of such DNA sequences due to allelic differences. The sequences of the invention can be used to obtain such identification sequences from individuals and from tissue. Allelic variation occurs to some degree in the coding regions of these sequences, and to a greater degree in the noncoding regions. The allelic variation between individual humans occurs with a frequency of about once ever 500 bases. Much of the allelic variation is due to single nucleotide polymorphisms (SNPs), which include RFLPs.

Each of the sequences described herein can, to some degree, be used as a standard against which DNA from an individual can be compared for identification purposes. Because greater numbers of polymorphisms occur in noncoding regions', fewer sequences are necessary to differentiate individuals. Noncoding sequences can positively identify individuals with a panel of 10 to 1,000 primers that each yield a noncoding amplified sequence of 100 bases. If predicted coding sequences, such as those in SEQ ID NOs: 1 and 2 are used, a more appropriate number of primers for positive individual identification would be 500-2,000.

Predictive Medicine

The invention also pertains to the field of predictive medicine in which diagnostic assays, prognostic assays, pharmacogenetics, and monitoring clinical trials are used for prognostic (predictive) purposes to treat an individual prophylactically. Accordingly, one aspect of the invention relates to diagnostic assays for determining T-Box protein and/or nucleic acid expression as well as T-Box and N-Myc gene expression activity, in the context of a biological sample (e.g., blood, serum, cells, tissue) to determine whether an individual is afflicted with a disease or disorder, or is at risk of developing a disorder, associated with aberrant T-Box protein and N-Myc gene expression or activity, including cancer and heart disease. The invention also provides for prognostic (or predictive) assays for determining whether an individual is at risk of developing a disorder associated with T-Box and N-Myc protein, nucleic acid expression or activity. For example, mutations in T-Box genes or proteins can be assayed in a biological sample. Such assays can be used for prognostic or predictive purpose, to prophylactically treat an individual prior to the onset of a disorder characterized by or associated with T-Box and N-Myc protein, nucleic acid expression, or biological activity.

Another aspect of the invention provides methods for determining T-Box and N-Myc activity, or nucleic acid expression, in an individual to select appropriate therapeutic or prophylactic agents for that individual (referred to herein as "pharmacogenomics"). Pharmacogenomics allows for the selection of modalities (e.g., drugs, foods) for therapeutic or prophylactic treatment of an individual based on the individual's genotype (e.g., the individual's genotype to determine the individual's ability to respond to a particular agent). Another aspect of the invention pertains to monitoring the influence of modalities (e.g., drugs, foods) on the expression or activity of T-Box and N-Myc in clinical trials.

Diagnostic Assays

An exemplary method for detecting the presence or absence of T-Box and N-Myc in a biological sample involves obtaining a biological sample from a subject and contacting the biological sample with a compound or an agent capable of detecting T-Box and N-Myc protein or T-Box and N-Myc nucleic acid (e.g., mRNA, genomic DNA) such that the presence of T-Box and N-Myc is confirmed in the sample. An agent for detecting T-Box or N-Myc mRNA or genomic DNA is a labeled nucleic acid probe that can hybridize to T-Box or N-Myc mRNA or genomic DNA. The nucleic acid probe can be, in a non-limiting example, a full-length T-Box nucleic acid, such as the nucleic acids of SEQ ID NOs: 1, 106 and 324, or portions thereof, such as an oligonucleotide of at least 15, 30, 50, 100, 250 or 500 nucleotides in length and sufficient to specifically hybridize under stringent conditions to T-Box mRNA or genomic DNA.

An agent for detecting T-Box polypeptide or N-Myc gene is an antibody capable of binding to T-Box protein or N-Myc gene or promoter, preferably an antibody with a detectable label. Abs can be polyclonal, or more preferably, monoclonal. An intact antibody, or a fragment (e.g., $F_{ab}$ or $F(ab')_2$) can be used. A labeled probe or antibody is coupled (i.e., physically linking) to a detectable substance, as well as indirect detection of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently-labeled streptavidin. The term "biological sample" includes tissues, cells and biological fluids isolated from a subject, as well as tissues, cells and fluids present within a subject. The detection method of the invention can be used to detect T-Box and N-Myc mRNA, protein, or genomic DNA in a biological sample in vitro as welt as in vivo. In one non-limiting example, in vitro techniques for defection of T-Box mRNA include Northern hybridizations and in situ hybridizations. In vitro techniques for detection of T-Box polypeptide include enzyme linked immunosorbent assays (ELISAs), Western blots, immunoprecipitation, and immunofluorescence. In vitro techniques for detection of T-Box genomic DNA include Southern hybridizations and fluorescence in situ hybridization (FISH). Furthermore, in vivo techniques for detecting T-Box include introducing into a subject a labeled anti-Tbx2 or anti-Tbx20 antibody. For example, the antibody can be labeled with a radioactive marker whose presence and location in a subject can be detected by standard imaging techniques.

In one embodiment, the biological sample from the subject contains protein molecules, and/or mRNA molecules, and/or genomic DNA molecules. A preferred biological sample is blood. In another embodiment, the methods further involve obtaining a biological sample from a subject to provide a control, contacting the sample with a compound or agent to detect T-Box protein, mRNA, or genomic DNA, and comparing the presence of T-Box protein, mRNA or genomic DNA in the control sample with the presence of T-Box protein, mRNA or genomic DNA in the test sample.

The invention also encompasses kits for detecting T-Box protein and/or N-Myc gene in a biological sample. For example, the kit can comprise: a labeled compound or agent capable of detecting T-Box protein or T-Box mRNA in a sample; reagent and/or equipment for determining the amount of T-Box in the sample; and reagent and/or equipment for comparing the amount of T-Box in the sample with a standard. The compound or agent can be packaged in a suitable container. The kit can further comprise instructions for using the kit to detect T-Box protein or nucleic acid.

Prognostic Assays

The diagnostic methods described herein can furthermore be utilized to identify subjects having or at risk of developing a disease or disorder associated with aberrant T-Box and N-Myc expression or activity. For example, the assays described herein, can be used to identify a subject having or at risk of developing a disorder associated with T-Box protein, nucleic acid expression or activity and N-Myc expression. Alternatively, the prognostic assays can be used to identify a subject having or at risk for developing a disease or disorder. The invention provides a method for identifying a disease or disorder associated with aberrant T-Box and N-Myc expression or activity in which a test sample is obtained from a subject and T-Box protein or nucleic acid (e.g., mRNA, genomic DNA) and N-Myc nucleic acid is detected. A test sample is a biological sample obtained from a subject. For example, a test sample can be a biological fluid (e.g., serum), cell sample, or tissue.

Prognostic assays can be used to determine whether a subject can be administered a modality (e.g., an agonist, antagonist, peptidomimetic, protein, peptide, nucleic acid, small molecule, food, etc.) to treat a disease or disorder associated with aberrant T-Box and N-Myc expression or activity. Such methods can be used to determine whether a subject can be effectively treated with an agent for a disorder. The invention provides methods for determining whether a subject can be effectively treated with an agent for a disorder associated with aberrant T-Box and N-Myc expression or activity in which a test sample is obtained and T-Box protein or nucleic acid and N-Myc nucleic acid is detected (e.g., where the presence of T-Box or nucleic acid and N-Myc nucleic acid is diagnostic for a subject that can be administered the agent to treat a disorder associated with aberrant T-Box and N-Myc expression or activity).

The methods of the invention can also be used to detect genetic lesions in a T-Box to determine if a subject with the genetic lesion is at risk for a disorder. Methods include detecting, in a sample from the subject, the presence or absence of a genetic lesion characterized by at an alteration affecting the integrity of a gene encoding a T-Box polypeptide, or the misexpression of T-Box. Such genetic lesions can be detected by ascertaining: (1) a deletion of one or more nucleotides from T-Box; (2) an addition of one or more nucleotides to T-Box; (3) a substitution of one or more nucleotides in T-Box, (4) a chromosomal rearrangement of a T-Box gene; (5) an alteration in the level of a T-Box mRNA transcripts, (6) aberrant modification of a T-Box, such as a change genomic DNA methylation, (7) the presence of a non-wild-type splicing pattern of a T-Box mRNA transcript, (8) a non-wild-type level of T-Box, (9) allelic loss of T-Box, and/or (10) inappropriate post-translational modification of T-Box polypeptide. There are a large number of known assay techniques that can be used to detect lesions in T-Box. Any biological sample containing nucleated cells may be used.

In certain embodiments, lesion detection may use a probe/primer in a polymerase chain reaction (PCR) (such as anchor PCR or rapid amplification of cDNA ends (RACE) PCR, or, alternatively, in a ligation chain reaction (LCR). This method may include collecting a sample from a patient, isolating nucleic acids from the sample, contacting the nucleic acids with one or more primers that specifically hybridize to T-Box under conditions such that hybridization and amplification of the T-Box (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication, transcriptional amplification system; Qβ Replicase, or any other nucleic acid amplification method, followed by the detection of the amplified molecules using techniques well known to those of skill in the art. These detection schemes are especially useful for the detection of nucleic acid molecules present in low abundance and are known to those of skill in the art.

Mutations in T-Box from a sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes can be used to score for the presence of specific mutations by development or loss of a ribozyme cleavage site.

Hybridizing a sample and control nucleic acids, e.g., DNA or RNA, to high-density arrays containing hundreds or thousands of oligonucleotides probes, can identify genetic mutations in T-Box. For example, genetic mutations in T-Box can be identified in two-dimensional arrays containing light-generated DNA probes. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the T-Box and detect mutations by comparing the sequence of the sample T-Box with the corresponding wild-type (control) sequence. Any of a variety of automated sequencing procedures can be used when performing diagnostic assays including sequencing by mass spectrometry.

Other methods for detecting mutations in the T-Box include those in which protection from cleavage agents is used to detect mismatched bases in RNA/RNA or RNA/DNA heteroduplexes. In general, the technique of "mismatch cleavage" starts by providing heteroduplexes formed by hybridizing (labeled) RNA or DNA containing the wild-type T-Box sequence with potentially mutant RNA or DNA obtained from a sample. The double-stranded duplexes are treated with an agent that cleaves single-stranded regions of the duplex such as those that arise from base pair mismatches between the control and sample strands. For instance, RNA/DNA duplexes can be treated with RNase and DNA/DNA hybrids treated with $S_1$ nuclease to enzymatically digest the mismatched regions. In other embodiments, either DNA/DNA or RNA/DNA duplexes can be treated with hydroxylamine or osmium tetroxide and with piperidine in order to digest mismatched regions. The digested material is then separated by size on denaturing polyacrylamide gels to determine the mutation site. The control DNA or RNA can be labeled for detection.

Mismatch cleavage reactions may employ one or more proteins that recognize mismatched base pairs in double-stranded DNA (DNA mismatch repair) in defined systems for defecting and mapping point mutations in T-Box cDNAs obtained from samples of cells. For example, the mutY enzyme of *E. coli* cleaves A at G/A mismatches and the thymidine DNA glycosylase from HeLa cells cleaves T at G/T mismatches. According to an exemplary embodiment, a probe based on a wild-type T-Box sequence is hybridized to a cDNA or other DNA product from a test cell(s). The duplex is treated with a DNA mismatch repair enzyme, and the cleavage products, if any, can be detected from electrophoresis protocols or the like.

Electrophoretic mobility alterations can be used to identify mutations in T-Box. For example, single strand conformation polymorphism (SSCP) may be used to detect differences in electrophoretic mobility between mutant and wild type nucleic acids. Single-stranded DNA fragments of sample and control T-Box nucleic acids are denatured and then renatured. The secondary structure of single-stranded nucleic acids varies according to sequence; the resulting alteration in electrophoretic mobility allows detection of even a single base change. The DNA fragments may be labeled or detected with labeled probes. The sensitivity of the assay may be enhanced by using RNA (rather than DNA), in which the secondary structure is more sensitive to a sequence changes. The subject method may use heteroduplex analysis to separate double stranded heteroduplex molecules on the basis of changes in electrophoretic mobility.

The migration of mutant or wild-type fragments can be assayed using denaturing gradient gel electrophoresis (DGGE). In DGGE, DNA is modified to prevent complete denaturation, for example by adding a GC clamp of approximately 40 bp of high-melting GC-rich DNA by PCR. A temperature gradient may also be used in place of a denaturing gradient to identify differences in the mobility of control and sample DNA.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. Such allele-specific oligonucleotides are hybridized to PCR-amplified target DNA or a number of different mutations when the oligonucleotides are attached to the hybridizing membrane and hybridized with labeled target DNA.

Alternatively, allele specific amplification technology that depends on selective PCR amplification may be used. Oligonucleotide primers for specific amplifications may carry the mutation of interest in the center of the molecule (so that amplification depends on differential hybridization) or at the extreme 3'-terminus of one primer where, under appropriate conditions, mismatch can prevent, or reduce polymerase extension. Novel restriction site in the region of the mutation may be introduced to create cleavage-based detection. Certain amplification may also be performed using Taq ligase for amplification. In such cases, ligation occurs only if there is a perfect match at the 3'-terminus of the 5' sequence, allowing detection of a known mutation by scoring for amplification.

The described methods may be performed, for example, by using pre-packaged kits comprising at least one probe (nucleic acid or antibody) that may be conveniently used, for example, in clinical settings to diagnose patients exhibiting symptoms or family history of a disease or illness involving T-Box.

Furthermore, any cell type or tissue in which T-Box is expressed may be utilized in the prognostic assays described herein.

Pharmacogenomics

Agents, or modulators that have a stimulatory or inhibitory effect on T-Box and N-Myc activity or expression, as identified by a screening assay can be administered to individuals to treat, prophylactically or therapeutically, disorders. In conjunction with such treatment, the pharmacogenomics (i.e., the study of the relationship between a subject's genotype and the subject's response to a foreign modality, such as a food, compound or drug) may be considered. Metabolic differences of therapeutics can lead to severe toxicity or therapeutic failure by altering the relation between dose and blood concentration of the pharmacologically active drug. Thus, the pharmacogenetics of the individual permits the selection of effective agents (e.g., drugs) for prophylactic or therapeutic treatments based on a consideration of the individual's genotype. Pharmacogenomics can further be used to determine appropriate dosages and therapeutic regimens. Accordingly, the activity of T-Box protein, expression of T-Box and N-Myc nucleic acid, or T-Box mutation(s) in an individual can be determined to guide the selection of appropriate agent(s) for therapeutic or prophylactic treatment.

Pharmacogenomics deals with clinically significant hereditary variations in the response to modalities due to altered modality disposition and abnormal action in affected persons. In general, two pharmacogenetic conditions can be differentiated: (1) genetic conditions transmitted as a single factor altering the interaction of a modality with the body (altered drug action) or (2) genetic conditions transmitted as single factors altering the way the body acts on a modality (altered drug metabolism). These pharmacogenetic conditions can occur either as rare defects or as nucleic acid polymorphisms. For example, glucose-6-phosphate dehydrogenase (G6PD) deficiency is a common inherited enzymopathy in which the main clinical complication is hemolysis after ingestion of oxidant drugs (antimalarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) explains the phenomena of some patients who show exaggerated drug response and/or serious toxicity after taking the standard and safe dose of a drug. These polymorphisms are expressed in two phenotypes in the population, the extensive metabolizer (EM) and poor metabolizer (PM). The prevalence of PM is different among different populations. For example, the CYP2D6 gene is highly polymorphic and several mutations have been identified in PM, which all lead to the absence of functional CYP2D6. Poor metabolizers due to mutant CYP2D6 and CYP2C19 frequently experience exaggerated drug responses and side effects when they receive standard doses. If a metabolite is the active therapeutic moiety, PM shows no therapeutic response, as demonstrated for the analgesic effect of codeine mediated by its CYP2D6-formed metabolite morphine. At the other extreme are the so-called ultra-rapid metabolizers who are unresponsive to standard doses. Recently, the molecular basis of ultra-rapid metabolism has been identified to be due to CYP2D6 gene amplification.

The activity of T-Box protein, expression of T-Box and N-Myc nucleic acid, or mutation content of T-Box in an individual can be determined to select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a T-Box and/or N-Myc modulator, such as a modulator identified by one of the described exemplary screening assays.

In another aspect of the present invention, a method for treating a cancer or a heart disease is provided comprising regulating the activity of T-Box and N-Myc. In various aspects, decreasing the activity can comprise regulating the expression of T-Box and N-Myc. In various aspects, decreasing the expression comprises transforming a cell to express a polynucleotide anti-sense to at least a portion of an endogenous polynucleotide encoding T-Box as described above. In various aspects, decreasing the activity comprises inhibiting, preventing, or reversing at least one activity of T-Box as described above. In various other aspects, decreasing the activity can comprise transforming a cell to express an aptamer to T-Box as described above. In various aspects, decreasing the activity can comprise introducing into a cell an aptamer to T-box as described above. In a further aspect, decreasing the activity can comprise administering to a cell an antibody that selectively binds T-Box as described above.

As a therapy, antisense nucleic acids, ribozymes, triplex-forming oligonucleotides, siRNAs, probes, primers, T-Box- or N-Myc-specific antibodies, and other compositions identified herein which modulate the expression of an T-Box or N-Myc can be used to stabilize normal T-Box or N-Myc expression. The present invention may also be used in a variety of assays and therapeutic techniques to detect heart disease at its earliest stages and treat it before significant damage is done to the heart tissue.

For example, in one non-limiting embodiment, the methods comprise the step of administering to the animal in need of treatment, a therapeutically effective amount of an T-Box inhibitor. The T-Box inhibitors of the present invention effectively inhibit the activity of the T-Box protein or inhibit the expression of the T-Box protein. In one embodiment, the activity or expression of T-Box in an animal is inhibited by about 10%. Preferably, the activity or expression of T-Box in an animal is inhibited by about 30%. More preferably, the activity or expression of T-Box in an animal is inhibited by 50% or more.

The reduction of the expression of T-Box or N-Myc may be measured in any body fluid, tissue or organ of the animal. Preferably, the cells contained within such fluids, tissues or organs being analyzed-contain a nucleic acid molecule encoding T-Box or N-Myc protein and/or the T-Box or N-Myc protein itself.

The antisense nucleic acids, ribozymes, triplex-forming oligonucleotides, siRNAs, probes, primers, T-Box or N-Myc-specific antibodies, and other compositions identified herein which modulate the expression of T-Box or N-Myc can be utilized in pharmaceutical preparations according to the Pharmaceutical Preparations and Methods of Administration section below.

Biological Methods

Methods involving conventional molecular biology techniques are generally known in the art and are described in detail in methodology treatises such as MOLECULAR CLONING: A LABORATORY MANUAL, 2nd ed., vol. 1-3, ed. Sambrook et al., Cold Spring Harbor Laboratory Press, Cold Spring Harbor, N.Y., 1989; and CURRENT PROTOCOLS IN MOLECULAR BIOLOGY, ed, Ausubel et al., Greene Publishing and Wiley-Interscience, New York, 1992 (with periodic updates). Various techniques using polymerase chain reaction (PCR) are described, e.g., in Innis et al., PCR PROTOCOLS: A GUIDE TO METHODS AND APPLICATIONS, Academic Press: San Diego, 1990. PCR-primer pairs can be derived from known sequences by known techniques such as using computer programs intended for that purpose. The Reverse Transcriptase Polymerase Chain Reaction (RT-PCR) method used to identify and amplify certain polynucleotide sequences within the invention may be performed as described in Elek et al., In vivo, 14:172-182, 2000). Methods and apparatus for chemical synthesis of nucleic acids are provided in several commercial embodiments, e.g., those provided by Applied Biosystems, Foster City, Calif., and Sigma-Genosys, The Woodlands, Tex. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., GENE THERAPY: PRINCIPLES AND APPLICATIONS, ed. T. Blackenstein, Springer Verlag, 1999; GENE THERAPY PROTOCOLS (METHODS IN MOLECULAR MEDICINE), ed. P. D. Robbins, Humana Press, 1997; and RETRO-VECTORS FOR HUMAN GENE THERAPY, ed. C. P. Hodgson, Springer Verlag, 1996.

Probes and Primers

The invention also provides oligonucleotide probes (i.e., isolated nucleic acid molecules conjugated with a detectable label or reporter molecule, e.g., a radioactive isotope, ligand, chemiluminescent agent, or enzyme); and oligonucleotide primers (i.e., isolated nucleic acid molecules that can be annealed to a complementary target DNA strand by nucleic acid hybridization to form a hybrid between the primer and the target DNA strand, then extended along the target DNA strand by a polymerase, e.g., a DNA polymerase). Primer pairs can be used for amplification of a nucleic acid sequence, e.g., by polymerase chain reaction (PCR) or other conventional nucleic-acid amplification methods. Probes and primers of the invention are generally 15, 16, 17, 18, and 19 nucleotides or more in length, preferably 20, 21, 22, 23, and 24 nucleotides or more, more preferably 25, 26, 27, 28, and 29 nucleotides, and most preferably 30, 31, 32, 33, 34, 35, 36, 37, 38, 39, and 40 nucleotides or more.

Preferred probes and primers are those that hybridize to a native T-Box or N-Myc gene (or cDNA or mRNA) sequence under high stringency conditions, and those that hybridize to T-Box or N-Myc gene homologs under at least moderately stringent conditions. Preferably, probes and primers according to the present invention have complete sequence identity with a native T-Box or N-Myc nucleic acid sequence. However, probes differing from this sequence that retain the ability to hybridize to a native T-Box or N-Myc gene sequence under stringent conditions may be designed by conventional methods and used in the invention. Primers and probes based on the T-Box or N-Myc gene sequences disclosed herein can be used to confirm (and, if necessary, to correct) the disclosed T-Box or N-Myc gene sequences by conventional methods, e.g., by re-cloning and sequencing a native T-Box or N-Myc gene or cDNA.

T-Box and N-Myc Proteins

In other aspects, the present invention utilizes a purified T-Box or N-Myc protein encoded by a nucleic acid of the invention. A preferred form of T-Box or N-Myc is a purified native T-Box or N-Myc protein that has the deduced amino acid sequence provided in Appendix A below. Variants of native T-Box or N-Myc proteins such as fragments, analogs and derivatives of native T-Box or N-Myc proteins are also within the invention. Such variants include, e.g., a polypeptide encoded by a naturally occurring allelic variant of a native T-Box or N-Myc gene, a polypeptide encoded by an alternative splice form of a native T-Box or N-Myc gene, a polypeptide encoded by a homolog of a native T-Box or N-Myc gene, and a polypeptide encoded by a non-naturally occurring variant of a native T-Box or N-Myc gene.

T-Box or N-Myc protein variants have a peptide sequence that differs from a native T-Box or N-Myc protein in one or more amino acids. The peptide sequence of such variants can feature a deletion, addition, or substitution of one or more amino acids of a native T-Box or N-Myc polypeptide. Amino acid insertions are preferably of about 1, 2, 3, and 4 to 5 contiguous amino acids, and deletions are preferably of about 1, 2, 3, 4, 5, 6, 7, 8, and 9 to 10 contiguous amino acids. In some applications, variant T-Box or N-Myc proteins substantially maintain a native T-Box or N-Myc protein functional activity. For other applications, variant T-Box or N-Myc proteins lack or feature a significant reduction in an T-Box or N-Myc protein functional activity. Where it is desired to retain a functional activity of native T-Box or N-Myc protein, preferred T-Box or N-Myc protein variants can be made by expressing nucleic acid molecules within the invention that feature silent or conservative changes. Variant T-Box or N-Myc proteins with substantial changes in functional activity can be made by expressing nucleic acid molecules within the invention that feature less than conservative changes.

T-Box or N-Myc protein fragments corresponding to one or more particular motifs and/or domains or to arbitrary sizes, for example, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 75, 100, 125, 150, 200, 250, 300 and 350 amino acids in length are intended to be within the scope of the present invention. Isolated peptidyl portions of T-Box or N-Myc proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an T-Box protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a native T-Box protein.

Another aspect of the present invention concerns recombinant forms of the T-Box or N-Myc proteins. Recombinant polypeptides preferred by the present invention, in addition to native T-Box or N-Myc protein, are encoded by a nucleic acid that has at least 85% sequence identity (e.g., 85%, 86%, 87%, 88%, 89%, 90%, 91%, 92%, 93%, 94%, 95%, 96%, 97%, 98%, and 99%) with the nucleic acid sequence provided in Appendix A. In a preferred embodiment, variant T-Box or N-Myc proteins have one or more functional activities of native T-Box or N-Myc protein.

T-Box or N-Myc protein variants can be generated through various techniques known in the art. For example, T-Box or N-Myc protein variants can be made by mutagenesis, such as by introducing discrete point mutation(s), or by truncation. Mutation can give rise to an T-Box or N-Myc protein variant having substantially the same, or merely a subset of the functional activity of a native T-Box or N-Myc protein. Alternatively, antagonistic forms of the protein can be generated which are able to inhibit the function of the naturally occurring form of the protein, such as by competitively binding to another molecule that interacts with T-Box or N-Myc protein. In addition, agonistic forms of the protein may be generated that constitutively express one or more T-Box or N-Myc functional activities. Other variants of T-Box or N-Myc proteins that can be generated include those that are resistant to proteolytic cleavage, as for example, due to mutations which alter protease target sequences. Whether a change in the amino acid sequence of a peptide results in an T-Box or N-Myc protein variant having one or more functional activities of a native T-Box or N-Myc protein can be readily determined by testing the variant for a native T-Box or N-Myc protein functional activity.

As another example, T-Box or N-Myc protein variants can be generated from a degenerate oligonucleotide sequence. Chemical synthesis of a degenerate gene sequence can be carried out in an automatic DNA synthesizer, and the synthetic genes then ligated into an appropriate expression vector. One purpose for a degenerate set of genes is to provide, in one mixture, all of the sequences encoding the desired set of potential T-Box or N-Myc protein sequences. The synthesis of degenerate oligonucleotides is well known in the art (see, e.g., Narang, S A (1983) Tetrahedron 39:3; Itakura et al. (1981) RECOMBINANT DNA, PROC 3RD CLEVELAND SYMPOS, MACROMOLECULES, ed. AG Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, e.g., Scott et al. (1990) Science 249:386-390; Roberts et al. (1992) Proc. Natl. Acad. Sci. USA 89:2429-2433; Devlin et al. (1990) Science 249:404-406; Cwirla et al. (1990) Proc. Natl. Acad. Sci. USA 87:6378-6382; as well as U.S. Pat. Nos. 5,223,409; 5,198,346; and 5,096,815).

Similarly, a library of coding sequence fragments can be provided for an T-Box or N-Myc gene clone in order to generate a variegated population of T-Box or N-Myc protein fragments for screening and subsequent selection of fragments having one or more native T-Box or N-Myc protein functional activities. A variety of techniques are known in the art for generating such libraries, including chemical synthesis. In one embodiment, a library of coding sequence fragments can be generated by (i) treating a double-stranded PCR fragment of an T-Box or N-Myc gene coding sequence with a nuclease under conditions wherein nicking occurs only about once per molecule; (ii) denaturing the double-stranded DNA; (iii) denaturing the DNA to form double-stranded DNA which can include sense/antisense pairs from different nicked products; (iv) removing single-stranded portions from reformed duplexes by treatment with SI nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of T-Box or N-Myc gene variants. The most widely used techniques for screening large gene libraries typically involve cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Combinatorial mutagenesis has a potential to generate very large libraries of mutant proteins. To screen a large number of protein mutants, techniques that allow one to avoid the very high proportion of non-functional proteins in a random library and simply enhance the frequency of functional proteins (thus decreasing the complexity required to achieve a useful sampling of sequence space) can be used. For example, recursive ensemble mutagenesis (REM), an algorithm that enhances the frequency of functional mutants in a library when an appropriate selection or screening method is employed, might be used. Arkin and Yourvan (1992) Proc. Natl. Acad. Sci. USA 89:7811-7815; Yourvan et al. (1992)

Parallel Problem Solving from Nature, Maenner and Manderick, eds., Elsevier Publishing Co., Amsterdam, pp. 401-410; Delgrave et al. (1993) Protein Engineering 6(3): 327-331.

The invention also provides for reduction of T-Box or N-Myc proteins to generate mimetics, e.g., peptide or non-peptide agents, that are able to disrupt binding of an T-Box or N-Myc protein to other proteins or molecules with which the native T-Box or N-Myc protein interacts. Thus, the techniques described herein can also be used to map which determinants of T-Box or N-Myc protein participate in the intermolecular interactions involved in, e.g., binding of an T-Box or N-Myc protein to other proteins which may fendion upstream (e.g., activators or repressors of T-Box or N-Myc functional activity) of the T-Box or N-Myc protein or to proteins or nucleic acids which may function downstream of the T-Box or N-Myc protein, and whether such molecules are positively or negatively regulated by the T-Box or N-Myc protein. To illustrate, the critical residues of an T-Box or N-Myc protein, similar to the RGD motif described above, which are involved in molecular recognition of, e.g., the T-Box or N-Myc protein or other components upstream or downstream of the T-Box or N-Myc protein can be determined and used to generate T-Box or N-Myc protein-derived peptidomimetics which competitively inhibit binding of the T-Box or N-Myc protein to that moiety. By employing scanning mutagenesis to map the amino acid residues of an T-Box or N-Myc protein that are involved in binding other extracellular proteins, peptidomimetic compounds can be generated which mimic those residues of a native T-Box or N-Myc protein. Such mimetics may then be used to interfere with the normal function of an T-Box or N-Myc protein.

For example, non-hydrolyzable peptide analogs of such residues can be generated using benzodiazepine (see, e.g., Freidinger et al., in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Polisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J. Med. Chem. 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J. Chem. Soc. Perkin. Trans. 1: 1231), and beta-aminoalcohols (Gordon et al. (1985) Biochem. Biophys. Res. Commun. 126:419; and Dann et al. (1986) Biochem. Biophys. Res. Commun. 134: 71). T-Box or N-Myc proteins may also be chemically modified to create T-Box or N-Myc protein derivatives by forming covalent or aggregate conjugates with other chemical moieties, such as glycosyl groups, lipids, phosphate, acetyl groups and the like. Covalent derivatives of T-Box or N-Myc protein can be prepared by linking the chemical moieties to functional groups on amino acid side chains of the protein or at the N-terminus or at the C-terminus of the polypeptide.

The present invention further pertains to methods of producing the subject T-Box or N-Myc proteins. For example, a host cell transfected with a nucleic acid vector directing expression of a nucleotide sequence encoding the subject polypeptides can be cultured under appropriate conditions to allow expression of the peptide to occur. The cells may be harvested, lysed, and the protein isolated. A recombinant T-Box or N-Myc protein can be isolated from host cells using techniques known in the art for purifying proteins including ion-exchange chromatography, gel filtration chromatography, ultrafiltration, electrophoresis, and immunoaffinity purification with antibodies specific for such protein.

For example, after an T-Box or N-Myc protein has been expressed in a cell, it can be isolated using any immunoaffinity chromatography. More specifically, an anti-T-Box or N-Myc antibody (e.g., produced as described below) can be immobilized on a column chromatography matrix, and the matrix can be used for immuno-affinity chromatography to purify the T-Box or N-Myc protein from cell lysates by standard methods (see, e.g., Ausubel et al., supra). After immunoaffinity chromatography, the T-Box or N-Myc protein can be further purified by other standard techniques, e.g., high performance liquid chromatography (see, e.g., Fisher, Laboratory Techniques In Biochemistry And Molecular Biology, Work and Burdon, eds., Elsevier, 1980). In another embodiment, an T-Box or N-Myc protein is expressed as a fusion protein containing an affinity tag (e.g., GST) that facilitates its purification.

T-Box- or N-Myc-Specific Antibodies

T-Box or N-Myc proteins, fragments, and variants thereof, can be used to raise antibodies useful in the invention. Such proteins can be produced by recombinant techniques or synthesized as described above. In general, T-Box or N-Myc proteins can be coupled to a carrier protein, such as keyhole limpet hemocyanin (KLH) or transferrin, as described in Ausubel et al., supra, mixed with an adjuvant, and injected into a host mammal. Antibodies produced in that animal can then be purified by peptide antigen affinity chromatography. In particular, various host animals can be immunized by injection with an T-Box or N-Myc protein or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin; transferrin, and dinitrophenol.

Polyclonal antibodies are heterogeneous populations of antibody molecules that are contained in the sera of the immunized animals. Antibodies intended to be within the scope of the present invention, therefore, include polyclonal antibodies and monoclonal antibodies, single chain antibodies, Fab fragments, F(ab')$_2$ fragments, and molecules produced using a Fab expression library. Monoclonal antibodies, which are homogeneous populations of antibodies to a particular antigen, can be prepared using the T-Box or N-Myc proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra). In particular, monoclonal antibodies can be obtained by any technique that provides for the production of antibody molecules by continuous cell lines in culture such as described in Kohler et al., Nature 256:495, 1975, and U.S. Pat. No. 4,376, 110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy" Alan R. Liss, Inc., pp. 77-96, 1983). Such antibodies can be of any immunoglobulin class including IgG, IgM, IgE, IgA, IgD and any subclass thereof. A hybridoma producing a mAb of the invention may be cultivated in vitro or in vivo. The ability to produce high titers of mAbs in vivo makes this a particularly useful method of production.

Once produced, polyclonal or monoclonal antibodies can be tested for specific T-Box or N-Myc recognition by Western blot or immunoprecipitation analysis by standard methods, e.g., as described in Ausubel et al., supra. Antibodies that specifically recognize and bind to T-Box or N-Myc protein are useful in the invention. For example, such antibodies can be used in an immunoassay to monitor the level of an T-Box or N-Myc protein produced by a mammal (e.g., to determine the amount or subcellular location of an T-Box or N-Myc protein).

Preferably, T-Box or N-Myc protein selective antibodies of the invention are produced using fragments of the T-Box or N-Myc protein that lie outside highly conserved regions and appear likely to be antigenic, by criteria such as high frequency of charged residues. Cross-reactive anti-T-Box or anti-N-Myc protein antibodies are produced using a fragment of T-Box or N-Myc protein that is conserved amongst members of this family of proteins. In one specific example, such fragments are generated by standard techniques of PCR, and are then cloned into the pGEX expression vector (Ausubel et al., supra). Fusion proteins are expressed in E. Coli and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two host animals. Antisera can be raised by injections in a series, preferably including at least three booster injections. Antiserum is also checked for its ability to immunoprecipitate recombinant T-Box or N-Myc proteins or control proteins, such as glucocorticoid receptor, CAT, or luciferase.

The antibodies of the invention can be used, e.g., in the detection of an T-Box or N-Myc protein in a biological sample. Antibodies also can be used in a screening assay to measure the effect of a candidate compound on expression or localization of an T-Box or N-Myc protein. Other assays using T-Box- or N-Myc-specific antibodies are provided herein. Additionally, such antibodies can be used to interfere with the interaction of an T-Box or N-Myc protein and other molecules that bind the T-Box or N-Myc protein.

Techniques described for producing single chain antibodies (e.g., U.S. Pat. Nos. 4,946,778, 4,946,778, and 4,704,692) can be adapted to make single chain antibodies against an T-Box or N-Myc protein, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed (Huse et al., Science 246:1275, 1989) to allow rapid and easy identification of monoclonal Fab fragments with the desired specificity.

In addition to known antibodies to T-Box or N-Myc proteins, human or humanoid antibodies that specifically bind an T-Box or N-Myc protein can also be produced using known methods. For example, polyclonal antibodies can also be collected from human subjects having such antibodies in their sera, e.g., subjects administered antigens that stimulate antibody production against an T-Box or N-Myc protein. As another example, human antibodies against an T-Box or N-Myc protein can be made by adapting known techniques for producing human antibodies in animals such as mice. See, e.g., Fishwild, D. M, et al., Nature Biotechnology 14 (1996): 845-851; Heijnen, I. et al., Journal of Clinical Investigation 97 (1996): 331-338; Lonberg, N. et al., Nature 368 (1994): 856-859; Morrison, S. L., Nature 368 (1994): 812-813; Neuberger, M., Nature Biotechnology 14 (1996): 826; and U.S. Pat. Nos. 5,545,806; 5,569,825; 5,877,397; 5,939,598; 6,075,181; 6,091,001; 6,114,598; and 6,130,314. Humanoid antibodies against an T-Box or N-Myc can be made from non-human antibodies by adapting known methods such as those described in U.S. Pat. Nos. 5,530,101; 5,585,089; 5,693,761; and 5,693,762.

Proteins that Associate with T-Box or N-Myc Proteins

The invention also features methods for identifying polypeptides that can associate with an T-Box or N-Myc protein. Any method that is suitable for detecting protein-protein interactions can be employed to detect polypeptides that associate with an T-Box or N-Myc protein. Examples of such methods include co-immunoprecipitation, crosslinking, and co-purification through gradients or chromatographic columns of cell lysates or proteins obtained from cell lysates and the use of an T-Box or N-Myc protein to identify proteins in the lysate that interact with the T-Box or N-Myc protein. For these assays, the T-Box or N-Myc protein can be a full length T-Box or N-Myc protein, a particular domain of T-Box or N-Myc protein, or some other suitable fragment of T-Box or N-Myc protein. Once isolated, such an interacting protein can be identified and cloned and then used, in conjunction with standard techniques, to alter the activity of the protein with which it interacts. For example, at least a portion of the amino acid sequence of a protein that interacts with T-Box or N-Myc protein can be ascertained using techniques well known to those of skill in the art, such as via the Edman degradation technique. The amino acid sequence obtained can be used as a guide for the generation of oligonucleotide mixtures that can be used to screen for gene sequences encoding the interacting protein. Screening can be accomplished, for example, by standard hybridization or PCR techniques. Techniques for the generation of oligonucleotide mixtures and the screening are well-known (Ausubel et al., supra; and PCR Protocols: A Guide to Methods and Applications, Innis et al., eds. Academic Press, Inc., NY, 1990).

Additionally, methods can be employed that result directly in the identification of genes that encode proteins that interact with an T-Box or N-Myc protein. These methods include, e.g., screening expression libraries, in a manner similar to the well known technique of antibody probing of lgt11 libraries, using labeled T-Box or N-Myc protein or an T-Box or N-Myc fusion protein, e.g., an T-Box or N-Myc protein or domain fused to a marker such as an enzyme, fluorescent dye, a luminescent protein, or to an IgFc domain.

There are also methods available that can detect protein-protein interaction in vivo. For example, as described herein the two-hybrid system can be used to detect such interactions in vivo. See, e.g., Chien et al., Proc. Natl. Acad. Sci. USA 88:9578, 1991. Briefly, as one example of utilizing such a system, plasmids are constructed that encode two hybrid proteins: one plasmid includes a nucleotide sequence encoding the DNA-binding domain of a transcription activator protein fused to a nucleotide sequence encoding an T-Box or N-Myc protein, an T-Box or N-Myc protein variant or fragment, or an T-Box or N-Myc fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, an T-Box or N-Myc protein may be used as the bait. Total genomic or cDNA sequences are fused to the DNA encoding an activation domain. This library and a plasmid encoding a hybrid of bait T-Box or N-Myc protein fused to the DNA-binding domain are co-transformed into a yeast reporter strain, and the resulting transformants are screened for those that express the reporter gene. For example, a bait T-Box or N-Myc gene sequence, such as that encoding an T-Box or N-Myc protein or domain of an T-Box or N-Myc protein can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait T-Box or N-Myc protein are to be detected can be made using methods routinely practiced in the art. According to the particular system described herein, e.g., the cDNA fragments can be inserted into a vector such that they are translationally fused to the transcriptional activation domain of GAL4. This library can be co-transformed along with the T-Box, -GAL4 encoding fusion plasmid into a yeast strain which contains a lacZ gene driven by a promoter which contains GAL4 activation sequence. A cDNA encoded protein, fused to GAL4 transcriptional activation domain, that interacts with bait T-Box or N-Myc protein will reconstitute an active GAL4 protein and thereby drive expression of the HIS3 gene. Colonies that express HIS3 can then be purified from these strains and used to produce and isolate bait T-Box or N-Myc protein-interacting proteins using techniques routinely practiced in the art.

Detection of T-Box or N-Myc Polynucleotides and Proteins

The invention encompasses methods for detecting the presence of an T-Box or N-Myc protein or an T-Box or N-Myc nucleic acid in a biological sample as well as methods for measuring the level of an T-Box or N-Myc protein or an T-Box or N-Myc nucleic acid in a biological sample. Such methods are useful for diagnosing heart disease associated with T-Box or N-Myc expression.

An exemplary method for detecting the presence or absence of an T-Box or N-Myc protein or T-Box or N-Myc nucleic acid in a biological sample involves obtaining a biological sample from a test subject (e.g., a human patient), contacting the biological sample with a compound or an agent capable of detecting an T-Box or N-Myc protein or a nucleic acid encoding an T-Box or N-Myc protein (e.g., mRNA or genomic DNA), and analyzing binding of the compound or agent to the sample after washing. Those samples having specifically bound compound or agent express an T-Box or N-Myc protein or a nucleic acid encoding an T-Box or N-Myc protein.

A preferred agent for detecting a nucleic acid encoding an T-Box or N-Myc protein is a labeled nucleic acid probe capable of hybridizing to the nucleic acid encoding the T-Box or N-Myc protein. The nucleic acid probe can be, e.g., all or a portion of an T-Box or N-Myc gene itself or all or a portion of a complement of an T-Box or N-Myc gene. Similarly, the probe can also be all or a portion of an T-Box or N-Myc gene variant, or all or a portion of a complement of an T-Box or N-Myc gene variant. For example, oligonucleotides at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 75, 100, 125, 150, 200, 250, or 500 nucleotides in length that specifically hybridize under stringent conditions to a native T-Box or N-Myc nucleic acid or a complement of a native T-Box or N-Myc nucleic can be used as probes within the invention. A preferred agent for detecting an T-Box or N-Myc protein is an antibody capable of binding to an T-Box or N-Myc protein, preferably an antibody with a detectable label. Such antibodies can be polyclonal or, more preferably, monoclonal. An intact antibody, or a fragment thereof (e.g., Fab or F(ab')$_2$), can also be used.

Detection methods of the invention can be used to detect an mRNA encoding an T-Box or N-Myc protein, a genomic DNA encoding an T-Box or N-Myc protein, or an T-Box or N-Myc protein in a biological sample in vitro as well as in vivo. For example, in vitro techniques for detection of mRNAs encoding an T-Box or N-Myc protein include PCR amplification methods, Northern hybridizations, and in situ hybridizations. In vitro techniques for detection of an T-Box or N-Myc protein include enzyme linked immunosorbent assays (ELISAs), Western blots, immunoprecipitations and immunofluorescence. Such assays are more specifically described below. In vitro techniques for detection of genomic DNA encoding T-Box or N-Myc nucleic acid include Southern hybridizations. Moreover, in vivo techniques for detection of an T-Box or N-Myc protein include introducing a labelled anti-T-Box or anti-N-Myc antibody into a biological sample or test subject. For example, the antibody can be labeled with a radioactive marker whose presence and location in a biological sample or test subject can be detected by standard imaging techniques.

Use of T-Box- or N-Myc-Specific Antibodies

Antibodies of this invention can be used as inhibitors of T-Box or N-Myc function and expression. Standard methods using antibodies can be used to detect and quantitate T-Box or N-Myc expression, including but not limited to: radioimmunoassays ("RIA"), receptor assays, enzyme immunoassays ("EIA"), cytochemical bioassays, ligand assays, immunoradiometric assays, fluoroimmunoassays, and enzyme-linked immunosorbent assays ("ELISA"). These methods are well known and will be understood by those skilled in the art to require a reasonable amount of experimentation to optimize the interaction between antibodies and antigens and the detection of the antigens by the antibodies. These and other immunoassay techniques may be found in PRINCIPLES AND PRACTICE OF IMMUNOASSAY, 2nd Ed., Price and Newman, eds., MacMillan (1997) and ANTIBODIES, A LABORATORY MANUAL, Harlow and Lane, eds., Cold Spring Harbor Laboratory, Ch. 9 (1988), each of which is incorporated herein by reference in its entirety.

The use of antibodies described herein can be used to screen samples of heart tissue for the presence of a specific T-Box or N-Myc proteins. Obtaining samples of heart tissues from human patients is a well known technique that can be practiced by anyone skilled in the art. The antibodies used in such methods are preferably monoclonal antibodies.

Particularly preferred, for ease of detection and because of its quantitative nature, is the sandwich or double antibody assay of which a number of variations exist, all of which are intended to be encompassed by the present invention. For example, in a typical forward sandwich assay, unlabeled antibody is immobilized on a solid substrate, e.g., microtiter plate wells, and the sample to be tested is brought into contact with the bound molecule. After incubation for a period of time sufficient to allow formation of an antibody-antigen binary complex, a second antibody labeled with a reporter molecule capable of inducing a detectable signal is then added. Incubation is continued allowing sufficient time for binding with the antigen at a different site and the formation of a ternary complex of antibody-antigen-labeled antibody. Any unreacted material is washed away, and the presence of the antigen is determined by observation of a signal which may be quantitated by comparison with a control sample containing known amounts of antigen. Variations on the forward sandwich assay include the simultaneous assay in which both sample and antibody are added simultaneously to the bound antibody, or a reverse sandwich assay in which the labeled antibody and sample to be tested are first combined, incubated and added to the unlabeled surface bound antibody. These techniques are well known to those skilled in the art, and the possibility of minor variations will be readily apparent. As used herein, the term "sandwich assay" is intended to encompass all variations on the basic two-site technique.

A number of possible combinations are possible in the identity and the way that antibodies are used for sandwich assays. As a more specific example, in a typical forward sandwich assay, a primary antibody is either covalently or non-covalently bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art.

Following binding, the solid phase-antibody complex is washed in preparation for the test sample. An aliquot of the heart tissue to be tested is then added to the solid phase complex and incubated at 25° C. for a period of time sufficient to allow binding of any T-Box or N-Myc present to the antibody specific for a particular subunit or combination of subunits. The second antibody is then added to the solid phase complex and incubated at 25° C. for an additional period of time sufficient to allow the second antibody to bind to the primary antibody-antigen solid phase complex. The second antibody is linked to a reporter molecule, the visible signal of which is used to indicate the binding of the second antibody to any antigen in the sample. The term "reporter molecule" as used in the present invention is meant a molecule which by its chemical nature provides an analytically detectable signal which allows the detection of antigen-bound antibody. Detection must be at least relatively quantifiable to allow determination of the amount of antigen in the sample. The signal may be calculated in absolute terms or may be calculated in comparison with a standard (or series of standards) containing a known normal level of antigen.

The most commonly used reporter molecules of this type of assay are either enzymes or fluorophores. In the case of an EIA, an enzyme is conjugated to the second antibody, often by means of glutaraldehyde or periodate. As will be apparent to those skilled in the art, a wide variety of different conjugation techniques exist. Commonly used enzymes include horseradish peroxidase, glucose oxidase, β-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates which yield a fluorescent product rather than the chromogenic substrates noted above. In all cases, the enzyme-labeled antibody is added to the first antibody-synthesis marker or antibody-degradation marker complex and allowed to bind to the complex, then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantitated, usually spectrophotometrically, to give an evaluation of the amount of antigen which is present in the biological fluid, tissue or organ sample.

Alternatively, fluorescent compounds such as fluorescein or rhodamine may be chemically coupled to antibodies without altering their binding capacity. When activated by illumination with light of a particular wavelength, the fluorochrome-labeled antibody absorbs the light energy inducing a state of excitability in the molecule followed by emission of the light at a longer wavelength. The emission appears as a characteristic color visually detectable with a light microscope. As in the EIA, the fluorescent-labeled antibody is allowed to bind to the first antibody-synthesis marker or antibody-degradation marker complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to those skilled in the art how to vary the procedure to suit the required use.

In yet another alternative embodiment, the sample to be tested which contains the T-Box or N-Myc may be used in a single site immunoassay wherein it is adhered to a solid substrate either covalently or noncovalently. An unlabeled anti-T-Box or anti-N-Myc antibody is brought into contact with the sample bound on the solid substrate. After a suitable period of incubation sufficient to allow formation of an antibody-antigen binary complex, a second antibody, labeled with a reporter molecule capable of inducing a detectable signal is added and incubation is continued allowing sufficient time for the formation of a ternary complex of antigen-antibody-labeled antibody. For the single site immunoassay, the second antibody may be a general antibody, i.e., zenogeneic antibody to immunoglobulin, particularly anti-(IgM and IgG) linked to a reporter molecule, capable of binding an antibody that is specific for the T-Box or N-Myc.

Antibodies against T-Box or N-Myc can also be used to detect T-Box or N-Myc in histological and cytological specimens, and in particular, to determine the progression of heart diseases (such as heart disease) based on staining patterns and intensities. For example, staining patterns can be observed by using an immunostaining technique and monoclonal antibodies against an T-Box or N-Myc protein. Using this method, abnormal myocytes can generally be seen to exhibit an increased degree of staining when compared to normal cells. Non-specific staining will preferably be absent.

Immunofluorescent histological techniques can also be used to examine human specimens with monoclonal antibodies. In a typical protocol, slides containing cryostat sections of frozen, unfixed tissue biopsy samples or cytological smears are air dried, formalin-fixed and incubated with the monoclonal antibody preparation in a humidified chamber at room temperature. The slides are then layered with a preparation of antibody directed against the monoclonal antibody, usually an anti-mouse immunoglobulin if the monoclonal antibodies used are derived from the fusion of a mouse spleen lymphocyte and a mouse myeloma cell line. This antimouse immunoglobulin is tagged with a compound that fluoresces at a particular wavelength, e.g., rhodamine or fluorescein isothiocyanate. The staining pattern and intensities within the sample are then determined by fluorescent light microscopy and optionally photographically recorded.

Monoclonal antibodies which can be used in the invention can be produced by a hybridoma using methods well known in the art. Various additional procedures known in the art may be used for the production of antibodies to epitopes of particular T-Box or N-Myc protein, both preferably including the T-Box or N-Myc protein. Such antibodies include but are not limited to polyclonal, monoclonal, chimeric, single chain, Fab fragments and a Fab expression library. The production of antibodies may be accomplishes as described above.

Solid Phase Assays

The solid phase used in the assays of this invention may be any surface commonly used in immunoassays. For example, the solid phase may be particulate; it may be the surface of beads, e.g., glass or polystyrene beads, or it may be the solid wall surface of any of a variety of containers, e.g., centrifuge tubes, columns, microtiter plate wells, filters, membranes and tubing, among other containers.

When particles are used as the solid phase, they will preferably be of a size in the range of from about 0.4 to 200 microns, preferably from about 0.8 to 4.0 microns. Magnetic or magnetizable particles, such as paramagnetic particles (PMP), are a preferred particulate solid phase, and microtiter plate wells are a preferred solid wall surface. Magnetic or magnetizable particles may be particularly preferred when the steps of the methods of this invention are performed in an automated immunoassay system.

Preferred detection/quantitation systems of this invention may be luminescent, and a luminescent detection/quantitation system in conjunction with a signal amplification system could be used, if necessary. Exemplary luminescent labels, preferably chemiluminescent labels, are detailed below, as are signal amplification systems.

The invention also includes solid supports which may be attached to the surface of a surgical device or other instrument which directly contacts heart tissue to be studied while the instrument is within a patient. The tissue in direct contact with the instrument may be in areas of the heart in which T-Box or N-Myc are expressed in the most abundance.

Signal Detection/Quantitation Systems

The complexes formed by the assays of this invention can be detected, or detected and quantitated by any known detection/quantitation systems used in immunoassays. As appropriate, the antibodies of this invention used as tracers may be labeled in any manner directly or indirectly, that results in a signal that is visible or can be rendered visible, Detectable marker substances include radionuclides, such as $^3H$, $^{125}I$, and $^{131}I$; fluorescers, such as, fluorescein isothiocyanate and other fluorochromes, phycobiliproteins, phycoerythrin, rare earth chelates, Texas red, dansyl and rhodamine; colorimetric reagents (chromogens); electron-opaque materials, such as colloidal gold; bioluminescers; chemiluminescers; dyes; enzymes, such as, horseradish peroxidase, alkaline phosphatase, glucose oxidase, glucose-6-phosphate dehydrogenase, acetylcholinesterase, $\alpha$-, $\beta$-galactosidase, among others; coenzymes; enzyme substrates; enzyme cofactors; enzyme inhibitors; enzyme subunits; metal ions; free radicals; or any other immunologically active or inert substance which provides a means of detecting or measuring the presence or amount of immunocomplex formed. Exemplary of enzyme substrate combinations are horseradish peroxidase and tetramethyl benzidine (TMB), and alkaline phosphatase and paranitrophenyl phosphate (pNPP).

Preferred detection, or detection and quantitation systems according to this invention produce luminescent signals, bioluminescent (BL) or chemiluminescent (CL). In CL or BL assays, the intensity or the total light emission is measured and related to the concentration of the analyte. Light can be measured quantitatively using a luminometer (photomultiplier tube as the detector) or charge-coupled device, or qualitatively by means of photographic or X-ray film. The main advantages of using such assays is their simplicity and analytical sensitivity, enabling the detection and/or quantitation of very small amounts of analyte.

Exemplary luminescent labels are acridinium esters, acridinium sulfonyl carboxamides, luminol, umbelliferone, isoluminol derivatives, photoproteins, such as aequorin, and luciferases from fireflies, marine bacteria, Vargulla and *Renilla*. Luminol can be used optionally with an enhancer molecule, preferably selected from the group consisting of 4-iodophenol or 4-hydroxycinnamic acid. Acridinium esters are one of the preferred types of CL labels according to this invention. A signal is generated by treatment with an oxidant under basic conditions.

Also preferred luminescent detection systems are those wherein the signal is produced by an enzymatic reaction upon a substrate. CL and BL detection schemes have been developed for assaying alkaline phosphatase (AP), glucose oxidase, glucose 6-phosphate dehydrogenase, horseradish peroxidase (HRP), and xanthine-oxidase labels, among others. AP and HRP are two preferred enzyme labels which can be quantitated by a range of CL and BL reactions. For example, AP can be used with a substrate, such as an adamantyl 1,2-dioxetane aryl phosphate substrate (e.g., AMPPD or CSPD; (Kricka, L. J., "Chemiluminescence and Bioluminescence, Analysis by," at p. 167, Molecular Biology and Biotechnology: A Comprehensive Desk Reference, ed. R. A. Meyers, VCH Publishers; N.Y., N.Y.; 1995)); preferably a disodium salt of 4-methoxy-4-(3-phosphatephenyl)spiro[1,2-dioxetane-3,2-adamantane], with or without an enhancer molecule, preferably, 1-(trioctylphosphonium methyl)-4-(tributylphosphonium methyl) benzene dichloride. HRP is preferably used with substrates, such as, 2',3',6'-trifluorophenyl 3-methoxy-10-methylacridan-9-carboxylate.

CL and BL reactions can also be adapted for analysis of not only enzymes, but other substrates, cofactors, inhibitors, metal ions and the like. For example, luminol, firefly luciferase, and marine bacterial luciferase reactions are indicator reactions for the production or consumption of peroxide, ATP, and NADPH, respectively. They can be coupled to other reactions involving oxidases, kinases, and dehydrogenases, and can be used to measure any component of the coupled reaction (enzyme, substrate, cofactor).

The detectable marker may be directly or indirectly linked to an antibody used in an assay of this invention. Exemplary of an indirect linkage of the detectable label is the use of a binding pair between the antibody and the marker, or the use of well known signal amplification signals, such as, using a biotinylated antibody complexed to UGP and then adding streptavidin conjugated to HRP and then TMB.

Exemplary of binding pairs that can be used to link antibodies of assays of this invention to detectable markers are biotin/avidin, streptavidin, or anti-biotin; avidin/anti-avidin; thyroxine/thyroxine-binding globulin; antigen/antibody; antibody/anti-antibody; carbohydrate/lectins; hapten/anti-hapten antibody; dyes and hydrophobic molecules/hydrophobic protein binding sites; enzyme inhibitor, coenzyme or cofactor/enzyme; polynucleic acid/homologous polynucleic acid sequence; fluorescein/anti-fluorescein; dinitrophenol/anti-dinitrophenol; vitamin B12/intrinsic factor; cortisone, cortisol/cortisol binding protein; and ligands for specific receptor protein/membrane associated specific receptor proteins. Preferred binding pairs according to this invention are biotin/avidin or streptavidin, more preferably biotin/streptavidin.

Various means for linking labels directly or indirectly to antibodies are known in the art. For example, labels may be bound either covalently or non-covalently. Exemplary antibody conjugation methods are described in: Avarmeas, et al., Scan. J. Immunol., 8 (Suppl. 7):7 (1978); Bayer, et al., Meth. Enzymol., 62:308 (1979); Chandler, et al., J. Immunol. Meth., 53:187 (1982); Ekeke and Abuknesha, J. Steroid Biochem., 11:1579 (1979); Engvall and Perlmann, J. Immunol., 109:129 (1972); Geoghegan, et al. Immunol. Comm., 7.1 (1978); and Wilson and Nakane, Immunofluorescence and Related Techniques, p. 215 (Elsevier/North Holland Biomedical Press; Amsterdam (1978)).

Depending upon the nature of the label, various techniques can be employed for detecting, or detecting and quantitating the label. For fluorescers, a large number of fluorometers are available. For chemiluminescers, luminometers or films are available. With enzymes, a fluorescent, chemiluminescent, or colored product can be determined or measured fluorometrically, luminometrically, spectrophotometrically or visually.

Automated Immunoassay System

The methods of this invention can be readily adapted to automated immunochemistry analyzers. To facilitate automation of the methods of this invention and to reduce the turn-around time, anti-UGP antibodies may be coupled to magnetizable particles.

Preferred automated/immunoassay systems include the DPC Immulite® system (Los Angeles, Calif. (USA)), Advia, IMS (Bayer Corp., Pittsburgh, Pa. (USA)), Bayer ACS:180™ Automated Chemiluminescence System (CCD; Medfield, Mass. (USA), Beckman Access (South San Francisco, Calif. (USA), Abbott AxSYM (Chicago, Ill. (USA)), and the like. The systems use chemiluminescent labels as tracers and paramagnetic particles as solid-phase reagents. The ACS:180 system accommodates both competitive binding and sandwich-type assays, wherein each of the steps are automated. The ACS:180 uses micron-sized paramagnetic particles that maximize the available surface area, and provide a means of rapid magnetic separation of bound tracer from unbound tracer without centrifugation. Reagents can be added simultaneously or sequentially. Other tags, such as an enzymatic tag, can be used in place of a chemiluminescent label, such as, acridinium ester.

Nucleic Acids Encoding T-Box or N-Myc Proteins

Preferred nucleic acid molecules for use in the invention are the native T-Box or N-Myc polynucleotides shown, as a non-limiting example in Appendix A. Another nucleic acid that can be used in various aspects of the invention includes a purified nucleic acid or polynucleotide that encodes a polypeptide.

Nucleic acid molecules utilized in the present invention may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence which encodes a native T-Box or N-Myc protein may be identical to the nucleotide sequence of those in Appendix A, or it may also be a different coding sequence which, as a result of the redundancy or degeneracy of the genetic code, encodes the same polypeptide as the polynucleotides of those in Appendix A. Examples of nucleotide codons which provide the same expressed amino acid are summarized in Table 1:

TABLE 1

| Codon | Full Name | Abbreviation (3 Letter) | Abbreviation (1 Letter) |
|---|---|---|---|
| TTT | Phenylalanine | Phe | F |
| TTC | Phenylalanine | Phe | F |
| TTA | Leucine | Leu | L |
| TTG | Leucine | Leu | L |
| TCT | Serine | Ser | S |
| TCC | Serine | Ser | S |
| TCA | Serine | Ser | S |
| TCG | Serine | Ser | S |
| TAT | Tyrosine | Tyr | Y |
| TAC | Tyrosine | Tyr | Y |
| TAA | Termination | Ter | X |
| TAG | Termination | Ter | X |
| TGT | Cysteine | Cys | C |
| TGC | Cysteine | Cys | C |
| TGA | Termination | Ter | X |
| TGG | Tryptophan | Trp | W |
| CTT | Leucine | Leu | L |
| CTC | Leucine | Leu | L |
| CTA | Leucine | Leu | L |
| CTG | Leucine | Leu | L |
| CCT | Proline | Pro | P |
| CCC | Proline | Pro | P |
| CCA | Proline | Pro | P |
| CCG | Proline | Pro | P |
| CAT | Histidine | His | H |
| CAC | Histidine | His | H |
| CAA | Glutamine | Gln | Q |
| CAG | Glutamine | Gln | Q |

TABLE 1-continued

| Codon | Full Name | Abbreviation (3 Letter) | Abbreviation (1 Letter) |
|---|---|---|---|
| CGT | Arginine | Arg | R |
| CGC | Arginine | Arg | R |
| CGA | Arginine | Arg | R |
| CGG | Arginine | Arg | R |
| ATT | Isoleucine | Ile | I |
| ATC | Isoleucine | Ile | I |
| ATA | Isoleucine | Ile | I |
| ATG | Methionine | Met | M |
| ACT | Threonine | Thr | T |
| ACC | Threonine | Thr | T |
| ACA | Threonine | Thr | T |
| ACG | Threonine | Thr | T |
| AAT | Asparagine | Asn | N |
| AAC | Asparagine | Asn | N |
| AAA | Lysine | Lys | K |
| AAG | Lysine | Lys | K |
| AGT | Serine | Ser | S |
| AGC | Serine | Ser | S |
| AGA | Arginine | Arg | R |
| AGG | Arginine | Arg | R |
| GTT | Valine | Val | V |
| GTC | Valine | Val | V |
| GTA | Valine | Val | V |
| GTG | Valine | Val | V |
| GCT | Alanine | Ala | A |
| GCC | Alanine | Ala | A |
| GCA | Alanine | Ala | A |
| GCG | Alanine | Ala | A |
| GAT | Aspartate | Asp | D |
| GAC | Aspartate | Asp | D |
| GAA | Glutamate | Glu | E |
| GAG | Glutamate | Glu | E |
| GGT | Glycine | Gly | G |
| GGC | Glycine | Gly | G |
| GGA | Glycine | Gly | G |
| GGG | Glycine | Gly | G |

Other nucleic acid molecules intended to be within the scope of the present invention include variants of the native T-Box or N-Myc gene such as those that encode fragments, analogs and derivatives of a native T-Box or N-Myc protein. Such variants may be, e.g., a naturally occurring allelic variant of the native T-Box or N-Myc gene, a homolog of the native T-Box or N-Myc gene, or a non-naturally occurring variant of the native T-Box or N-Myc gene. These variants have a nucleotide sequence that differs from the native T-Box or N-Myc gene in one or more bases. For example, the nucleotide sequence of such variants can feature a deletion, addition, or substitution of one or more nucleotides of the native T-Box or N-Myc gene. Nucleic acid insertions are preferably of about 1 to 10 contiguous nucleotides, and deletions are preferably of about 1 to 30 contiguous nucleotides.

In other applications, variant T-Box or N-Myc proteins displaying substantial changes in structure can be generated by making nucleotide substitutions that cause less than conservative changes in the encoded polypeptide. Examples of such nucleotide substitutions, as shown in Table 1, are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histamine, for (or by) an electronegative residue, e.g., glutamine or aspartine; or (d) a residue having a bulky side chain, e.g., phenylalanine, for (or by) one not having a side chain, e.g., glycine. Table 2 provides similar possible substitution possibilities:

TABLE 2

| Amino Acid | 3-letter code | 1-letter code | Properties |
|---|---|---|---|
| Alanine | Ala | A | Aliphatic, hydrophobic, neutral |
| Arginine | Arg | R | polar, hydrophilic, charged (+) |
| Asparagine | Asn | N | polar, hydrophilic, neutral |
| Aspartate | Asp | D | polar, hydrophilic, charged (−) |
| Cysteine | Cys | C | polar, hydrophobic, neutral |
| Glutamine | Gln | Q | polar, hydrophilic, neutral |
| Glutamate | Glu | E | polar, hydrophilic, charged (−) |
| Glycine | Gly | G | aliphatic, neutral |
| Histidine | His | H | aromatic, polar, hydrophilic, charged (+) |
| Isoleucine | Ile | I | aliphatic, hydrophobic, neutral |
| Leucine | Leu | L | aliphatic, hydrophobic, neutral |
| Lysine | Lys | K | polar, hydrophilic, charged (+) |
| Methionine | Met | M | hydrophobic, neutral |
| Phenylalanine | Phe | F | aromatic, hydrophobic, neutral |
| Proline | Pro | P | hydrophobic, neutral |
| Serine | Ser | S | polar, hydrophilic, neutral |
| Threonine | Thr | T | polar, hydrophilic, neutral |
| Tryptophan | Trp | W | aromatic, hydrophobic, neutral |
| Tyrosine | Tyr | Y | aromatic, polar, hydrophobic |
| Valine | Val | V | aliphatic, hydrophobic, neutral |

Naturally occurring allelic variants of a native T-Box or N-Myc gene or native T-Box or N-Myc mRNAs within the invention are nucleic acids isolated from human tissue that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native T-Box or N-Myc gene or native T-Box or N-Myc mRNAs, and encode polypeptides having structural similarity to a native T-Box or N-Myc protein.

Homologs of the native T-Box or N-Myc gene or native T-Box or N-Myc mRNAs within the invention are nucleic acids isolated from other species that have at least 75% (e.g., 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native T-Box or N-Myc gene or native T-Box or N-Myc mRNAs, and encode polypeptides having structural similarity to native T-Box or N-Myc protein. Public and/or proprietary nucleic acid databases can be searched to identify other nucleic acid molecules having a high percent (e.g., 75, 85, 95% or more) sequence identity to the native T-Box or N-Myc gene or native T-Box or N-Myc mRNAs.

Non-naturally occurring T-Box or N-Myc gene or mRNA variants are nucleic acids that do not occur in nature (e.g., are made by the hand of man), have at least 75% (e.g., 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native T-Box or N-Myc gene or native T-Box or N-Myc mRNAs, and encode polypeptides having structural similarity to native T-Box or N-Myc protein. Examples of non-naturally occurring T-Box or N-Myc gene variants are those that encode a fragment of an T-Box or N-Myc protein, those that hybridize to the native T-Box or N-Myc gene or a complement of the native T-Box or N-Myc gene under stringent conditions, those that share at least 75% sequence identity with the native T-Box or N-Myc gene or a complement thereof, and those that encode an T-Box or N-Myc fusion protein.

Nucleic acids encoding fragments of a native T-Box or N-Myc protein within the invention are those that encode, e.g., 2, 3, 4, 5, 10, 25, 50, 100, 150, 200, 250, 300, or more amino acid residues of the native T-Box or N-Myc protein. Shorter oligonucleotides (e.g., those of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 100, 125, 150 or 200 base pairs in length) that encode or hybridize with nucleic acids that encode fragments of a native T-Box or N-Myc protein can be used as probes, primers, or antisense molecules. Longer polynucleotides (e.g., those of 300, 400, 500, 600, 700, 800, 900, 1000, 1100, 1200, 1300, 1400, 1500, 1600, 1700, 1800, 1900 or 2000 base pairs) that encode or hybridize with nucleic acids that encode fragments of a native T-Box or N-Myc protein can also be used in various aspects of the invention. Nucleic acids encoding fragments of a native T-Box or N-Myc protein can be made by enzymatic digestion (e.g., using a restriction enzyme) or chemical degradation of the full length native T-Box or N-Myc gene, an T-Box or N-Myc mRNA or cDNA, or variants of the foregoing.

Nucleic adds that hybridize under stringent conditions to the nucleic acids of Appendix A or the complements of Appendix A can also be used in the invention. For example, such nucleic acids can be those that hybridize to the nucleic acids of Appendix A or the complement of the nucleic acids of Appendix A under low stringency conditions, moderate stringency conditions, or high stringency conditions are within the invention. Preferred nucleotide acids are those having a nucleotide sequence that is the complement of all or a portion of the nucleic acids of Appendix A. Other variants of the native T-Box or N-Myc gene within the invention are polynucleotides that share at least 65% (e.g., 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity to the nucleic acids of Appendix A or the complement of the nucleic acids of Appendix A. Nucleic acids that hybridize under stringent conditions to or share at least 65% sequence identity with the nucleic acids of Appendix A or the complement of the nucleic acids of Appendix A can be obtained by techniques known in the art such as by making mutations in the native T-Box or N-Myc gene, or by isolation from an organism expressing such a nucleic acid (e.g., an allelic variant).

Nucleic acid molecules encoding T-Box or N-Myc fusion proteins are also within the invention. Such nucleic acids can be made by preparing a construct (e.g., an expression vector) that expresses an T-Box or N-Myc fusion protein when introduced into a suitable host. For example, such a construct can be made by ligating a first polynucleotide encoding an T-Box or N-Myc protein fused in frame with a second polynucleotide encoding another protein such that expression of the construct in a suitable expression system yields a fusion protein.

The nucleic acid molecules of the invention can be modified at a base moiety, sugar moiety, or the phosphate backbone, e.g., to improve stability of the molecule, hybridization, and the like. For example the nucleic acid molecules of the invention can be conjugated to groups such as peptides (e.g., for targeting host cell receptors in vivo), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. USA 84:648-652; PCT Publication No. WO 88/09810, published Dec. 15, 1988), hybridization-triggered cleavage agents. (See, e.g., Krol et al. (1988) BioTechniques 6:958-976) or intercalating agents (see, e.g., Zon (1988) Pharm. Res. 5:539-549).

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are T-Box or N-Myc nucleic acids and proteins, in particular oligonucleotides, which contain two or more chemically distinct regions, each made up of at least one monomer unit, i.e., a nucleotide in the case of an oligonucleotide compound. Such oligonucleotides typically contain at least one region wherein the oligonucleotide is modified so as to confer upon the oligonucleotide increased resistance to nuclease degradation, increased cellular uptake; increased stability and/or increased binding affinity for the target nucleic acid. An additional region of the oligonucleotide may serve as a substrate for enzymes capable of cleaving RNA:DNA or RNA:RNA hybrids. For example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric T-Box or N-Myc nucleic acids and proteins of the invention may be formed as composite structures of, e.g., two or more oligonucleotides, modified oligonucleotides, oligonucleosides and/or oligonucleotide mimetics as described above. Such compounds have also been referred to in the art as hybrids or gapmers.

Vectors

Vectors are tools used to shuttle DNA between host cells or as a means to express a nucleotide sequence. Some vectors function only in prokaryotes, while others function in both prokaryotes and eukaryotes, enabling large-scale DNA preparation from prokaryotes for expression in eukaryotes. Inserting the DNA of interest, such as T-Box nucleotide sequence or a fragment, is accomplished by ligation techniques and/or mating protocols well known to the skilled artisan. Such DNA is inserted such that its integration does not disrupt any necessary components of the vector. In the case of vectors that are used to express the inserted DNA protein, the introduced DNA is operably-linked to the vector elements that govern its transcription and translation.

Vectors can be divided into two general classes: Cloning vectors are replicating plasmid or phage with regions that are non-essential for propagation in an appropriate host cell, and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA. In expression vectors, the introduced DNA is operably-linked to elements, such as promoters, that signal to the host cell to transcribe the inserted DNA. Some promoters are exceptionally useful, such as inducible promoters that control gene transcription in response to specific factors. Operably-linking T-Box or anti-sense construct to an inducible promoter can control the expression of T-Box or fragments, or anti-sense constructs. Examples of classic inducible promoters include those that are responsive to α-interferon, heat-shock, heavy metal ions, and steroids such as glucocorticoids and tetracycline. Other desirable inducible promoters include those that are not endogenous to the cells in which the construct is being introduced, but, however, is responsive in those cells when the induction agent is exogenously supplied.

Vectors have many difference manifestations. A "plasmid" is a circular double stranded DNA molecule into which additional DNA segments can be introduced. Viral vectors can accept additional DNA segments into the viral genome. Certain vectors are capable of autonomous replication in a host cell (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. In general, useful expression vectors are often plasmids. However, other forms of expression vectors, such as viral vectors (e.g., replication defective retroviruses, adenoviruses and adeno-associated viruses) are contemplated.

Recombinant expression vectors that comprise T-Box (or fragments) regulate T-Box transcription by exploiting one or more host cell-responsive (or that can be manipulated in vitro) regulatory sequences that is operably-linked to T-Box. "Operably-linked" indicates that a nucleotide sequence of interest is linked to regulatory sequences such that expression of the nucleotide sequence is achieved.

Vectors can be introduced in a variety of organisms and/or cells (Table 12). Alternatively, the vectors can be transcribed and translated in vitro, for example using T7 promoter regulatory sequences and T7 polymerase.

TABLE 12

Examples of hosts for cloning or expression

| Organisms | Examples |
|---|---|
| Prokaryotes | |
| Enterobacteriaceae | E coli |
| | K 12 strain MM294 |
| | X1776 |
| | W3110 |
| | K5 772 |
| | Enterobacter |
| | Erwinia |
| | Klebsiella |
| | Proteus |
| | Salmonella (S. tyhpimurium) |
| | Serratia (S. marcescans) |
| | Shigelia |
| | Bacilli (B. subtilis and B. licheniformis) |
| | Pseudomonas (P. aeruginosa) |
| | Streptomyces |
| Eukaryotes | |
| Yeasts | Saccharomyces cerevisiae |
| | Schizosaccharomyces pombe |
| | Kluyveromyces |
| | K. lactis MW98-8C, CBS683, CBS4574 |
| | K. fragilis |
| | K. bulgaricus |
| | K. wickeramii |
| | K. waltii |
| | K. drosophilarum |
| | K. thermotolerans |
| | K. marxianus; yarrowia |
| | Pichia pastoris |
| | Candida |
| | Trichoderma reesia |
| | Neurospora crassa |
| | Torulopsis |
| | Rhodotorula |
| | Schwanniomyces (S. occidentalis) |
| Filamentous Fungi | Neurospora |
| | Penicillium |
| | Tolypocladium |
| | Aspergilius (A. nidulans and A. niger) |
| Invertebrate cells | Drosophila S2 |
| | Spodoptera Sf9 |
| Vertebrate cells | Chinese Hamster Ovary (CHO) |
| | simian COS |
| | COS-7 |
| | HEK 293 |

Vector choice is dictated by the organism or cells being used and the desired fate of the vector. Vectors may replicate once in the target cells, or may be "suicide" vectors. In general, vectors comprise signal sequences, origins of replication, marker genes, enhancer elements, promoters, and transcription termination sequences. The choice of these elements depends on the organisms in which the vector will be used and are easily determined. Some of these elements may be conditional, such as an inducible or conditional promoter that is turned "on" when conditions are appropriate. Examples of inducible promoters include those that are tissue-specific, which relegate expression to certain cell types, steroid-responsive, or heat-shock reactive. Some bacterial repression systems, such as the lac operon, have been exploited in mammalian cells and transgenic animals. Vectors often use a selectable marker to facilitate identifying those cells that have incorporated the vector. Many selectable markers are well known in the art for the use with prokaryotes, usually antibiotic-resistance genes or the use of autotrophy and auxotrophy mutants.

Antisense, Ribozyme, Triplex Techniques

Another aspect of the invention relates to the use of purified antisense nucleic acids to inhibit expression of T-Box or N-Myc proteins. Antisense nucleic acid molecules within the invention are those that specifically hybridize (e.g., bind) under cellular conditions to cellular mRNA and/or genomic DNA encoding an T-Box or N-Myc protein in a manner that inhibits expression of the T-Box or N-Myc protein, e.g., by inhibiting transcription and/or translation. The binding may be by conventional base pair complementarily, or, for example, in the case of binding to DNA duplexes, through specific interactions in the major groove of the double helix.

Antisense constructs can be delivered, for example, as an expression plasmid which, when transcribed in the cell, produces RNA which is complementary to at least a unique portion of the cellular mRNA which encodes an T-Box or N-Myc protein. Alternatively, the antisense construct can take the form of an oligonucleotide probe generated ex vivo which, when introduced into an T-Box or N-Myc protein expressing cell, causes inhibition of T-Box or N-Myc protein expression by hybridizing with an mRNA and/or genomic sequences coding for T-Box or N-Myc protein. Such oligonucleotide probes are preferably modified oligonucleotides that are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see, e.g., U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958-976; and Stein et al. (1988) Cancer Res 48:2659-2668. With respect to antisense DNA, oligodeoxyribonucleotides derived from the translation initiation site, e.g., between the −10 and +10 regions of an T-Box or N-Myc protein encoding nucleotide sequence, are preferred.

Antisense approaches involve the design of oligonucleotides (either DNA or RNA) that are complementary to T-Box or N-Myc mRNA. The antisense oligonucleotides will bind to T-Box or N-Myc mRNA transcripts and prevent translation. Absolute complementarity, although preferred, is not required. The ability to hybridize will depend on both the degree of complementarity and the length of the antisense nucleic acid. Generally, the longer the hybridizing nucleic acid, the more base mismatches with an RNA it may contain and still form a stable duplex or triplex. One skilled in the art can ascertain a tolerable degree of mismatch by use of standard procedures to determine the melting point of the hybridized complex. Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well (Wagner, R. (1994) Nature 372:333). Therefore, oligonucleotides complementary to either the 5' or 3' untranslated, non-coding regions of an T-Box or N-Myc gene could be used in an antisense approach to inhibit translation of endogenous T-Box or N-Myc mRNA. Oligonucleotides complementary to the 5' untranslated region of the mRNA should preferably include the complement of the AUG start codon. Although antisense oligonucleotides complementary to mRNA coding regions are generally less efficient inhibitors of translation, these could still be used in the invention. Whether designed to hybridize to the 5', 3' or coding region of an T-Box or N-Myc mRNA, preferred antisense nucleic acids are less that about 100 (e.g., less than about 30, 25, 20, or 18) nucleotides in length. Generally, in order to be effective, the antisense oligonucleotide should be 18 or more nucleotides in length, but may be shorter depending on the conditions.

Specific antisense oligonucleotides can be tested for effectiveness using in vitro studies to assess the ability of the antisense oligonucleotide to inhibit gene expression. Preferably such studies (1) utilize controls (e.g., a non-antisense oligonucleotide of the same size as the antisense oligonucleotide) to distinguish between antisense gene inhibition and nonspecific biological effects of oligonucleotides, and (2) compare levels of the target RNA or protein with that of an internal control RNA or protein.

Antisense oligonucleotides of the invention may include at least one modified base or sugar moiety such as those provided above. Antisense oligonucleotides within the invention might also be an alpha-anomeric oligonucleotide. See, Gautier et al. (1987) Nucl. Acids Res. 15:6625-6641. For example, the antisense oligonucleotide can be a 2'-β-methylribonucleotide (Inoue et al. (1987) Nucl. Acids Res. 15:6131-6148), or a chimeric RNA-DNA analogue (Inoue et al. (1987) FEBS Lett. 215:327-330).

Oligonucleotides of the invention may be synthesized by standard methods known in the art, e.g., by use of an automated DNA synthesizer, as described above. Phosphorothioate oligonucleotides may be synthesized by the method of Stein et al. (1988) Nucl. Acids Res. 16:3209). Methylphosphonate oligonucleotides can be prepared by use of controlled pore glass polymer supports (e.g., as described in Sarin et al. (1988) Proc. Natl. Acad. Sci. U.S.A. 85:7448-7451).

The invention also provides a method for delivering one or more of the above-described nucleic acid molecules into cells that express T-Box or N-Myc protein. A number of methods have been developed for delivering antisense DNA or RNA into cells. For example, antisense molecules can be introduced directly into a cell by electroporation, liposome-mediated transfection, CaCl-mediated transfection, or using a gene gun. Modified nucleic acid molecules designed to target the desired cells (e.g., antisense oligonucleotides linked to peptides or antibodies that specifically bind receptors or antigens expressed on the target cell surface) can be used. To achieve high intracellular concentrations of antisense oligonucleotides (as may be required to suppress translation on endogenous mRNAs), a preferred approach utilizes a recombinant DNA construct in which the antisense oligonucleotide is placed under the control of a strong promoter (e.g., the CMV promoter).

Ribozymes

Ribozyme molecules designed to catalytically cleave T-Box or N-Myc mRNA transcripts can also be used to prevent translation of T-Box or N-Myc mRNAs and expression of T-Box or N-Myc proteins (see, e.g., Wright and Kearney, Cancer Invest. 19:495, 2001; Lewin and Hauswirth, Trends Mol. Med. 7:221, 2001; Sarver et al. (1990) Science 247: 1222-1225 and U.S. Pat. No. 5,093,246). As one example, hammerhead ribozymes that cleave mRNAs at locations dictated by flanking regions that form complementary base pairs with the target mRNA might be used so long as the target mRNA has the following common sequence: 5'-UG-3'. See, e.g., Haseloff and Gerlach (1988) Nature 334:585-591. As another example, hairpin and hepatitis delta virus ribozymes may also be used. See, e.g., Bartolome et al. (2004) Minerva Med. 95(1):11-24. To increase efficiency and minimize the intracellular accumulation of non-functional mRNA transcripts, a ribozyme should be engineered so that the cleavage recognition site is located near the 5' end of the target T-Box or N-Myc mRNA. Ribozymes within the invention can be delivered to a cell using a vector as described below.

Other methods can also be used to reduce T-Box or N-Myc gene expression in a cell. For example, T-Box or N-Myc gene expression can be reduced by inactivating or "knocking out" the T-Box or N-Myc gene or its promoter using targeted homologous recombination. See, e.g., Kempin et al., Nature 389: 802 (1997); Smithies et al. (1985) Nature 317:230-234; Thomas and Capecchi (1987) Cell 51:503-512; and Thompson et al. (1989) Cell 5:313-321. For example, a mutant, non-functional T-Box or N-Myc gene variant (or a completely unrelated DNA sequence) flanked by DNA homologous to the endogenous T-Box or N-Myc gene (either the coding regions or regulatory regions of the T-Box or N-Myc gene) can be used, with or without a selectable marker and/or a negative selectable marker, to transfect cells that express T-Box or N-Myc protein in vivo.

T-Box or N-Myc gene expression might also be reduced by targeting deoxyribonucleotide sequences complementary to the regulatory region of the T-Box or N-Myc gene (i.e., the T-Box or N-Myc promoter and/or enhancers) to form triple helical structures that prevent transcription of the T-Box or N-Myc gene in target cells. See generally, Helene, C. (1991) Anticancer Drug Des. 6(6): 569-84; Helene, C., et al. (1992) Ann. N.Y. Acad. Sci. 660:27-36; and Maher, L. J. (1992) Bioassays 14(12): 807-15. Nucleic acid molecules to be used in this technique are preferably single stranded and composed of deoxyribonucleotides. The base composition of these oligonucleotides should be selected to promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, e.g., containing a stretch of G residues. These molecules will form a triple helix with a DNA duplex that is rich in GC pairs, in which the majority of the purine residues are located on a single strand of the targeted duplex, resulting in CGC triplets across the three strands in the triplex. The potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

The antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be introduced stably into cell tines.

RNA Interference (RNAi)

The use of short-interfering RNA (siRNA) is a technique known in the art for inhibiting expression of a target gene by introducing exogenous RNA into a living cell (Elbashir et al. 2001. Nature, 411:494-498). siRNAs suppress gene expression through a highly regulated enzyme-mediated process called RNA interference (RNAi). RNAi involves multiple RNA-protein interactions characterized by four major steps: assembly of siRNA with the RNA-induced silencing complex (RISC), activation of the RISC, target recognition and target cleavage. Therefore, identifying siRNA-specific features likely to contribute to efficient processing at each step is beneficial efficient RNAi. Reynolds et al. provide methods for identifying such features. A. Reynolds et al., "Rational siRNA design for RNA interference", Nature Biotechnology 22(3), March 2004. In that study, eight characteristics associated with siRNA functionality were identified: low G/C content, a bias towards low internal stability at the sense strand 3'-terminus, lack of inverted repeats, and sense strand base preferences (positions 3, 10, 13 and 19). Further analyses revealed that application of an algorithm incorporating all eight criteria significantly improves potent siRNA selection. siRNA sequences that contain internal repeats or palindromes may form internal fold-back structures. These hairpin-tike structures may exist in equilibrium with the duplex form, reducing the effective concentration and silencing potential of the siRNA. The relative stability and propensity to form internal hairpins can be estimated by the predicted melting temperatures ($T_M$). Sequences with high Tm values would favor internal hairpin structures.

siRNA can be used either ex vivo or in vivo, making it useful in both research and therapeutic settings. Unlike in other antisense technologies, the RNA used in the siRNA technique has a region with double-stranded structure that is made identical to a portion of the target gene, thus making inhibition sequence-specific. Double-stranded RNA-mediated inhibition has advantages both in the stability of the material to be delivered and the concentration required for effective inhibition.

The extent to which there is loss of function of the target gene can be titrated using the dose of double stranded RNA delivered. A reduction or loss of gene expression in at least 99% of targeted cells has been shown. See, e.g., U.S. Pat. No. 6,506,559. Lower doses of injected material and longer times after administration of siRNA may result in inhibition in a smaller fraction of cells. Quantitation of gene expression in a cell show similar amounts of inhibition at the level of accumulation of target mRNA or translation of target protein.

The RNA used in this technique can comprise one or more strands of polymerized ribonucleotides, and modification can be made to the sugar-phosphate backbone as disclosed above. The double-stranded structure is often formed using either a single self-complementary RNA strand (hairpin) or two complementary RNA strands. RNA containing a nucleotide sequences identical to a portion of the target gene is preferred for inhibition, although sequences with insertions, deletions, and single point mutations relative to the target sequence can also be used for inhibition. Sequence identity may be optimized using alignment algorithms known in the art and through calculating the percent difference between the nucleotide sequences. The duplex region of the RNA could also be described in functional terms as a nucleotide sequence that is capable of hybridizing with a portion of the target gene transcript.

siRNA can often be a more effective therapeutic tool than other types of gene suppression due to siRNA's potent gene inhibition and ability to target receptors with a specificity can reach down to the level of single-nucleotide polymorphisms. Such specificity generally results in fewer side effects than is seen in conventional therapies, because other genes are not be affected by application of a sufficiently sequence-specific siRNA.

There are multiple ways to deliver siRNA to the appropriate target. Standard transfection techniques may be used, in which siRNA duplexes are incubated with cells of interest and then processed using standard commercially available kits. Electroporation techniques of transfection may also be appropriate. Cells or organisms can be soaked in a solution of the siRNA, allowing the natural uptake processes of the cells or organism to introduce the siRNA into the system. Viral constructs packaged into a viral particle would both introduce the siRNA into the cell line or organism and also initiate transcription through the expression construct. Other methods known in the art for introducing nucleic acids to cells may also be used, including lipid-mediated carrier transport, chemical-mediated transport, such as calcium phosphate, and the like.

For therapeutic uses, tissue-targeted nanoparticles may serve as a delivery vehicle for siRNA. These nanoparticles carry the siRNA exposed on the surface, which is then available to bind to the target gene to be silenced. Schiffelers, et al., Nucleic Acids Research 2004 32(19):e149. These nanoparticles may be introduced into the cells or organisms using the above described techniques already known in the art. RGD peptides have been shown to be effective at targeting the neovasculature that accompanies the growth of tumors. Designing the appropriate nanoparticles for a particular illness is a matter of determining the appropriate targets for the particular disease. In the case of cancer and heart disease, the present invention has already revealed potential targets for this powerful therapy.

Other delivery vehicles for therapeutic uses in humans include pharmaceutical compositions, intracellular injection, and intravenous introduction into the vascular system. Inhibition of gene expression can be confirmed by using biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression may be assayed using a reporter or drug resistance gene whose protein product can be easily detected and quantified. Such reporter genes include acetohydroxyacid synthase (AHAS), alkaline phosphatase (AP), beta galactosidase (LacZ), beta glucuronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. These techniques are well known and easily practiced by those skilled in the art. For in vivo use in humans, reduction or elimination of symptoms of illness will confirm inhibition of the target gene's expression.

Exemplary siRNAs of the invention are described above and provided in the Sequence Listing.

Kits, Research Reagents, Diagnostics, and Therapeutics

The T-Box or N-Myc polynucleotides and T-Box or N-Myc proteins identified herein can be utilized for diagnostics, therapeutics, prophylaxis, as research reagents and kits. Furthermore, antisense nucleic acid, a ribozyme, a triplex-forming oligonucleotide, a siRNA, a probe, a primer, and the like may be provided in a kit.

For use in kits and diagnostics, the T-Box or N-Myc polynucleotides and proteins of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more T-Box or N-Myc polynucleotides are compared to control cells or tissues not treated with antisense T-Box or N-Myc polynucleotides and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), fluorescent in situ hybridization (FISH) techniques (Going and Gusterson, Eur. J. Cancer, 1999, 35, 1895-904) and mass spectrometry methods (To, Comb. Chem. High Throughput Screen, 2000, 3, 235-41).

FIG. 1 depicts the generation of Tbx20 targeted allele, whole mount and histological view of Tbx20-null mice and littermate controls at E8.5 and E9.5. (A) Two LoxP sites were induced into Tbx20 exon 2 where T-Box domain starts. (B) Southern Blot of ES cell DNA digested with NcoI and hybridized with a genomic fragment external to the targeting construct with wild type band 5.5 kb and recombinant band 4.3 kb. Recombinant ES cells were then transfected with a Cre plasmid in order to remove PGKNeo, HSV-TKcassettes. Tbx20 null mice were obtained by crossing mice with Tbx20 floxed allele toprotamine-Cre mice. (C) RT-PCR using whole heart RNA obtained from adult wild type (C-1) and heterozygous mice (C-2) with primers located in exon 1 (P-RT-5') and exon 3(P-RT-3') showed the wild type band 677 bp and mutant band 427 bp. Excision of exon2 of Tbx20 created a new immediate stop codon within exon 3. (D) Genotypes determined by PCR of one littermate embryos from heterozygous cross. The wild type allele band was 310 bp and the mutant allele band was 650 bp. (E-L) Embryonic stages are indicated. Hearts of Tbx20 null mice are severely hypoplastic relative to control littermates at both stages. Arrows indicate heart region.

A 2.6 kb Smal-Smal fragment within intron 1 and a 4.4 kbSmal-NotI fragment were cloned into the vector as the 5' arm or 3' arm, respectively. Targeted vector was linearized with NotI and electroporated into SM-1 ES cells derived from 129/svmice. After G418 selection, homologous recombinants were identified by digesting genomic DNA with NcoI and hybridizing with a 176 bp NcoI-Smal 5' probe. Recombinant ES cells were then transfected with a Cre plasmid in order to remove PGKNeo, HSV-TK cassettes (FIG. 1). ES cells with a floxed Tbx20 allele were injected into C57BL/6 blastocysts. Chimeras were mated with C57BL/6 females and offspring were genotyped by PCR and Southern blot analysis of tail DNA. Tbx20 null mice were obtained by crossing mice with Tbx20 foxed allele to protamine-Cre mice (O'Gorman et al., 1997). Genotypes were determined by PCR with primers: P-810, 5'-AGTGCTACCCTCTGCAGCTGCAAA-3' (SEQ ID NO: 568), P-1120, 5'-AGTAGGAAGGAGCTGGGAA-GAGTA-3' (SEQ ID NO: 569), P-2320, 5'-CAGAAAATGA-CACGCGGATGGTGG-3' (SEQ ID NO: 570). The wild type allele band was 310 bp and the mutant allele band was 650 bp (FIG. 1).

Whole-Mount RNA in Situ Hybridization and Histological Analyses

Whole-mount RNA in situ hybridization was carried out according to Wilkinson's protocol (Wilkinson, 1992). For sectioning, mouse embryos were fixed in 4% paraformaldehyde, dehydrated in ethanol and embedded in paraffin. Transverse sections were cut and stained with hematoxylin-erosin according to a standard method.

Further, the present invention provides a kit for detecting the progression of diseases of the heart. The kit comprises a T-Box- or N-Myc-specific antibody, whereby the detection of heart illness can be carried out using the antibody in an assay as described above. The kit may comprise first and second antibodies specific to one or more T-Box or N-Myc proteins or fragments. The second antibody is preferably capable of binding to a conjugate of the T-Box or N-Myc protein and the first antibody. For this purpose, for example, an antibody that recognizes an epitope different from that recognized by the first antibody may be used as the second antibody. It is preferable that the first and second antibodies be monoclonal antibodies.

The kit of the present invention may further comprise a substance and/or a device suitable for the detection of antibodies, the immobilization of antibodies, and the like. To immobilize the antibodies, the kit may further comprise a carrier (e.g., a microtiter plate), a solution for the immobilization (e.g., carbonate buffer) and a blocking solution (e.g., gelatin-containing phosphate buffered saline (PBS)). For the detection of the antibodies, it is preferable that the antibodies be labeled previously. In this case, the kit may further comprise a detecting reagent for detecting the label. For example, when biotin is used as the labeling substance, the detecting reagent may comprise a conjugate of streptavidin with horseradish peroxidase (HRP) as well as a color-developing solution that is capable of developing a color by the action of HRP.

The kit may further comprise instructions for performing the assays of the present invention in any media, including but not limited to paper, CD-ROM, via the Internet or other means of transmitting such instructions.

EXAMPLES

Aspects of the present teachings may be further understood in light of the following examples, which should not be construed as limiting true scope of the present teachings in any way.

Example 1

Targeted Disruption of Murine Tbx20

Tbx20 genomic clones were isolated by screening a mouse 129/sv genomic library (Stratagene). The targeting vector was constructed in a plasmid containing PGKNeo and HSVTK cassettes flanked by two LoxP sites. To generate a foxed allele targeting construct, aSmaI-SmaI 1 kb genomic DNA fragment containing the second exon was cloned into a site flanked by two LoxP sites (FIG. 1).

Chromatin Immunoprecipitation (ChIP) Assay

For in vivo ChIP experiments, extracts were prepared from 20 E8.75-9.5 wild type mouse hearts. Embryos were dissected in ice-cold PBS. Following gentle pipetting, tissue was crosslinked with 2% formaldehyde for 2 hours at room temperature. Chromatin extraction and immunoprecipitations were performed using a ChIP assay kit (Upstate, 17 295) according to manufacturer's protocol. Protein-DNA crosslinking was reversed by overnight incubation at 65° C. A PCR purification kit (QIAGEN, 28106) was used to recover DNA in 50 ul. The following PCR primers against the 5' Tbx2 promoter region were used: P-813 (5'-CTCCCTCTGAAGT-GCATGGAC-3') (SEQ ID NO: 571) and P-573 (5'-AGCG-CAGAGGACCGATCTGAC-3') (SEQ ID NO: 572). As control, primers against an unrelated region of Tbx2 promoter region were used, primer E (5'-CTCTGGTTCCTAGGCAG-GACTCGG-3') (SEQ ID NO: 573) and primer F (5'-TC-CTCTGCAGTCTGCCTGTCTGTG-3') (SEQ ID NO: 574). The following PRC primers against the N-myc intron 1 promoter region were used. P-4030 (5'-CCAGGCAGAGAAAT-AGCTTTAGCG-3') (SEQ ID NO: 575) and P-4330 (5'-CCTTTCCATTCCCCTTCCTTCAGA-3') (SEQ ID NO: 576); P4630 (5'-CCAGGCAGTGCCTTGTGTGAAT-3') (SEQ ID NO: 577) and P-4930 (5'-GCCAACCTCCAACTC-TACAACC-3') (SEQ ID NO: 578). As control, primers against an unrelated region of N-myc promoter region were used: primer G (5'-GAGGCTATGTGGCTTCTAGGAGAG-3') (SEQ ID NO: 579) and primer H (5'-GGATGTTAGAT-GTCCAGTCTCACC-3') (SEQ ID NO: 580).

Promoter Cloning and Luciferase Transfection Assay

The following PCR primers against the Isl1 5' promoter region were used: P-842 (5'-CGGGAGGAAAGGAAC-CAACCT-3') (SEQ ID NO: 581) and P-581 (5'-CCCGGAG-TAGGACGGTTAGACC-3') (SEQ ID NO: 582). As controls, primers against an unrelated region of Isl1 promoter region were used: primer I (5'-CTCTGGTTCCTAGGCAG-GACTCGG-3') (SEQ ID NO: 583) and primer J (5'-GCG-GTCTGCTGCTCGGCTCTCAGC-3') (SEQ ID NO: 584). Tbx20 polyclonal antibody was obtained from Orbigen (PAB-11248) and Tbx2 polyclonal antibody was obtained from Upstate (07-318).

Promoter Cloning and Luciferase Transfection Assay

A 1 kb genomic DNA fragment upstream of Tbx2 ATG was amplified with high fidelity DNA polymerase (Novagen, 71086-3) and cloned into pGL3-basic vector (Promega, E1751). Primers were: 5' primer 5'-CATCAGGGTTCTGC-CATGGCTC-3' (SEQ ID NO: 585), 3' primer 5'-GGCTCTCTCATCGGGACATCC-3' (SEQ ID NO: 586). A full-length 1.3 kb N-myc intron 1 promoter fragment was cloned into pGL3-basic vector following PCR. Primers were 5' primer 5'-AGCGGTACTTGCGAAGCTTCGA-3' (SEQ ID NO: 587), 3' primer 5'-CGCCTCTCTTTTAATATCTC-CGCT-3' (SEQ ID NO: 588). A 1.5 kb genomic DNA fragment upstream of Isl1 ATG was amplified and cloned into pGL3-basic vector. Primers were: 5' primer 5'-GAATTCT-GTGTGTCCCCTAATAAC-3' (SEQ ID NO: 589), 3' primer 5'-AGAGGGAGTAATGTCCACAGTGAA-3' (SEQ ID NO: 590). Transfections were carried out in HEK 293 cells according to standard techniques by FUGENE6 (Roche). Cells were lysed 48 hr after transfection, and luciferase and β-galactosidase activities were measured on a Luminoskan Ascent luminometer (ThermoLabsystems). For luciferase reporters, CMV-β-galactosidase was used to control for transfection efficiency. Normalized luciferase activities were compared with a pGL3 control to calculate fold-repression. Results are from one representative experiment carried out in triplicates and expressed as mean±SD. At least three independent transfection experiments were performed.

Site-Directed Mutagenesis

The QuickChange sited-directed mutagenesis kit (Stratagene, 200518) was used to make point mutations in T-Box binding sites in the promoter region according to the manufacture's protocol.

Whole-Mount Cell Death (TUNEL) Assay

Whole mount TUNEL staining was performed with in Situ Cell Death Detection Kit (Roche, 1684 817) followed a modified protocol (Chi et al., 2003; Hensey and Gautier, 1998; Yamamoto and Henderson, 1999).

Whole-Mount Proliferation Assay

The whole-mount mouse embryo cell proliferation assay was performed as described (Nagy et al., 2003). Anti-phospho-Histone H3 (Ser10) (1:100 dilution) was obtained from Upstate (06-570).

Results

Tbx20 Null Mice are Embryonic Lethal and Exhibit Unlooped Severely Hypoplastic Hearts To investigate the role of Tbx20 in mammalian heart development, Tbx20 knockout mice were generated. Homozygous null mice arrested development at E9.0 and died at E10.5. Hearts of Tbx20 mutants exhibited an unusual cardiac phenotype, somewhat resembling an "hourglass", and were unlooped and severely hypoplastic (FIG. 1 E-L).

Myocardial Differentiation and Anterioposterior Patterning Occur in Tbx20 Mutant Hearts Tbx20 is expressed in throughout early differentiating myocardium, suggesting that it might play a role in differentiation. To investigate this, we performed whole mount in situ hybridization to examine RNAs encoding myofibrillar proteins myosin light chain 2a (MLC2a) and β myosin heavy chain (β-MHC), both expressed throughout myocardium, myosin light chain 2v (MLC2v), restricted to ventricle and atrioventricular canal, and α myosin heavy chain (α-MHC), restricted to the atrioventricular canal and forming atrium at early stages. Expression of MLC2a, MLC2v, and myosin heavy chain was intact in Tbx20 mutants, demonstrating that myocardial differentiation had occurred. Expression of α-MHC, however, was greatly reduced relative to wildtype controls, suggesting that some aspects of specification or differentiation may be perturbed in Tbx20 null mice (FIG. 2 A-H).

FIG. 2 depicts whole mount in situ analysis of Tbx20 null mutants and control littermates. (A-H) Differentiation markers MLC2a, β-MHC, MLC2v are normally expressed in Tbx20 mutants. α-MHC, however, is downregulated (G,H). (I-N) Tbx5 is expressed in left ventricular, atrioventricular, and atrial progenitors in an anteriorposterior gradient. This expression profile is maintained in Tbx20 mutants, Wnt11 is expressed in outflow tract and atrioventricular canal. In Tbx20 mutants, outflow tract expression is present, but atrioventricular canal expression is lacking. GATA4 is expressed throughout the heart in an anterior-posterior gradient which is maintained in Tbx20 mutants.

To determine whether individual cardiac segments were present, we performed whole mount RNA in situ analysis for markers of distinct cardiac segments and anterior posterior polarity, namely, Tbx5 (left ventricle and atria), Wnt11 (outflow tract, right ventricle and atrioventricular canal), and GATA4 (expressed throughout the heart in an anterior posterior gradient) (FIG. 2 IN). Results demonstrated that overall anterior-posterior patterning had occurred in Tbx20 mutants, although Wnt11 expression in a putative atrioventricular canal region was absent in Tbx20 mutants. This could indicate regional down regulation of Wnt11 or an absence of atrioventricular canal identity.

Tbx2 is Up Regulated in Tbx20 Mutants and is Directly Repressed by Tbx20

Hearts in Tbx20 null mice closely resembled those described for transgenic mice overexpressing Tbx2 in myocardium (Christoffels et al., 2004). Indeed, we found that Tbx2 is highly up regulated in Tbx20 null mice, beginning at early cardiac crescent stages (FIG. 3 A-F).

FIG. 3 depicts Tbx2 being up regulated in Tbx20 mutants and is a direct target for repression by Tbx20. (A-F) Whole mount RNA in situ and section analysis for Tbx2 expression in Tbx20 null embryos and wildtype littermates. (G-P) Whole mount RNA in situ demonstrates down regulation of Nppa, chisel, and cited1 in Tbx20 mutants. Expression of Tbx20 and Tbx3 is unaffected. (Q) ChIP analysis with embryonic heart extracts revealed binding of Tbx20 to region containing conserved T-Box sites within Tbx2 promoter (Q-1, primer P-813, P-573). Chip analysis with primers against an unrelated promoter region revealed no Tbx20 recruitment (Q-2) (see Methods for primers). No recruitment was found with Beads, IgG or $H_2O$. (R) Cotransfection of Tbx20 expression vector (500 ng) with Tbx2 promote-luciferase constructs (100 ng) into HEK293 cells demonstrated repression by Tbx20 which was abrogated by mutation (Mu) of conserved T-Box elements within the Tbx2 promoter. *$P<0.05$, paired t-test.

These data suggested that upregulation of Tbx2 could account for the heart phenotype in Tbx20 mutants. Transgenic mice overexpressing Tbx2 in myocardium exhibit decreased expression of several genes, including atrial natriuretic peptide, Nppa, the muscle specific gene chisel, and the transcriptional co-activator, cited 1. Expression of each of these genes is greatly reduced or absent in Tbx20 mutants (FIG. 3 G-L). To investigate a potential feedback loop between Tbx20 and Tbx2, we examined expression of Tbx20 mRNA in Tbx20 mutants. Although no Tbx20 protein is present in homozygous null mice, Tbx20 mRNA can still be detected.

We observed no differences between Tbx20 expression in wildtype and null mice, demonstrating that the observed regulatory interaction between Tbx20 and Tbx2 is unidirectional, and suggesting lack of autoregulation of Tbx20 at the transcriptional level (FIG. 3 M-N). Tbx2 is most closely related to Tbx3, and the two genes are expressed in an overlapping pattern in developing heart (Hoogaars et al., 2004), suggesting that they may, in some instances, be regulated coordinately. However, Tbx3 expression was unaltered in Tbx20 mutants (FIG. 3 O-P). We investigated whether upregulation of Tbx2 in Tbx20 mutants reflected direct repression by Tbx20 in wildtype hearts. Analysis revealed two conserved T-Box recognition sites between 677-688 bp upstream of a putative transcription start site of the Tbx2 gene. ChIP analysis was performed on extracts from E8.75-E9.5 hearts and demonstrated that Tbx20 protein was recruited to this region, but not to an unrelated 5' genomic region of Tbx2 (FIG. 3 Q). Cotransfection assays with a luciferase reporter driven by a 1 kb Tbx2 promoter and a Tbx20 expression vector demonstrated a four-fold repression of the Tbx2 promoter by Tbx20. This repression was relieved by mutation of the conserved T-Box sites (FIG. 3 R). These data demonstrated that Tbx20 directly represses Tbx2 within developing heart.

Proliferation, but not Apoptosis, is Affected in Tbx20 Mutants

Reduced heart size in Tbx20 null mutants suggested an increase in cell death, or decrease in cell proliferation, or both. TUNEL assays demonstrated no differences in apoptosis between wildtype or mutant embryos at E7.5 or E8.5 (FIG. 4 A-D).

FIG. 4 depicts apoptosis and proliferation assays in Tbx20 null mutants and control littermates. (A-D) TUNEL analysis revealed no increase in apoptosis in Tbx20 null embryos relative to control littermates. Arrows indicate cardiac crescent (A,B) and heart tube (C,D). (E-L) Antibody staining for phosphorylated histone H3 reveals decreased proliferation in Tbx20 null mutants relative to control littermates. Arrows indicate positive phosphorylated histone H3 staining in cardiomyocytes.

Wholemount immunostaining with antibody to phosphorylated histone H3, however, demonstrated decreased proliferation in Tbx20 mutant hearts relative to hearts of wildtype littermates at E8.0 and E8.5 (FIG. 4 E-L). Proliferation rates were assessed by examination of sections. At E8.0, the number of phosphorylated histone H3 positive nuclei within myocardium of Tbx20 mutants was reduced more than two-fold, from 3.5% in wildtype to 1.4% in mutants. At E8.5, the number of positive nuclei was reduced more than three-fold, from 3.7% in wildtype to 1.0% in mutants, indicating significant reduction in proliferation rate in myocardium of Tbx20 mutants. To ensure that the proliferative decrease in heart was specific, we assessed proliferation rates in neural folds which do not express Tbx20 at this stage, and found no significant difference between wildtype and mutant embryos (5.9% vs. 5.7%, respectively).

N-myc and Cyclin A2 are Downregulated in Tbx20 Mutant Hearts

Decreased proliferation in Tbx20 mutant hearts suggested down regulation of genes important for cell cycle regulation in cardiomyocytes. N-myc is required for early myocardial proliferation (Davis and Bradley, 1993). Cyclin A2 is required for proliferation in early embryos, and is implicated in myocyte proliferation (Chaudhry et al., 2004; Murphy et al., 1997). We found expression of both genes was severely downregulated in Tbx20 mutant hearts, consistent with observed defects in proliferation (FIG. 5 A-H).

FIG. 5 shows that Tbx2 directly binds and represses N-myc expression in regions of relatively low proliferation within the heart. Regions of relatively low proliferation, outfow tract (OFT) and atrioventricular canal (AV) are indicated by arrows, (A-H). Expression of Nmyc (A-D) and cyclin A2 (E-H) is downregulated in Tbx20 null mutants. Section analysis of wildtype littermates reveals regional differences in expression of N-myc (C) and cyclinA2 (G), with relatively low levels in OFT and AV canal. (1-K) Wildtype Tbx2 expression is complementary to that of N-myc and cyclinA2. (L) Expression of phosphorylated histone H3 in wildtype embryos revealed regions of low proliferation within developing heart. (M) ChIP analysis with embryonic heart extracts demonstrated recruitment of Tbx2 and Tbx20 to regions containing T-Box consensus sites within intron 1 of the N-myc gene (M-1, primer P-4030, P-4330; M-2, primer P-4630, P-4930). ChIP analysis with primers against an unrelated promoter region revealed no Tbx2 recruitment (M-3) (see Methods for primers). No recruitment was found with IgG. (N) Cotransfections of Tbx2 or Tbx20 expression vectors with N-myc intron 1-luciferase reporter into HEK293 cells demonstrated repression or activation, respectively. **$P<0.005$, paired t-test; *$P<0.05$, paired t-test. (O) Co-transfections of Tbx2 expression vector with N-myc intron 1-luciferase reporter into HEK293 cells demonstrated dose-dependent repression by Tbx2. **$P<0.005$, paired t-test.

Regional Variation in Expression of N-Myc, Cyclin A2, and Phosphorylated Histone H3 Correlates with Tbx2 Expression During our analysis we observed focal differences in expression of cyctin A2 and N-myc within wildtype heart (FIG. 5 A,E,C,G). Regions which had relatively low levels of expression were similar for cyclin A2 and N-myc, and included the outflow tract and atrioventricular canal. These regions are those in which Tbx2 is expressed, and suggested that one of these genes might be a direct target of Tbx2. Bioinformatic analysis of 2 kb upstream of the translation start codon or 2 kb downstream, including intron 1, of cyclin A2 did not reveal any conserved T-Box sites between human and mouse. However, similar analysis of sequences within the N-myc gene revealed two clusters of conserved T-Box sites within intron 1 (FIG. 5 M). These sites are within regions previously defined to be required for expression of N-myc both in vitro and in vivo (Strieder and Lutz, 2002).

Tbx2 Directly Represses N-Myc

ChIP analysis with E8.75-E9.5 embryonic heart extracts revealed that Tbx2 was recruited to both clusters of T-Box sites within intron1 of N-myc (FIG. 5 M-1,2). Control sites further upstream were negative (FIG. 5 M-3). Co-transfection of an N-myc intron 1-luciferase reporter with a Tbx2 expression vector in HEK293 cells demonstrated significant down regulation of the N-myc promoter fragment by Tbx2 (FIG. 5 O). In contrast, similar studies with Tbx20 demonstrated in vivo binding, and in vitro activation of the N-myc promoter fragment by Tbx20, demonstrating specificity of repression by Tbx2 (FIG. 5 N). Repression by Tbx2 of the N-myc promoter was dose dependent. These data demonstrated that Tbx2 directly binds to T-Box consensus sites within intron 1 of the N-myc gene to repress transcriptional activity of N-myc.

Tbx20 is Required for Expression of BMP2 and BMP5

Our data demonstrated down regulation of N-myc in Tbx20 mutants. Cardiac hypoplasia in Tbx20 mutants, or myocardial-Tbx2 transgenics (Christoffels et al., 2004), however, appears to be more severe than observed in N-myc null mice (Charron et al., 1992; Moens et al., 1993; Sawai et al., 1993), suggesting that perturbation of genes in addition to N-myc might account for the severity of the growth phenotype in Tbx20 null mice. Accordingly, we examined expression of bone morphogenetic growth factors which have been demonstrated to play a role in early myocardial growth, often in a redundant fashion (Kim et al., 2001; Liu et al., 2004; Solloway and Robertson, 1999; Zhang and Bradley, 1996). Results demonstrated that expression of BMP4 and BMP7 was not downregulated in Tbx20 null mice, whereas expression of BMP2 and BMP5 was severely downregulated (FIG. 6).

FIG. 6 shows that Tbx20 Regulates Expression of a subset of BMP genes. Expression of BMPs 4 and 7 (C,D; G,H) are not downregulated in Tbx20 mutants, whereas expression of BMPs 2 and 5 (A,B; E,F) is severely downregulated specifically in the heart, as indicated by arrows.

Tbx20 is Required for Expression of Genes which Also Require Nkx2.5 Expression Several genes downregulated in transgenic mice overexpressing Tbx2 in myocardium (Christoffels et al., 2004), and in Tbx20 knockouts, are also downregulated in Nkx2.5 knockout mice (Harvey, 2002), including Nppa, chisel and cited1. Accordingly, we investigated whether Nkx2.5 was downregulated in Tbx20 mutants. We found no evidence for down regulation of Nkx2.5 in Tbx20 mutants from E8.5-E9.25, suggesting that down regulation of Nppa, chisel and cited1 in Tbx20 mutants was not a consequence of down regulation of Nkx2.5. Two other genes downregulated in Nkx2.5 mutants, Hand1 and Irx4, were also downregulated in Tbx20 mutants (FIG. 7).

FIG. 7 shows that Tbx20 and Nkx2.5 independently regulate common downstream targets. (A-F) Expression of Hand1 and Irx4 is downregulated in Tbx20 mutants. Hand2 expression is unaffected. (G-J) Nkx2.5 expression is unaffected in Tbx20 mutants.

Expression of these genes was not examined in transgenics overexpressing Tbx2. Expression of Hand2 was not affected in Tbx20 mutants.

Tbx20 Directly Represses Expression of Isl1 in Myocardium

The LIM-homeodomain transcription factor Isl1 is required for proliferation, survival and migration of a subset of undifferentiated cardiac progenitors, and is downregulated as they enter the heart and differentiate (Cai et al., 2003). We observed that Isl1 is up regulated throughout the heart of Tbx20 mutants (FIG. 8 A-D) and subsequently demonstrated by ChIP analysis and transfection studies that Tbx20 directly binds and represses conserved T-Box sites within Isl1 promoter sequences (1.5 kb upstream of ATG) (FIG. 8 E-F). Functional consequences of this upregulation are not yet clear, but it is unlikely that Isl1 upregulation contributes substantially to the Tbx20 null phenotype, as hearts of transgenic mice expressing Isl1 at comparable levels throughout myocardium appear relatively normal at E10.5 (FIG. 8 GJ).

FIG. 8 shows that Tbx20 directly binds and represses Isl1 in myocardium. (A-D) Isl1 is expressed throughout myocardium in Tbx20 mutants (B,D). (E) ChIP analysis revealed Tbx20 recruitment to region of Isl1 promoter with conserved T-Box site (E-1, primer P-842, P-581). ChIP analysis with primers against an unrelated promoter region revealed no Tbx20 recruitment (E-2) (see Methods for primers). No recruitment was found with Beads, IgG or $H_2O$. (F) Co-transfection of Tbx20 expression vector (500 ng) with Isl1 promoter-luciferase reporter (100 ng) demonstrated repression of Isl1 by Tbx20. Repression was abrogated by mutation of the consensus T-Box element within the Isl1 promoter. *$P<0.05$, paired t-test. (G-J) The nebulette promoter, expressed exclusively in myocardium during early embryogenesis (Ju Chen, personal communication) was utilized to drive expression of Isl1 in transient transgenic mice. Whole mount in situ hybridization revealed expression of Isl1 throughout myocardium in transgenic mice. Hearts of transgenics appeared normal at E10.5.

Other Embodiments

The detailed description set forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention. Specifically intended to be within the scope of the present invention, and incorporated herein by reference in its entirety, is the following forthcoming publication: Cai, C-L. Zhou, W, Yang, L. Bu, L. Qyang, Y., Zhang, X., Li, X., Rosenfeld, M. G., Chen, J and Evans, S. (2005) T-Box genes coordinate regional rates of proliferation and regional specification during cardiogenesis. *Development and Disease* 132(10):2475-2487.

OTHER PUBLICATIONS INCORPORATED HEREIN BY REFERENCE IN THEIR ENTIRETY INCLUDE

Agulnik, S. I., Garvey, H., Hancock, S., Ruvinsky, I., Chapman, D. L., Agulnik, I., Bollag, R., Papaioannou, V. and Silver, L. M. (1996). Evolution of mouse T-box genes by tandem duplication and cluster dispersion. *Genetics* 144, 249-54.

Bamshad, M., Le, T., Watkins, W. S., Dixon, M. E., Kramer, B. E., Roeder, A. D., Carey, J. C., Root, S. Schinzel, A., Van Maldergem, L. et al. (1999). The spectrum of mutations in TBX3; Genotype/Phenotype relationship in ulnar-mammary syndrome. *Am J Hum Genet*. 64, 1550-62.

Brown, D. D., Martz, S. N., Binder, O., Goetz, S. C., Price, B. M., Smith, J. C. and Conlon, F. L. (2005). Tbx5 and Tbx20 act synergistically to control vertebrate heart morphogenesis. *Development*.

Brummelkamp, T. R., Kortlever, R. M., Lingbeek, M., Trettel, F., MacDonald, M. E., vanLohuizen, M. and Bernards, R. (2002). TBX-3, the gene mutated in Ulnar-Mammary Syndrome, is a negative regulator of p19ARF and inhibits senescence. *J Biol Chem* 277, 6567-72.

Bruneau, B. G., Bao, Z. Z., Tanaka, M., Schott, J. J. Izumo, S., Cepko, C. L., Seidman, J. G. and Seidman, C. E. (2000). Cardiac expression of the ventricle-specific homeobox geneIrx4 is modulated by Nkx2-5 and dHand, *Dev Bio* 217, 266-77.

Cai, C. L., Liang, X., Shi, Y., Chu, P. H. (Pfaff, S. L. Chen, J. and Evans, S. (2003), Isl1 identifies a cardiac progenitor population that proliferates prior to differentiation and contributes a majority of cells to the heart. *Dev Cell* 5, 877-89.

Carlson, C. C., Burnham, L. L., Shanks, R. A. and Dransfield, D. T. (2001). 8-Cl-adenosine induces differentiation in LS174T cells. *Dig Dis Sci* 46, 757-64.

Carlson, H. Ota, S., Song, Y., Chen, Y. and Hurlin, P. J. (2002). Tbx3 impinges on the p53 pathway to suppress apoptosis, facilitate cell transformation and block myogenic differentiation. *Oncogene* 21, 3827-35.

Carraway, K. L., 3rd. (1996). Involvement of the neuregulins and their receptors in cardiac and neural development. *Bioessays* 18, 263-6.

Charron, J., Malynn, B. A., Fisher, P., Stewart, V., Jeannotte, L., Goff, S. P., Robertson, E. J. and Alt, F. W. (1992). Embryonic lethality in mice homozygous for a targeted disruption of the N-myc gene. *Genes Dev* 6, 2248-57.

Chaudhry, H. W., Dashoush, N. H., Tang, H., Zhang, L., Wang, X., Wu, E. X. and Wolgemuth, D. J. (2004). Cyclin A2 mediates cardiomyocyte mitosis in the post mitotic myocardium. *J Biol Chem* 279, 35858-66.

Chen, H., Shi, S., Acosta, L., Li, W., Lu, J., Bao, S., Chen, Z., Yang, Z., Schneider, M. D., Chien, K. R. et al. (2004).

BMP10 is essential for maintaining cardiac growth during murine cardiogenesis. *Development* 131, 2219-31.

Chi, C. L., Martinez, S., Wurst, W. and Martin, G. R. (2003). The isthmic organizer signal FGF8 is required for cell survival in the prospective midbrain and cerebellum. *Development* 130, 2633-44.

Christoffels, V. M., Hoogaars, W. M., Tessari, A., Clout, D. E., Moorman, A. F. and Campione, M. (2004). T-box transcription factor Tbx2 represses differentiation and formation of the cardiac chambers. *Dev Dyn* 229, 763-70.

Davis, A. and Bradley, A. (1993). Mutation of N-myc in mice: what does the phenotype tell us? *Bioessays* 15, 273-5.

de Jong, F., Opthof, T., Wilde, A. A., Janse, M. J., Charles, R., Lamers, W. H. and Moorman, A. F. (1992). Persisting zones of slow impulse conduction in developing chicken hearts. *Circ Res* 71, 240-50.

Fan, W., Huang, X., Chen, C., Gray, J. and Huang, T. (2004). TBX3 and its isoform TBX3+2a are functionally distinctive in inhibition of senescence and are overexpressed in a subset of breast cancer cell lines. *Cancer Res* 64, 5132-9.

Harrelson, Z., Kelly, R, G., Goldin, S. N., Gibson-Brown, J. J., Bollag, R. J., Silver, L. M. and Papaioannou, V. E. (2004). Tbx2 is essential for patterning the atrioventricular canal and for morphogenesis of the outflow tract during heart development *Development* 131, 5041-52.

Harvey, R. P. (2002). Patterning the vertebrate heart. *Nat Rev Genet.* 3, 544-56.

Hatcher, C. J., Kim, M. S., Mah, C. S., Goldstein, M. M., Wong, B., Mikawa, T. and Basson, C. T. (2001). TBX5 transcription factor regulates cell proliferation during cardiogenesis. *Dev Biol* 230, 177-88. Hensey, C. and Gautier, J. (1998). Programmed cell death during *Xenopus* development: aspatio-temporal analysis. *Dev Biol* 203, 36-48.

Hoogaars, W. M., Tessari, A., Moorman, A. F., de Boer, P. A., Hagoort, J., Soufan, A. T., Campione, M. and Christoffels, V. M. (2004). The transcriptional repressor Tbx3 delineates the developing central conduction system of the heart. *Cardiovasc Res* 62, 489-99.

Iio, A., Koide, M., Hidaka, K. and Morisaki, T. (2001). Expression pattern of novel chick Tbox gene, Tbx20. *Dev Genes Biol* 211, 559-62.

Jacobs, J. J., Keblusek, P., Robanus-Maandag, E., Kristet, P., Lingbeek, M., Nederlof, P. M., van Welsem, T., van de Vijver, M. J., Koh, E. Y., Daley, G. Q. et al. (2000). Senescence bypass screen identifies TBX2, which represses Cdkn2a (p19(ARF)) and is amplified in a subset of human breast cancers. *Nat Genet.* 26, 291-9.

Kamijo, T., Zindy, F., Roussel, M. F., Quelle, D. E., Downing, J. R., Ashmun, R. A., Grosveld, G. and Sherr, C. J. (1997). Tumor suppression at the mouse INK4a locus mediated by the alternative reading frame product p19ARF. *Cell* 91, 649-39.

Kiefer, J. C. (2004). The Tbx-files: the truth is out there. *Dev Dyn* 231, 232-6.

Kim, R. Y., Robertson, E. J. and Solloway, M. J. (2001). Bmp6 and Bmp7 are required for cushion formation and septation in the developing mouse heart. *Dev Biol* 235, 449-66.

Kraus, F., Haenig, B. and Kispert, A. (2001). Cloning and expression analysis of the mouse T-box gene tbx20. *Mech Dev* 100, 87-91.

Lavine, K. J. Yu, K., White, A. C., Zhang, X., Smith, C., Partanen, J. and Omitz, D. M. (2005). Endocardial and epicardial derived FGF signals regulate myocardial proliferation and differentiation in vivo. *Dev Cell* 8, 85-95.

Lingbeek, M. E., Jacobs, J. J. and van Lohuizen, M. (2002). The T-box repressors TBX2 and TBX3 specifically regulate the tumor suppressor gene p14ARF via a variant T-site in the initiator. *J Boil Chem* 277, 26120-7.

Liu, W., Selever, J., Wang, D., Lu, M. F., Moses, K. A., Schwartz, R. J. and Martin, J. F. (2004). Bmp4 signaling is required for outflow-tract septation and bronchial-arch artery remodeiing. *Proc Natl Acad Sci USA* 101, 4489-94.

Moens, C. B., Stanton, B. R., Parada, L. F. and Rossant, J. (1993). Defects in heart and lung development in compound heterozygotes for two different targeted mutations at the Nmyclocus. *Development* 119, 485-99.

Murphy, M., Stinnakre, M. G., Senamaud-Beaufort, C., Winston, N. J., Sweeney, C., Kubelka, M., Carrington, M., Brechot, C. and Sobczak-Thepot, J. (1997). Delayed early embryonic lethality following disruption of the murine cyclin A2 gene. *Nat Genet.* 15, 83-6.

Nagy, A., Gersenstein, M., Vintersten, K. and Behringer, R. (2003). Manipulating the Mouse Embryo: A Laboratory Manual: Cold Spring Harbor Laboratory Press.

Negro, A., Brar, B. K. and Lee, K. F. 2004). Essential roles of Her2/erbB2 in cardiac development and function. *Recent Prog Horm Res* 59, 1-12.

Niles, R. M. (2003). Vitamin A (retinoids) regulation of mouse melanoma growth and differentiation. *J Nutr* 133, 282S-286S.

O'Gorman, S., Dagenais, N. A., Qian, M. and Marchuk, Y. (1997). Protamine-Cre recombinase transgenes efficiently recombine target sequences in the male germ line of mice, but not in embryonic stem cells. *Proc Natl Acad Sci USA* 94, 14602-7.

Olson, E. N. (2004). A decade of discoveries in cardiac biology. *Nat Med* 10, 467-74.

Packham, E. A. and Brook, J. D. (2003). T-box genes in human disorders. *Hum Mol Genet.* 12 Spec No 1, R37-44.

Park, I. K., Morrison, S. J. and Clarke, M. F. (2004). Bmi1, stem cells, and senescence regulation. *J Clin Invest* 113, 175-9.

Pashmforoush, M., Lu, J. T., Chen, H., Amand, T. S., Kondo, R., Pradervand, S., Evans, S. M. Clark, B., Feramisco, J. R., Giles, W. et al. (2004). Nkx2-5 pathways and congenital heart disease; loss of ventricular myocyte lineage specification leads to progressive cardiomyopathy and complete heart block. *Cell* 117, 373-86.

Plageman, T. F., Jr. and Yutzey, K. E. (2005). T-box genes and heart development: Putting the "T" in heart. *Dev Dyn* 232, 11-20.

Prince, S., Carreira, S., Vancet K. W., Abrahams, A. and Goding, C. R. (2004). Tbx2 directly represses the expression of the p21(WAF1) cyclin-dependent kinase inhibitor. *Cancer Res* 64, 1669-74.

Rowley, M., Grothey, E. and Couch, F. J. (2004). The role of Tbx2 and Tbx3 in mammary development and tumorigenesis. *J Mammary Gland Biol Neoplasia* 9, 109-18.

Rumyantsev, P. P. (1991). Growth and hyperplasia of cardiac muscle cells. London: Harwood Acad. Publishers.

Sawai, S., Shimono, A., Wakamatsu, Y., Palmes, C., Hanaoka, K. and Kondoh, H. (1993). Defects of embryonic organogenesis resulting from targeted disruption of the N-myc gene in the mouse. *Development* 117, 1445-55.

Schulte, J. H., Schramm, A., Klein-Hitpass, L., Klenk, M., Wessels, H., Hauffa, B. P., Eils. J., Eils, R., Brodeur, G. M., Schweigerer, L. et al. (2005), Microarray analysis reveals differential gene expression patterns and regulation of single target genes contributing to the opposing phenotype of TrkA- and TrkB-expressing neuroblastomas. *Oncogene* 24, 165-77.

Sedmera, D., Reckova, M., DeAlmeida, A., Coppen, S. R., Kubalak, S. W., Gourdie, R. G. and Thompson, R. P.

(2003). Spatiotemporal pattern of commitment to slowed proliferation in the embryonic mouse heart indicates progressive differentiation of the cardiac conduction system. *Anat Rec A Discov Mol Cell Evol Biol* 274, 773-7.

Seidman, J. G. and Seidman, C. (2002). Transcription factor haploinsufficiency: when half a loaf is not enough. *J Clin Invest* 109, 451-5.

Sherr, C. J. and Weber, J. D. (2000). The ARF/p53 pathway. *Curr Opin Genet Dev* 10, 94-9.

Solloway, M. J. and Robertson, E. J. (1999). Early embryonic lethality in Bmp5; Bmp7 double mutant mice suggests functional redundancy within the 60A subgroup. *Development* 126, 1753-68.

Srivastava, O. (1999). Developmental and genetic aspects of congenital heart disease. *Curr Opin Cardiol* 14, 263-8.

Stennard, F. A., Costa, M. W., Elliott, D. A., Rankin, S., Haast, S. J., Lai, D., McDonald, L. P., Niederreither, K., Dolle, P., Bruneau, B. G. et al. (2003). Cardiac T-box factor Tbx20 directly interacts with Nkx2-5, GATA4, and GATA5 in regulation of gene expression in the developing heart. *Dev Biol* 262, 206-24.

Strieder, V. and Lutz, W. (2002). Regulation of N-myc expression in development and disease. *Cancer Lett* 180, 107-19.

Szeto, D. P., Griffin, K. J. and Kimelman, D. (2002). HrT is required for cardiovascular development in zebrafish. *Development* 129, 5093-101.

Thiele, C. J., Reynolds, C. P. and Israel, M. A. (1985). Decreased expression of N-myc precedes retinoic acid-induced morphological differentiation of human neuroblastoma, *Nature* 313, 404-6.

Turney, M. K., Nicholson, W. E. and Kovacs, W. J. (2004). Gene expression phenotyping of an ACTH-producing small cell lung cancer line. *Mol Cell Endocrinol* 219, 105-13.

Vance, K. W. and Goding, C. R. (2004). The transcription network regulating melanocyte development and melanoma. *Pigment Cell Res* 17, 318-25.

Wilkinson, D. G. (1992). In Situ Hybridization: A Practical Approach. New York: Oxford University Press.

Xu, H., Morishima, M., Wylie, J. N., Schwartz, R. J., Bruneau, B. G., Lindsay, E. A. and Baldini, A. (2004). Tbx1 has a dual role in the morphogenesis of the cardiac outflow tract. *Development* 131, 3217-27.

Yamada, M., Revelli, J. P., Eichele, G., Barron, M. and Schwartz, R. J. (2000). Expression of chick Tbx-2, Tbx-3, and Tbx-5 genes during early heart development: evidence for BMP2 induction of Tbx2. *Dev Biol* 228, 95-105.

Yamamoto, Y. and Henderson, C. E. (1999). Patterns of programmed cell death in populations of developing spinal motoneurons in chicken, mouse, and rat. *Dev Biol* 214, 60-71.

Zhang, H. and Bradley, A. (1996). Mice deficient for BMP2 are nonviable and have defects in amnion/chorion and cardiac development. *Development* 122, 2977-88.

Zimmerman, K., Legouy, E., Stewart, V., Depinho, R. and Alt, F. W. (1990). Differential regulation of the N-myc gene in transfected cells and transgenic mice. *Mol Cell Biol* 10, 2096-103.

What is claimed is:

1. A method for identifying a Tbx2 up regulating compound, the method comprising:
   (a) contacting a sample comprising a nucleic acid sequence encoding a Tbx20 gene as set forth in SEQ ID NO: 1 with a candidate compound; and
   (b) detecting an increase in expression of a Tbx2 gene encoding a Tbx2 gene as set forth in SEQ ID NO: 106 as compared to expression of the Tbx2 gene in the absence of the candidate compound, thereby identifying the candidate compound as a Tbx2 up regulating compound.

2. A method according to claim 1, wherein the test compound is an antibody.

3. A method according to claim 2, wherein the antibody is a monoclonal antibody.

4. The method of claim 1, wherein the compound is an siRNA.

5. The method of claim 4, wherein the siRNA comprises a sequence selected from the group consisting of SEQ ID NOs: 2-105.

6. The method of claim 5, wherein the siRNA sequence is SEQ ID NO: 2.

7. The method of claim 1, wherein the method is performed in vivo or ex vivo.

* * * * *

SEQUENCE LISTING

```
<160> NUMBER OF SEQ ID NOS: 590

<210> SEQ ID NO 1
<211> LENGTH: 905
<212> TYPE: DNA
<213> ORGANISM: Homo sapiens

<400> SEQUENCE: 1
tgctggggac catggagttc acggcgtccc ccaagcccca actctcctct cgggccaacg      60
ccttctccat tgccgcgctc atgtcgagcg gcggctctaa ggagaaggag gcgacggaga     120
acacaatcaa accctggag caatttgtgg agaagtcgtc ctgtgcccag cccctgggtg      180
agctgaccag cctggatgct catgggagt ttggtggagg cagtggcagc agcccgtcct     240
cctcctctct gtgcactgag ccactgatcc ccaccacccc catcatcccc agtgaggaaa     300
tggccaaaat tgcctgcagc ctggagacca aggagctttg ggacaaattc catgagctgg     360
gcaccgagat gatcatcacc aagtcgggca ggaggatgtt tccaaccatc cgggtgtcct     420 tttcggggt ggatcctgag gccaagtaca tagtcctgat ggacatcgtc cctgtggaca     480
acaagaggta ccgctacgcc taccaccggt cctcctggct ggtggctggc aaggccgacc     540
cgccgttgcc agccaggctc tatgtgcatc cagattctcc ttttaccggt gagcaactac     600
tcaaacagat ggtgtctttt gaaaaggtga aactcaccaa caatgaactg gatcaacatg     660
gccatataat tttgaactca atgcataagt accagccaag ggtgcacatc attaagaaga     720
aagaccacac agcctcattg ctcaacctga agtctgaaga atttagaact ttcatcttc     780 cagaaacagt tttacggca gtcactgcct accagaatca actgataacg aagctgaaaa     840
tagatagcaa tccttttgcc aaaggattcc gggattcctc caggctcact gacattgaga     900
ggtaa                                                                 905
```

```
<210> SEQ ID NO 2
<211> LENGTH: 19
<212> TYPE: RNA
<213> ORGANISM: Homo sapiens

<400> SEQUENCE: 2
gccccaacuc uccucucgg                                                19

<210> SEQ ID NO 3
<211> LENGTH: 19
<212> TYPE: RNA
<213> ORGANISM: Homo sapiens

<400> SEQUENCE: 3
ccgagaggag aguuggggc                                                19

<210> SEQ ID NO 4
<211> LENGTH: 19
<212> TYPE: RNA
<213> ORGANISM: Homo sapiens

<400> SEQUENCE: 4
cucuccucuc gggccaacg                                                19

<210> SEQ ID NO 5
<211> LENGTH: 19
<212> TYPE: RNA
<213> ORGANISM: Homo sapiens

<400> SEQUENCE: 5
cguuggcccg agaggagag                                                19

<210> SEQ ID NO 6
<211> LENGTH: 19
<212> TYPE: RNA
<213> ORGANISM: Homo sapiens

<400> SEQUENCE: 6
cgccuucucc auugccgcg                                                19

<210> SEQ ID NO 7
<211> LENGTH: 19
<212> TYPE: RNA
<213> ORGANISM: Homo sapiens

<400> SEQUENCE: 7
cgcggcaaug gagaaggcg                                                19

<210> SEQ ID NO 8
<211> LENGTH: 19
<212> TYPE: RNA
<213> ORGANISM: Homo sapiens

<400> SEQUENCE: 8
ggagaaggag gcgacggag                                                19

<210> SEQ ID NO 9
<211> LENGTH: 19
<212> TYPE: RNA
<213> ORGANISM: Homo sapiens

<400> SEQUENCE: 9
cuccgucgcc uccuucucc                                                19
```

```
<210> SEQ ID NO 10
<211> LENGTH: 19
<212> TYPE: RNA
<213> ORGANISM: Homo sapiens

<400> SEQUENCE: 10
ggaggcgacg gagaacaca                                                    19

<210> SEQ ID NO 11
<211> LENGTH: 19
<212> TYPE: RNA
<213> ORGANISM: Homo sapiens

<400> SEQUENCE: 11
uguguucucc gucgccucc                                                    19

<210> SEQ ID NO 12
<211> LENGTH: 19
<212> TYPE: RNA
<213> ORGANISM: Homo sapiens

<400> SEQUENCE: 12
cacaaucaaa ccccuggag                                                    19

<210> SEQ ID NO 13
<211> LENGTH: 19
<212> TYPE: RNA
<213> ORGANISM: Homo sapiens

<400> SEQUENCE: 13
cuccaggggu uugauugug                                                    19

<210> SEQ ID NO 14
<211> LENGTH: 19
<212> TYPE: RNA
<213> ORGANISM: Homo sapiens

<400> SEQUENCE: 14
ucaaaccccu ggagcaauu                                                    19

<210> SEQ ID NO 15
<211> LENGTH: 19
<212> TYPE: RNA
<213> ORGANISM: Homo sapiens

<400> SEQUENCE: 15
aauugcucca gggguuuga                                                    19

<210> SEQ ID NO 16
<211> LENGTH: 19
<212> TYPE: RNA
<213> ORGANISM: Homo sapiens

<400> SEQUENCE: 16
accccuggag caauuugug                                                    19

<210> SEQ ID NO 17
<211> LENGTH: 19
<212> TYPE: RNA
<213> ORGANISM: Homo sapiens

<400> SEQUENCE: 17
cacaaauugc uccaggggu                                                    19
```

```
<210> SEQ ID NO 18
<211> LENGTH: 19
<212> TYPE: RNA
<213> ORGANISM: Homo sapiens

<400> SEQUENCE: 18
uuuguggaga agucguccu                                                    19

<210> SEQ ID NO 19
<211> LENGTH: 19
<212> TYPE: RNA
<213> ORGANISM: Homo sapiens

<400> SEQUENCE: 19
aggacgacuu cuccacaaa                                                    19

<210> SEQ ID NO 20
<211> LENGTH: 19
<212> TYPE: RNA
<213> ORGANISM: Homo sapiens

<400> SEQUENCE: 20
gucguccugu gcccagccc                                                    19

<210> SEQ ID NO 21
<211> LENGTH: 19
<212> TYPE: RNA
<213> ORGANISM: Homo sapiens

<400> SEQUENCE: 21
gggcugggca caggacgac                                                    19

<210> SEQ ID NO 22
<211> LENGTH: 19
<212> TYPE: RNA
<213> ORGANISM: Homo sapiens

<400> SEQUENCE: 22
auggccaaaa uugccugca                                                    19

<210> SEQ ID NO 23
<211> LENGTH: 19
<212> TYPE: RNA
<213> ORGANISM: Homo sapiens

<400> SEQUENCE: 23
ugcaggcaau uuuggccau                                                    19

<210> SEQ ID NO 24
<211> LENGTH: 19
<212> TYPE: RNA
<213> ORGANISM: Homo sapiens

<400> SEQUENCE: 24
aauugccugc agccuggag                                                    19

<210> SEQ ID NO 25
<211> LENGTH: 19
<212> TYPE: RNA
<213> ORGANISM: Homo sapiens

<400> SEQUENCE: 25
cuccaggcug caggcaauu                                                    19
```

```
<210> SEQ ID NO 26
<211> LENGTH: 18
<212> TYPE: RNA
<213> ORGANISM: Homo sapiens

<400> SEQUENCE: 26
uugccugcag ccuggaga                                                   18

<210> SEQ ID NO 27
<211> LENGTH: 19
<212> TYPE: RNA
<213> ORGANISM: Homo sapiens

<400> SEQUENCE: 27
gucuccaggc ugcaggcaa                                                  19

<210> SEQ ID NO 28
<211> LENGTH: 19
<212> TYPE: RNA
<213> ORGANISM: Homo sapiens

<400> SEQUENCE: 28
ggagcuuugg gacaaauuc                                                  19

<210> SEQ ID NO 29
<211> LENGTH: 19
<212> TYPE: RNA
<213> ORGANISM: Homo sapiens

<400> SEQUENCE: 29
gaauuugucc caaagcucc                                                  19

<210> SEQ ID NO 30
<211> LENGTH: 19
<212> TYPE: RNA
<213> ORGANISM: Homo sapiens

<400> SEQUENCE: 30
auuccaugag cugggcacc                                                  19

<210> SEQ ID NO 31
<211> LENGTH: 19
<212> TYPE: RNA
<213> ORGANISM: Homo sapiens

<400> SEQUENCE: 31
ggugcccagc ucauggaau                                                  19

<210> SEQ ID NO 32
<211> LENGTH: 19
<212> TYPE: RNA
<213> ORGANISM: Homo sapiens

<400> SEQUENCE: 32
gucgggcagg aggauguuu                                                  19

<210> SEQ ID NO 33
<211> LENGTH: 19
<212> TYPE: RNA
<213> ORGANISM: Homo sapiens

<400> SEQUENCE: 33
aaacauccuc cugcccgac                                                  19
```

```
<210> SEQ ID NO 34
<211> LENGTH: 19
<212> TYPE: RNA
<213> ORGANISM: Homo sapiens

<400> SEQUENCE: 34
ccauccgggu guccuuuuc                                                    19

<210> SEQ ID NO 35
<211> LENGTH: 19
<212> TYPE: RNA
<213> ORGANISM: Homo sapiens

<400> SEQUENCE: 35
gaaaaggaca cccggaugg                                                    19

<210> SEQ ID NO 36
<211> LENGTH: 19
<212> TYPE: RNA
<213> ORGANISM: Homo sapiens

<400> SEQUENCE: 36
guacauaguc cugauggac                                                    19

<210> SEQ ID NO 37
<211> LENGTH: 19
<212> TYPE: RNA
<213> ORGANISM: Homo sapiens

<400> SEQUENCE: 37
guccaucagg acuauguac                                                    19

<210> SEQ ID NO 38
<211> LENGTH: 19
<212> TYPE: RNA
<213> ORGANISM: Homo sapiens

<400> SEQUENCE: 38
caagagguac cgcuacgcc                                                    19

<210> SEQ ID NO 39
<211> LENGTH: 19
<212> TYPE: RNA
<213> ORGANISM: Homo sapiens

<400> SEQUENCE: 39
ggcguagcgg uaccucuug                                                    19

<210> SEQ ID NO 40
<211> LENGTH: 19
<212> TYPE: RNA
<213> ORGANISM: Homo sapiens

<400> SEQUENCE: 40
gagguaccgc uacgccuac                                                    19

<210> SEQ ID NO 41
<211> LENGTH: 19
<212> TYPE: RNA
<213> ORGANISM: Homo sapiens

<400> SEQUENCE: 41
guaggcguag cgguaccuc                                                    19
```

```
<210> SEQ ID NO 42
<211> LENGTH: 19
<212> TYPE: RNA
<213> ORGANISM: Homo sapiens

<400> SEQUENCE: 42
ggccgacccg ccguugcca                                              19

<210> SEQ ID NO 43
<211> LENGTH: 19
<212> TYPE: RNA
<213> ORGANISM: Homo sapiens

<400> SEQUENCE: 43
uggcaacggc gggucggcc                                              19

<210> SEQ ID NO 44
<211> LENGTH: 19
<212> TYPE: RNA
<213> ORGANISM: Homo sapiens

<400> SEQUENCE: 44
cuacucaaac agauggugu                                              19

<210> SEQ ID NO 45
<211> LENGTH: 19
<212> TYPE: RNA
<213> ORGANISM: Homo sapiens

<400> SEQUENCE: 45
acaccaucug uuugaguag                                              19

<210> SEQ ID NO 46
<211> LENGTH: 19
<212> TYPE: RNA
<213> ORGANISM: Homo sapiens

<400> SEQUENCE: 46
acagauggug ucuuuugaa                                              19

<210> SEQ ID NO 47
<211> LENGTH: 19
<212> TYPE: RNA
<213> ORGANISM: Homo sapiens

<400> SEQUENCE: 47
uucaaaagac accaucugu                                              19

<210> SEQ ID NO 48
<211> LENGTH: 19
<212> TYPE: RNA
<213> ORGANISM: Homo sapiens

<400> SEQUENCE: 48
aaggugaaac ucaccaaca                                              19

<210> SEQ ID NO 49
<211> LENGTH: 19
<212> TYPE: RNA
<213> ORGANISM: Homo sapiens

<400> SEQUENCE: 49
uguuggugag uuucaccuu                                              19
```

-continued

```
<210> SEQ ID NO 50
<211> LENGTH: 19
<212> TYPE: RNA
<213> ORGANISM: Homo sapiens

<400> SEQUENCE: 50
ggugaaacuc accaacaau                                              19

<210> SEQ ID NO 51
<211> LENGTH: 19
<212> TYPE: RNA
<213> ORGANISM: Homo sapiens

<400> SEQUENCE: 51
auuguuggug aguuucacc                                              19

<210> SEQ ID NO 52
<211> LENGTH: 19
<212> TYPE: RNA
<213> ORGANISM: Homo sapiens

<400> SEQUENCE: 52
acucaccaac aaugaacug                                              19

<210> SEQ ID NO 53
<211> LENGTH: 19
<212> TYPE: RNA
<213> ORGANISM: Homo sapiens

<400> SEQUENCE: 53
caguucauug uuggugagu                                              19

<210> SEQ ID NO 54
<211> LENGTH: 19
<212> TYPE: RNA
<213> ORGANISM: Homo sapiens

<400> SEQUENCE: 54
caaugaacug gaucaacau                                              19

<210> SEQ ID NO 55
<211> LENGTH: 19
<212> TYPE: RNA
<213> ORGANISM: Homo sapiens

<400> SEQUENCE: 55
auguugaucc aguucauug                                              19

<210> SEQ ID NO 56
<211> LENGTH: 18
<212> TYPE: RNA
<213> ORGANISM: Homo sapiens

<400> SEQUENCE: 56
ugaacuggau caacaugg                                               18

<210> SEQ ID NO 57
<211> LENGTH: 19
<212> TYPE: RNA
<213> ORGANISM: Homo sapiens

<400> SEQUENCE: 57
gccauguuga uccaguuca                                              19
```

```
<210> SEQ ID NO 58
<211> LENGTH: 19
<212> TYPE: RNA
<213> ORGANISM: Homo sapiens

<400> SEQUENCE: 58
cuggaucaac auggccaua                                               19

<210> SEQ ID NO 59
<211> LENGTH: 19
<212> TYPE: RNA
<213> ORGANISM: Homo sapiens

<400> SEQUENCE: 59
uauggccaug uugauccag                                               19

<210> SEQ ID NO 60
<211> LENGTH: 19
<212> TYPE: RNA
<213> ORGANISM: Homo sapiens

<400> SEQUENCE: 60
cauggccaua uaauuuga                                                19

<210> SEQ ID NO 61
<211> LENGTH: 19
<212> TYPE: RNA
<213> ORGANISM: Homo sapiens

<400> SEQUENCE: 61
ucaaaauuau auggccaug                                               19

<210> SEQ ID NO 62
<211> LENGTH: 19
<212> TYPE: RNA
<213> ORGANISM: Homo sapiens

<400> SEQUENCE: 62
uuuugaacuc aaugcauaa                                               19

<210> SEQ ID NO 63
<211> LENGTH: 19
<212> TYPE: RNA
<213> ORGANISM: Homo sapiens

<400> SEQUENCE: 63
uuaugcauug aguucaaaa                                               19

<210> SEQ ID NO 64
<211> LENGTH: 19
<212> TYPE: RNA
<213> ORGANISM: Homo sapiens

<400> SEQUENCE: 64
cucaaugcau aaguaccag                                               19

<210> SEQ ID NO 65
<211> LENGTH: 19
<212> TYPE: RNA
<213> ORGANISM: Homo sapiens

<400> SEQUENCE: 65
cugguacuua ugcauugag                                               19
```

<210> SEQ ID NO 66
<211> LENGTH: 19
<212> TYPE: RNA
<213> ORGANISM: Homo sapiens

<400> SEQUENCE: 66
ugcauaagua ccagccaag                                                19

<210> SEQ ID NO 67
<211> LENGTH: 19
<212> TYPE: RNA
<213> ORGANISM: Homo sapiens

<400> SEQUENCE: 67
cuuggcuggu acuuaugca                                                19

<210> SEQ ID NO 68
<211> LENGTH: 19
<212> TYPE: RNA
<213> ORGANISM: Homo sapiens

<400> SEQUENCE: 68
guaccagcca agggugcac                                                19

<210> SEQ ID NO 69
<211> LENGTH: 19
<212> TYPE: RNA
<213> ORGANISM: Homo sapiens

<400> SEQUENCE: 69
gugcacccuu ggcugguac                                                19

<210> SEQ ID NO 70
<211> LENGTH: 19
<212> TYPE: RNA
<213> ORGANISM: Homo sapiens

<400> SEQUENCE: 70
gggugcacau cauuaagaa                                                19

<210> SEQ ID NO 71
<211> LENGTH: 19
<212> TYPE: RNA
<213> ORGANISM: Homo sapiens

<400> SEQUENCE: 71
uucuuaauga ugugcaccc                                                19

<210> SEQ ID NO 72
<211> LENGTH: 19
<212> TYPE: RNA
<213> ORGANISM: Homo sapiens

<400> SEQUENCE: 72
gaagaaagac cacacagcc                                                19

<210> SEQ ID NO 73
<211> LENGTH: 19
<212> TYPE: RNA
<213> ORGANISM: Homo sapiens

<400> SEQUENCE: 73
ggcugugugg ucuuucuuc                                                19

<210> SEQ ID NO 74
<211> LENGTH: 19
<212> TYPE: RNA
<213> ORGANISM: Homo sapiens

<400> SEQUENCE: 74
gaaagaccac acagccuca					19

<210> SEQ ID NO 75
<211> LENGTH: 19
<212> TYPE: RNA
<213> ORGANISM: Homo sapiens

<400> SEQUENCE: 75
ugaggcugug uggucuuuc					19

<210> SEQ ID NO 76
<211> LENGTH: 19
<212> TYPE: RNA
<213> ORGANISM: Homo sapiens

<400> SEQUENCE: 76
agaccacaca gccucauug					19

<210> SEQ ID NO 77
<211> LENGTH: 19
<212> TYPE: RNA
<213> ORGANISM: Homo sapiens

<400> SEQUENCE: 77
caaugaggcu guguggucu					19

<210> SEQ ID NO 78
<211> LENGTH: 19
<212> TYPE: RNA
<213> ORGANISM: Homo sapiens

<400> SEQUENCE: 78
ccugaagucu gaagaauuu					19

<210> SEQ ID NO 79
<211> LENGTH: 19
<212> TYPE: RNA
<213> ORGANISM: Homo sapiens

<400> SEQUENCE: 79
aaauucuuca gacuucagg					19

<210> SEQ ID NO 80
<211> LENGTH: 19
<212> TYPE: RNA
<213> ORGANISM: Homo sapiens

<400> SEQUENCE: 80
gucugaagaa uuuagaacu					19

<210> SEQ ID NO 81
<211> LENGTH: 19
<212> TYPE: RNA
<213> ORGANISM: Homo sapiens

<400> SEQUENCE: 81
aguucuaaau ucuucagac					19

<210> SEQ ID NO 82
<211> LENGTH: 19
<212> TYPE: RNA
<213> ORGANISM: Homo sapiens

<400> SEQUENCE: 82
gaauuuagaa cuuucaucu                                        19

<210> SEQ ID NO 83
<211> LENGTH: 19
<212> TYPE: RNA
<213> ORGANISM: Homo sapiens

<400> SEQUENCE: 83
agaugaaagu ucuaaauuc                                        19

<210> SEQ ID NO 84
<211> LENGTH: 19
<212> TYPE: RNA
<213> ORGANISM: Homo sapiens

<400> SEQUENCE: 84
uuuagaacuu ucaucuuuc                                        19

<210> SEQ ID NO 85
<211> LENGTH: 19
<212> TYPE: RNA
<213> ORGANISM: Homo sapiens

<400> SEQUENCE: 85
gaaagaugaa aguucuaaa                                        19

<210> SEQ ID NO 86
<211> LENGTH: 19
<212> TYPE: RNA
<213> ORGANISM: Homo sapiens

<400> SEQUENCE: 86
cuuucaucuu uccagaaac                                        19

<210> SEQ ID NO 87
<211> LENGTH: 19
<212> TYPE: RNA
<213> ORGANISM: Homo sapiens

<400> SEQUENCE: 87
guuucuggaa agaugaaag                                        19

<210> SEQ ID NO 88
<211> LENGTH: 19
<212> TYPE: RNA
<213> ORGANISM: Homo sapiens

<400> SEQUENCE: 88
acaguuuuua cggcaguca                                        19

<210> SEQ ID NO 89
<211> LENGTH: 19
<212> TYPE: RNA
<213> ORGANISM: Homo sapiens

<400> SEQUENCE: 89
ugacugccgu aaaaacugu                                        19

<210> SEQ ID NO 90
<211> LENGTH: 19
<212> TYPE: RNA
<213> ORGANISM: Homo sapiens

<400> SEQUENCE: 90
ucaacugaua acgaagcug                                            19

<210> SEQ ID NO 91
<211> LENGTH: 19
<212> TYPE: RNA
<213> ORGANISM: Homo sapiens

<400> SEQUENCE: 91
cagcuucguu aucaguuga                                            19

<210> SEQ ID NO 92
<211> LENGTH: 19
<212> TYPE: RNA
<213> ORGANISM: Homo sapiens

<400> SEQUENCE: 92
cugauaacga agcugaaaa                                            19

<210> SEQ ID NO 93
<211> LENGTH: 19
<212> TYPE: RNA
<213> ORGANISM: Homo sapiens

<400> SEQUENCE: 93
uuuucagcuu cguuaucag                                            19

<210> SEQ ID NO 94
<211> LENGTH: 19
<212> TYPE: RNA
<213> ORGANISM: Homo sapiens

<400> SEQUENCE: 94
cgaagcugaa aauagauag                                            19

<210> SEQ ID NO 95
<211> LENGTH: 19
<212> TYPE: RNA
<213> ORGANISM: Homo sapiens

<400> SEQUENCE: 95
cuaucuauuu ucagcuucg                                            19

<210> SEQ ID NO 96
<211> LENGTH: 19
<212> TYPE: RNA
<213> ORGANISM: Homo sapiens

<400> SEQUENCE: 96
gcugaaaaua gauagcaau                                            19

<210> SEQ ID NO 97
<211> LENGTH: 19
<212> TYPE: RNA
<213> ORGANISM: Homo sapiens

<400> SEQUENCE: 97
auugcuaucu auuuucagc                                            19

```
<210> SEQ ID NO 98
<211> LENGTH: 19
<212> TYPE: RNA
<213> ORGANISM: Homo sapiens

<400> SEQUENCE: 98
aauagauagc aauccuuuu                                                    19

<210> SEQ ID NO 99
<211> LENGTH: 19
<212> TYPE: RNA
<213> ORGANISM: Homo sapiens

<400> SEQUENCE: 99
aaaaggauug cuaucuauu                                                    19

<210> SEQ ID NO 100
<211> LENGTH: 19
<212> TYPE: RNA
<213> ORGANISM: Homo sapiens

<400> SEQUENCE: 100
uagauagcaa uccuuuugc                                                    19

<210> SEQ ID NO 101
<211> LENGTH: 19
<212> TYPE: RNA
<213> ORGANISM: Homo sapiens

<400> SEQUENCE: 101
gcaaaaggau ugcuaucua                                                    19

<210> SEQ ID NO 102
<211> LENGTH: 19
<212> TYPE: RNA
<213> ORGANISM: Homo sapiens

<400> SEQUENCE: 102
uccuuuugcc aaaggauuc                                                    19

<210> SEQ ID NO 103
<211> LENGTH: 19
<212> TYPE: RNA
<213> ORGANISM: Homo sapiens

<400> SEQUENCE: 103
gaauccuuug gcaaaagga                                                    19

<210> SEQ ID NO 104
<211> LENGTH: 19
<212> TYPE: RNA
<213> ORGANISM: Homo sapiens

<400> SEQUENCE: 104
aggauuccgg gauuccucc                                                    19

<210> SEQ ID NO 105
<211> LENGTH: 19
<212> TYPE: RNA
<213> ORGANISM: Homo sapiens

<400> SEQUENCE: 105
ggaggaaucc cggaauccu                                                    19
```

<210> SEQ ID NO 106
<211> LENGTH: 3396
<212> TYPE: DNA
<213> ORGANISM: Homo sapiens

<400> SEQUENCE: 106

```
cagagatcac gacaagatct aaccagtcgc gcgtggtccc cggcgccgga gcgggccagc      60
tcagcccggc ccagcccggc cccgcgcaga gccccgccg ccccgcgca cagagccggg       120 tgccccttgc ggtgcgccgg acgggaagcc ccgaggagca gctgctgcgc ccgccacccg     180
ggtcgtccgt ccaccgcgcg cgccgccgcc cgggccgggg gtccgagccg cgcgcccccg     240
gccccggccc cggcccccgg gcgcctgggc cggatgtccc gatgagagag ccggcgctgg     300
cggccagcgc catggcttac cacccgttcc acgcgccacg gccgccgac ttccccatgt      360 ccgcctttct ggcggcggcg cagccctcct tcttcccggc actcgcgctg ccgcccggcg     420
cgctggccaa gccgctgccc gacccgggcc tggcgggggc ggcggccgcg gcggcggcgg     480
cggcagcagc ggccgaggcg gggctgcacg tctcggcact gggcccgcac ccgcccgccg     540
cgcatctgcg ctccctcaag agcctggagc ccgaggacga ggtggaggac gaccccaagg     600
tgacgctgga ggccaaggag ctgtgggacc agttccacaa gctaggcacg gagatggtca     660
tcaccaagtc cgggaggcgg atgttccccc ccttcaaggt gcgagtcagc ggcctggaca     720
agaaggccaa gtatatcctg ctgatggaca ttgtagccgc tgacgattgc gctataagt      780 tccacaactc gcgctggatg gtggcgggca aggccgaccc tgagatgccc aaacgcatgt     840
acatccaccc agacagccca gccacggggg agcagtggat ggctaagcct gtggccttcc     900
acaagctgaa gctgaccaac aacatctctg acaagcacgg cttcaccatc ctaaactcca     960
tgcacaagta ccagccgcgc ttccacatag tgcgagccaa cgacatcctg aagctgcctt    1020
acagcacctt ccgcacctac gtgttcccgg agaccgactt catcgccgtc actgcctacc    1080
agaatgacaa gatcacacag ctgaagatcg acaacaaccc gtttgccaag ggcttccggg    1140
acaccgggaa cggccggcgg gagaaaagga agcagctgac gctgccgtct ctacgcttgt    1200
acgaggagca ctgcaaaccc gagcgcgatg gcgcggagtc agacgcctcg tcgtgcgacc    1260 ctcccccgc gcgggaacca cccacctccc cgggcgcagc gcccagtccg ctgcgcctgc    1320
accgggcccg agctgaggag aagtcgtgcg ccgcggacag cgacccggag cctgagcggt    1380
tgagcgagga gcgtgcgggg cgccgctag gccgcagccc ggctccagac agcgccagcc     1440
ccactcgctt gaccgaaccc gagcgcgccc gggagcggcg tagtcccgag aggggcaagg    1500
agccggccga gagcggcggg gacggcccgt tcggcctgag gagcctggag aaggagcgcg    1560
ccgaagctcg gaggaaggac gaggggcgca aggaggcggc cgagggcaag gagcagggcc    1620
tggcgccgct ggtggtgcag acagacagtg cgtcccccct gggcgccgga cacctgcccg    1680
gcctggcctt ttcagccac ttgcacgggc agcagttctt tgggccgctg ggagccggcc     1740
agccgctctt cctgcacccct ggacagttca ccatgggccc tggcgccttc tccgccatgg    1800
gcatgggtca cctactggcc tcggtggcag gcggcggcaa cggcggaggt ggcgggcctg    1860
ggaccgccgc ggggctggac gcaggcgggc tgggtcccgc ggccagcgca gcaagcaccg    1920
ccgcgccctt cccgttccac ctctcccagc acatgctgga atctcaggga attccaatgc    1980
ccactttcgg aggcctcttc ccctacccct acacctacat ggcagcagca gccgcagccg    2040
cctcggcttt gccgccact agtgctgcag ctgccgccgc cgcagccgcc ggctccctct    2100
cccggagccc cttcctgggc agtgcccggc cccgactgcg tttcagcccc tatcagatcc    2160
```

```
cggtcaccat cccgcctagc actagcctcc tcaccaccgg gctggcctct gagggctcca    2220
aggccgctgg tggaaacagc cgggagccta gcccctgcc cgagctggct ctccgcaaag     2280
taggggcccc atcccgcggt gccctgtcgc ccagtggctc ggccaaggag gcggccaatg    2340
aactgcagag catccagaga ctggtgagtg ggctggagag ccagcgagcc ctctccccag    2400
gccgggagtc gcccaagtga ggggctgccc agctgctccc ctgccacgca ggccacccgg    2460
gctgcctgcc cctgctgctt gggacgtgta cagcacagaa tgagtattta tttaaataaa    2520
ggagaaaagt gggctgcagc agccggaata gagcctcgtc tggcaagtcg gggcctggga    2580
cacttccctg ggcctcaaca aggatcaggc tgctggaaac acagtcactt gggagctgct    2640
gggctaggtc cagatccgct ccagcgtcaa ggtggcatcc gaaggtgtct ctggtcttcc    2700
agcgaggtgg gagaggcctc atccagggcc cagcggtccc tgcagaagcc agaaggtgca    2760
ggggccaggg gtgggagcat cggagggagt cccagagccc tggaccttgg gcctagaccg    2820
cgtgataaaa ctgggttgag ggatgctgga accagttacg actgaagtca gtgtagacct    2880
gagctgggag ggaacctgtt agtctcccca cctcttccct gaagagacag gcacccctcc    2940
cagccgtggt caacggaggg agtggcactt ctgccttgag tccccagggg aaaaaaaaaa    3000
aagatattta tgaaataaat ggtaatttgt gtaaataagc tttaaggttc ccagaatatg    3060
caaattggta ttaatttatt caaggtgta cattgctgtg tacatatatt tagagattaa     3120
ctcatacatt taaagttttt ttcattttac gtgagcatct atattgtaca gggctggggg    3180
ggcccttggc tgcgggagaa ggcccagagc cctggaggag ccaccacccc gccggccc ct   3240 cgaccctcg gcccctcggc cctccgccc gggtttggct cgcccggccc gcgggctcca      3300
cctcaggttt tcacttttcg ctccggagcg agaacgaaac gacaaaaacg caagaaaaca    3360
ataaaacgct agaaagcgaa aaaaaaaaaa aaaaaa                              3396

<210> SEQ ID NO 107
<211> LENGTH: 19
<212> TYPE: RNA
<213> ORGANISM: Homo sapiens

<400> SEQUENCE: 107
gaucuaacca gucgcgcgu                                                  19

<210> SEQ ID NO 108
<211> LENGTH: 19
<212> TYPE: RNA
<213> ORGANISM: Homo sapiens

<400> SEQUENCE: 108
acgcgcgacu gguuagauc                                                  19

<210> SEQ ID NO 109
<211> LENGTH: 19
<212> TYPE: RNA
<213> ORGANISM: Homo sapiens

<400> SEQUENCE: 109
ccagucgcgc gugguccc                                                   19

<210> SEQ ID NO 110
<211> LENGTH: 19
<212> TYPE: RNA
<213> ORGANISM: Homo sapiens

<400> SEQUENCE: 110
```

```
ggggaccacg cgcgacugg                                              19

<210> SEQ ID NO 111
<211> LENGTH: 19
<212> TYPE: RNA
<213> ORGANISM: Homo sapiens

<400> SEQUENCE: 111
gccccgagga gcagcugcu                                              19

<210> SEQ ID NO 112
<211> LENGTH: 19
<212> TYPE: RNA
<213> ORGANISM: Homo sapiens

<400> SEQUENCE: 112
agcagcugcu ccucggggc                                              19

<210> SEQ ID NO 113
<211> LENGTH: 19
<212> TYPE: RNA
<213> ORGANISM: Homo sapiens

<400> SEQUENCE: 113
gccgcugccc gacccgggc                                              19

<210> SEQ ID NO 114
<211> LENGTH: 19
<212> TYPE: RNA
<213> ORGANISM: Homo sapiens

<400> SEQUENCE: 114
gcccgggucg ggcagcggc                                              19

<210> SEQ ID NO 115
<211> LENGTH: 19
<212> TYPE: RNA
<213> ORGANISM: Homo sapiens

<400> SEQUENCE: 115
gagccuggag cccgaggac                                              19

<210> SEQ ID NO 116
<211> LENGTH: 19
<212> TYPE: RNA
<213> ORGANISM: Homo sapiens

<400> SEQUENCE: 116
guccucgggc uccaggcuc                                              19

<210> SEQ ID NO 117
<211> LENGTH: 19
<212> TYPE: RNA
<213> ORGANISM: Homo sapiens

<400> SEQUENCE: 117
ggugacgcug gaggccaag                                              19

<210> SEQ ID NO 118
<211> LENGTH: 19
<212> TYPE: RNA
<213> ORGANISM: Homo sapiens

<400> SEQUENCE: 118
```
cuuggccucc agcgucacc 19

<210> SEQ ID NO 119
<211> LENGTH: 19
<212> TYPE: RNA
<213> ORGANISM: Homo sapiens

<400> SEQUENCE: 119
ggagcugugg gaccaguuc 19

<210> SEQ ID NO 120
<211> LENGTH: 19
<212> TYPE: RNA
<213> ORGANISM: Homo sapiens

<400> SEQUENCE: 120
gaacuggucc cacagcucc 19

<210> SEQ ID NO 121
<211> LENGTH: 19
<212> TYPE: RNA
<213> ORGANISM: Homo sapiens

<400> SEQUENCE: 121
gcuaggcacg gagaugguc 19

<210> SEQ ID NO 122
<211> LENGTH: 19
<212> TYPE: RNA
<213> ORGANISM: Homo sapiens

<400> SEQUENCE: 122
gaccaucucc gugccuagc 19

<210> SEQ ID NO 123
<211> LENGTH: 19
<212> TYPE: RNA
<213> ORGANISM: Homo sapiens

<400> SEQUENCE: 123
guccgggagg cggauguuc 19

<210> SEQ ID NO 124
<211> LENGTH: 19
<212> TYPE: RNA
<213> ORGANISM: Homo sapiens

<400> SEQUENCE: 124
gaacauccgc cucccggac 19

<210> SEQ ID NO 125
<211> LENGTH: 19
<212> TYPE: RNA
<213> ORGANISM: Homo sapiens

<400> SEQUENCE: 125
ggugcgaguc agcggccug 19

<210> SEQ ID NO 126
<211> LENGTH: 19
<212> TYPE: RNA
<213> ORGANISM: Homo sapiens

<400> SEQUENCE: 126

-continued caggccgcug acucgcacc                                    19

<210> SEQ ID NO 127
<211> LENGTH: 19
<212> TYPE: RNA
<213> ORGANISM: Homo sapiens

<400> SEQUENCE: 127
gaaggccaag uauauccug                                    19

<210> SEQ ID NO 128
<211> LENGTH: 19
<212> TYPE: RNA
<213> ORGANISM: Homo sapiens

<400> SEQUENCE: 128
caggauauac uuggccuuc                                    19

<210> SEQ ID NO 129
<211> LENGTH: 19
<212> TYPE: RNA
<213> ORGANISM: Homo sapiens

<400> SEQUENCE: 129
ggccaaguau auccgcug                                     19

<210> SEQ ID NO 130
<211> LENGTH: 19
<212> TYPE: RNA
<213> ORGANISM: Homo sapiens

<400> SEQUENCE: 130
cagcaggaua uacuuggcc                                    19

<210> SEQ ID NO 131
<211> LENGTH: 19
<212> TYPE: RNA
<213> ORGANISM: Homo sapiens

<400> SEQUENCE: 131
guauauccug cugauggac                                    19

<210> SEQ ID NO 132
<211> LENGTH: 19
<212> TYPE: RNA
<213> ORGANISM: Homo sapiens

<400> SEQUENCE: 132
guccaucagc aggauauac                                    19

<210> SEQ ID NO 133
<211> LENGTH: 19
<212> TYPE: RNA
<213> ORGANISM: Homo sapiens

<400> SEQUENCE: 133
guuccacaac ucgcgcugg                                    19

<210> SEQ ID NO 134
<211> LENGTH: 19
<212> TYPE: RNA
<213> ORGANISM: Homo sapiens

<400> SEQUENCE: 134
ccagcgcgag uuguggaac                                                19

<210> SEQ ID NO 135
<211> LENGTH: 19
<212> TYPE: RNA
<213> ORGANISM: Homo sapiens

<400> SEQUENCE: 135
cucgcgcugg augguggcg                                                19

<210> SEQ ID NO 136
<211> LENGTH: 19
<212> TYPE: RNA
<213> ORGANISM: Homo sapiens

<400> SEQUENCE: 136
cgccaccauc cagcgcgag                                                19

<210> SEQ ID NO 137
<211> LENGTH: 19
<212> TYPE: RNA
<213> ORGANISM: Homo sapiens

<400> SEQUENCE: 137
ggccgacccu gagaugccc                                                19

<210> SEQ ID NO 138
<211> LENGTH: 19
<212> TYPE: RNA
<213> ORGANISM: Homo sapiens

<400> SEQUENCE: 138
gggcaucuca gggucggcc                                                19

<210> SEQ ID NO 139
<211> LENGTH: 19
<212> TYPE: RNA
<213> ORGANISM: Homo sapiens

<400> SEQUENCE: 139
acgcauguac auccaccca                                                19

<210> SEQ ID NO 140
<211> LENGTH: 19
<212> TYPE: RNA
<213> ORGANISM: Homo sapiens

<400> SEQUENCE: 140
uggguggaug uacaugcgu                                                19

<210> SEQ ID NO 141
<211> LENGTH: 19
<212> TYPE: RNA
<213> ORGANISM: Homo sapiens

<400> SEQUENCE: 141
gccuguggcc uuccacaag                                                19

<210> SEQ ID NO 142
<211> LENGTH: 19
<212> TYPE: RNA
<213> ORGANISM: Homo sapiens

<400> SEQUENCE: 142
cuuguggaag gccacaggc                          19

<210> SEQ ID NO 143
<211> LENGTH: 19
<212> TYPE: RNA
<213> ORGANISM: Homo sapiens

<400> SEQUENCE: 143
gcugaagcug accaacaac                          19

<210> SEQ ID NO 144
<211> LENGTH: 19
<212> TYPE: RNA
<213> ORGANISM: Homo sapiens

<400> SEQUENCE: 144
guuguugguc agcuucagc                          19

<210> SEQ ID NO 145
<211> LENGTH: 19
<212> TYPE: RNA
<213> ORGANISM: Homo sapiens

<400> SEQUENCE: 145
gcugaccaac aacaucucu                          19

<210> SEQ ID NO 146
<211> LENGTH: 19
<212> TYPE: RNA
<213> ORGANISM: Homo sapiens

<400> SEQUENCE: 146
agagauguug uuggucagc                          19

<210> SEQ ID NO 147
<211> LENGTH: 19
<212> TYPE: RNA
<213> ORGANISM: Homo sapiens

<400> SEQUENCE: 147
caacaucucu gacaagcac                          19

<210> SEQ ID NO 148
<211> LENGTH: 19
<212> TYPE: RNA
<213> ORGANISM: Homo sapiens

<400> SEQUENCE: 148
gugcuuguca gagauguug                          19

<210> SEQ ID NO 149
<211> LENGTH: 19
<212> TYPE: RNA
<213> ORGANISM: Homo sapiens

<400> SEQUENCE: 149
caucucugac aagcacggc                          19

<210> SEQ ID NO 150
<211> LENGTH: 19
<212> TYPE: RNA
<213> ORGANISM: Homo sapiens

<400> SEQUENCE: 150

```
gccgugcuug ucagagaug                                              19

<210> SEQ ID NO 151
<211> LENGTH: 19
<212> TYPE: RNA
<213> ORGANISM: Homo sapiens

<400> SEQUENCE: 151
gcacggcuuc accauccua                                              19

<210> SEQ ID NO 152
<211> LENGTH: 19
<212> TYPE: RNA
<213> ORGANISM: Homo sapiens

<400> SEQUENCE: 152
uaggauggug aagccgugc                                              19

<210> SEQ ID NO 153
<211> LENGTH: 19
<212> TYPE: RNA
<213> ORGANISM: Homo sapiens

<400> SEQUENCE: 153
acuccaugca caaguacca                                              19

<210> SEQ ID NO 154
<211> LENGTH: 19
<212> TYPE: RNA
<213> ORGANISM: Homo sapiens

<400> SEQUENCE: 154
ugguacuugu gcauggagu                                              19

<210> SEQ ID NO 155
<211> LENGTH: 19
<212> TYPE: RNA
<213> ORGANISM: Homo sapiens

<400> SEQUENCE: 155
guaccagccg cgcuuccac                                              19

<210> SEQ ID NO 156
<211> LENGTH: 19
<212> TYPE: RNA
<213> ORGANISM: Homo sapiens

<400> SEQUENCE: 156
guggaagcgc ggcugguac                                              19

<210> SEQ ID NO 157
<211> LENGTH: 19
<212> TYPE: RNA
<213> ORGANISM: Homo sapiens

<400> SEQUENCE: 157
cgacauccug aagcugccu                                              19

<210> SEQ ID NO 158
<211> LENGTH: 19
<212> TYPE: RNA
<213> ORGANISM: Homo sapiens

<400> SEQUENCE: 158
```
aggcagcuuc aggaugucg                                              19

<210> SEQ ID NO 159
<211> LENGTH: 19
<212> TYPE: RNA
<213> ORGANISM: Homo sapiens

<400> SEQUENCE: 159
gcugccuuac agcaccuuc                                              19

<210> SEQ ID NO 160
<211> LENGTH: 19
<212> TYPE: RNA
<213> ORGANISM: Homo sapiens

<400> SEQUENCE: 160
gaaggugcug uaaggcagc                                              19

<210> SEQ ID NO 161
<211> LENGTH: 19
<212> TYPE: RNA
<213> ORGANISM: Homo sapiens

<400> SEQUENCE: 161
ugacaagauc acacagcug                                              19

<210> SEQ ID NO 162
<211> LENGTH: 19
<212> TYPE: RNA
<213> ORGANISM: Homo sapiens

<400> SEQUENCE: 162
cagcugugug aucuuguca                                              19

<210> SEQ ID NO 163
<211> LENGTH: 19
<212> TYPE: RNA
<213> ORGANISM: Homo sapiens

<400> SEQUENCE: 163
gaucacacag cugaagauc                                              19

<210> SEQ ID NO 164
<211> LENGTH: 19
<212> TYPE: RNA
<213> ORGANISM: Homo sapiens

<400> SEQUENCE: 164
gaucuucagc ugugugauc                                              19

<210> SEQ ID NO 165
<211> LENGTH: 19
<212> TYPE: RNA
<213> ORGANISM: Homo sapiens

<400> SEQUENCE: 165
gaucgacaac aacccguuu                                              19

<210> SEQ ID NO 166
<211> LENGTH: 19
<212> TYPE: RNA
<213> ORGANISM: Homo sapiens

<400> SEQUENCE: 166
aaacggguug uugucgauc 19

<210> SEQ ID NO 167
<211> LENGTH: 19
<212> TYPE: RNA
<213> ORGANISM: Homo sapiens

<400> SEQUENCE: 167
caacccguuu gccaagggc 19

<210> SEQ ID NO 168
<211> LENGTH: 19
<212> TYPE: RNA
<213> ORGANISM: Homo sapiens

<400> SEQUENCE: 168
gcccuuggca aacggguug 19

<210> SEQ ID NO 169
<211> LENGTH: 19
<212> TYPE: RNA
<213> ORGANISM: Homo sapiens

<400> SEQUENCE: 169
cccguuugcc aagggcuuc 19

<210> SEQ ID NO 170
<211> LENGTH: 19
<212> TYPE: RNA
<213> ORGANISM: Homo sapiens

<400> SEQUENCE: 170
gaagcccuug gcaaacggg 19

<210> SEQ ID NO 171
<211> LENGTH: 19
<212> TYPE: RNA
<213> ORGANISM: Homo sapiens

<400> SEQUENCE: 171
gggcuuccgg gacaccggg 19

<210> SEQ ID NO 172
<211> LENGTH: 19
<212> TYPE: RNA
<213> ORGANISM: Homo sapiens

<400> SEQUENCE: 172 cccgugucc cggaagccc 19

<210> SEQ ID NO 173
<211> LENGTH: 19
<212> TYPE: RNA
<213> ORGANISM: Homo sapiens

<400> SEQUENCE: 173
cggccggcgg gagaaaagg 19

<210> SEQ ID NO 174
<211> LENGTH: 19
<212> TYPE: RNA
<213> ORGANISM: Homo sapiens

<400> SEQUENCE: 174
ccuuuucucc cgccggccg                                                19

<210> SEQ ID NO 175
<211> LENGTH: 19
<212> TYPE: RNA
<213> ORGANISM: Homo sapiens

<400> SEQUENCE: 175
aaggaagcag cugacgcug                                                19

<210> SEQ ID NO 176
<211> LENGTH: 19
<212> TYPE: RNA
<213> ORGANISM: Homo sapiens

<400> SEQUENCE: 176
cagcgucagc ugcuuccuu                                                19

<210> SEQ ID NO 177
<211> LENGTH: 19
<212> TYPE: RNA
<213> ORGANISM: Homo sapiens

<400> SEQUENCE: 177
ggaagcagcu gacgcugcc                                                19

<210> SEQ ID NO 178
<211> LENGTH: 19
<212> TYPE: RNA
<213> ORGANISM: Homo sapiens

<400> SEQUENCE: 178
ggcagcguca gcugcuucc                                                19

<210> SEQ ID NO 179
<211> LENGTH: 19
<212> TYPE: RNA
<213> ORGANISM: Homo sapiens

<400> SEQUENCE: 179
gcagcugacg cugccgucu                                                19

<210> SEQ ID NO 180
<211> LENGTH: 19
<212> TYPE: RNA
<213> ORGANISM: Homo sapiens

<400> SEQUENCE: 180
agacggcagc gucagcugc                                                19

<210> SEQ ID NO 181
<211> LENGTH: 19
<212> TYPE: RNA
<213> ORGANISM: Homo sapiens

<400> SEQUENCE: 181
acccgagcgc gauggcgcg                                                19

<210> SEQ ID NO 182
<211> LENGTH: 19
<212> TYPE: RNA
<213> ORGANISM: Homo sapiens

<400> SEQUENCE: 182

| | |
|---|---|
| cgcgccaucg cgcucgggu | 19 |

\<210\> SEQ ID NO 183
\<211\> LENGTH: 19
\<212\> TYPE: RNA
\<213\> ORGANISM: Homo sapiens

\<400\> SEQUENCE: 183

| | |
|---|---|
| ccacccaccu ccccgggcg | 19 |

\<210\> SEQ ID NO 184
\<211\> LENGTH: 19
\<212\> TYPE: RNA
\<213\> ORGANISM: Homo sapiens

\<400\> SEQUENCE: 184

| | |
|---|---|
| cgcccggga ggugggugg | 19 |

\<210\> SEQ ID NO 185
\<211\> LENGTH: 19
\<212\> TYPE: RNA
\<213\> ORGANISM: Homo sapiens

\<400\> SEQUENCE: 185

| | |
|---|---|
| gucgugcgcc gcggacagc | 19 |

\<210\> SEQ ID NO 186
\<211\> LENGTH: 19
\<212\> TYPE: RNA
\<213\> ORGANISM: Homo sapiens

\<400\> SEQUENCE: 186

| | |
|---|---|
| gcuguccgcg gcgcacgac | 19 |

\<210\> SEQ ID NO 187
\<211\> LENGTH: 19
\<212\> TYPE: RNA
\<213\> ORGANISM: Homo sapiens

\<400\> SEQUENCE: 187

| | |
|---|---|
| cccgagcgcg cccgggagc | 19 |

\<210\> SEQ ID NO 188
\<211\> LENGTH: 19
\<212\> TYPE: RNA
\<213\> ORGANISM: Homo sapiens

\<400\> SEQUENCE: 188

| | |
|---|---|
| gcuccccgggc gcgcucggg | 19 |

\<210\> SEQ ID NO 189
\<211\> LENGTH: 19
\<212\> TYPE: RNA
\<213\> ORGANISM: Homo sapiens

\<400\> SEQUENCE: 189

| | |
|---|---|
| ggagccggcc gagagcggc | 19 |

\<210\> SEQ ID NO 190
\<211\> LENGTH: 19
\<212\> TYPE: RNA
\<213\> ORGANISM: Homo sapiens

\<400\> SEQUENCE: 190

```
gccgcucucg gccggcucc                                              19
```

<210> SEQ ID NO 191
<211> LENGTH: 19
<212> TYPE: RNA
<213> ORGANISM: Homo sapiens

<400> SEQUENCE: 191

```
ggagcgcgcc gaagcucgg                                              19
```

<210> SEQ ID NO 192
<211> LENGTH: 19
<212> TYPE: RNA
<213> ORGANISM: Homo sapiens

<400> SEQUENCE: 192

```
ccgagcuucg gcgcgcucc                                              19
```

<210> SEQ ID NO 193
<211> LENGTH: 19
<212> TYPE: RNA
<213> ORGANISM: Homo sapiens

<400> SEQUENCE: 193

```
gcucggagga aggacgagg                                              19
```

<210> SEQ ID NO 194
<211> LENGTH: 19
<212> TYPE: RNA
<213> ORGANISM: Homo sapiens

<400> SEQUENCE: 194

```
ccucguccuu ccuccgagc                                              19
```

<210> SEQ ID NO 195
<211> LENGTH: 19
<212> TYPE: RNA
<213> ORGANISM: Homo sapiens

<400> SEQUENCE: 195

```
ggacgagggg cgcaaggag                                              19
```

<210> SEQ ID NO 196
<211> LENGTH: 19
<212> TYPE: RNA
<213> ORGANISM: Homo sapiens

<400> SEQUENCE: 196

```
cuccuugcgc cccucgucc                                              19
```

<210> SEQ ID NO 197
<211> LENGTH: 19
<212> TYPE: RNA
<213> ORGANISM: Homo sapiens

<400> SEQUENCE: 197

```
ggaggcggcc gagggcaag                                              19
```

<210> SEQ ID NO 198
<211> LENGTH: 19
<212> TYPE: RNA
<213> ORGANISM: Homo sapiens

<400> SEQUENCE: 198

```
cuugcccucg gccgccucc                                                    19

<210> SEQ ID NO 199
<211> LENGTH: 19
<212> TYPE: RNA
<213> ORGANISM: Homo sapiens

<400> SEQUENCE: 199
ggagcagggc cuggcgccg                                                    19

<210> SEQ ID NO 200
<211> LENGTH: 19
<212> TYPE: RNA
<213> ORGANISM: Homo sapiens

<400> SEQUENCE: 200
cggcgccagg cccugcucc                                                    19

<210> SEQ ID NO 201
<211> LENGTH: 19
<212> TYPE: RNA
<213> ORGANISM: Homo sapiens

<400> SEQUENCE: 201
cggcggaggu ggcgggccu                                                    19

<210> SEQ ID NO 202
<211> LENGTH: 19
<212> TYPE: RNA
<213> ORGANISM: Homo sapiens

<400> SEQUENCE: 202
aggcccgcca ccuccgccg                                                    19

<210> SEQ ID NO 203
<211> LENGTH: 19
<212> TYPE: RNA
<213> ORGANISM: Homo sapiens

<400> SEQUENCE: 203
gcaccgccgc gcccuuccc                                                    19

<210> SEQ ID NO 204
<211> LENGTH: 19
<212> TYPE: RNA
<213> ORGANISM: Homo sapiens

<400> SEQUENCE: 204
gggaagggcg cggcggugc                                                    19

<210> SEQ ID NO 205
<211> LENGTH: 19
<212> TYPE: RNA
<213> ORGANISM: Homo sapiens

<400> SEQUENCE: 205
uuccaaugcc cacuuucgg                                                    19

<210> SEQ ID NO 206
<211> LENGTH: 19
<212> TYPE: RNA
<213> ORGANISM: Homo sapiens

<400> SEQUENCE: 206
```

-continued

```
ccgaaagugg gcauuggaa                                          19

<210> SEQ ID NO 207
<211> LENGTH: 19
<212> TYPE: RNA
<213> ORGANISM: Homo sapiens

<400> SEQUENCE: 207
ugcccacuuu cggaggccu                                          19

<210> SEQ ID NO 208
<211> LENGTH: 19
<212> TYPE: RNA
<213> ORGANISM: Homo sapiens

<400> SEQUENCE: 208
aggccuccga aagugggca                                          19

<210> SEQ ID NO 209
<211> LENGTH: 19
<212> TYPE: RNA
<213> ORGANISM: Homo sapiens

<400> SEQUENCE: 209
ggccgcuggu ggaaacagc                                          19

<210> SEQ ID NO 210
<211> LENGTH: 19
<212> TYPE: RNA
<213> ORGANISM: Homo sapiens

<400> SEQUENCE: 210
gcuguuucca ccagcggcc                                          19

<210> SEQ ID NO 211
<211> LENGTH: 19
<212> TYPE: RNA
<213> ORGANISM: Homo sapiens

<400> SEQUENCE: 211
acagccggga gccuagccc                                          19

<210> SEQ ID NO 212
<211> LENGTH: 19
<212> TYPE: RNA
<213> ORGANISM: Homo sapiens

<400> SEQUENCE: 212
gggcuaggcu cccggcugu                                          19

<210> SEQ ID NO 213
<211> LENGTH: 19
<212> TYPE: RNA
<213> ORGANISM: Homo sapiens

<400> SEQUENCE: 213
aguaggggcc ccaucccgc                                          19

<210> SEQ ID NO 214
<211> LENGTH: 19
<212> TYPE: RNA
<213> ORGANISM: Homo sapiens

<400> SEQUENCE: 214
```

-continued gcgggauggg gccccuacu                                                19

<210> SEQ ID NO 215
<211> LENGTH: 19
<212> TYPE: RNA
<213> ORGANISM: Homo sapiens

<400> SEQUENCE: 215
ggaggcggcc aaugaacug                                                19

<210> SEQ ID NO 216
<211> LENGTH: 19
<212> TYPE: RNA
<213> ORGANISM: Homo sapiens

<400> SEQUENCE: 216
caguucauug gccgccucc                                                19

<210> SEQ ID NO 217
<211> LENGTH: 19
<212> TYPE: RNA
<213> ORGANISM: Homo sapiens

<400> SEQUENCE: 217
ugaacugcag agcauccag                                                19

<210> SEQ ID NO 218
<211> LENGTH: 19
<212> TYPE: RNA
<213> ORGANISM: Homo sapiens

<400> SEQUENCE: 218
cuggaugcuc ugcaguuca                                                19

<210> SEQ ID NO 219
<211> LENGTH: 19
<212> TYPE: RNA
<213> ORGANISM: Homo sapiens

<400> SEQUENCE: 219
cugcagagca uccagagac                                                19

<210> SEQ ID NO 220
<211> LENGTH: 19
<212> TYPE: RNA
<213> ORGANISM: Homo sapiens

<400> SEQUENCE: 220
gucucuggau gcucugcag                                                19

<210> SEQ ID NO 221
<211> LENGTH: 19
<212> TYPE: RNA
<213> ORGANISM: Homo sapiens

<400> SEQUENCE: 221
gugaggggcu gcccagcug                                                19

<210> SEQ ID NO 222
<211> LENGTH: 19
<212> TYPE: RNA
<213> ORGANISM: Homo sapiens

<400> SEQUENCE: 222
cagcugggca gccccucac                                             19

<210> SEQ ID NO 223
<211> LENGTH: 19
<212> TYPE: RNA
<213> ORGANISM: Homo sapiens

<400> SEQUENCE: 223
ugaguauuua uuuaaauaa                                             19

<210> SEQ ID NO 224
<211> LENGTH: 19
<212> TYPE: RNA
<213> ORGANISM: Homo sapiens

<400> SEQUENCE: 224
uuauuuaaau aaauacuca                                             19

<210> SEQ ID NO 225
<211> LENGTH: 19
<212> TYPE: RNA
<213> ORGANISM: Homo sapiens

<400> SEQUENCE: 225
auaaaggaga aaagugggc                                             19

<210> SEQ ID NO 226
<211> LENGTH: 19
<212> TYPE: RNA
<213> ORGANISM: Homo sapiens

<400> SEQUENCE: 226
gcccacuuuu cuccuuuau                                             19

<210> SEQ ID NO 227
<211> LENGTH: 19
<212> TYPE: RNA
<213> ORGANISM: Homo sapiens

<400> SEQUENCE: 227
aggagaaaag ugggcugca                                             19

<210> SEQ ID NO 228
<211> LENGTH: 19
<212> TYPE: RNA
<213> ORGANISM: Homo sapiens

<400> SEQUENCE: 228
ugcagcccac uuuucuccu                                             19

<210> SEQ ID NO 229
<211> LENGTH: 19
<212> TYPE: RNA
<213> ORGANISM: Homo sapiens

<400> SEQUENCE: 229
aagugggcug cagcagccg                                             19

<210> SEQ ID NO 230
<211> LENGTH: 19
<212> TYPE: RNA
<213> ORGANISM: Homo sapiens

<400> SEQUENCE: 230

```
cggcugcugc agcccacuu                                                19

<210> SEQ ID NO 231
<211> LENGTH: 19
<212> TYPE: RNA
<213> ORGANISM: Homo sapiens

<400> SEQUENCE: 231
gugggcugca gcagccgga                                                19

<210> SEQ ID NO 232
<211> LENGTH: 19
<212> TYPE: RNA
<213> ORGANISM: Homo sapiens

<400> SEQUENCE: 232
uccggcugcu gcagcccac                                                19

<210> SEQ ID NO 233
<211> LENGTH: 19
<212> TYPE: RNA
<213> ORGANISM: Homo sapiens

<400> SEQUENCE: 233
uagagccucg ucuggcaag                                                19

<210> SEQ ID NO 234
<211> LENGTH: 19
<212> TYPE: RNA
<213> ORGANISM: Homo sapiens

<400> SEQUENCE: 234
cuugccagac gaggcucua                                                19

<210> SEQ ID NO 235
<211> LENGTH: 19
<212> TYPE: RNA
<213> ORGANISM: Homo sapiens

<400> SEQUENCE: 235
gucggggccu gggacacuu                                                19

<210> SEQ ID NO 236
<211> LENGTH: 19
<212> TYPE: RNA
<213> ORGANISM: Homo sapiens

<400> SEQUENCE: 236
aagugcccca ggccccgac                                                19

<210> SEQ ID NO 237
<211> LENGTH: 19
<212> TYPE: RNA
<213> ORGANISM: Homo sapiens

<400> SEQUENCE: 237
caaggaucag gcugcugga                                                19

<210> SEQ ID NO 238
<211> LENGTH: 19
<212> TYPE: RNA
<213> ORGANISM: Homo sapiens

<400> SEQUENCE: 238
```

```
uccagcagcc ugauccuug                                                19

<210> SEQ ID NO 239
<211> LENGTH: 19
<212> TYPE: RNA
<213> ORGANISM: Homo sapiens

<400> SEQUENCE: 239
ggaucaggcu gcuggaaac                                                19

<210> SEQ ID NO 240
<211> LENGTH: 19
<212> TYPE: RNA
<213> ORGANISM: Homo sapiens

<400> SEQUENCE: 240 guuccagca gccugaucc                                                 19

<210> SEQ ID NO 241
<211> LENGTH: 19
<212> TYPE: RNA
<213> ORGANISM: Homo sapiens

<400> SEQUENCE: 241
acacagucac uugggagcu                                                19

<210> SEQ ID NO 242
<211> LENGTH: 19
<212> TYPE: RNA
<213> ORGANISM: Homo sapiens

<400> SEQUENCE: 242
agcucccaag ugacugugu                                                19

<210> SEQ ID NO 243
<211> LENGTH: 19
<212> TYPE: RNA
<213> ORGANISM: Homo sapiens

<400> SEQUENCE: 243
gguggcaucc gaagguguc                                                19

<210> SEQ ID NO 244
<211> LENGTH: 19
<212> TYPE: RNA
<213> ORGANISM: Homo sapiens

<400> SEQUENCE: 244
gacaccuucg gaugccacc                                                19

<210> SEQ ID NO 245
<211> LENGTH: 19
<212> TYPE: RNA
<213> ORGANISM: Homo sapiens

<400> SEQUENCE: 245
ggugucucug gucuuccag                                                19

<210> SEQ ID NO 246
<211> LENGTH: 19
<212> TYPE: RNA
<213> ORGANISM: Homo sapiens

<400> SEQUENCE: 246
```

-continued cuggaagacc agagacacc                                         19

<210> SEQ ID NO 247
<211> LENGTH: 19
<212> TYPE: RNA
<213> ORGANISM: Homo sapiens

<400> SEQUENCE: 247
gccagaaggu gcaggggcc                                         19

<210> SEQ ID NO 248
<211> LENGTH: 19
<212> TYPE: RNA
<213> ORGANISM: Homo sapiens

<400> SEQUENCE: 248
ggccccugca ccuucuggc                                         19

<210> SEQ ID NO 249
<211> LENGTH: 19
<212> TYPE: RNA
<213> ORGANISM: Homo sapiens

<400> SEQUENCE: 249
ggugcagggg ccaggggug                                         19

<210> SEQ ID NO 250
<211> LENGTH: 19
<212> TYPE: RNA
<213> ORGANISM: Homo sapiens

<400> SEQUENCE: 250
caccccuggc cccugcacc                                         19

<210> SEQ ID NO 251
<211> LENGTH: 19
<212> TYPE: RNA
<213> ORGANISM: Homo sapiens

<400> SEQUENCE: 251
aacuggguug agggaugcu                                         19

<210> SEQ ID NO 252
<211> LENGTH: 19
<212> TYPE: RNA
<213> ORGANISM: Homo sapiens

<400> SEQUENCE: 252
agcaucccuc aacccaguu                                         19

<210> SEQ ID NO 253
<211> LENGTH: 19
<212> TYPE: RNA
<213> ORGANISM: Homo sapiens

<400> SEQUENCE: 253
cuggguugag ggaugcugg                                         19

<210> SEQ ID NO 254
<211> LENGTH: 19
<212> TYPE: RNA
<213> ORGANISM: Homo sapiens

<400> SEQUENCE: 254
ccagcauccc ucaacccag                                              19

<210> SEQ ID NO 255
<211> LENGTH: 19
<212> TYPE: RNA
<213> ORGANISM: Homo sapiens

<400> SEQUENCE: 255
ccaguuacga cugaaguca                                              19

<210> SEQ ID NO 256
<211> LENGTH: 19
<212> TYPE: RNA
<213> ORGANISM: Homo sapiens

<400> SEQUENCE: 256
ugacuucagu cguaacugg                                              19

<210> SEQ ID NO 257
<211> LENGTH: 19
<212> TYPE: RNA
<213> ORGANISM: Homo sapiens

<400> SEQUENCE: 257
gucaguguag accugagcu                                              19

<210> SEQ ID NO 258
<211> LENGTH: 19
<212> TYPE: RNA
<213> ORGANISM: Homo sapiens

<400> SEQUENCE: 258
agcucagguc uacacugac                                              19

<210> SEQ ID NO 259
<211> LENGTH: 19
<212> TYPE: RNA
<213> ORGANISM: Homo sapiens

<400> SEQUENCE: 259
ccuguuaguc uccccaccu                                              19

<210> SEQ ID NO 260
<211> LENGTH: 19
<212> TYPE: RNA
<213> ORGANISM: Homo sapiens

<400> SEQUENCE: 260 aggugggag acuaacagg                                               19

<210> SEQ ID NO 261
<211> LENGTH: 19
<212> TYPE: RNA
<213> ORGANISM: Homo sapiens

<400> SEQUENCE: 261
gagacaggca ccccuccca                                              19

<210> SEQ ID NO 262
<211> LENGTH: 19
<212> TYPE: RNA
<213> ORGANISM: Homo sapiens

<400> SEQUENCE: 262

```
ugggaggggu gccugucuc                                              19

<210> SEQ ID NO 263
<211> LENGTH: 19
<212> TYPE: RNA
<213> ORGANISM: Homo sapiens

<400> SEQUENCE: 263
cggagggagu ggcacuucu                                              19

<210> SEQ ID NO 264
<211> LENGTH: 19
<212> TYPE: RNA
<213> ORGANISM: Homo sapiens

<400> SEQUENCE: 264
agaagugcca cucccuccg                                              19

<210> SEQ ID NO 265
<211> LENGTH: 19
<212> TYPE: RNA
<213> ORGANISM: Homo sapiens

<400> SEQUENCE: 265
aaaaaaaaaa gauauuuau                                              19

<210> SEQ ID NO 266
<211> LENGTH: 19
<212> TYPE: RNA
<213> ORGANISM: Homo sapiens

<400> SEQUENCE: 266
auaaauaucu uuuuuuuu                                               19

<210> SEQ ID NO 267
<211> LENGTH: 19
<212> TYPE: RNA
<213> ORGANISM: Homo sapiens

<400> SEQUENCE: 267 aaaaaaaga uauuuauga                                               19

<210> SEQ ID NO 268
<211> LENGTH: 19
<212> TYPE: RNA
<213> ORGANISM: Homo sapiens

<400> SEQUENCE: 268
ucauaaauau cuuuuuuuu                                              19

<210> SEQ ID NO 269
<211> LENGTH: 19
<212> TYPE: RNA
<213> ORGANISM: Homo sapiens

<400> SEQUENCE: 269 aaaaagaua uuuaugaaa                                               19

<210> SEQ ID NO 270
<211> LENGTH: 19
<212> TYPE: RNA
<213> ORGANISM: Homo sapiens

<400> SEQUENCE: 270
```
uuucauaaau aucuuuuuu       19

<210> SEQ ID NO 271
<211> LENGTH: 19
<212> TYPE: RNA
<213> ORGANISM: Homo sapiens

<400> SEQUENCE: 271
aaaagauauu uaugaaaua       19

<210> SEQ ID NO 272
<211> LENGTH: 19
<212> TYPE: RNA
<213> ORGANISM: Homo sapiens

<400> SEQUENCE: 272
uauuucauaa auaucuuuu       19

<210> SEQ ID NO 273
<211> LENGTH: 19
<212> TYPE: RNA
<213> ORGANISM: Homo sapiens

<400> SEQUENCE: 273
aagauauuua ugaauaaa        19

<210> SEQ ID NO 274
<211> LENGTH: 19
<212> TYPE: RNA
<213> ORGANISM: Homo sapiens

<400> SEQUENCE: 274
uuuauuucau aaauaucuu       19

<210> SEQ ID NO 275
<211> LENGTH: 19
<212> TYPE: RNA
<213> ORGANISM: Homo sapiens

<400> SEQUENCE: 275
gauauuuaug aaauaaaug       19

<210> SEQ ID NO 276
<211> LENGTH: 19
<212> TYPE: RNA
<213> ORGANISM: Homo sapiens

<400> SEQUENCE: 276
cauuuauuuc auaaauauc       19

<210> SEQ ID NO 277
<211> LENGTH: 19
<212> TYPE: RNA
<213> ORGANISM: Homo sapiens

<400> SEQUENCE: 277
auaaauggua auuugugua       19

<210> SEQ ID NO 278
<211> LENGTH: 19
<212> TYPE: RNA
<213> ORGANISM: Homo sapiens

<400> SEQUENCE: 278

| | |
|---|---|
| uacacaaauu accauuuau | 19 |

<210> SEQ ID NO 279
<211> LENGTH: 19
<212> TYPE: RNA
<213> ORGANISM: Homo sapiens

<400> SEQUENCE: 279

| | |
|---|---|
| augguaauuu guguaaaua | 19 |

<210> SEQ ID NO 280
<211> LENGTH: 19
<212> TYPE: RNA
<213> ORGANISM: Homo sapiens

<400> SEQUENCE: 280

| | |
|---|---|
| uauuuacaca aauuaccau | 19 |

<210> SEQ ID NO 281
<211> LENGTH: 19
<212> TYPE: RNA
<213> ORGANISM: Homo sapiens

<400> SEQUENCE: 281

| | |
|---|---|
| uuuguguaaa uaagcuuua | 19 |

<210> SEQ ID NO 282
<211> LENGTH: 19
<212> TYPE: RNA
<213> ORGANISM: Homo sapiens

<400> SEQUENCE: 282

| | |
|---|---|
| uaaagcuuau uuacacaaa | 19 |

<210> SEQ ID NO 283
<211> LENGTH: 19
<212> TYPE: RNA
<213> ORGANISM: Homo sapiens

<400> SEQUENCE: 283

| | |
|---|---|
| auaagcuuua agguuccca | 19 |

<210> SEQ ID NO 284
<211> LENGTH: 19
<212> TYPE: RNA
<213> ORGANISM: Homo sapiens

<400> SEQUENCE: 284

| | |
|---|---|
| ugggaaccuu aaagcuuau | 19 |

<210> SEQ ID NO 285
<211> LENGTH: 19
<212> TYPE: RNA
<213> ORGANISM: Homo sapiens

<400> SEQUENCE: 285

| | |
|---|---|
| gcuuuaaggu ucccagaau | 19 |

<210> SEQ ID NO 286
<211> LENGTH: 19
<212> TYPE: RNA
<213> ORGANISM: Homo sapiens

<400> SEQUENCE: 286 auucuggaa ccuuaaagc                                              19

<210> SEQ ID NO 287
<211> LENGTH: 19
<212> TYPE: RNA
<213> ORGANISM: Homo sapiens

<400> SEQUENCE: 287
gguucccaga auaugcaaa                                             19

<210> SEQ ID NO 288
<211> LENGTH: 19
<212> TYPE: RNA
<213> ORGANISM: Homo sapiens

<400> SEQUENCE: 288
uuugcauauu cugggaacc                                             19

<210> SEQ ID NO 289
<211> LENGTH: 19
<212> TYPE: RNA
<213> ORGANISM: Homo sapiens

<400> SEQUENCE: 289
uaugcaaauu gguauuaau                                             19

<210> SEQ ID NO 290
<211> LENGTH: 19
<212> TYPE: RNA
<213> ORGANISM: Homo sapiens

<400> SEQUENCE: 290
auuaauacca auuugcaua                                             19

<210> SEQ ID NO 291
<211> LENGTH: 19
<212> TYPE: RNA
<213> ORGANISM: Homo sapiens

<400> SEQUENCE: 291
auugguauua auuuauuca                                             19

<210> SEQ ID NO 292
<211> LENGTH: 19
<212> TYPE: RNA
<213> ORGANISM: Homo sapiens

<400> SEQUENCE: 292
ugaauaaauu aauaccaau                                             19

<210> SEQ ID NO 293
<211> LENGTH: 19
<212> TYPE: RNA
<213> ORGANISM: Homo sapiens

<400> SEQUENCE: 293
uuuauucaaa gguguacau                                             19

<210> SEQ ID NO 294
<211> LENGTH: 19
<212> TYPE: RNA
<213> ORGANISM: Homo sapiens

<400> SEQUENCE: 294
auguacaccu uugaauaaa                                                19

<210> SEQ ID NO 295
<211> LENGTH: 19
<212> TYPE: RNA
<213> ORGANISM: Homo sapiens

<400> SEQUENCE: 295
agguguacau ugcugugua                                                19

<210> SEQ ID NO 296
<211> LENGTH: 19
<212> TYPE: RNA
<213> ORGANISM: Homo sapiens

<400> SEQUENCE: 296
uacacagcaa uguacaccu                                                19

<210> SEQ ID NO 297
<211> LENGTH: 19
<212> TYPE: RNA
<213> ORGANISM: Homo sapiens

<400> SEQUENCE: 297
cucauacauu uaaaguuuu                                                19

<210> SEQ ID NO 298
<211> LENGTH: 19
<212> TYPE: RNA
<213> ORGANISM: Homo sapiens

<400> SEQUENCE: 298
aaaacuuuaa auguaugag                                                19

<210> SEQ ID NO 299
<211> LENGTH: 19
<212> TYPE: RNA
<213> ORGANISM: Homo sapiens

<400> SEQUENCE: 299 aguuuuuuc auuuuacgu                                                 19

<210> SEQ ID NO 300
<211> LENGTH: 19
<212> TYPE: RNA
<213> ORGANISM: Homo sapiens

<400> SEQUENCE: 300
acguaaaaug aaaaaaacu                                                19

<210> SEQ ID NO 301
<211> LENGTH: 19
<212> TYPE: RNA
<213> ORGANISM: Homo sapiens

<400> SEQUENCE: 301
ggcccagagc ccuggagga                                                19

<210> SEQ ID NO 302
<211> LENGTH: 19
<212> TYPE: RNA
<213> ORGANISM: Homo sapiens

<400> SEQUENCE: 302
uccuccaggg cucugggcc                                            19

<210> SEQ ID NO 303
<211> LENGTH: 19
<212> TYPE: RNA
<213> ORGANISM: Homo sapiens

<400> SEQUENCE: 303
cgaaacgaca aaacgcaa                                             19

<210> SEQ ID NO 304
<211> LENGTH: 19
<212> TYPE: RNA
<213> ORGANISM: Homo sapiens

<400> SEQUENCE: 304
uugcguuuuu gucguuucg                                            19

<210> SEQ ID NO 305
<211> LENGTH: 19
<212> TYPE: RNA
<213> ORGANISM: Homo sapiens

<400> SEQUENCE: 305
acgacaaaaa cgcaagaaa                                            19

<210> SEQ ID NO 306
<211> LENGTH: 19
<212> TYPE: RNA
<213> ORGANISM: Homo sapiens

<400> SEQUENCE: 306
uuucuugcgu uuugucgu                                             19

<210> SEQ ID NO 307
<211> LENGTH: 19
<212> TYPE: RNA
<213> ORGANISM: Homo sapiens

<400> SEQUENCE: 307
aaacgcaaga aaacaauaa                                            19

<210> SEQ ID NO 308
<211> LENGTH: 19
<212> TYPE: RNA
<213> ORGANISM: Homo sapiens

<400> SEQUENCE: 308
uuauuguuuu cuugcguuu                                            19

<210> SEQ ID NO 309
<211> LENGTH: 19
<212> TYPE: RNA
<213> ORGANISM: Homo sapiens

<400> SEQUENCE: 309
acgcaagaaa acaauaaaa                                            19

<210> SEQ ID NO 310
<211> LENGTH: 19
<212> TYPE: RNA
<213> ORGANISM: Homo sapiens

<400> SEQUENCE: 310
uuuuauuguu uucuugcgu					19

<210> SEQ ID NO 311
<211> LENGTH: 19
<212> TYPE: RNA
<213> ORGANISM: Homo sapiens

<400> SEQUENCE: 311
gaaaacaaua aaacgcuag					19

<210> SEQ ID NO 312
<211> LENGTH: 19
<212> TYPE: RNA
<213> ORGANISM: Homo sapiens

<400> SEQUENCE: 312
cuagcguuuu auuguuuuc					19

<210> SEQ ID NO 313
<211> LENGTH: 19
<212> TYPE: RNA
<213> ORGANISM: Homo sapiens

<400> SEQUENCE: 313
aacaauaaaa cgcuagaaa					19

<210> SEQ ID NO 314
<211> LENGTH: 19
<212> TYPE: RNA
<213> ORGANISM: Homo sapiens

<400> SEQUENCE: 314
uuucuagcgu uuuauuguu					19

<210> SEQ ID NO 315
<211> LENGTH: 19
<212> TYPE: RNA
<213> ORGANISM: Homo sapiens

<400> SEQUENCE: 315
caauaaaacg cuagaaagc					19

<210> SEQ ID NO 316
<211> LENGTH: 19
<212> TYPE: RNA
<213> ORGANISM: Homo sapiens

<400> SEQUENCE: 316
gcuuucuagc guuuuauug					19

<210> SEQ ID NO 317
<211> LENGTH: 19
<212> TYPE: RNA
<213> ORGANISM: Homo sapiens

<400> SEQUENCE: 317
uaaaacgcua gaaagcgaa					19

<210> SEQ ID NO 318
<211> LENGTH: 19
<212> TYPE: RNA
<213> ORGANISM: Homo sapiens

<400> SEQUENCE: 318

```
uucgcuuucu agcguuuua                                              19

<210> SEQ ID NO 319
<211> LENGTH: 19
<212> TYPE: RNA
<213> ORGANISM: Homo sapiens

<400> SEQUENCE: 319
aacgcuagaa agcgaaaaa                                              19

<210> SEQ ID NO 320
<211> LENGTH: 19
<212> TYPE: RNA
<213> ORGANISM: Homo sapiens

<400> SEQUENCE: 320
uuuuucgcuu ucuagcguu                                              19

<210> SEQ ID NO 321
<211> LENGTH: 19
<212> TYPE: RNA
<213> ORGANISM: Homo sapiens

<400> SEQUENCE: 321
cgcuagaaag cgaaaaaaa                                              19

<210> SEQ ID NO 322
<211> LENGTH: 19
<212> TYPE: RNA
<213> ORGANISM: Homo sapiens

<400> SEQUENCE: 322 uuuuuucgc uuucuagcg                                               19

<210> SEQ ID NO 323
<211> LENGTH: 19
<212> TYPE: RNA
<213> ORGANISM: Homo sapiens

<400> SEQUENCE: 323
agcgaaaaaa aaaaaaaaa                                              19

<210> SEQ ID NO 324
<211> LENGTH: 19
<212> TYPE: RNA
<213> ORGANISM: Homo sapiens

<400> SEQUENCE: 324
uuuuuuuuuu uuuuucgcu                                              19

<210> SEQ ID NO 325
<211> LENGTH: 2429
<212> TYPE: DNA
<213> ORGANISM: Homo sapiens

<400> SEQUENCE: 325
tcgcccgcgc gactatgttt gctgattttt cgccttgccc tctttaaaag cggcctccca    60
ttctccaaaa gacacttccc ctcctcccct tgaagtgcat tagttgtgat ttctgcctcc   120
ttttcttttt tctttctttt ttgtttgctt tttccccccct tttgaattat gtgctgctgt   180
taaacaacaa caaaaaaaca acaaaacaca gcagctgcgg acttgtcccc ggctggagcc   240
cagcgccccg cctggagtgg atgagcctct ccatgagaga tccggtcatt cctgggacaa   300
```

```
gcatggccta ccatccgttc ctacctcacc gggcgccgga cttcgccatg agcgcggtgc    360
tgggtcacca gccgccgttc ttccccgcgc tgacgctgcc tcccaacggc gcggcggcgc    420
tctcgctgcc gggcgccctg gccaagccga tcatggatca attggtgggg gcggccgaga    480
ccggcatccc gttctcctcc ctggggcccc aggcgcatct gaggcctttg aagaccatgg    540
agcccgaaga gaggtggag gacgacccca aggtgcacct ggaggctaaa gaactttggg     600
atcagtttca caagcggggc accgagatgg tcattaccaa gtcgggaagg cgaatgtttc    660
ctccatttaa agtgagatgt tctgggctgg ataaaaaagc caaatacatt ttattgatgg    720
acattatagc tgctgatgac tgtcgttata aatttcacaa ttctcggtgg atggtggctg    780
gtaaggccga ccccgaaatg ccaaagagga tgtacattca cccggacagc cccgctactg    840
gggaacagtg gatgtccaaa gtcgtcactt tccacaaact gaaactcacc aacaacattt    900
cagacaaaca tggatttact atattgaact ccatgcacaa ataccagccc cggttccaca    960
ttgtaagagc caatgacatc ttgaaactcc cttatagtac atttcggaca tacttgttcc   1020
ccgaaactga attcatcgct gtgactgcat accagaatga taagataacc cagttaaaaa   1080
tagacaacaa ccccttttgca aaggtttccc gggacactgg aaatggccga agagaaaaaa   1140
gaaaacagct caccctgcag tccatgaggg tgtttgatga agacacaaa aaggagaatg    1200
ggacctctga tgagtcctcc agtgaacaag cagctttcaa ctgcttcgcc caggcttctt   1260
ctccagccgc ctccactgta gggacatcga acctcaaaga tttatgtccc agcgagggtg   1320
agagcgacgc cgaggccgag agcaaagagg agcacggccc cgaggcctgc gacgcggcca   1380
agatctccac caccacgtcg gaggagccct gccgtgacaa gggcagcccc gcggtcaagg   1440
ctcacctttt cgctgctgag cggccccggg acagcgggcg gctggacaaa gcgtcgcccg   1500
actcacgcca tagccccgcc accatctcgt ccagcactcg cggcctgggc gcggaggagc   1560
gcaggagccc ggttcgcgag ggcacagcgc cggccaaggt ggaagaggcg cgcgcgctcc   1620
cgggcaagga ggccttcgcg ccgctcacgg tgcagacgga cgcggccgcc gcgcacctgg   1680
cccagggccc cctgcctggc ctcggcttcg ccccggggcct ggcgggccaa cagttcttca   1740
acgggcaccc gctcttcctg cacccagcc agtttgccat ggggggcgcc ttctccagca   1800
tggcggccgc tggcatgggt cccctcctgg ccacggtttc tggggcctcc accggtgtct   1860
cgggcctgga ttccacggcc atggcctctg ccgctgcggc gcagggactg tccggggcgt   1920
ccgcggccac cctgccccttc cacctccagc agcacgtcct ggcctctcag ggcctggcca   1980
tgtcccttt cggaagcctg ttcccttacc cctacacgta catggccgca gcggcggccg   2040
cttctctgcg gcagcctcag cttcggtgca ccgcacccct tcttaatctg aacaccatgc   2100
gcccgcggtt gcgctacagc ccctactcca tcccggtgcc ggtcccggac ggcagcagtc   2160
tgctcaccac cgcccctgccc tccatggcgg cggccgcggg gccctggac ggcaaagccg   2220
ccgccctggc cgccagcccg gcctcggtgg cagtggactc gggctctgaa cccaacagcc   2280
gctcctccac gctctcctcc agttccatgt ccttgtcccc caaactctgc gcggagaaag   2340
aggcggccac cagcgaactg cagagcatcc agcggttggt tagcggcttg gaagccaagc   2400
cggacaggtc ccgcagcgcg tccccgtag                                     2429
```

<210> SEQ ID NO 326
<211> LENGTH: 19
<212> TYPE: RNA
<213> ORGANISM: Homo sapiens

<400> SEQUENCE: 326
aagcggccuc ccauucucc					19

<210> SEQ ID NO 327
<211> LENGTH: 19
<212> TYPE: RNA
<213> ORGANISM: Homo sapiens

<400> SEQUENCE: 327
ggagaauggg aggccgcuu					19

<210> SEQ ID NO 328
<211> LENGTH: 19
<212> TYPE: RNA
<213> ORGANISM: Homo sapiens

<400> SEQUENCE: 328
gcggccuccc auucuccaa					19

<210> SEQ ID NO 329
<211> LENGTH: 19
<212> TYPE: RNA
<213> ORGANISM: Homo sapiens

<400> SEQUENCE: 329
uuggagaaug ggaggccgc					19

<210> SEQ ID NO 330
<211> LENGTH: 19
<212> TYPE: RNA
<213> ORGANISM: Homo sapiens

<400> SEQUENCE: 330
aagacacuuc cccuccucc					19

<210> SEQ ID NO 331
<211> LENGTH: 19
<212> TYPE: RNA
<213> ORGANISM: Homo sapiens

<400> SEQUENCE: 331
ggaggagggg aagugucuu					19

<210> SEQ ID NO 332
<211> LENGTH: 19
<212> TYPE: RNA
<213> ORGANISM: Homo sapiens

<400> SEQUENCE: 332
gacacuuccc cuccuccu					19

<210> SEQ ID NO 333
<211> LENGTH: 19
<212> TYPE: RNA
<213> ORGANISM: Homo sapiens

<400> SEQUENCE: 333
agggaggagg ggaaguguc					19

<210> SEQ ID NO 334
<211> LENGTH: 19
<212> TYPE: RNA
<213> ORGANISM: Homo sapiens

<400> SEQUENCE: 334

-continued

| | |
|---|---|
| gugcauuagu ugugauuuc | 19 |

<210> SEQ ID NO 335
<211> LENGTH: 19
<212> TYPE: RNA
<213> ORGANISM: Homo sapiens

<400> SEQUENCE: 335

| | |
|---|---|
| gaaaucacaa cuaaugcac | 19 |

<210> SEQ ID NO 336
<211> LENGTH: 19
<212> TYPE: RNA
<213> ORGANISM: Homo sapiens

<400> SEQUENCE: 336

| | |
|---|---|
| uuaugugcug cuguuaaac | 19 |

<210> SEQ ID NO 337
<211> LENGTH: 19
<212> TYPE: RNA
<213> ORGANISM: Homo sapiens

<400> SEQUENCE: 337

| | |
|---|---|
| guuuaacagc agcacauaa | 19 |

<210> SEQ ID NO 338
<211> LENGTH: 19
<212> TYPE: RNA
<213> ORGANISM: Homo sapiens

<400> SEQUENCE: 338

| | |
|---|---|
| acaacaacaa aaaaacaac | 19 |

<210> SEQ ID NO 339
<211> LENGTH: 19
<212> TYPE: RNA
<213> ORGANISM: Homo sapiens

<400> SEQUENCE: 339

| | |
|---|---|
| guuguuuuuu uguuguugu | 19 |

<210> SEQ ID NO 340
<211> LENGTH: 19
<212> TYPE: RNA
<213> ORGANISM: Homo sapiens

<400> SEQUENCE: 340

| | |
|---|---|
| caacaaaaaa acaacaaaa | 19 |

<210> SEQ ID NO 341
<211> LENGTH: 19
<212> TYPE: RNA
<213> ORGANISM: Homo sapiens

<400> SEQUENCE: 341

| | |
|---|---|
| uuuuguuguu uuuuuguug | 19 |

<210> SEQ ID NO 342
<211> LENGTH: 19
<212> TYPE: RNA
<213> ORGANISM: Homo sapiens

<400> SEQUENCE: 342

```
caaaaaaaca acaaaacac                                              19

<210> SEQ ID NO 343
<211> LENGTH: 19
<212> TYPE: RNA
<213> ORGANISM: Homo sapiens

<400> SEQUENCE: 343
guguuuuguu guuuuuuug                                              19

<210> SEQ ID NO 344
<211> LENGTH: 19
<212> TYPE: RNA
<213> ORGANISM: Homo sapiens

<400> SEQUENCE: 344
aaaaacaaca aaacacagc                                              19

<210> SEQ ID NO 345
<211> LENGTH: 19
<212> TYPE: RNA
<213> ORGANISM: Homo sapiens

<400> SEQUENCE: 345
gcuguguuuu guuguuuuu                                              19

<210> SEQ ID NO 346
<211> LENGTH: 21
<212> TYPE: RNA
<213> ORGANISM: Homo sapiens

<400> SEQUENCE: 346
aaacaacaaa acacagcagu u                                           21

<210> SEQ ID NO 347
<211> LENGTH: 19
<212> TYPE: RNA
<213> ORGANISM: Homo sapiens

<400> SEQUENCE: 347
cugcuguguu uuguuguuu                                              19

<210> SEQ ID NO 348
<211> LENGTH: 19
<212> TYPE: RNA
<213> ORGANISM: Homo sapiens

<400> SEQUENCE: 348
acaacaaaac acagcagcu                                              19

<210> SEQ ID NO 349
<211> LENGTH: 19
<212> TYPE: RNA
<213> ORGANISM: Homo sapiens

<400> SEQUENCE: 349
agcugcugug uuuuguugu                                              19

<210> SEQ ID NO 350
<211> LENGTH: 19
<212> TYPE: RNA
<213> ORGANISM: Homo sapiens

<400> SEQUENCE: 350
```

| | |
|---|---|
| caaaacacag cagcugcgg | 19 |

<210> SEQ ID NO 351
<211> LENGTH: 19
<212> TYPE: RNA
<213> ORGANISM: Homo sapiens

<400> SEQUENCE: 351

| | |
|---|---|
| ccgcagcugc uguguuug | 19 |

<210> SEQ ID NO 352
<211> LENGTH: 19
<212> TYPE: RNA
<213> ORGANISM: Homo sapiens

<400> SEQUENCE: 352

| | |
|---|---|
| aacacagcag cugcggacu | 19 |

<210> SEQ ID NO 353
<211> LENGTH: 19
<212> TYPE: RNA
<213> ORGANISM: Homo sapiens

<400> SEQUENCE: 353

| | |
|---|---|
| aguccgcagc ugcuguguu | 19 |

<210> SEQ ID NO 354
<211> LENGTH: 19
<212> TYPE: RNA
<213> ORGANISM: Homo sapiens

<400> SEQUENCE: 354

| | |
|---|---|
| cacagcagcu gcggacuug | 19 |

<210> SEQ ID NO 355
<211> LENGTH: 19
<212> TYPE: RNA
<213> ORGANISM: Homo sapiens

<400> SEQUENCE: 355

| | |
|---|---|
| caaguccgca gcugcugug | 19 |

<210> SEQ ID NO 356
<211> LENGTH: 19
<212> TYPE: RNA
<213> ORGANISM: Homo sapiens

<400> SEQUENCE: 356

| | |
|---|---|
| gcauggccua ccauccguu | 19 |

<210> SEQ ID NO 357
<211> LENGTH: 19
<212> TYPE: RNA
<213> ORGANISM: Homo sapiens

<400> SEQUENCE: 357

| | |
|---|---|
| aacggauggu aggccaugc | 19 |

<210> SEQ ID NO 358
<211> LENGTH: 19
<212> TYPE: RNA
<213> ORGANISM: Homo sapiens

<400> SEQUENCE: 358

-continued cggcgcggcg gcgcucucg                                         19

<210> SEQ ID NO 359
<211> LENGTH: 19
<212> TYPE: RNA
<213> ORGANISM: Homo sapiens

<400> SEQUENCE: 359
cgagagcgcc gccgcgccg                                         19

<210> SEQ ID NO 360
<211> LENGTH: 19
<212> TYPE: RNA
<213> ORGANISM: Homo sapiens

<400> SEQUENCE: 360
gccgaucaug gaucaauug                                         19

<210> SEQ ID NO 361
<211> LENGTH: 19
<212> TYPE: RNA
<213> ORGANISM: Homo sapiens

<400> SEQUENCE: 361
caauugaucc augaucggc                                         19

<210> SEQ ID NO 362
<211> LENGTH: 19
<212> TYPE: RNA
<213> ORGANISM: Homo sapiens

<400> SEQUENCE: 362 uuggugggg cggccgaga                                          19

<210> SEQ ID NO 363
<211> LENGTH: 19
<212> TYPE: RNA
<213> ORGANISM: Homo sapiens

<400> SEQUENCE: 363
ucucggccgc ccccaccaa                                         19

<210> SEQ ID NO 364
<211> LENGTH: 19
<212> TYPE: RNA
<213> ORGANISM: Homo sapiens

<400> SEQUENCE: 364
gaccauggag cccgaagaa                                         19

<210> SEQ ID NO 365
<211> LENGTH: 19
<212> TYPE: RNA
<213> ORGANISM: Homo sapiens

<400> SEQUENCE: 365
uucuucgggc uccaugguc                                         19

<210> SEQ ID NO 366
<211> LENGTH: 19
<212> TYPE: RNA
<213> ORGANISM: Homo sapiens

<400> SEQUENCE: 366

```
gaagaggugg aggacgacc                                                19

<210> SEQ ID NO 367
<211> LENGTH: 19
<212> TYPE: RNA
<213> ORGANISM: Homo sapiens

<400> SEQUENCE: 367
ggucguccuc caccucuuc                                                19

<210> SEQ ID NO 368
<211> LENGTH: 19
<212> TYPE: RNA
<213> ORGANISM: Homo sapiens

<400> SEQUENCE: 368
gagguggagg acgacccca                                                19

<210> SEQ ID NO 369
<211> LENGTH: 19
<212> TYPE: RNA
<213> ORGANISM: Homo sapiens

<400> SEQUENCE: 369
uggggucguc cuccaccuc                                                19

<210> SEQ ID NO 370
<211> LENGTH: 19
<212> TYPE: RNA
<213> ORGANISM: Homo sapiens

<400> SEQUENCE: 370
ggugcaccug gaggcuaaa                                                19

<210> SEQ ID NO 371
<211> LENGTH: 19
<212> TYPE: RNA
<213> ORGANISM: Homo sapiens

<400> SEQUENCE: 371
uuuagccucc aggugcacc                                                19

<210> SEQ ID NO 372
<211> LENGTH: 19
<212> TYPE: RNA
<213> ORGANISM: Homo sapiens

<400> SEQUENCE: 372
agaacuuugg gaucaguuu                                                19

<210> SEQ ID NO 373
<211> LENGTH: 19
<212> TYPE: RNA
<213> ORGANISM: Homo sapiens

<400> SEQUENCE: 373
aaacugaucc caaaguucu                                                19

<210> SEQ ID NO 374
<211> LENGTH: 19
<212> TYPE: RNA
<213> ORGANISM: Homo sapiens

<400> SEQUENCE: 374
```
cuuugggauc aguuucaca                                    19

<210> SEQ ID NO 375
<211> LENGTH: 19
<212> TYPE: RNA
<213> ORGANISM: Homo sapiens

<400> SEQUENCE: 375
ugugaaacug aucccaaag                                    19

<210> SEQ ID NO 376
<211> LENGTH: 19
<212> TYPE: RNA
<213> ORGANISM: Homo sapiens

<400> SEQUENCE: 376
gcggggcacc gagaugguc                                    19

<210> SEQ ID NO 377
<211> LENGTH: 19
<212> TYPE: RNA
<213> ORGANISM: Homo sapiens

<400> SEQUENCE: 377
gaccaucucg gugccccgc                                    19

<210> SEQ ID NO 378
<211> LENGTH: 19
<212> TYPE: RNA
<213> ORGANISM: Homo sapiens

<400> SEQUENCE: 378
gucgggaagg cgaauguuu                                    19

<210> SEQ ID NO 379
<211> LENGTH: 19
<212> TYPE: RNA
<213> ORGANISM: Homo sapiens

<400> SEQUENCE: 379
aaacauucgc cuucccgac                                    19

<210> SEQ ID NO 380
<211> LENGTH: 19
<212> TYPE: RNA
<213> ORGANISM: Homo sapiens

<400> SEQUENCE: 380
ggcgaauguu uccuccauu                                    19

<210> SEQ ID NO 381
<211> LENGTH: 19
<212> TYPE: RNA
<213> ORGANISM: Homo sapiens

<400> SEQUENCE: 381
aauggaggaa acauucgcc                                    19

<210> SEQ ID NO 382
<211> LENGTH: 19
<212> TYPE: RNA
<213> ORGANISM: Homo sapiens

<400> SEQUENCE: 382

```
uguuuccucc auuuaaagu                                                 19

<210> SEQ ID NO 383
<211> LENGTH: 19
<212> TYPE: RNA
<213> ORGANISM: Homo sapiens

<400> SEQUENCE: 383
acuuuaaaug gaggaaaca                                                 19

<210> SEQ ID NO 384
<211> LENGTH: 19
<212> TYPE: RNA
<213> ORGANISM: Homo sapiens

<400> SEQUENCE: 384
agugagaugu ucugggcug                                                 19

<210> SEQ ID NO 385
<211> LENGTH: 19
<212> TYPE: RNA
<213> ORGANISM: Homo sapiens

<400> SEQUENCE: 385
cagcccagaa caucucacu                                                 19

<210> SEQ ID NO 386
<211> LENGTH: 19
<212> TYPE: RNA
<213> ORGANISM: Homo sapiens

<400> SEQUENCE: 386
aaaagccaaa uacauuuua                                                 19

<210> SEQ ID NO 387
<211> LENGTH: 19
<212> TYPE: RNA
<213> ORGANISM: Homo sapiens

<400> SEQUENCE: 387
uaaaauguau uuggcuuuu                                                 19

<210> SEQ ID NO 388
<211> LENGTH: 19
<212> TYPE: RNA
<213> ORGANISM: Homo sapiens

<400> SEQUENCE: 388
aagccaaaua cauuuuauu                                                 19

<210> SEQ ID NO 389
<211> LENGTH: 19
<212> TYPE: RNA
<213> ORGANISM: Homo sapiens

<400> SEQUENCE: 389
aauaaaaugu auuuggcuu                                                 19

<210> SEQ ID NO 390
<211> LENGTH: 19
<212> TYPE: RNA
<213> ORGANISM: Homo sapiens

<400> SEQUENCE: 390
```

-continued gccaaauaca uuuuauuga                                                19

<210> SEQ ID NO 391
<211> LENGTH: 19
<212> TYPE: RNA
<213> ORGANISM: Homo sapiens

<400> SEQUENCE: 391
ucaauaaaau guauuuggc                                                19

<210> SEQ ID NO 392
<211> LENGTH: 19
<212> TYPE: RNA
<213> ORGANISM: Homo sapiens

<400> SEQUENCE: 392
auacauuuua uugauggac                                                19

<210> SEQ ID NO 393
<211> LENGTH: 19
<212> TYPE: RNA
<213> ORGANISM: Homo sapiens

<400> SEQUENCE: 393
guccaucaau aaaauguau                                                19

<210> SEQ ID NO 394
<211> LENGTH: 19
<212> TYPE: RNA
<213> ORGANISM: Homo sapiens

<400> SEQUENCE: 394
auuucacaau ucucggugg                                                19

<210> SEQ ID NO 395
<211> LENGTH: 19
<212> TYPE: RNA
<213> ORGANISM: Homo sapiens

<400> SEQUENCE: 395
ccaccgagaa uugugaaau                                                19

<210> SEQ ID NO 396
<211> LENGTH: 19
<212> TYPE: RNA
<213> ORGANISM: Homo sapiens

<400> SEQUENCE: 396
uucucggugg augguggcu                                                19

<210> SEQ ID NO 397
<211> LENGTH: 19
<212> TYPE: RNA
<213> ORGANISM: Homo sapiens

<400> SEQUENCE: 397
agccaccauc caccgagaa                                                19

<210> SEQ ID NO 398
<211> LENGTH: 19
<212> TYPE: RNA
<213> ORGANISM: Homo sapiens

<400> SEQUENCE: 398
ggccgacccc gaaaugcca                                                19

<210> SEQ ID NO 399
<211> LENGTH: 19
<212> TYPE: RNA
<213> ORGANISM: Homo sapiens

<400> SEQUENCE: 399
uggcauuucg ggucggcc                                                 19

<210> SEQ ID NO 400
<211> LENGTH: 19
<212> TYPE: RNA
<213> ORGANISM: Homo sapiens

<400> SEQUENCE: 400
augccaaaga ggauguaca                                                19

<210> SEQ ID NO 401
<211> LENGTH: 19
<212> TYPE: RNA
<213> ORGANISM: Homo sapiens

<400> SEQUENCE: 401
uguacauccu cuuuggcau                                                19

<210> SEQ ID NO 402
<211> LENGTH: 19
<212> TYPE: RNA
<213> ORGANISM: Homo sapiens

<400> SEQUENCE: 402
agaggaugua cauucaccc                                                19

<210> SEQ ID NO 403
<211> LENGTH: 19
<212> TYPE: RNA
<213> ORGANISM: Homo sapiens

<400> SEQUENCE: 403
gggugaaugu acauccucu                                                19

<210> SEQ ID NO 404
<211> LENGTH: 19
<212> TYPE: RNA
<213> ORGANISM: Homo sapiens

<400> SEQUENCE: 404
caguggaugu ccaaagucg                                                19

<210> SEQ ID NO 405
<211> LENGTH: 19
<212> TYPE: RNA
<213> ORGANISM: Homo sapiens

<400> SEQUENCE: 405
cgacuuugga cauccacug                                                19

<210> SEQ ID NO 406
<211> LENGTH: 19
<212> TYPE: RNA
<213> ORGANISM: Homo sapiens

<400> SEQUENCE: 406

```
agucgucacu uuccacaaa                                             19

<210> SEQ ID NO 407
<211> LENGTH: 19
<212> TYPE: RNA
<213> ORGANISM: Homo sapiens

<400> SEQUENCE: 407
uuuguggaaa gugacgacu                                             19

<210> SEQ ID NO 408
<211> LENGTH: 19
<212> TYPE: RNA
<213> ORGANISM: Homo sapiens

<400> SEQUENCE: 408
acugaaacuc accaacaac                                             19

<210> SEQ ID NO 409
<211> LENGTH: 19
<212> TYPE: RNA
<213> ORGANISM: Homo sapiens

<400> SEQUENCE: 409
guuguuggug aguuucagu                                             19

<210> SEQ ID NO 410
<211> LENGTH: 19
<212> TYPE: RNA
<213> ORGANISM: Homo sapiens

<400> SEQUENCE: 410
acucaccaac aacauuuca                                             19

<210> SEQ ID NO 411
<211> LENGTH: 19
<212> TYPE: RNA
<213> ORGANISM: Homo sapiens

<400> SEQUENCE: 411
ugaaauguug uuggugagu                                             19

<210> SEQ ID NO 412
<211> LENGTH: 19
<212> TYPE: RNA
<213> ORGANISM: Homo sapiens

<400> SEQUENCE: 412
caacauuuca gacaaacau                                             19

<210> SEQ ID NO 413
<211> LENGTH: 19
<212> TYPE: RNA
<213> ORGANISM: Homo sapiens

<400> SEQUENCE: 413
auguuugucu gaaauguug                                             19

<210> SEQ ID NO 414
<211> LENGTH: 19
<212> TYPE: RNA
<213> ORGANISM: Homo sapiens

<400> SEQUENCE: 414
```

-continued

```
cauuucagac aaacaugga                                              19

<210> SEQ ID NO 415
<211> LENGTH: 19
<212> TYPE: RNA
<213> ORGANISM: Homo sapiens

<400> SEQUENCE: 415
uccauguuug ucugaaaug                                              19

<210> SEQ ID NO 416
<211> LENGTH: 19
<212> TYPE: RNA
<213> ORGANISM: Homo sapiens

<400> SEQUENCE: 416
acauggauuu acuauauug                                              19

<210> SEQ ID NO 417
<211> LENGTH: 19
<212> TYPE: RNA
<213> ORGANISM: Homo sapiens

<400> SEQUENCE: 417
caauauagua aauccaugu                                              19

<210> SEQ ID NO 418
<211> LENGTH: 19
<212> TYPE: RNA
<213> ORGANISM: Homo sapiens

<400> SEQUENCE: 418
cuccaugcac aaauaccag                                              19

<210> SEQ ID NO 419
<211> LENGTH: 19
<212> TYPE: RNA
<213> ORGANISM: Homo sapiens

<400> SEQUENCE: 419
cugguauuug ugcauggag                                              19

<210> SEQ ID NO 420
<211> LENGTH: 19
<212> TYPE: RNA
<213> ORGANISM: Homo sapiens

<400> SEQUENCE: 420
auaccagccc cgguuccac                                              19

<210> SEQ ID NO 421
<211> LENGTH: 19
<212> TYPE: RNA
<213> ORGANISM: Homo sapiens

<400> SEQUENCE: 421
guggaaccgg ggcugguau                                              19

<210> SEQ ID NO 422
<211> LENGTH: 19
<212> TYPE: RNA
<213> ORGANISM: Homo sapiens

<400> SEQUENCE: 422
```

-continued

```
gagccaauga caucuugaa                                              19

<210> SEQ ID NO 423
<211> LENGTH: 19
<212> TYPE: RNA
<213> ORGANISM: Homo sapiens

<400> SEQUENCE: 423
uucaagaugu cauuggcuc                                              19

<210> SEQ ID NO 424
<211> LENGTH: 19
<212> TYPE: RNA
<213> ORGANISM: Homo sapiens

<400> SEQUENCE: 424
ugacaucuug aaacucccu                                              19

<210> SEQ ID NO 425
<211> LENGTH: 19
<212> TYPE: RNA
<213> ORGANISM: Homo sapiens

<400> SEQUENCE: 425
agggaguuuc aagauguca                                              19

<210> SEQ ID NO 426
<211> LENGTH: 19
<212> TYPE: RNA
<213> ORGANISM: Homo sapiens

<400> SEQUENCE: 426
acucccuuau aguacauuu                                              19

<210> SEQ ID NO 427
<211> LENGTH: 19
<212> TYPE: RNA
<213> ORGANISM: Homo sapiens

<400> SEQUENCE: 427
aaauguacua uaagggagu                                              19

<210> SEQ ID NO 428
<211> LENGTH: 19
<212> TYPE: RNA
<213> ORGANISM: Homo sapiens

<400> SEQUENCE: 428
acugaauuca ucgcuguga                                              19

<210> SEQ ID NO 429
<211> LENGTH: 19
<212> TYPE: RNA
<213> ORGANISM: Homo sapiens

<400> SEQUENCE: 429
ucacagcgau gaauucagu                                              19

<210> SEQ ID NO 430
<211> LENGTH: 19
<212> TYPE: RNA
<213> ORGANISM: Homo sapiens

<400> SEQUENCE: 430
```
uucaucgcug ugacugcau                                              19

<210> SEQ ID NO 431
<211> LENGTH: 19
<212> TYPE: RNA
<213> ORGANISM: Homo sapiens

<400> SEQUENCE: 431
augcagucac agcgaugaa                                              19

<210> SEQ ID NO 432
<211> LENGTH: 19
<212> TYPE: RNA
<213> ORGANISM: Homo sapiens

<400> SEQUENCE: 432
ugauaagaua acccaguua                                              19

<210> SEQ ID NO 433
<211> LENGTH: 19
<212> TYPE: RNA
<213> ORGANISM: Homo sapiens

<400> SEQUENCE: 433
uaacuggguu aucuuauca                                              19

<210> SEQ ID NO 434
<211> LENGTH: 19
<212> TYPE: RNA
<213> ORGANISM: Homo sapiens

<400> SEQUENCE: 434
gauaacccag uuaaaaaua                                              19

<210> SEQ ID NO 435
<211> LENGTH: 19
<212> TYPE: RNA
<213> ORGANISM: Homo sapiens

<400> SEQUENCE: 435 uauuuuaac uggguuauc                                               19

<210> SEQ ID NO 436
<211> LENGTH: 19
<212> TYPE: RNA
<213> ORGANISM: Homo sapiens

<400> SEQUENCE: 436
cccaguuaaa aauagacaa                                              19

<210> SEQ ID NO 437
<211> LENGTH: 19
<212> TYPE: RNA
<213> ORGANISM: Homo sapiens

<400> SEQUENCE: 437
uugucuauuu uuaacuggg                                              19

<210> SEQ ID NO 438
<211> LENGTH: 19
<212> TYPE: RNA
<213> ORGANISM: Homo sapiens

<400> SEQUENCE: 438

-continued

```
aaauagacaa caacccuuu                                          19

<210> SEQ ID NO 439
<211> LENGTH: 19
<212> TYPE: RNA
<213> ORGANISM: Homo sapiens

<400> SEQUENCE: 439 aaagguugu ugucuauuu                                           19

<210> SEQ ID NO 440
<211> LENGTH: 19
<212> TYPE: RNA
<213> ORGANISM: Homo sapiens

<400> SEQUENCE: 440
auagacaaca acccuuuug                                          19

<210> SEQ ID NO 441
<211> LENGTH: 19
<212> TYPE: RNA
<213> ORGANISM: Homo sapiens

<400> SEQUENCE: 441 caaaagguu guugucuau                                           19

<210> SEQ ID NO 442
<211> LENGTH: 19
<212> TYPE: RNA
<213> ORGANISM: Homo sapiens

<400> SEQUENCE: 442
caacccuuuu gcaaaaggu                                          19

<210> SEQ ID NO 443
<211> LENGTH: 19
<212> TYPE: RNA
<213> ORGANISM: Homo sapiens

<400> SEQUENCE: 443
accuuuugca aaagguug                                           19

<210> SEQ ID NO 444
<211> LENGTH: 19
<212> TYPE: RNA
<213> ORGANISM: Homo sapiens

<400> SEQUENCE: 444
cccuuuugca aagguuuc                                           19

<210> SEQ ID NO 445
<211> LENGTH: 19
<212> TYPE: RNA
<213> ORGANISM: Homo sapiens

<400> SEQUENCE: 445
gaaaccuuuu gcaaaaggg                                          19

<210> SEQ ID NO 446
<211> LENGTH: 19
<212> TYPE: RNA
<213> ORGANISM: Homo sapiens

<400> SEQUENCE: 446
```

```
aagguuuccg ggacacugg                                                 19

<210> SEQ ID NO 447
<211> LENGTH: 19
<212> TYPE: RNA
<213> ORGANISM: Homo sapiens

<400> SEQUENCE: 447
ccaguguccc ggaaaccuu                                                 19

<210> SEQ ID NO 448
<211> LENGTH: 19
<212> TYPE: RNA
<213> ORGANISM: Homo sapiens

<400> SEQUENCE: 448 gguuccggg acacuggaa                                                  19

<210> SEQ ID NO 449
<211> LENGTH: 21
<212> TYPE: RNA
<213> ORGANISM: Homo sapiens

<400> SEQUENCE: 449
uuccaguguc ccggaaaccu u                                              21

<210> SEQ ID NO 450
<211> LENGTH: 19
<212> TYPE: RNA
<213> ORGANISM: Homo sapiens

<400> SEQUENCE: 450
auggccgaag agaaaaaag                                                 19

<210> SEQ ID NO 451
<211> LENGTH: 19
<212> TYPE: RNA
<213> ORGANISM: Homo sapiens

<400> SEQUENCE: 451 cuuuuucuc uucggccau                                                  19

<210> SEQ ID NO 452
<211> LENGTH: 19
<212> TYPE: RNA
<213> ORGANISM: Homo sapiens

<400> SEQUENCE: 452 gagaaaaag aaaacagcu                                                  19

<210> SEQ ID NO 453
<211> LENGTH: 19
<212> TYPE: RNA
<213> ORGANISM: Homo sapiens

<400> SEQUENCE: 453 agcuguuuc uuuuucuc                                                   19

<210> SEQ ID NO 454
<211> LENGTH: 19
<212> TYPE: RNA
<213> ORGANISM: Homo sapiens

<400> SEQUENCE: 454
```
aaaagaaaac agcucaccc                                            19

<210> SEQ ID NO 455
<211> LENGTH: 19
<212> TYPE: RNA
<213> ORGANISM: Homo sapiens

<400> SEQUENCE: 455
gggugagcug uuuucuuuu                                            19

<210> SEQ ID NO 456
<211> LENGTH: 19
<212> TYPE: RNA
<213> ORGANISM: Homo sapiens

<400> SEQUENCE: 456
aagaaaacag cucacccug                                            19

<210> SEQ ID NO 457
<211> LENGTH: 21
<212> TYPE: RNA
<213> ORGANISM: Homo sapiens

<400> SEQUENCE: 457
cagggugagc uguuucuuu u                                          21

<210> SEQ ID NO 458
<211> LENGTH: 21
<212> TYPE: RNA
<213> ORGANISM: Homo sapiens

<400> SEQUENCE: 458
gaaaacagcu cacccugcau u                                         21

<210> SEQ ID NO 459
<211> LENGTH: 21
<212> TYPE: RNA
<213> ORGANISM: Homo sapiens

<400> SEQUENCE: 459
ugcaggguga gcuguuucu u                                          21

<210> SEQ ID NO 460
<211> LENGTH: 19
<212> TYPE: RNA
<213> ORGANISM: Homo sapiens

<400> SEQUENCE: 460
aacagcucac ccugcaguc                                            19

<210> SEQ ID NO 461
<211> LENGTH: 19
<212> TYPE: RNA
<213> ORGANISM: Homo sapiens

<400> SEQUENCE: 461
gacugcaggg ugagcuguu                                            19

<210> SEQ ID NO 462
<211> LENGTH: 19
<212> TYPE: RNA
<213> ORGANISM: Homo sapiens

<400> SEQUENCE: 462
cagcucaccc ugcagucca                                        19

<210> SEQ ID NO 463
<211> LENGTH: 19
<212> TYPE: RNA
<213> ORGANISM: Homo sapiens

<400> SEQUENCE: 463
uggacugcag ggugagcug                                        19

<210> SEQ ID NO 464
<211> LENGTH: 19
<212> TYPE: RNA
<213> ORGANISM: Homo sapiens

<400> SEQUENCE: 464
agacacaaaa aggagaaug                                        19

<210> SEQ ID NO 465
<211> LENGTH: 19
<212> TYPE: RNA
<213> ORGANISM: Homo sapiens

<400> SEQUENCE: 465
cauucuccuu uuugugucu                                        19

<210> SEQ ID NO 466
<211> LENGTH: 19
<212> TYPE: RNA
<213> ORGANISM: Homo sapiens

<400> SEQUENCE: 466
aaaggagaau gggaccucu                                        19

<210> SEQ ID NO 467
<211> LENGTH: 19
<212> TYPE: RNA
<213> ORGANISM: Homo sapiens

<400> SEQUENCE: 467
agagguccca uucuccuuu                                        19

<210> SEQ ID NO 468
<211> LENGTH: 19
<212> TYPE: RNA
<213> ORGANISM: Homo sapiens

<400> SEQUENCE: 468
aggagaaugg gaccucuga                                        19

<210> SEQ ID NO 469
<211> LENGTH: 19
<212> TYPE: RNA
<213> ORGANISM: Homo sapiens

<400> SEQUENCE: 469 ucagagaggucc cauucuccu                                      19

<210> SEQ ID NO 470
<211> LENGTH: 19
<212> TYPE: RNA
<213> ORGANISM: Homo sapiens

<400> SEQUENCE: 470

-continued ugggaccucu gaugagucc								19

<210> SEQ ID NO 471
<211> LENGTH: 19
<212> TYPE: RNA
<213> ORGANISM: Homo sapiens

<400> SEQUENCE: 471
ggacucauca gagguccca								19

<210> SEQ ID NO 472
<211> LENGTH: 19
<212> TYPE: RNA
<213> ORGANISM: Homo sapiens

<400> SEQUENCE: 472
caagcagcuu ucaacugcu								19

<210> SEQ ID NO 473
<211> LENGTH: 19
<212> TYPE: RNA
<213> ORGANISM: Homo sapiens

<400> SEQUENCE: 473
agcaguugaa agcugcuug								19

<210> SEQ ID NO 474
<211> LENGTH: 19
<212> TYPE: RNA
<213> ORGANISM: Homo sapiens

<400> SEQUENCE: 474
gcagcuuuca acugcuucg								19

<210> SEQ ID NO 475
<211> LENGTH: 19
<212> TYPE: RNA
<213> ORGANISM: Homo sapiens

<400> SEQUENCE: 475
cgaagcaguu gaaagcugc								19

<210> SEQ ID NO 476
<211> LENGTH: 19
<212> TYPE: RNA
<213> ORGANISM: Homo sapiens

<400> SEQUENCE: 476
cugcuucgcc caggcuucu								19

<210> SEQ ID NO 477
<211> LENGTH: 19
<212> TYPE: RNA
<213> ORGANISM: Homo sapiens

<400> SEQUENCE: 477
agaagccugg gcgaagcag								19

<210> SEQ ID NO 478
<211> LENGTH: 19
<212> TYPE: RNA
<213> ORGANISM: Homo sapiens

<400> SEQUENCE: 478

| | |
|---|---|
| ccucaaagau uuauguccc | 19 |

<210> SEQ ID NO 479
<211> LENGTH: 19
<212> TYPE: RNA
<213> ORGANISM: Homo sapiens

<400> SEQUENCE: 479

| | |
|---|---|
| gggacauaaa ucuuugagg | 19 |

<210> SEQ ID NO 480
<211> LENGTH: 19
<212> TYPE: RNA
<213> ORGANISM: Homo sapiens

<400> SEQUENCE: 480

| | |
|---|---|
| agauuuaugu cccagcgag | 19 |

<210> SEQ ID NO 481
<211> LENGTH: 19
<212> TYPE: RNA
<213> ORGANISM: Homo sapiens

<400> SEQUENCE: 481

| | |
|---|---|
| cucgcuggga cauaaaucu | 19 |

<210> SEQ ID NO 482
<211> LENGTH: 19
<212> TYPE: RNA
<213> ORGANISM: Homo sapiens

<400> SEQUENCE: 482

| | |
|---|---|
| agaggagcac ggccccgag | 19 |

<210> SEQ ID NO 483
<211> LENGTH: 19
<212> TYPE: RNA
<213> ORGANISM: Homo sapiens

<400> SEQUENCE: 483

| | |
|---|---|
| cucggggccg ugcuccucu | 19 |

<210> SEQ ID NO 484
<211> LENGTH: 19
<212> TYPE: RNA
<213> ORGANISM: Homo sapiens

<400> SEQUENCE: 484

| | |
|---|---|
| gaucuccacc accacgucg | 19 |

<210> SEQ ID NO 485
<211> LENGTH: 19
<212> TYPE: RNA
<213> ORGANISM: Homo sapiens

<400> SEQUENCE: 485

| | |
|---|---|
| cgacguggug guggagauc | 19 |

<210> SEQ ID NO 486
<211> LENGTH: 19
<212> TYPE: RNA
<213> ORGANISM: Homo sapiens

<400> SEQUENCE: 486
gggcagcccc gcggucaag 19

<210> SEQ ID NO 487
<211> LENGTH: 19
<212> TYPE: RNA
<213> ORGANISM: Homo sapiens

<400> SEQUENCE: 487
cuugaccgcg gggcugccc 19

<210> SEQ ID NO 488
<211> LENGTH: 19
<212> TYPE: RNA
<213> ORGANISM: Homo sapiens

<400> SEQUENCE: 488
ggcucaccuu uucgcugcu 19

<210> SEQ ID NO 489
<211> LENGTH: 19
<212> TYPE: RNA
<213> ORGANISM: Homo sapiens

<400> SEQUENCE: 489
agcagcgaaa aggugagcc 19

<210> SEQ ID NO 490
<211> LENGTH: 19
<212> TYPE: RNA
<213> ORGANISM: Homo sapiens

<400> SEQUENCE: 490
agcgucgccc gacucacgc 19

<210> SEQ ID NO 491
<211> LENGTH: 19
<212> TYPE: RNA
<213> ORGANISM: Homo sapiens

<400> SEQUENCE: 491
gcgugagucg ggcgacgcu 19

<210> SEQ ID NO 492
<211> LENGTH: 19
<212> TYPE: RNA
<213> ORGANISM: Homo sapiens

<400> SEQUENCE: 492
gguggaagag gcgcgcgcg 19

<210> SEQ ID NO 493
<211> LENGTH: 19
<212> TYPE: RNA
<213> ORGANISM: Homo sapiens

<400> SEQUENCE: 493
cgcgcgcgcc ucuuccacc 19

<210> SEQ ID NO 494
<211> LENGTH: 19
<212> TYPE: RNA
<213> ORGANISM: Homo sapiens

<400> SEQUENCE: 494

-continued gaggcgcgcg cgcucccgg                                                    19

<210> SEQ ID NO 495
<211> LENGTH: 19
<212> TYPE: RNA
<213> ORGANISM: Homo sapiens

<400> SEQUENCE: 495
ccgggagcgc gcgcgccuc                                                    19

<210> SEQ ID NO 496
<211> LENGTH: 19
<212> TYPE: RNA
<213> ORGANISM: Homo sapiens

<400> SEQUENCE: 496
ggaggccuuc gcgccgcuc                                                    19

<210> SEQ ID NO 497
<211> LENGTH: 19
<212> TYPE: RNA
<213> ORGANISM: Homo sapiens

<400> SEQUENCE: 497
gagcggcgcg aaggccucc                                                    19

<210> SEQ ID NO 498
<211> LENGTH: 19
<212> TYPE: RNA
<213> ORGANISM: Homo sapiens

<400> SEQUENCE: 498
caguucuuca acgggcacc                                                    19

<210> SEQ ID NO 499
<211> LENGTH: 19
<212> TYPE: RNA
<213> ORGANISM: Homo sapiens

<400> SEQUENCE: 499
ggugcccguu gaagaacug                                                    19

<210> SEQ ID NO 500
<211> LENGTH: 19
<212> TYPE: RNA
<213> ORGANISM: Homo sapiens

<400> SEQUENCE: 500
cgggcacccg cucuuccug                                                    19

<210> SEQ ID NO 501
<211> LENGTH: 19
<212> TYPE: RNA
<213> ORGANISM: Homo sapiens

<400> SEQUENCE: 501
caggaagagc gggugcccg                                                    19

<210> SEQ ID NO 502
<211> LENGTH: 19
<212> TYPE: RNA
<213> ORGANISM: Homo sapiens

<400> SEQUENCE: 502

| | |
|---|---|
| gccuguccc uuaccccua | 19 |

<210> SEQ ID NO 503
<211> LENGTH: 19
<212> TYPE: RNA
<213> ORGANISM: Homo sapiens

<400> SEQUENCE: 503

| | |
|---|---|
| uaggguaag ggaacaggc | 19 |

<210> SEQ ID NO 504
<211> LENGTH: 19
<212> TYPE: RNA
<213> ORGANISM: Homo sapiens

<400> SEQUENCE: 504

| | |
|---|---|
| ucugaacacc augcgcccg | 19 |

<210> SEQ ID NO 505
<211> LENGTH: 19
<212> TYPE: RNA
<213> ORGANISM: Homo sapiens

<400> SEQUENCE: 505

| | |
|---|---|
| cgggcgcaug guguucaga | 19 |

<210> SEQ ID NO 506
<211> LENGTH: 19
<212> TYPE: RNA
<213> ORGANISM: Homo sapiens

<400> SEQUENCE: 506

| | |
|---|---|
| caccaugcgc ccgcgguug | 19 |

<210> SEQ ID NO 507
<211> LENGTH: 19
<212> TYPE: RNA
<213> ORGANISM: Homo sapiens

<400> SEQUENCE: 507

| | |
|---|---|
| caaccgcggg cgcauggug | 19 |

<210> SEQ ID NO 508
<211> LENGTH: 19
<212> TYPE: RNA
<213> ORGANISM: Homo sapiens

<400> SEQUENCE: 508

| | |
|---|---|
| agccgccgcc cuggccgcc | 19 |

<210> SEQ ID NO 509
<211> LENGTH: 19
<212> TYPE: RNA
<213> ORGANISM: Homo sapiens

<400> SEQUENCE: 509

| | |
|---|---|
| ggcggccagg gcggcggcu | 19 |

<210> SEQ ID NO 510
<211> LENGTH: 19
<212> TYPE: RNA
<213> ORGANISM: Homo sapiens

<400> SEQUENCE: 510
cccaacagcc gcuccucca                                          19

<210> SEQ ID NO 511
<211> LENGTH: 19
<212> TYPE: RNA
<213> ORGANISM: Homo sapiens

<400> SEQUENCE: 511
uggaggagcg gcuguuggg                                          19

<210> SEQ ID NO 512
<211> LENGTH: 19
<212> TYPE: RNA
<213> ORGANISM: Homo sapiens

<400> SEQUENCE: 512
cagccgcucc uccacgcuc                                          19

<210> SEQ ID NO 513
<211> LENGTH: 19
<212> TYPE: RNA
<213> ORGANISM: Homo sapiens

<400> SEQUENCE: 513
gagcguggag gagcggcug                                          19

<210> SEQ ID NO 514
<211> LENGTH: 19
<212> TYPE: RNA
<213> ORGANISM: Homo sapiens

<400> SEQUENCE: 514
acucugcgcg gagaaagag                                          19

<210> SEQ ID NO 515
<211> LENGTH: 19
<212> TYPE: RNA
<213> ORGANISM: Homo sapiens

<400> SEQUENCE: 515
cucuuucucc gcgcagagu                                          19

<210> SEQ ID NO 516
<211> LENGTH: 19
<212> TYPE: RNA
<213> ORGANISM: Homo sapiens

<400> SEQUENCE: 516
agaggcggcc accagcgaa                                          19

<210> SEQ ID NO 517
<211> LENGTH: 19
<212> TYPE: RNA
<213> ORGANISM: Homo sapiens

<400> SEQUENCE: 517
uucgcuggug gccgccucu                                          19

<210> SEQ ID NO 518
<211> LENGTH: 19
<212> TYPE: RNA
<213> ORGANISM: Homo sapiens

<400> SEQUENCE: 518
cugcagagca uccagcggu          19

<210> SEQ ID NO 519
<211> LENGTH: 19
<212> TYPE: RNA
<213> ORGANISM: Homo sapiens

<400> SEQUENCE: 519
accgcuggau gcucugcag          19

<210> SEQ ID NO 520
<211> LENGTH: 19
<212> TYPE: RNA
<213> ORGANISM: Homo sapiens

<400> SEQUENCE: 520
gccaagccgg acagguccc          19

<210> SEQ ID NO 521
<211> LENGTH: 19
<212> TYPE: RNA
<213> ORGANISM: Homo sapiens

<400> SEQUENCE: 521
gggaccuguc cggcuuggc          19

<210> SEQ ID NO 522
<211> LENGTH: 19
<212> TYPE: RNA
<213> ORGANISM: Homo sapiens

<400> SEQUENCE: 522
gccggacagg ucccgcagc          19

<210> SEQ ID NO 523
<211> LENGTH: 19
<212> TYPE: RNA
<213> ORGANISM: Homo sapiens

<400> SEQUENCE: 523
gcugcgggac cuguccggc          19

<210> SEQ ID NO 524
<211> LENGTH: 376
<212> TYPE: DNA
<213> ORGANISM: Homo sapiens

<400> SEQUENCE: 524
atctgtctgg acgcgctggg tggatgcggg gggctcctgg gaactgtgtt ggagccgagc      60
aagcgctagc caggcgcaag cgcgcacaga ctgtagccat ccgaggacac ccccgccccc     120
ccggcccacc cggagacacc cgcgcagaat cgcctccgga tccctgcag tcggcggag      180 tgttggaggt cggcgccggc ccccgccttc cgcgccccc acgggaagga agcaccccg      240 gtattaaaac gaacggggcg gaaagaagcc ctcagtcgcc ggccgggagg cgagccgatg    300
ccgagctgct ccacgtccac catgccgggc atgatctgca agaacccaga cctcgagttt    360
gactcgctac agccct                                                    376

<210> SEQ ID NO 525
<211> LENGTH: 19
<212> TYPE: RNA
<213> ORGANISM: Homo sapiens

```
<400> SEQUENCE: 525
cuguguugga gccgagcaa                                                19

<210> SEQ ID NO 526
<211> LENGTH: 19
<212> TYPE: RNA
<213> ORGANISM: Homo sapiens

<400> SEQUENCE: 526
uugcucggcu ccaacacag                                                19

<210> SEQ ID NO 527
<211> LENGTH: 19
<212> TYPE: RNA
<213> ORGANISM: Homo sapiens

<400> SEQUENCE: 527
gcgcuagcca ggcgcaagc                                                19

<210> SEQ ID NO 528
<211> LENGTH: 19
<212> TYPE: RNA
<213> ORGANISM: Homo sapiens

<400> SEQUENCE: 528
gcuugcgccu ggcuagcgc                                                19

<210> SEQ ID NO 529
<211> LENGTH: 19
<212> TYPE: RNA
<213> ORGANISM: Homo sapiens

<400> SEQUENCE: 529
gcgcgcacag acuguagcc                                                19

<210> SEQ ID NO 530
<211> LENGTH: 19
<212> TYPE: RNA
<213> ORGANISM: Homo sapiens

<400> SEQUENCE: 530
ggcuacaguc ugugcgcgc                                                19

<210> SEQ ID NO 531
<211> LENGTH: 19
<212> TYPE: RNA
<213> ORGANISM: Homo sapiens

<400> SEQUENCE: 531
ucgccuccgg auccccugc                                                19

<210> SEQ ID NO 532
<211> LENGTH: 19
<212> TYPE: RNA
<213> ORGANISM: Homo sapiens

<400> SEQUENCE: 532
gcaggggauc cggaggcga                                                19

<210> SEQ ID NO 533
<211> LENGTH: 19
<212> TYPE: RNA
<213> ORGANISM: Homo sapiens
```

```
<400> SEQUENCE: 533
ggaagcaccc ccgguauua                                              19

<210> SEQ ID NO 534
<211> LENGTH: 19
<212> TYPE: RNA
<213> ORGANISM: Homo sapiens

<400> SEQUENCE: 534
uaauaccggg ggugcucc                                               19

<210> SEQ ID NO 535
<211> LENGTH: 19
<212> TYPE: RNA
<213> ORGANISM: Homo sapiens

<400> SEQUENCE: 535 gcaccccgg uauuaaaac                                               19

<210> SEQ ID NO 536
<211> LENGTH: 19
<212> TYPE: RNA
<213> ORGANISM: Homo sapiens

<400> SEQUENCE: 536
guuuuaauac cgggggugc                                              19

<210> SEQ ID NO 537
<211> LENGTH: 19
<212> TYPE: RNA
<213> ORGANISM: Homo sapiens

<400> SEQUENCE: 537
aacgaacggg gcggaaaga                                              19

<210> SEQ ID NO 538
<211> LENGTH: 19
<212> TYPE: RNA
<213> ORGANISM: Homo sapiens

<400> SEQUENCE: 538 ucuuccgcc ccguucguu                                               19

<210> SEQ ID NO 539
<211> LENGTH: 19
<212> TYPE: RNA
<213> ORGANISM: Homo sapiens

<400> SEQUENCE: 539 cgaacgggc ggaaagaag                                               19

<210> SEQ ID NO 540
<211> LENGTH: 19
<212> TYPE: RNA
<213> ORGANISM: Homo sapiens

<400> SEQUENCE: 540
cuucuuuccg ccccguucg                                              19

<210> SEQ ID NO 541
<211> LENGTH: 19
<212> TYPE: RNA
<213> ORGANISM: Homo sapiens
```

<400> SEQUENCE: 541
cggggcggaa agaagcccu                                          19

<210> SEQ ID NO 542
<211> LENGTH: 19
<212> TYPE: RNA
<213> ORGANISM: Homo sapiens

<400> SEQUENCE: 542
agggcuucuu uccgccccg                                          19

<210> SEQ ID NO 543
<211> LENGTH: 19
<212> TYPE: RNA
<213> ORGANISM: Homo sapiens

<400> SEQUENCE: 543
agaagcccuc agucgccgg                                          19

<210> SEQ ID NO 544
<211> LENGTH: 19
<212> TYPE: RNA
<213> ORGANISM: Homo sapiens

<400> SEQUENCE: 544
ccggcgacug agggcuucu                                          19

<210> SEQ ID NO 545
<211> LENGTH: 19
<212> TYPE: RNA
<213> ORGANISM: Homo sapiens

<400> SEQUENCE: 545
gcccucaguc gccggccgg                                          19

<210> SEQ ID NO 546
<211> LENGTH: 19
<212> TYPE: RNA
<213> ORGANISM: Homo sapiens

<400> SEQUENCE: 546
ccggccggcg acugagggc                                          19

<210> SEQ ID NO 547
<211> LENGTH: 19
<212> TYPE: RNA
<213> ORGANISM: Homo sapiens

<400> SEQUENCE: 547
gaacccagac cucgaguuu                                          19

<210> SEQ ID NO 548
<211> LENGTH: 19
<212> TYPE: RNA
<213> ORGANISM: Homo sapiens

<400> SEQUENCE: 548
aaacucgagg ucuggguuc                                          19

<210> SEQ ID NO 549
<211> LENGTH: 19
<212> TYPE: RNA
<213> ORGANISM: Homo sapiens

```
<400> SEQUENCE: 549
cccagaccuc gaguuugac                                                    19

<210> SEQ ID NO 550
<211> LENGTH: 19
<212> TYPE: RNA
<213> ORGANISM: Homo sapiens

<400> SEQUENCE: 550
gucaaacucg aggucuggg                                                    19

<210> SEQ ID NO 551
<211> LENGTH: 1341
<212> TYPE: DNA
<213> ORGANISM: Homo sapiens

<400> SEQUENCE: 551
atggagttca cggcgtcccc caagccccaa ctctcctctc gggccaacgc cttctccatt       60
gccgcgctca tgtcgagcgg cggctctaag gagaaggagg cgacggagaa cacaatcaaa      120
cccctggagc aatttgtgga gaagtcgtcc tgtgcccagc cctgggtga gctgaccagc       180 ctggatgctc atggggagtt tggtggaggc agtggcagca gccgtcctc ctcctctctg       240 tgcactgagc cactgatccc caccaccccc atcatcccca gtgaggaaat ggccaaaatt      300
gcctgcagcc tggagaccaa ggagctttgg gacaaattcc atgagctggg caccgagatg      360 atcatccacca gtcgggcag gaggatgttt ccaaccatcc gggtgtcctt ttcggggtg       420 gatcctgagg ccaagtacat agtcctgatg gacatcgtcc ctgtggacaa caagaggtac     480
cgctacgcct accaccggtc ctcctggctg gtggctggca aggccgaccc gccgttgcca      540
gccaggctct atgtgcatcc agattctcct tttaccggtg agcaactact caaacagatg     600 gtgtctttg aaaaggtgaa actcaccaac aatgaactgg atcaacatgg ccatataatt      660
ttgaactcaa tgcataagta ccagccaagg gtgcacatca ttaagaagaa agaccacaca     720
gcctcattgc tcaacctgaa gtctgaagaa tttagaactt tcatctttcc agaaacagtt     780
tttacggcag tcactgccta ccagaatcaa ctgataacga agctgaaaat agatagcaat     840
ccttttgcca aaggattccg ggattcctcc aggctcactg acattgagag ggaaagtgtg    900
gagagcctga ttcaaaagca ttcctatgca cgctcaccca tccgtaccta cggaggagaa    960
gaagatgtct tggggatga gagtcagaca ccccaaaatc gagggtcagc ctttacaaca   1020
tctgataatt tgtctctcag ctcctgggta tcatcttctt ccagttttcc tgggtttcag    1080
cacccacagt ccctgactgc tcttggcacc agcacagcat ccatagcaac acccattcct   1140
caccccatcc agggttctct gccaccatat agccgactgg gaatgcctct gacaccatcg   1200
gccattgcca gctccatgca agggagtggc cccacattcc cttcattcca catgccgcga   1260
taccatcact attttcagca ggggccctat gctgccattc aaggactacg ccattcctct   1320
gctgtgatga cgccatttgt a                                             1341

<210> SEQ ID NO 552
<211> LENGTH: 2109
<212> TYPE: DNA
<213> ORGANISM: Homo sapiens

<400> SEQUENCE: 552
atggcttacc acccgttcca cgcgccacgg cccgccgact cccccatgtc cgcctttctg      60
gcggcggcgc agccctcctt cttcccggca ctcgcgctgc cgcccggcgc gctggccaag     120
```

```
ccgctgcccg acccgggcct ggcggggggcg gcggccgcgg cggcggcggc ggcagcagcg    180
gccgaggcgg ggctgcacgt ctcggcactg ggcccgcacc cgcccgccgc gcatctgcgc    240
tccctcaaga gcctggagcc cgaggacgag gtggaggacg accccaaggt gacgctggag    300
gccaaggagc tgtgggacca gttccacaag ctaggcacgg agatggtcat caccaagtcc    360
gggaggcgga tgttcccccc cttcaaggtg cgagtcagcg gcctggacaa gaaggccaag    420
tatatcctgc tgatggacat tgtagccgct gacgattgcc gctataagtt ccacaactcg    480
cgctggatgg tggcgggcaa ggccgaccct gagatgccca acgcatgta catccaccca    540
gacagcccag ccacggggga gcagtggatg gctaagcctg tggccttcca caagctgaag    600
ctgaccaaca acatctctga caagcacggc ttcaccatcc taaactccat gcacaagtac    660
cagccgcgct tccacatagt gcgagccaac gacatcctga agctgcctta cagcaccttc    720
cgcacctacg tgttcccgga gaccgacttc atcgccgtca ctgcctacca gaatgacaag    780
atcacacagc tgaagatcga caacaacccg tttgccaagg gcttccggga caccgggaac    840
ggccggcggg agaaaaggaa gcagctgacg ctgccgtctc tacgcttgta cgaggagcac    900
tgcaaacccg agcgcgatgg cgcggagtca gacgcctcgt cgtgcgaccc tccccccgcg    960
cgggaaccac ccacctcccc gggcgcagcg cccagtccgc tgcgcctgca ccgggcccga   1020
gctgaggaga agtcgtgcgc cgcggacagc gaccccgagc tgagcggtt gagcgaggag   1080
cgtgcggggg cgccgctagg ccgcagcccg gctccagaca gcgccagccc cactcgcttg   1140
accgaacccg agcgcgcccg ggagcggcgt agtcccgaga ggggcaagga gccggccgag   1200
agcggcgggg acggcccgtt cggcctgagg agcctggaga aggagcgcgc cgaagctcgg   1260
aggaaggacg aggggcgcaa ggaggcggcc gagggcaagg agcagggcct ggcgccgctg   1320
gtggtgcaga cagacagtgc gtcccccctg ggcgccggac acctgccggg cctggccttt   1380
tccagccact gcacgggca gcagttcttt gggccgctgg gagccggcca gccgctcttc   1440
ctgcaccctg gacagttcac catgggccct ggcgccttct ccgccatggg catgggtcac   1500
ctactggcct cggtggcagg cggcggcaac ggcggaggtg gcgggcctgg gaccgccgcg   1560
gggctggacg caggcgggct gggtcccgcg gccagcgcag caagcaccgc cgcgcccttc   1620
ccgttccacc tctcccagca catgctggca tctcagggaa ttccaatgcc cactttcgga   1680
ggcctcttcc cctaccccta cacctacatg gcagcagcag ccgcagccgc ctcggctttg   1740
cccgccacta gtgctgcagc tgccgccgcc gcagccgccg gctccctctc ccggagcccc   1800
ttcctgggca gtgcccggcc ccgactgcgt ttcagcccct atcagatccc ggtcaccatc   1860
ccgcctagca ctagcctcct caccaccggg ctggcctctg agggctccaa ggccgctggt   1920
ggaaacagcc gggagcctag cccctgcccc gagctggctc tccgcaaagt aggggcccca   1980
tcccgcggtg ccctgtcgcc cagtggctcg gccaaggagg cggccaatga actgcagagc   2040
atccagagac tggtgagtgg gctggagagc cagcgagccc tctccccagg ccgggagtcg   2100
cccaagtga                                                           2109
```

<210> SEQ ID NO 553
<211> LENGTH: 1788
<212> TYPE: DNA
<213> ORGANISM: Homo sapiens

<400> SEQUENCE: 553

```
atgagcctct ccatgagaga tccggtcatt cctgggacaa gcatggccta ccatccgttc     60
ctacctcacc gggcgccgga cttcgccatg agcgcggtgc tgggtcacca gccgccgttc    120
```

-continued

```
ttccccgcgc tgacgctgcc tcccaacggc gcggcggcgc tctcgctgcc gggcgccctg    180
gccaagccga tcatggatca attggtgggg gcggccgaga ccggcatccc gttctcctcc    240
ctggggcccc aggcgcatct gaggcctttg aagaccatgg agcccgaaga agaggtggag    300
gacgacccca aggtgcacct ggaggctaaa gaactttggg atcagtttca aagcggggc     360 accgagatgg tcattaccaa gtcgggaagg cgaatgtttc ctccatttaa agtgagatgt    420
tctgggctgg ataaaaaagc caaatacatt ttattgatgg acattatagc tgctgatgac    480 tgtcgtttata aatttcacaa ttctcggtgg atggtggctg gtaaggccga ccccgaaatg    540
ccaaagagga tgtacattca cccggacagc cccgctactg gggaacagtg gatgtccaaa    600
gtcgtcactt tccacaaact gaaactcacc aacaacattt cagacaaaca tggatttact    660
ttggccttcc caagtgatca cgctacgtgg caggggaatt atagttttgg tactcagact    720
atattgaact ccatgcacaa ataccagccc cggttccaca ttgtaagagc caatgacatc    780
ttgaaactcc cttatagtac atttcggaca tacttgttcc ccgaaactga attcatcgct    840
gtgactgcat accagaatga taagataacc cagttaaaaa tagacaacaa cccttttgca    900 aaaggttttcc gggacactgg aaatggccga agagaaaaaa gaaaacagct caccctgcag    960
tccatgaggg tgtttgatga agacacaaa aaggagaatg ggacctctga tgagtcctcc    1020
agtgaacaag cagcttttcaa ctgcttcgcc caggcttctt ctccagccgc ctccactgta    1080
gggacatcga acctcaaaga tttatgtccc agcgagggtg agagcgacgc cgaggccgag    1140
agcaaagagg agcatggccc cgaggcctgc gacgcggcca agatctccac caccacgtcg    1200
gaggagccct gccgtgacaa gggcagcccc gcggtcaagg ctcacctttt cgctgctgag    1260
cggccccggg acagcgggcg gctggacaaa gcgtcgcccg actcacgcca tagccccgcc    1320
accatctcgt ccagcactcg cggcctgggc gcggaggagc gcaggagccc ggttcgcgag    1380
ggcacagcgc cggccaaggt ggaagaggcg cgcgcgctcc cgggcaagga ggccttcgcg    1440
ccgctcacgc ggcgggcctc ctctgcggca gcctccagct cggtgcaccg ccacccttc     1500 ctcaatctga acaccatgcg cccgcggctg cgctacagcc cctactccat cccggtgccg    1560
gtcccggacg gcagcatcgc cgccctggcc gccagcccgg cctcggtggc agtggactcg    1620
ggctctgaac tcaacagccg ctcctccacg ctctcctcca gctccatgtc cttgtcgccc    1680
aaactctgcg cggagaaaga ggcggccacc agcgaactgc agagcatcca gcggttggtt    1740
agcggcttgg aagccaagcc ggacaggtcc cgcagcgcgt ccccgtag                  1788
```

<210> SEQ ID NO 554
<211> LENGTH: 44
<212> TYPE: DNA
<213> ORGANISM: Mouse

<400> SEQUENCE: 554

```
tccggaacgt gtcaatgctt tgcacttggg gccggcatgc ggct                       44
```

<210> SEQ ID NO 555
<211> LENGTH: 44
<212> TYPE: DNA
<213> ORGANISM: Rat

<400> SEQUENCE: 555

```
tcccgaacgt gtcaatgctt tgcacttggg gccggcatgc ggct                       44
```

<210> SEQ ID NO 556
<211> LENGTH: 44

```
<212> TYPE: DNA
<213> ORGANISM: Homo sapiens

<400> SEQUENCE: 556
tcggggtcgt gtcaatgctt tgcacttggg gccggcgtgc ggct            44

<210> SEQ ID NO 557
<211> LENGTH: 32
<212> TYPE: DNA
<213> ORGANISM: Mouse

<400> SEQUENCE: 557
ccctggacgc ggctccgcac cctgcaccca aa                         32

<210> SEQ ID NO 558
<211> LENGTH: 39
<212> TYPE: DNA
<213> ORGANISM: Homo sapiens

<400> SEQUENCE: 558
ccctggacgg gattgcgacg tgcgcaccgg gcgccctaa                  39

<210> SEQ ID NO 559
<211> LENGTH: 27
<212> TYPE: DNA
<213> ORGANISM: Mouse

<400> SEQUENCE: 559
ccggtgcgtc cccaccccaa gctgggg                               27

<210> SEQ ID NO 560
<211> LENGTH: 27
<212> TYPE: DNA
<213> ORGANISM: Homo sapiens

<400> SEQUENCE: 560
ccggtgcgtc cccacccag gctgggg                                27

<210> SEQ ID NO 561
<211> LENGTH: 29
<212> TYPE: DNA
<213> ORGANISM: Mouse

<400> SEQUENCE: 561
cagtgccttg tgtgaatgaa acggcagtt                             29

<210> SEQ ID NO 562
<211> LENGTH: 29
<212> TYPE: DNA
<213> ORGANISM: Homo sapiens

<400> SEQUENCE: 562
cagtgccttg tgtgaatgaa atggcagtt                             29

<210> SEQ ID NO 563
<211> LENGTH: 54
<212> TYPE: DNA
<213> ORGANISM: Mouse

<400> SEQUENCE: 563
atctgcaagc ccctcccac tcccagtctt agacagcttg tacacaaaag gagg  54

<210> SEQ ID NO 564
<211> LENGTH: 54
```

```
<212> TYPE: DNA
<213> ORGANISM: Homo sapiens

<400> SEQUENCE: 564
atctgcatgc cccctcccac ccctgtcgt agacagcttg tacacaaaag gagg      54

<210> SEQ ID NO 565
<211> LENGTH: 45
<212> TYPE: DNA
<213> ORGANISM: Mouse

<400> SEQUENCE: 565
ggagacaagc tcccctttcc tcccacccca agtctttgga gagct             45

<210> SEQ ID NO 566
<211> LENGTH: 45
<212> TYPE: DNA
<213> ORGANISM: Rat

<400> SEQUENCE: 566
ggtgacaagc gcccctttcc tcccacccca agtcttttg gagag              45

<210> SEQ ID NO 567
<211> LENGTH: 46
<212> TYPE: DNA
<213> ORGANISM: Homo sapiens

<400> SEQUENCE: 567
agcaagaagc gcccctttcc tcccacccaa cgttttaga tatctg             46

<210> SEQ ID NO 568
<211> LENGTH: 24
<212> TYPE: DNA
<213> ORGANISM: Artificial Sequence
<220> FEATURE:
<223> OTHER INFORMATION: Primer

<400> SEQUENCE: 568
agtgctaccc tctgcagctg caaa                                    24

<210> SEQ ID NO 569
<211> LENGTH: 24
<212> TYPE: DNA
<213> ORGANISM: Artificial Sequence
<220> FEATURE:
<223> OTHER INFORMATION: Primer

<400> SEQUENCE: 569
agtaggaagg agctgggaag agta                                    24

<210> SEQ ID NO 570
<211> LENGTH: 24
<212> TYPE: DNA
<213> ORGANISM: Artificial Sequence
<220> FEATURE:
<223> OTHER INFORMATION: Primer

<400> SEQUENCE: 570
cagaaaatga cacgcggatg gtgg                                    24

<210> SEQ ID NO 571
<211> LENGTH: 21
<212> TYPE: DNA
<213> ORGANISM: Artificial Sequence
<220> FEATURE:
<223> OTHER INFORMATION: Primer
```

-continued

```
<400> SEQUENCE: 571
ctccctctga agtgcatgga c                                              21

<210> SEQ ID NO 572
<211> LENGTH: 21
<212> TYPE: DNA
<213> ORGANISM: Artificial Sequence
<220> FEATURE:
<223> OTHER INFORMATION: Primer

<400> SEQUENCE: 572
agcgcagagg accgatctga c                                              21

<210> SEQ ID NO 573
<211> LENGTH: 24
<212> TYPE: DNA
<213> ORGANISM: Artificial Sequence
<220> FEATURE:
<223> OTHER INFORMATION: Primer

<400> SEQUENCE: 573
ctctggttcc taggcaggac tcgg                                           24

<210> SEQ ID NO 574
<211> LENGTH: 24
<212> TYPE: DNA
<213> ORGANISM: Artificial Sequence
<220> FEATURE:
<223> OTHER INFORMATION: Primer

<400> SEQUENCE: 574
tcctctgcag tctgcctgtc tgtg                                           24

<210> SEQ ID NO 575
<211> LENGTH: 24
<212> TYPE: DNA
<213> ORGANISM: Artificial Sequence
<220> FEATURE:
<223> OTHER INFORMATION: Primer

<400> SEQUENCE: 575
ccaggcagag aaatagcttt agcg                                           24

<210> SEQ ID NO 576
<211> LENGTH: 24
<212> TYPE: DNA
<213> ORGANISM: Artificial Sequence
<220> FEATURE:
<223> OTHER INFORMATION: Primer

<400> SEQUENCE: 576
cctttccatt cccttcctt caga                                            24

<210> SEQ ID NO 577
<211> LENGTH: 22
<212> TYPE: DNA
<213> ORGANISM: Artificial Sequence
<220> FEATURE:
<223> OTHER INFORMATION: Primer

<400> SEQUENCE: 577
ccaggcagtg ccttgtgtga at                                             22

<210> SEQ ID NO 578
<211> LENGTH: 22
```

```
<212> TYPE: DNA
<213> ORGANISM: Artificial Sequence
<220> FEATURE:
<223> OTHER INFORMATION: Primer

<400> SEQUENCE: 578
gccaacctcc aactctacaa cc                                          22

<210> SEQ ID NO 579
<211> LENGTH: 24
<212> TYPE: DNA
<213> ORGANISM: Artificial Sequence
<220> FEATURE:
<223> OTHER INFORMATION: Primer

<400> SEQUENCE: 579
gaggctatgt ggcttctagg agag                                        24

<210> SEQ ID NO 580
<211> LENGTH: 24
<212> TYPE: DNA
<213> ORGANISM: Artificial Sequence
<220> FEATURE:
<223> OTHER INFORMATION: Primer

<400> SEQUENCE: 580
ggatgttaga tgtccagtct cacc                                        24

<210> SEQ ID NO 581
<211> LENGTH: 21
<212> TYPE: DNA
<213> ORGANISM: Artificial Sequence
<220> FEATURE:
<223> OTHER INFORMATION: Primer

<400> SEQUENCE: 581
cgggaggaaa ggaaccaacc t                                           21

<210> SEQ ID NO 582
<211> LENGTH: 22
<212> TYPE: DNA
<213> ORGANISM: Artificial Sequence
<220> FEATURE:
<223> OTHER INFORMATION: Primer

<400> SEQUENCE: 582
cccggagtag gacggttaga cc                                          22

<210> SEQ ID NO 583
<211> LENGTH: 24
<212> TYPE: DNA
<213> ORGANISM: Artificial Sequence
<220> FEATURE:
<223> OTHER INFORMATION: Primer

<400> SEQUENCE: 583
ctctggttcc taggcaggac tcgg                                        24

<210> SEQ ID NO 584
<211> LENGTH: 24
<212> TYPE: DNA
<213> ORGANISM: Artificial Sequence
<220> FEATURE:
<223> OTHER INFORMATION: Primer

<400> SEQUENCE: 584
gcggtctgct gctcggctct cagc                                        24
```

```
<210> SEQ ID NO 585
<211> LENGTH: 22
<212> TYPE: DNA
<213> ORGANISM: Artificial Sequence
<220> FEATURE:
<223> OTHER INFORMATION: Primer

<400> SEQUENCE: 585
catcagggtt ctgccatggc tc                                          22

<210> SEQ ID NO 586
<211> LENGTH: 21
<212> TYPE: DNA
<213> ORGANISM: Artificial Sequence
<220> FEATURE:
<223> OTHER INFORMATION: Primer

<400> SEQUENCE: 586
ggctctctca tcgggacatc c                                           21

<210> SEQ ID NO 587
<211> LENGTH: 22
<212> TYPE: DNA
<213> ORGANISM: Artificial Sequence
<220> FEATURE:
<223> OTHER INFORMATION: Primer

<400> SEQUENCE: 587
agcggtactt gcgaagcttc ga                                          22

<210> SEQ ID NO 588
<211> LENGTH: 24
<212> TYPE: DNA
<213> ORGANISM: Artificial Sequence
<220> FEATURE:
<223> OTHER INFORMATION: Primer

<400> SEQUENCE: 588
cgcctctctt ttaatatctc cgct                                        24

<210> SEQ ID NO 589
<211> LENGTH: 24
<212> TYPE: DNA
<213> ORGANISM: Artificial Sequence
<220> FEATURE:
<223> OTHER INFORMATION: Primer

<400> SEQUENCE: 589
gaattctgtg tgtcccctaa taac                                        24

<210> SEQ ID NO 590
<211> LENGTH: 24
<212> TYPE: DNA
<213> ORGANISM: Artificial Sequence
<220> FEATURE:
<223> OTHER INFORMATION: Primer

<400> SEQUENCE: 590
agagggagta atgtccacag tgaa                                        24
```